US008883454B2

(12) United States Patent
Borns

(10) Patent No.: US 8,883,454 B2
(45) Date of Patent: *Nov. 11, 2014

(54) DNA POLYMERASE FUSIONS AND USES THEREOF

(75) Inventor: Michael Borns, Escondido, CA (US)

(73) Assignee: Agilent Technologies, Inc., Loveland, CO (US)

( * ) Notice: Subject to any disclaimer, the term of this patent is extended or adjusted under 35 U.S.C. 154(b) by 215 days.

This patent is subject to a terminal disclaimer.

(21) Appl. No.: 12/646,565

(22) Filed: Dec. 23, 2009

(65) Prior Publication Data

US 2010/0173365 A1 Jul. 8, 2010

Related U.S. Application Data

(62) Division of application No. 11/606,865, filed on Nov. 29, 2006, now Pat. No. 7,659,100, which is a division of application No. 10/805,650, filed on Mar. 19, 2004, now Pat. No. 7,704,712.

(60) Provisional application No. 60/457,426, filed on Mar. 25, 2003.

(51) Int. Cl.

| | |
|---|---|
| ***C12P 19/34*** | (2006.01) |
| ***C12N 9/00*** | (2006.01) |
| ***C12Q 1/68*** | (2006.01) |
| ***C12N 9/12*** | (2006.01) |
| ***C12N 15/10*** | (2006.01) |

(52) U.S. Cl.

CPC .............. *C12N 15/102* (2013.01); *C12Q 1/686* (2013.01); *C12Q 1/6844* (2013.01); *C12N 9/1252* (2013.01)

USPC .......................................... 435/91.2; 435/183

(58) Field of Classification Search

None

See application file for complete search history.

(56) References Cited

U.S. PATENT DOCUMENTS

| | | | | |
|---|---|---|---|---|
| 4,545,933 | A * | 10/1985 | Ernster | 530/360 |
| 4,889,818 | A | 12/1989 | Gelfand et al. | |
| 5,466,591 | A | 11/1995 | Abramson et al. | |
| 5,541,311 | A | 7/1996 | Dahlberg et al. | |
| 5,814,506 | A | 9/1998 | Kong et al. | |
| 5,972,603 | A | 10/1999 | Bedford et al. | |
| 6,255,062 | B1 | 7/2001 | Campbell et al. | |
| 6,803,201 | B2 | 10/2004 | Sorge et al. | |
| 7,659,100 | B2 * | 2/2010 | Borns | 435/183 |
| 7,704,712 | B2 * | 4/2010 | Borns | 435/91.1 |
| 2002/0119461 | A1 * | 8/2002 | Chatterjee | 435/6 |
| 2003/0143577 | A1 | 7/2003 | Hogrefe et al. | |

(Continued)

FOREIGN PATENT DOCUMENTS

| | | | |
|---|---|---|---|
| EP | 0 751 226 | A2 | 1/1997 |
| EP | 1012248 | B1 | 6/2000 |

(Continued)

OTHER PUBLICATIONS

Hugli et al., Determination of the Tryptophan Content of Proteins by Ion Exchange Chromatography of Alkaline Hydrolysates, The Journal of Biological Chemistry, vol. 247, No. 9, Issue of May 10, pp. 2828-2834, 1972.*

(Continued)

*Primary Examiner* — Stephanie K Mummert

(57) ABSTRACT

The present invention discloses methods of using DNA polymerase fusions at high pH in PCR, DNA sequencing and mutagenesis protocols.

13 Claims, 186 Drawing Sheets

(56) References Cited

U.S. PATENT DOCUMENTS

| | | | |
|---|---|---|---|
| 2003/0149257 A1 | 8/2003 | Sorge et al. | |
| 2004/0086890 A1 | 5/2004 | Sorge et al. | |
| 2005/0069908 A1 | 3/2005 | Sorge et al. | |
| 2005/0118609 A1 | 6/2005 | Sorge et al. | |

FOREIGN PATENT DOCUMENTS

| | | | |
|---|---|---|---|
| WO | WO 97/29209 | 2/1997 | |
| WO | WO 01/11051 | 2/2001 | |
| WO | WO 01/61015 | 2/2001 | |
| WO | 01/32887 A1 | 5/2001 | |
| WO | WO 01/38546 | 5/2001 | |
| WO | WO 01 92501 A1 * | 6/2001 | ............... C12N 9/12 |

OTHER PUBLICATIONS

Drazic et al,., Kinetic and mechanistic study of hydroxyl ion electrosorption at the Pt(111) surface in alkaline media, Journal of Electroanalytical Chemistry 466 (1999) 155-164.*

Yates et al., Molecular Diagnosis of Thiopurine S-Methyltransferase Deficiency: Genetic Basis for Azathioprine and Mercaptopurine Intolerance, Ann Intern Med. 1997;126:608-614.*

Siegelman et al., Rapid, nonradioactive screening for mutations in exons 10, 11, and 16 of the RET protooncogene associated with inherited medullary thyroid carcinoma,Clinical Chemistry, Molecular Pathology, 43:3, pp. 453-457 (1997).*

Koonin et al. Comparison of archaeal and bacterail genomes, Molecular Microbiology (1997) 25(4), pp. 619-637.*

Stratagne 1988 Catalog, p. 39.*

Sigma, JumpStart™ AccuTaq™ LA DNA Polymerase Mix, Product Code D 5809, Technical Bulletin No. MB-1000, Dec. 2001, pp. 1-7.*

Cline, Janice, et al., PCR Fidelity of PFU DNA Polymerase and Other Thermostable DNA Polymerases, 1996, Nucleic Acids Research, vol. 24(18), pp. 3546-3551.

Shen, Yulong, et al., Invariant Asp-1122 and Asp-1124 are Essential Residues for Polymerization Catalysis of Family D DNA Polymerase from Pyrococcus horikoshii, Jul. 20, 2001, Journal of Biological Chemistry, vol. 276, No. 29, pp. 27376-27383.

Shimazaki, N., et al., Over-Expression of Human DNA Polymerase Lambda in *E.coli* and Characterization of the Recombinant Enzyme, Jul. 2002, Genes to Cells, vol. 7, pp. 639-651.

Braithwaite, Dan, et al., "Compilation, Alignment, and Phylogenetic Relationships of DNA Polymerases", (1993) Nucleic Acids Research, vol. 21, No. 4, pp. 787-802.

European Search Report received in European Publication No. EP2194123, mailed on May 4, 2010, pp. 1-10.

Barnes, "PCR amplification of up to 35-kb DNA with high fidelity and high yield from λ bacteriophage templates," Proc. Nat'l. Acad. Sci. USA 91:2216-2220 (1994).

Bedford et al., Proc. Nat'l. Acad. Sci. USA 94:479-484 (1997).

Motz et al., "Elucidation of an Archaeal Replicaton Protein Network to GenerateEnhanced PCR Enzymes," J. Biol. Chem. 277(18):16179-16188 (May 3, 2002).

Pavlov et al., "Helix-hairpin-helix motifs confer salt resistance and processivity on chimeric DNA polymerases," Proc. Nat'l. Acad. Sci. USA 99:13510-13515 (2002).

International Search Report and Written Opinion of the International Searching Authority, or the Declaration for International Application No. PCT/US04/08875.

Sanger et al., "DNA sequencing with chain-terminating inhibitors," Biochemistry, Proc. Nat'l. Acad. Sci. USA vol. 74 No. 12 pp. 5463-5467 (1977).

Böhlke et al., Nucleic Acids Research, 2000, vol. 28, No. 20, pp. 3910-3917.

Fogg et al., "Structural basis for uracil recognition by archaeal family B DNA polymerases," Nature Structural Biology, Dec. 2002, vol. 9, No. 12, pp. 922-927.

Gardner et al., "Determinants of nucleotide sugar recognition in an archaeon DNA polymerase," Nucleic Acids Research, 1999, vol. 27, No. 12, pp. 2545-3553.

Miettinen et al., "Impaired migration and delayed differentiation of pancreatic islet cells in mice lacking EGF-receptors," Development, 2000, vol. 127, pp. 2617-2627.

Siegelman et al., Clinical Chemistry, 1997, vol. 43, No. 3, pp. 453-457.

Yates et al., Ann. Intern. Med., 1997, vol. 126, pp. 608-614.

European Search Report, EP 04758266.7—2402; PCT.US2004/008875, Apr. 10, 2007.

Hugli et al., "Determination of the Tryptophan Content of Proteins by Ion Exchange Chromatography of Alkaline Hydrolysates," J. Biol. Chem. 274:9, pp. 2828-2834, (1972).

Drazic et al., "Kinetic and mechanistic study of hydroxyl ion electrosorbtion at the Pt (111) surface in akaline media," Journal of Electroanalytical Chemistry 466:155-164.

Dietrich et al., "PCR Performance of the Highly Thermostable Proof-Reading B-Type DNA Polymerase from Pyrococcus abyssi," FEMS Microbiology Letters, vol. 217, pp. 89-94, 2002.

* cited by examiner

6kb BG
15”/kb - 1’-30”

1X Cloned buffer

19kb BG
30"/kb - 9.5' extension

19kb BG
30”/kb - 9.5’ extension

19kb BG
30"/kb - 9.5' extension

900bp HαAT
1"/kb - 1" extension

2.6kb HαAT
2"/kb - 5" extension

6kb BG
10"/kb - 1' extension

2.6kb HαAT
30"/kb - 1'. 18" extension

FIGURE 10

Figure 10. Oligonucleotide Primers for QuikChange Mutagenesis

V93E#1

5'-gAACATCCCCAAgATgAACCCACTATTAgAgAAAAAg-3' (SEQ ID NO: 5)

V93E#2

5'-CTTTTTCTCTAATAgTgggTTCATCTTggggATgTTC-3' (SEQ ID NO: 6)

V93R#1

5'-gAACATCCCCAAgATAgACCCACTATTAgAgAAAAAg-3' (SEQ ID NO: 7)

V93R#2

5'-CTTTTTCTCTAATAgTgggTCTATCTTggggATgTTC-3' (SEQ ID NO: 8)

V93N#1

5'-gAACATCCCCAAgATAACCCCACTATTAgAgAAAAAg-3' (SEQ ID NO: 9)

V93N#2

5'-CTTTTTCTCTAATAgTggggTTATCTTggggATgTTC-3' (SEQ ID NO: 10)

V93H#1

5'-gAACATCCCCAAgATCACCCCACTATTAgAgAAAAAg-3' (SEQ ID NO: 11)

V93H#2

5'-CTTTTTCTCTAATAgTggggTgATCTTggggATgTTC-3' (SEQ ID NO: 12)

V93X (for saturation mutagenesis; obtained V93G and V93L mutants from library)

5'-(Phosphate)gAACATCCCCAAgATNNKCCCACTATTAgAgAAAAAg-3' (SEQ ID NO: 13)

5'-gAACATCCCCAAgATAAACCCACTATTAgAg-3' (SEQ ID NO: 14)

V93K#2

5'-CTCTAATAgTgggTTTATCTTggggATgTTC-3' (SEQ ID NO: 15)

QCM#1 5'-(Phosphate)gAACATCCCCAAgATgCACCCACTATTAgAgAAAAAg-(SEQ ID NO: 16)'

Alanine

QCM#2 5'-(Phosphate)gAACATCCCCAAgATgACCCCACTATTAgAgAAAAAg-3'(SEQ ID NO: 17)

Aspartic Acid

QCM#3 5'-(Phosphate)gAACATCCCCAAgATTgCCCCCACTATTAgAgAAAAAg-3' (SEQ ID NO: 18)

Cysteine

QCM#4 5'-(Phosphate)gAACATCCCCAAgATATACCCACTATTAgAgAAAAAg-3' (SEQ ID NO: 19)

Isoleucine

QCM#5 5'-(Phosphate)gAACATCCCCAAgATATgCCCACTATTAgAgAAAAAg-3' (SEQ ID NO: 20)

Methionine

QCM#6 5'-(Phosphate)gAACATCCCCAAgATTTCCCCACTATTAgAgAAAAAg-3' (SEQ ID NO: 21)

FIGURE 10 (Cont.)

Phenylalanine

QCM#7 5'-(Phosphate)gAACATCCCCAAgATCCTCCCACTATTAgAgAAAAAg-3' (SEQ ID NO: 22)

Proline

QCM#8 5'-(Phosphate)gAACATCCCCAAgATAgCCCCACTATTAgAgAAAAAg-3' (SEQ ID NO: 23)

Serine

QCM#9 5'-(Phosphate)gAACATCCCCAAgATACACCCACTATTAgAgAAAAAg- 3' (SEQ ID NO: 24)

Threonine

QCM#10 5'-(Phosphate)gAACATCCCCAAgATTACCCCACTATTAgAgAAAAAg-3' (SEQ ID NO: 25)

Tyrosine

QCM#11 5'-(Phosphate)gAACATCCCCAAgATTggCCCACTATTAgAgAAAAAg-3'

(SEQ ID NO: 26)

Tryptophan

Figure 11
a.)
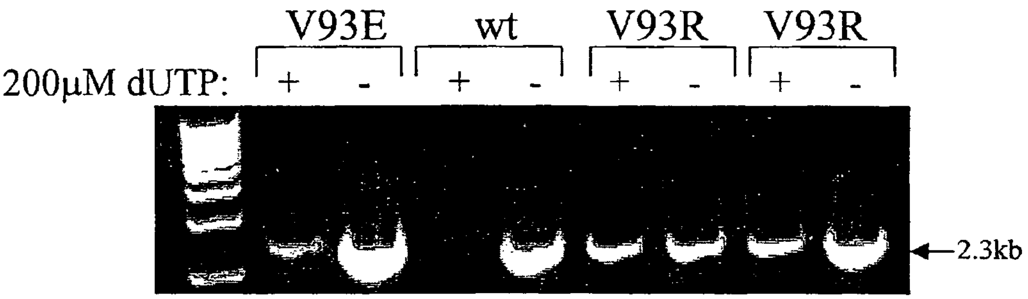
b.)
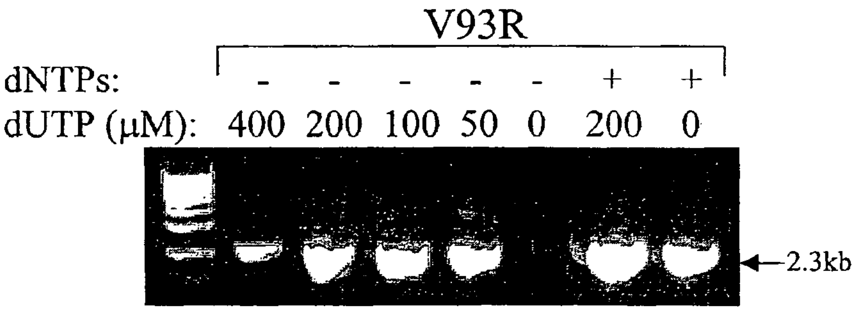

FIGURE 13A

PFU DNA POLYMERASE
V93R MUTANT: NNN = AGA, AGG, CGA, CGC, CGG, CGT (ALL POSSIBLE CODONS FOR ARGININE) (SEQ ID NO: 27)

V93E MUTANT: NNN = GAA, GAG (ALL CODONS FOR GLUTAMIC ACID) (SEQ ID NO: 28)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATNNNC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG 2328
```

FIGURE 13A (Cont.)

PFU DNA POLYMERASE
G387P Mutant (CCN is the codon for Proline where N = C, G, A, or T)
V93R MUTANT: NNN = AGA, AGG, CGA, CGC, CGG, CGT (ALL POSSIBLE CODONS FOR ARGININE) (SEQ ID NO: 29)
V93E MUTANT: NNN = GAA, GAG (ALL CODONS FOR GLUTAMIC ACID) (SEQ ID NO: 30)

ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATNNNC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG 2328

PFU DNA POLYMERASE
D141A/E143A Mutant (GCN is the codon for alanine where N = C, G, A, or T)
V93R MUTANT: NNN = AGA, AGG, CGA, CGC, CGG, CGT (ALL POSSIBLE CODONS FOR ARGININE) (SEQ ID NO: 31)
V93E MUTANT: NNN = GAA, GAG (ALL CODONS FOR GLUTAMIC ACID) (SEQ ID NO: 32)

ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120

FIGURE 13A (Cont.)

CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATNNNC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGGTGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG 2328

KOD DNA POLYMERASE
V93R MUTANT: NNN = AGA, AGG, CGA, CGC, CGG, CGT (ALL POSSIBLE CODONS FOR ARGININE) (SEQ ID NO: 33)
V93E MUTANT: NNN = GAA, GAG (ALL CODONS FOR GLUTAMIC ACID) (SEQ ID NO: 34)

ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACNNNC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780

FIGURE 13A (Cont.)

```
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CTTGA  2325
```

Vent DNA POLYMERASE
V93R MUTANT: NNN = AGA, AGG, CGA, CGC, CGG, CGT (ALL POSSIBLE CODONS FOR ARGININE) (SEQ ID NO: 35)
V93E MUTANT: NNN = GAA, GAG (ALL CODONS FOR GLUTAMIC ACID) (SEQ ID NO: 36)

```
ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACNNNC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
```

FIGURE 13A (Cont.)

GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325

Deep Vent
V93R MUTANT: NNN = AGA, AGG, CGA, CGC, CGG, CGT (ALL POSSIBLE CODONS FOR ARGININE) (SEQ ID NO: 37)
V93E MUTANT: NNN = GAA, GAG (ALL CODONS FOR GLUTAMIC ACID) (SEQ ID NO: 38)

ATGATACTTG ACGCTGACTA CATCACCGAG GATGGGAAGC CGATTATAAG GATTTTCAAG 60
AAAGAAAACG GCGAGTTTAA GGTTGAGTAC GACAGAAACT TTAGACCTTA CATTTACGCT 120
CTCCTCAAAG ATGACTCGCA GATTGATGAG GTTAGGAAGA TAACCGCCGA GAGGCATGGG 180
AAGATAGTGA GAATTATAGA TGCCGAAAAG GTAAGGAAGA AGTTCCTGGG GAGGCCGATT 240
GAGGTATGGA GGCTGTACTT TGAACACCCT CAGGACNNNC CCGCAATAAG GGATAAGATA 300
AGAGAGCATT CCGCAGTTAT TGACATCTTT GAGTACGACA TTCCGTTCGC GAAGAGGTAC 360
CTAATAGACA AAGGCCTAAT TCCAATGGAA GGCGATGAAG AGCTCAAGTT GCTCGCATTT 420
GACATAGAAA CCCTCTATCA CGAAGGGGAG GAGTTCGCGA AGGGGCCCAT TATAATGATA 480
AGCTATGCTG ATGAGGAAGA AGCCAAAGTC ATAACGTGGA AAAAGATCGA TCTCCCGTAC 540
GTCGAGGTAG TTTCCAGCGA GAGGGAGATG ATAAAGCGGT TCCTCAAGGT GATAAGGGAG 600
AAAGATCCCG ATGTTATAAT TACCTACAAC GGCGATTCTT TCGACCTTCC CTATCTAGTT 660
AAGAGGGCCG AAAAGCTCGG GATAAAGCTA CCCCTGGGAA GGGACGGTAG TGAGCCAAAG 720
ATGCAGAGGC TTGGGGATAT GACAGCGGTG GAGATAAAGG GAAGGATACA CTTTGACCTC 780
TACCACGTGA TTAGGAGAAC GATAAACCTC CCAACATACA CCCTCGAGGC AGTTTATGAG 840
GCAATCTTCG GAAAGCCAAA GGAGAAAGTT TACGCTCACG AGATAGCTGA GGCCTGGGAG 900
ACTGGAAAGG GACTGGAGAG AGTTGCAAAG TATTCAATGG AGGATGCAAA GGTAACGTAC 960
GAGCTCGGTA GGGAGTTCTT CCCAATGGAG GCCCAGCTTT CAAGGTTAGT CGGCCAGCCC 1020
CTGTGGGATG TTTCTAGGTC TTCAACTGGC AACTTGGTGG AGTGGTACCT CCTCAGGAAG 1080
GCCTACGAGA GGAATGAATT GGCTCCAAAC AAGCCGGATG AGAGGGAGTA CGAGAGAAGG 1140
CTAAGGGAGA GCTACGCTGG GGGATACGTT AAGGAGCCGG AGAAAGGGCT CTGGGAGGGG 1200
TTAGTTTCCC TAGATTTCAG GAGCCTGTAC CCCTCGATAA TAATCACCCA TAACGTCTCA 1260
CCGGATACGC TGAACAGGGA AGGGTGTAGG GAATACGATG TCGCCCCAGA GGTTGGGCAC 1320
AAGTTCTGCA AGGACTTCCC GGGGTTTATC CCCAGCCTGC TCAAGAGGTT ATTGGATGAA 1380
AGGCAAGAAA TAAAAAGGAA GATGAAAGCT TCTAAAGACC CAATCGAGAA GAAGATGCTT 1440
GATTACAGGC AACGGGCAAT CAAAATCCTG GCAAACAGCT ATTATGGGTA TTATGGGTAC 1500
GCAAAAGCCC GTTGGTACTG TAAGGAGTGC GCAGAGAGCG TTACGGCCTG GGGGAGGGAA 1560
TATATAGAGT TCGTAAGGAA GGAACTGGAG GAAAAGTTCG GGTTCAAAGT CTTATACATA 1620
GACACAGATG GACTCTACGC CACAATTCCT GGGGCAAAAC CCGAGGAGAT AAAGAAGAAA 1680
GCCCTAGAGT TCGTAGATTA TATAAACGCC AAGCTCCCAG GGCTGTTGGA GCTTGAGTAC 1740
GAGGGCTTCT ACGTGAGAGG GTTCTTCGTG ACGAAGAAGA AGTATGCGTT GATAGATGAG 1800
GAAGGGAAGA TAATCACTAG GGGGCTTGAA ATAGTCAGGA GGGACTGGAG CGAAATAGCC 1860
AAAGAAACCC AAGCAAAAGT CCTAGAGGCT ATCCTAAAGC ATGGCAACGT TGAGGAGGCA 1920
GTAAAGATAG TTAAGGAGGT AACTGAAAAG CTGAGCAAGT ACGAAATACC TCCAGAAAAG 1980
CTAGTTATTT ACGAGCAGAT CACGAGGCCC CTTCACGAGT ACAAGGCTAT AGGTCCGCAC 2040
GTTGCCGTGG CAAAAAGGTT AGCCGCTAGA GGAGTAAAGG TGAGGCCTGG CATGGTGATA 2100
GGGTACATAG TGCTGAGGGG AGACGGGCCA ATAAGCAAGA GGGCTATCCT TGCAGAGGAG 2160
TTCGATCTCA GGAAGCATAA GTATGACGCT GAGTATTACA TAGAAAATCA GGTTTTACCT 2220

FIGURE 13A (Cont.)

GCCGTTCTTA GAATATTAGA GGCCTTTGGG TACAGGAAAG AAGACCTCAG GTGGCAGAAG 2280
ACTAAACAGA CAGGTCTTAC GGCATGGCTT AACATCAAGA AGAAGTAA 2328

JDF-3
V93R MUTANT: NNN = AGA, AGG, CGA, CGC, CGG, CGT (ALL POSSIBLE CODONS FOR ARGININE) (SEQ ID NO: 39)
V93E MUTANT: NNN = GAA, GAG (ALL CODONS FOR GLUTAMIC ACID) (SEQ ID NO: 40)

ATGATCCTTGACGTTGATTACATCACCGAGAATGGAAAGCCCGTCATCAGGGTCTTCAAGAAGGAGAACGGCGAGTTCA
GGATTGAATACGACCGCGAGTTCGAGCCCTACTTCTACGCGCTCCTCAGGGACGACTCTGCCATCGAAGAAATCAAAAA
GATAACCGCGGAGAGGCACGGCAGGGTCGTTAAGGTTAAGCGCGCGGAGAAGGTGAAGAAAAAGTTCCTCGGCAGGTCT
GTGGAGGTCTGGGTCCTCTACTTCACGCACCCGCAGGACNNNCCGGCAATCCGCGACAAAATAAGGAAGCACCCCGCGG
TCATCGACATCTACGAGTACGACATACCCTTCGCCAAGCGCTACCTCATAGACAAGGGCCTAATCCCGATGGAAGGTGA
GGAAGAGCTTAAACTCATGTCCTTCGACATCGAGACGCTCTACCACGAGGGAGAAGAGTTTGGAACCGGGCCGATTCTG
ATGATAAGCTACGCCGATGAAAGCGAGGCGCGCGTGATAACCTGGAAGAAGATCGACCTTCCTTACGTTGAGGTTGTCT
CCACCGAGAAGGAGATGATTAAGCGCTTCTTGAGGGTCGTTAAGGAGAAGGACCCGGACGTGCTGATAACATACAACGG
CGACAACTTCGACTTCGCCTACCTGAAAAAGCGCTGTGAGAAGCTTGGCGTGAGCTTTACCCTCGGGAGGGACGGGAGC
GAGCCGAAGATACAGCGCATGGGGGACAGGTTTGCGGTCGAGGTGAAGGGCAGGGTACACTTCGACCTTTATCCAGTCA
TAAGGCGCACCATAAACCTCCCGACCTACACCCTTGAGGCTGTATACGAGGCGGTTTTCGGCAAGCCCAAGGAGAAGGT
CTACGCCGAGGAGATAGCCACCGCCTGGGAGACCGGCGAGGGGCTTGAGAGGGTCGCGCGCTACTCGATGGAGGACGCG
AGGGTTACCTACGAGCTTGGCAGGGAGTTCTTCCCGATGGAGGCCCAGCTTTCCAGGCTCATCGGCCAAGGCCTCTGGG
ACGTTTCCCGCTCCAGCACCGGCAACCTCGTCGAGTGGTTCCTCCTAAGGAAGGCCTACGAGAGGAACGAACTCGCTCC
CAACAAGCCCGACGAGAGGGAGCTGGCGAGGAGAAGGGGGGCTACgcCGGTGGCTACGTCAAGGAGCCGGAGCGGGGA
CTGTGGGACAATATCGTGTATCTAGACTTTCGTAGTCTCTACCCTTCAATCATAATCACCCACAACGTCTCGCCAGATA
CGCTCAACCGCGAGGGGTGTAGGAGCTACGACGTTGCCCCCGAGGTCGGTCACAAGTTCTGCAAGGACTTCCCCGGCTT
CATTCCGAGCCTGCTCGGAAACCTGCTGGAGGAAAGGCAGAAGATAAAGAGGAAGATGAAGGCAACTCTCGACCCGCTG
GAGAAGAATCTCCTCGATTACAGGCAACGCGCCATCAAGATTCTCGCCAACAGCTACTACGGCTACTACGGCTATGCCA
GGGCAAGATGGTACTGCAGGGAGTGCGCCGAGAGCGTTACGGCATGGGGAAGGGAGTACATCGAAATGGTCATCAGAGA
GCTTGAGGAAAAGTTCGGTTTTAAAGTCCTCTATGCAGACACAGACGGTCTCCATGCCACCATTCCTGGAGCGGACGCT
GAAACAGTCAAGAAAAAGGCAATGGAGTTCTTAAACTATATCAATCCCAAACTGCCCGGCCTTCTCGAACTCGAATACG
AGGGCTTCTACGTCAGGGGCTTCTTCGTCACGAAGAAAAAGTACGCGGTCATCGACGAGGAGGGCAAGATAACCACGCG
CGGGCTTGAGATAGTCAGGCGCGACTGGAGCGAGATAGCGAAGGAGACGCAGGCGAGGGTTTTGGAGGCGATACTCAGG
CACGGTGACGTTGAAGAGGCCGTCAGAATTGTCAGGGAAGTCACCGAAAAGCTGAGCAAGTACGAGGTTCCGCCGGAGA
AGCTGCTTATCCACGAGCAGATAACGCGCGAGCTCAAGGACTACAAGGCCACCGGCCCGCACGTAGCCATAGCGAAgcG
TTTGGCCGCCAGAGGTGTTAAAATCCGGCCCGGAACTGTGATAAGCTACATCGTTCTGAAGGGCTCCGGAAGGATAGGC
GACAGGGCGATTCCCTTCGACGAGTTCGACCCGACGAAGCACAAGTACGATGCGGACTACTACATCGAGAACCAGGTTC
TGCCGGCAGTTGAGAGAATCCTCAGGGCCTTCGGCTACCGCAAGGAAGACCTGCGCTACCAGAAGACGAGGCAGGTCGG
GCTTGGCGCGTGGCTGAAGCCGAAGGGAAGAAGAAGTGA

Figure 13B

>Pfu V93R (SEQ ID NO:41)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS //

>Pfu V93E (SEQ ID NO:42)
MILDVDYITEEGKPVIRLFKKENGKFKIEHDRTFRPYIYALLRDDSKIEEVKKITGERHGKIVRIVDVEKVEKKFLG
KPITVWKLYLEHPQDEPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

>Pfu V93R/G387P (SEQ ID NO:43)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TPGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

>Pfu V93R/D141A/E143A(SEQ ID NO:44)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFAIATLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

FIGURE 13B (Cont.)

>Pfu V93E/G387P(SEQ ID NO:45)
MILDVDYITEEGKPVIRLFKKENGKFKIEHDRTFRPYIYALLRDDSKIEEVKKITGERHGKIVRIVDVEKVEKKFLG
KPITVWKLYLEHPQDEPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TPGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

>Pfu V93E/D141A/E143A(SEQ ID NO:46)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFAIATLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

>DEEP VENT V93R(SEQ ID NO:47)
MILDADYITEDGKPIIRIFKKENGEFKVEYDRNFRPYIYALLKDDSQIDEVRKITAERHGKIVRIIDAEKVRKKFLG
RPIEVWRLYFEHPQDRPAIRDKIREHSAVIDIFEYDIPFAKRYLIDKGLIPMEGDEELKLLAFDIETLYHEGEEFAK
GPIIMISYADEEEAKVITWKKIDLPYVEVVSSEREMIKRFLKVIREKDPDVIITYNGDSFDLPYLVKRAEKLGIKLP
LGRDGSEPKMQRLGDMTAVEIKGRIHFDLYHVIRRTINLPTYTLEAVYEAIFGKPKEKVYAHEIAEAWETGKGLERV
AKYSMEDAKVTYELGREFFPMEAQLSRLVGQPLWDVSRSSTGNLVEWYLLRKAYERNELAPNKPDEREYERRLRESY
AGGYVKEPEKGLWEGLVSLDFRSLYPSIIITHNVSPDTLNREGCREYDVAPEVGHKFCKDFPGFIPSLLKRLLDERQ
EIKRKMKASKDPIEKKMLDYRQRAIKILANSYYGYYGYAKARWYCKECAESVTAWGREYIEFVRKELEEKFGFKVLY
IDTDGLYATIPGAKPEEIKKKALEFVDYINAKLPGLLELEYEGFYVRGFFVTKKKYALIDEEGKIITRGLEIVRRDW
SEIAKETQAKVLEAILKHGNVEEAVKIVKEVTEKLSKYEIPPEKLVIYEQITRPLHEYKAIGPHVAVAKRLAARGVK
VRPGMVIGYIVLRGDGPISKRAILAEEFDLRKHKYDAEYYIENQVLPAVLRILEAFGYRKEDLRWQKTKQTGLTAWL
NIKKK

>DEEP VENT V93E(SEQ ID NO:48)
MILDADYITEDGKPIIRIFKKENGEFKVEYDRNFRPYIYALLKDDSQIDEVRKITAERHGKIVRIIDAEKVRKKFLG
RPIEVWRLYFEHPQDEPAIRDKIREHSAVIDIFEYDIPFAKRYLIDKGLIPMEGDEELKLLAFDIETLYHEGEEFAK
GPIIMISYADEEEAKVITWKKIDLPYVEVVSSEREMIKRFLKVIREKDPDVIITYNGDSFDLPYLVKRAEKLGIKLP
LGRDGSEPKMQRLGDMTAVEIKGRIHFDLYHVIRRTINLPTYTLEAVYEAIFGKPKEKVYAHEIAEAWETGKGLERV
AKYSMEDAKVTYELGREFFPMEAQLSRLVGQPLWDVSRSSTGNLVEWYLLRKAYERNELAPNKPDEREYERRLRESY
AGGYVKEPEKGLWEGLVSLDFRSLYPSIIITHNVSPDTLNREGCREYDVAPEVGHKFCKDFPGFIPSLLKRLLDERQ
EIKRKMKASKDPIEKKMLDYRQRAIKILANSYYGYYGYAKARWYCKECAESVTAWGREYIEFVRKELEEKFGFKVLY
IDTDGLYATIPGAKPEEIKKKALEFVDYINAKLPGLLELEYEGFYVRGFFVTKKKYALIDEEGKIITRGLEIVRRDW
SEIAKETQAKVLEAILKHGNVEEAVKIVKEVTEKLSKYEIPPEKLVIYEQITRPLHEYKAIGPHVAVAKRLAARGVK
VRPGMVIGYIVLRGDGPISKRAILAEEFDLRKHKYDAEYYIENQVLPAVLRILEAFGYRKEDLRWQKTKQTGLTAWL
NIKKK

>TGO V93R(SEQ ID NO:49)

FIGURE 13B (Cont.)

MILDTDYITEDGKPVIRIFKKENGEFKIDYDRNFEPYIYALLKDDSAIEDVKKITAERHGTTVRVVRAEKVKKKFLG
RPIEVWKLYFTHPQDRPAIRDKIKEHPAVVDIYEYDIPFAKRYLIDKGLIPMEGDEELKMLAFDIETLYHEGEEFAE
GPILMISYADEEGARVITWKNIDLPYVDVVSTEKEMIKRFLKVVKEKDPDVLITYNGDNFDFAYLKKRSEKLGVKFI
LGREGSEPKIQRMGDRFAVEVKGRIHFDLYPVIRRTINLPTYTLEAVYEAIFGQPKEKVYAEEIAQAWETGEGLERV
ARYSMEDAKVTYELGKEFFPMEAQLSRLVGQSLWDVSRSSTGNLVEWFLLRKAYERNELAPNKPDERELARRRESYA
GGYVKEPERGLWENIVYLDFRSLYPSIIITHNVSPDTLNREGCEEYDVAPQVGHKFCKDFPGFIPSLLGDLLEERQK
VKKKMKATIDPIEKKLLDYRQRAIKILANSFYGYYGYAKARWYCKECAESVTAWGRQYIETTIREIEEKFGFKVLYA
DTDGFFATIPGADAETVKKKAKEFLDYINAKLPGLLELEYEGFYKRGFFVTKKKYAVIDEEDKITTRGLEIVRRDWS
EIAKETQARVLEAILKHGDVEEAVRIVKEVTEKLSKYEVPPEKLVIYEQITRDLKDYKATGPHVAVAKRLAARGIKI
RPGTVISYIVLKGSGRIGDRAIPFDEFDPAKHKYDAEYYIENQVLPAVERILRAFGYRKEDLRYQKTRQVGLGAWLK
PKT

>TGO V93E(SEQ ID NO:50)
MILDTDYITEDGKPVIRIFKKENGEFKIDYDRNFEPYIYALLKDDSAIEDVKKITAERHGTTVRVVRAEKVKKKFLG
RPIEVWKLYFTHPQDEPAIRDKIKEHPAVVDIYEYDIPFAKRYLIDKGLIPMEGDEELKMLAFDIETLYHEGEEFAE
GPILMISYADEEGARVITWKNIDLPYVDVVSTEKEMIKRFLKVVKEKDPDVLITYNGDNFDFAYLKKRSEKLGVKFI
LGREGSEPKIQRMGDRFAVEVKGRIHFDLYPVIRRTINLPTYTLEAVYEAIFGQPKEKVYAEEIAQAWETGEGLERV
ARYSMEDAKVTYELGKEFFPMEAQLSRLVGQSLWDVSRSSTGNLVEWFLLRKAYERNELAPNKPDERELARRRESYA
GGYVKEPERGLWENIVYLDFRSLYPSIIITHNVSPDTLNREGCEEYDVAPQVGHKFCKDFPGFIPSLLGDLLEERQK
VKKKMKATIDPIEKKLLDYRQRAIKILANSFYGYYGYAKARWYCKECAESVTAWGRQYIETTIREIEEKFGFKVLYA
DTDGFFATIPGADAETVKKKAKEFLDYINAKLPGLLELEYEGFYKRGFFVTKKKYAVIDEEDKITTRGLEIVRRDWS
EIAKETQARVLEAILKHGDVEEAVRIVKEVTEKLSKYEVPPEKLVIYEQITRDLKDYKATGPHVAVAKRLAARGIKI
RPGTVISYIVLKGSGRIGDRAIPFDEFDPAKHKYDAEYYIENQVLPAVERILRAFGYRKEDLRYQKTRQVGLGAWLK
PKT

>KOD V93R(SEQ ID NO:51)
MILDTDYITEDGKPVIRIFKKENGEFKIEYDRTFEPYFYALLKDDSAIEEVKKITAERHGTVVTVKRVEKVQKKFLG
RPVEVWKLYFTHPQDRPAIRDKIREHGAVIDIYEYDIPFAKRYLIDKGLVPMEGDEELKMLAFDIQTLYHEGEEFAE
GPILMISYADEEGARVITWKNVDLPYVDVVSTEREMIKRFLRVVKEKDPDVLITYNGDNFDFAYLKKRCEKLGINFA
LGRDGSEPKIQRMGDRFAVEVKGRIHFDLYPVIRRTINLPTYTLEAVYEAVFGQPKEKVYAEEITPAWETGENLERV
ARYSMEDAKVTYELGKEFLPMEAQLSRLIGQSLWDVSRSSTGNLVEWFLLRKAYERNELAPNKPDEKELARRRQSYE
GGYVKEPERGLWENIVYLDFRSLYPSIIITHNVSPDTLNREGCKEYDVAPQVGHRFCKDFPGFIPSLLGDLLEERQK
IKKKMKATIDPIERKLLDYRQRAIKILANSYYGYYGYARARWYCKECAESVTAWGREYITMTIKEIEEKYGFKVIYS
DTDGFFATIPGADAETVKKKAMEFLNYINAKLPGALELEYEGFYKRGFFVTKKKYAVIDEEGKITTRGLEIVRRDWS
EIAKETQARVLEALLKDGDVEKAVRIVKEVTEKLSKYEVPPEKLVIHEQITRDLKDYKATGPHVAVAKRLAARGVKI
RPGTVISYIVLKGSGRIGDRAIPFDEFDPTKHKYDAEYYIENQVLPAVERILRAFGYRKEDLRYQKTRQVGLSAWLK
PKGT

>KOD V93E(SEQ ID NO:52)
MILDTDYITEDGKPVIRIFKKENGEFKIEYDRTFEPYFYALLKDDSAIEEVKKITAERHGTVVTVKRVEKVQKKFLG
RPVEVWKLYFTHPQDEPAIRDKIREHGAVIDIYEYDIPFAKRYLIDKGLVPMEGDEELKMLAFDIQTLYHEGEEFAE
GPILMISYADEEGARVITWKNVDLPYVDVVSTEREMIKRFLRVVKEKDPDVLITYNGDNFDFAYLKKRCEKLGINFA
LGRDGSEPKIQRMGDRFAVEVKGRIHFDLYPVIRRTINLPTYTLEAVYEAVFGQPKEKVYAEEITPAWETGENLERV
ARYSMEDAKVTYELGKEFLPMEAQLSRLIGQSLWDVSRSSTGNLVEWFLLRKAYERNELAPNKPDEKELARRRQSYE
GGYVKEPERGLWENIVYLDFRSLYPSIIITHNVSPDTLNREGCKEYDVAPQVGHRFCKDFPGFIPSLLGDLLEERQK
IKKKMKATIDPIERKLLDYRQRAIKILANSYYGYYGYARARWYCKECAESVTAWGREYITMTIKEIEEKYGFKVIYS
DTDGFFATIPGADAETVKKKAMEFLNYINAKLPGALELEYEGFYKRGFFVTKKKYAVIDEEGKITTRGLEIVRRDWS
EIAKETQARVLEALLKDGDVEKAVRIVKEVTEKLSKYEVPPEKLVIHEQITRDLKDYKATGPHVAVAKRLAARGVKI
RPGTVISYIVLKGSGRIGDRAIPFDEFDPTKHKYDAEYYIENQVLPAVERILRAFGYRKEDLRYQKTRQVGLSAWLK
PKGT

FIGURE 13B (Cont.)

>VENT V93R(SEQ ID NO:53)
MILDTDYITKDGKPIIRIFKKENGEFKIELDPHFQPYIYALLKDDSAIEEIKAIKGERHGKTVRVLDAVKVRKKFLG
REVEVWKLIFEHPQDRPAMRGKIREHPAVVDIYEYDIPFAKRYLIDKGLIPMEGDEELKLLAFDIETFYHEGDEFGK
GEIIMISYADEEEARVITWKNIDLPYVDVVSNEREMIKRFVQVVKEKDPDVIITYNGDNFDLPYLIKRAEKLGVRLV
LGRDKEHPEPKIQRMGDSFAVEIKGRIHFDLFPVVRRTINLPTYTLEAVYEAVLGKTKSKLGAEEIAAIWETEESMK
KLAQYSMEDARATYELGKEFFPMEAELAKLIGQSVWDVSRSSTGNLVEWYLLRVAYARNELAPNKPDEEEYKRRLRT
TYLGGYVKEPEKGLWENIIYLDFRSLYPSIIVTHNVSPDTLEKEGCKNYDVAPIVGYRFCKDFPGFIPSILGDLIAM
RQDIKKKMKSTIDPIEKKMLDYRQRAIKLLANSYYGYMGYPKARWYSKECAESVTAWGRHYIEMTIREIEEKFGFKV
LYADTDGFYATIPGEKPELIKKKAKEFLNYINSKLPGLLELEYEGFYLRGFFVTKKRYAVIDEEGRITTRGLEVVRR
DWSEIAKETQAKVLEAILKEGSVEKAVEVVRDVVEKIAKYRVPLEKLVIHEQITRDLKDYKAIGPHVAIAKRLAARG
IKVKPGTIISYIVLKGSGKISDRVILLTEYDPRKHKYDPDYYIENQVLPAVLRILEAFGYRKEDLRYQSSKQTGLDA
WLKR

>VENT V93E(SEQ ID NO:54)
MILDTDYITKDGKPIIRIFKKENGEFKIELDPHFQPYIYALLKDDSAIEEIKAIKGERHGKTVRVLDAVKVRKKFLG
REVEVWKLIFEHPQDEPAMRGKIREHPAVVDIYEYDIPFAKRYLIDKGLIPMEGDEELKLLAFDIETFYHEGDEFGK
GEIIMISYADEEEARVITWKNIDLPYVDVVSNEREMIKRFVQVVKEKDPDVIITYNGDNFDLPYLIKRAEKLGVRLV
LGRDKEHPEPKIQRMGDSFAVEIKGRIHFDLFPVVRRTINLPTYTLEAVYEAVLGKTKSKLGAEEIAAIWETEESMK
KLAQYSMEDARATYELGKEFFPMEAELAKLIGQSVWDVSRSSTGNLVEWYLLRVAYARNELAPNKPDEEEYKRRLRT
TYLGGYVKEPEKGLWENIIYLDFRSLYPSIIVTHNVSPDTLEKEGCKNYDVAPIVGYRFCKDFPGFIPSILGDLIAM
RQDIKKKMKSTIDPIEKKMLDYRQRAIKLLANSYYGYMGYPKARWYSKECAESVTAWGRHYIEMTIREIEEKFGFKV
LYADTDGFYATIPGEKPELIKKKAKEFLNYINSKLPGLLELEYEGFYLRGFFVTKKRYAVIDEEGRITTRGLEVVRR
DWSEIAKETQAKVLEAILKEGSVEKAVEVVRDVVEKIAKYRVPLEKLVIHEQITRDLKDYKAIGPHVAIAKRLAARG
IKVKPGTIISYIVLKGSGKISDRVILLTEYDPRKHKYDPDYYIENQVLPAVLRILEAFGYRKEDLRYQSSKQTGLDA
WLKR

>JDF-3 V93R(SEQ ID NO:55)
MILDVDYITENGKPVIRVFKKENGEFRIEYDREFEPYFYALLRDDSAIEEIKKITAERHGRVVKVKRAEKVKKKFLGR
SVEVWVLYFTHPQDRPAIRDKIRKHPAVIDIYEYDIPFAKRYLIDKGLIPMEGEEELKLMSFDIETLYHEGEEFGTGP
ILMISYADESEARVITWKKIDLPYVEVVSTEKEMIKRFLRVVKEKDPDVLITYNGDNFDFAYLKKRCEKLGVSFTLGR
DGSEPKIQRMGDRFAVEVKGRVHFDLYPVIRRTINLPTYTLEAVYEAVFGKPKEKVYAEEIATAWETGEGLERVARYS
MEDARVTYELGREFFPMEAQLSRLIGQGLWDVSRSSTGNLVEWFLLRKAYERNELAPNKPDERELARRRGGYAGGYVK
EPERGLWDNIVYLDFRSLYPSIIITHNVSPDTLNREGCRSYDVAPEVGHKFCKDFPGFIPSLLGNLLEERQKIKRKMK
ATLDPLEKNLLDYRQRAIKILANSYYGYYGYARARWYCRECAESVTAWGREYIEMVIRELEEKFGFKVLYADTDGLHA
TIPGADAETVKKKAMEFLNYINPKLPGLLELEYEGFYVRGFFVTKKKYAVIDEEGKITTRGLEIVRRDWSEIAKETQA
RVLEAILRHGDVEEAVRIVREVTEKLSKYEVPPEKLVIHEQITRELKDYKATGPHVAIAKRLAARGVKIRPGTVISYI
VLKGSGRIGDRAIPFDEFDPTKHKYDADYYIENQVLPAVERILRAFGYRKEDLRYQKTRQVGLGAWLKPKGKKK

>JDF-3 V93E(SEQ ID NO:56)
MILDVDYITENGKPVIRVFKKENGEFRIEYDREFEPYFYALLRDDSAIEEIKKITAERHGRVVKVKRAEKVKKKFLGR
SVEVWVLYFTHPQDEPAIRDKIRKHPAVIDIYEYDIPFAKRYLIDKGLIPMEGEEELKLMSFDIETLYHEGEEFGTGP
ILMISYADESEARVITWKKIDLPYVEVVSTEKEMIKRFLRVVKEKDPDVLITYNGDNFDFAYLKKRCEKLGVSFTLGR
DGSEPKIQRMGDRFAVEVKGRVHFDLYPVIRRTINLPTYTLEAVYEAVFGKPKEKVYAEEIATAWETGEGLERVARYS
MEDARVTYELGREFFPMEAQLSRLIGQGLWDVSRSSTGNLVEWFLLRKAYERNELAPNKPDERELARRRGGYAGGYVK
EPERGLWDNIVYLDFRSLYPSIIITHNVSPDTLNREGCRSYDVAPEVGHKFCKDFPGFIPSLLGNLLEERQKIKRKMK
ATLDPLEKNLLDYRQRAIKILANSYYGYYGYARARWYCRECAESVTAWGREYIEMVIRELEEKFGFKVLYADTDGLHA
TIPGADAETVKKKAMEFLNYINPKLPGLLELEYEGFYVRGFFVTKKKYAVIDEEGKITTRGLEIVRRDWSEIAKETQA
RVLEAILRHGDVEEAVRIVREVTEKLSKYEVPPEKLVIHEQITRELKDYKATGPHVAIAKRLAARGVKIRPGTVISYI
VLKGSGRIGDRAIPFDEFDPTKHKYDADYYIENQVLPAVERILRAFGYRKEDLRYQKTRQVGLGAWLKPKGKKK

Figure 14

Tgo 93:
NNN = AGA, AGG, CGA, CGC, CGG, CGT (R)
(NUCLEOTIDE SEQUENCE: SEQ ID NO: 57; AMINO ACID SEQUENCE: SEQ ID NO: 58)

NNN = GAA, GAG (E)
(NUCLEOTIDE SEQUENCE: SEQ ID NO: 59; AMINO ACID SEQUENCE: SEQ ID NO: 60)

```
5'
atg atc ctc gat aca gac tac ata act gag gat gga aag ccc gtc atc      48
Met Ile Leu Asp Thr Asp Tyr Ile Thr Glu Asp Gly Lys Pro Val Ile
1               5                   10                  15

agg atc ttc aag aag gag aac ggc gag ttc aaa ata gac tac gac aga      96
Arg Ile Phe Lys Lys Glu Asn Gly Glu Phe Lys Ile Asp Tyr Asp Arg
            20                  25                  30

aac ttt gag cca tac atc tac gcg ctc ttg aag gac gac tct gcg att      144
Asn Phe Glu Pro Tyr Ile Tyr Ala Leu Leu Lys Asp Asp Ser Ala Ile
        35                  40                  45

gag gac gtc aag aag ata act gcc gag agg cac ggc act acc gtt agg      192
Glu Asp Val Lys Lys Ile Thr Ala Glu Arg His Gly Thr Thr Val Arg
    50                  55                  60

gtt gtc agg gcc gag aaa gtg aag aag aag ttc cta ggc agg ccg ata      240
Val Val Arg Ala Glu Lys Val Lys Lys Lys Phe Leu Gly Arg Pro Ile
65                  70                  75                  80

gag gtc tgg aag ctc tac ttc act cac ccc cag gac nnn ccc gca atc      288
Glu Val Trp Lys Leu Tyr Phe Thr His Pro Gln Asp Xaa Pro Ala Ile
                85                  90                  95

agg gac aag ata aag gag cat cct gcc gtt gtg gac atc tac gag tac      336
Arg Asp Lys Ile Lys Glu His Pro Ala Val Val Asp Ile Tyr Glu Tyr
            100                 105                 110

gac atc ccc ttc gcg aag cgc tac ctc ata gac aaa ggc tta atc ccg      384
Asp Ile Pro Phe Ala Lys Arg Tyr Leu Ile Asp Lys Gly Leu Ile Pro
        115                 120                 125

atg gag ggc gac gag gaa ctt aag atg ctc gcc ttc gac atc gag acg      432
Met Glu Gly Asp Glu Glu Leu Lys Met Leu Ala Phe Asp Ile Glu Thr
    130                 135                 140

ctc tat cac gag ggc gag gag ttc gcc gaa ggg cct atc ctg atg ata      480
Leu Tyr His Glu Gly Glu Glu Phe Ala Glu Gly Pro Ile Leu Met Ile
145                 150                 155                 160

agc tac gcc gac gag gaa ggg gcg cgc gtt att acc tgg aag aat atc      528
Ser Tyr Ala Asp Glu Glu Gly Ala Arg Val Ile Thr Trp Lys Asn Ile
                165                 170                 175

gac ctt ccc tat gtc gac gtc gtt tcc acc gag aag gag atg ata aag      576
Asp Leu Pro Tyr Val Asp Val Val Ser Thr Glu Lys Glu Met Ile Lys
            180                 185                 190
```

FIGURE 14 (Cont.)

```
cgc ttc ctc aag gtc gtc aag gaa aag gat ccc gac gtc ctc ata acc      624
Arg Phe Leu Lys Val Val Lys Glu Lys Asp Pro Asp Val Leu Ile Thr
        195                 200                 205

tac aac ggc gac aac ttc gac ttc gcc tac ctc aag aag cgc tcc gag      672
Tyr Asn Gly Asp Asn Phe Asp Phe Ala Tyr Leu Lys Lys Arg Ser Glu
    210                 215                 220

aag ctc gga gtc aag ttc atc ctc gga agg gaa ggg agc gag ccg aaa      720
Lys Leu Gly Val Lys Phe Ile Leu Gly Arg Glu Gly Ser Glu Pro Lys
225                 230                 235                 240

atc cag cgc atg ggc gat cgc ttt gcg gtg gag gtc aag gga agg att      768
Ile Gln Arg Met Gly Asp Arg Phe Ala Val Glu Val Lys Gly Arg Ile
                245                 250                 255

cac ttc gac ctc tac ccc gtc att agg aga acg att aac ctc ccc act      816
His Phe Asp Leu Tyr Pro Val Ile Arg Arg Thr Ile Asn Leu Pro Thr
            260                 265                 270

tac acc ctt gag gca gta tat gaa gcc atc ttt gga cag ccg aag gag      864
Tyr Thr Leu Glu Ala Val Tyr Glu Ala Ile Phe Gly Gln Pro Lys Glu
        275                 280                 285

aag gtc tac gct gag gag ata gcg cag gcc tgg gaa acg ggc gag gga      912
Lys Val Tyr Ala Glu Glu Ile Ala Gln Ala Trp Glu Thr Gly Glu Gly
    290                 295                 300

tta gaa agg gtg gcc cgc tac tcg atg gag gac gca aag gta acc tat      960
Leu Glu Arg Val Ala Arg Tyr Ser Met Glu Asp Ala Lys Val Thr Tyr
305                 310                 315                 320

gaa ctc gga aaa gag ttc ttc cct atg gaa gcc cag ctc tcg cgc ctc     1008
Glu Leu Gly Lys Glu Phe Phe Pro Met Glu Ala Gln Leu Ser Arg Leu
                325                 330                 335

gta ggc cag agc ctc tgg gat gta tct cgc tcg agt acc gga aac ctc     1056
Val Gly Gln Ser Leu Trp Asp Val Ser Arg Ser Ser Thr Gly Asn Leu
            340                 345                 350

gtc gag tgg ttt ttg ctg agg aag gcc tac gag agg aat gaa ctt gca     1104
Val Glu Trp Phe Leu Leu Arg Lys Ala Tyr Glu Arg Asn Glu Leu Ala
        355                 360                 365

cca aac aag ccg gac gag agg gag ctg gca aga aga agg gag agc tac     1152
Pro Asn Lys Pro Asp Glu Arg Glu Leu Ala Arg Arg Arg Glu Ser Tyr
    370                 375                 380

gcg ggt gga tac gtc aag gag ccc gaa agg gga ctg tgg gag aac atc     1200
Ala Gly Gly Tyr Val Lys Glu Pro Glu Arg Gly Leu Trp Glu Asn Ile
385                 390                 395                 400

gtg tat ctg gac ttc cgc tcc ctg tat cct tcg ata ata atc acc cat     1248
Val Tyr Leu Asp Phe Arg Ser Leu Tyr Pro Ser Ile Ile Ile Thr His
                405                 410                 415

aac gtc tcc cct gat aca ctc aac agg gag ggt tgt gag gag tac gac     1296
```

FIGURE 14 (Cont.)

```
Asn Val Ser Pro Asp Thr Leu Asn Arg Glu Gly Cys Glu Glu Tyr Asp
            420                 425                 430

gtg gct cct cag gta ggc cat aag ttc tgc aag gac ttc ccc ggc ttc      1344
Val Ala Pro Gln Val Gly His Lys Phe Cys Lys Asp Phe Pro Gly Phe
        435                 440                 445

atc cca agc ctc ctc gga gac ctc ttg gag gag aga cag aag gta aag      1392
Ile Pro Ser Leu Leu Gly Asp Leu Leu Glu Glu Arg Gln Lys Val Lys
    450                 455                 460

aag aag atg aag gcc act ata gac cca atc gag aag aaa ctc ctc gat      1440
Lys Lys Met Lys Ala Thr Ile Asp Pro Ile Glu Lys Lys Leu Leu Asp
465                 470                 475                 480

tac agg caa cga gca atc aaa atc ctt gct aat agc ttc tac ggt tac      1488
Tyr Arg Gln Arg Ala Ile Lys Ile Leu Ala Asn Ser Phe Tyr Gly Tyr
                485                 490                 495

tac ggc tat gca aag gcc cgc tgg tac tgc aag gag tgc gcc gag agc      1536
Tyr Gly Tyr Ala Lys Ala Arg Trp Tyr Cys Lys Glu Cys Ala Glu Ser
            500                 505                 510

gtt acc gct tgg ggc agg cag tac atc gag acc acg ata agg gaa ata      1584
Val Thr Ala Trp Gly Arg Gln Tyr Ile Glu Thr Thr Ile Arg Glu Ile
        515                 520                 525

gag gag aaa ttt ggc ttt aaa gtc ctc tac gcg gac aca gat gga ttt      1632
Glu Glu Lys Phe Gly Phe Lys Val Leu Tyr Ala Asp Thr Asp Gly Phe
    530                 535                 540

ttc gca aca ata cct gga gcg gac gcc gaa acc gtc aaa aag aag gca      1680
Phe Ala Thr Ile Pro Gly Ala Asp Ala Glu Thr Val Lys Lys Lys Ala
545                 550                 555                 560

aag gag ttc ctg gac tac atc aac gcc aaa ctg ccc ggc ctg ctc gaa      1728
Lys Glu Phe Leu Asp Tyr Ile Asn Ala Lys Leu Pro Gly Leu Leu Glu
                565                 570                 575

ctc gaa tac gag ggc ttc tac aag cgc ggc ttc ttc gtg acg aag aag      1776
Leu Glu Tyr Glu Gly Phe Tyr Lys Arg Gly Phe Phe Val Thr Lys Lys
            580                 585                 590

aag tac gcg gtt ata gac gag gag gac aag ata acg acg cgc ggg ctt      1824
Lys Tyr Ala Val Ile Asp Glu Glu Asp Lys Ile Thr Thr Arg Gly Leu
        595                 600                 605

gaa ata gtt agg cgt gac tgg agc gag ata gcg aag gag acg cag gcg      1872
Glu Ile Val Arg Arg Asp Trp Ser Glu Ile Ala Lys Glu Thr Gln Ala
    610                 615                 620

agg gtt ctt gag gcg ata cta aag cac ggt gac gtt gaa gaa gcg gta      1920
Arg Val Leu Glu Ala Ile Leu Lys His Gly Asp Val Glu Glu Ala Val
625                 630                 635                 640

agg att gtc aaa gag gtt acg gag aag ctg agc aag tac gag gtt cca      1968
Arg Ile Val Lys Glu Val Thr Glu Lys Leu Ser Lys Tyr Glu Val Pro
```

FIGURE 14 (Cont.)

```
               645                 650                 655

ccg gag aag ctg gtc atc tac gag cag ata acc cgc gac ctg aag gac      2016
Pro Glu Lys Leu Val Ile Tyr Glu Gln Ile Thr Arg Asp Leu Lys Asp
            660                 665                 670

tac aag gcc acc ggg ccg cat gtg gct gtt gca aaa cgc ctc gcc gca      2064
Tyr Lys Ala Thr Gly Pro His Val Ala Val Ala Lys Arg Leu Ala Ala
        675                 680                 685

agg ggg ata aaa atc cgg ccc gga acg gtc ata agc tac atc gtg ctc      2112
Arg Gly Ile Lys Ile Arg Pro Gly Thr Val Ile Ser Tyr Ile Val Leu
    690                 695                 700

aaa ggc tcg gga agg att ggg gac agg gct ata ccc ttt gac gaa ttt      2160
Lys Gly Ser Gly Arg Ile Gly Asp Arg Ala Ile Pro Phe Asp Glu Phe
705                 710                 715                 720

gac ccg gca aag cac aag tac gat gca gaa tac tac atc gag aac cag      2208
Asp Pro Ala Lys His Lys Tyr Asp Ala Glu Tyr Tyr Ile Glu Asn Gln
                725                 730                 735

gtt ctt cca gct gtg gag agg att ctg agg gcc ttt ggt tac cgt aaa      2256
Val Leu Pro Ala Val Glu Arg Ile Leu Arg Ala Phe Gly Tyr Arg Lys
            740                 745                 750

gaa gat tta agg tat cag aaa acg cgg cag gtt ggc ttg ggg gcg tgg      2304
Glu Asp Leu Arg Tyr Gln Lys Thr Arg Gln Val Gly Leu Gly Ala Trp
        755                 760                 765

cta aaa cct aag aca tga                                              2322
Leu Lys Pro Lys Thr
```

Results: *Pfu* V93K and V93R mutants show significantly improved dUTP incorporation compared to wild type *Pfu*. In contrast, the *Pfu* V93W, V93Y, and V93M mutants show little-to-no improvement in dUTP incorporation.

Results: The *Pfu* V93D and V93R mutants show significantly improved dUTP incorporation compared to wild type *Pfu*.

Results: The *Pfu* V93N mutant shows a very small improvement in dUTP incorporation compared to wild type *Pfu*. In contrast, the *Pfu* V93G mutant shows little-to-no improvement.

Figure 16: Polymerase activity and Temperature optimum of Pfu N terminal truncation mutants

| Pfu clone # | Truncated after Pfu residue | Relative DNA polymerase activity | Temperature Optimum |
|---|---|---|---|
| 61 | H30 | Moderate | 65° |
| 72 | V66 | Similar to wild type | 70° |
| 81 | P128 | Low | Not tested |
| 92 | I158 | Low | Not tested |
| 3 | G125 | Similar to wild type | Not tested |
| 13/14 | K201 | low | 65° |

Figure 17A

Pyrococcus furiosus gene for archaeal histone (HMf-like)
(ACCESSION No: AB013081)
Nucleotide sequence (SEQ ID NO: 63)
Amino acid sequence (SEQ ID NO: 64)

```
 M   M   G   E   L   P   I   A   P   V   D   R   L   I   R   K   A   G      18
ATG ATG GGA GAA TTA CCA ATT GCC CCA GTT GAC AGA CTT ATA AGA AAG GCT GGT      54

 A   Q   R   V   S   E   Q   A   A   K   V   L   A   E   H   L   E   E      36
GCT CAG AGA GTT AGC GAG CAA GCA GCT AAG GTA CTT GCA GAG CAC CTT GAG GAA     108

 K   A   I   E   I   A   K   K   A   V   D   L   A   K   H   A   G   R      54
AAA GCT ATT GAG ATC GCA AAA AAG GCA GTA GAT CTT GCA AAG CAC GCA GGT AGA     162

 K   T   V   K   V   E   D   I   K   L   A   I   K   S   *                  69
AAG ACC GTT AAG GTC GAA GAC ATT AAG CTC GCA ATT AAG AGC TGA                 207
```

Figure 17B

(HMf-like)-Taq DNA polymerase fusion protein

Nucleotide sequence (SEQ ID NO: 63) // Nucleotide sequence (SEQ ID NO: 65)
Amino acid sequence (SEQ ID NO: 64) // Amino acid sequence (SEQ ID NO: 66)

```
 M   M   G   E   L   P   I   A   P   V   D   R   L   I   R   K   A   G      18
ATG ATG GGA GAA TTA CCA ATT GCC CCA GTT GAC AGA CTT ATA AGA AAG GCT GGT      54

 A   Q   R   V   S   E   Q   A   A   K   V   L   A   E   H   L   E   E      36
GCT CAG AGA GTT AGC GAG CAA GCA GCT AAG GTA CTT GCA GAG CAC CTT GAG GAA     108

 K   A   I   E   I   A   K   K   A   V   D   L   A   K   H   A   G   R      54
AAA GCT ATT GAG ATC GCA AAA AAG GCA GTA GAT CTT GCA AAG CAC GCA GGT AGA     162

 K   T   V   K   V   E   D   I   K   L   A   I   K   S                      69
AAG ACC GTT AAG GTC GAA GAC ATT AAG CTC GCA ATT AAG AGC
```

FIGURE 17B (Cont.)

```
    G   G   G
// GGC GGC GGT

 V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

 D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

 S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

 A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

 S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA
```

FIGURE 17B (Cont.)

```
 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG

 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC

 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC

 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC
```

FIGURE 17B (Cont.)

```
 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
```

```
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H   *
CAT CAT TAA
```

<u>Figure 17C</u>

<u>Taq DNA polymerase- (HMf-like) fusion protein</u>

Nucleotide sequence (SEQ ID NO: 65) //Nucleotide sequence (SEQ ID NO: 63)
Amino acid sequence (SEQ ID NO: 66) /Amino acid sequence (SEQ ID NO: 64)

```
 G   G   G
GGC GGC GGT

 V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG
```

FIGURE 17C (Cont.)

```
 D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

 S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

 A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

 S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG

 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
```

```
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC

 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC

 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC
```

FIGURE 17C (Cont.)

```
 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC
```

FIGURE 17C (Cont.)

```
T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

H   H   //
CAT CAT //


M   M   G   E   L   P   I   A   P   V   D   R   L   I   R   K   A   G      18
ATG ATG GGA GAA TTA CCA ATT GCC CCA GTT GAC AGA CTT ATA AGA AAG GCT GGT    54

A   Q   R   V   S   E   Q   A   A   K   V   L   A   E   H   L   E   E      36
GCT CAG AGA GTT AGC GAG CAA GCA GCT AAG GTA CTT GCA GAG CAC CTT GAG GAA   108

K   A   I   E   I   A   K   K   A   V   D   L   A   K   H   A   G   R      54
AAA GCT ATT GAG ATC GCA AAA AAG GCA GTA GAT CTT GCA AAG CAC GCA GGT AGA   162

K   T   V   K   V   E   D   I   K   L   A   I   K   S   *                  69
AAG ACC GTT AAG GTC GAA GAC ATT AAG CTC GCA ATT AAG AGC TGA
```

Figure 17D

Pfu DNA Polymerase (WT) -(HMf-like) fusion protein

Nucleotide sequence (SEQ ID NO: 61) //Nucleotide sequence (SEQ ID NO: 63)

FIGURE 17D (Cont.)

// ccctggtcct gggtccacat atatgttctt actcgccttt atgaagaatc ccccagtcgc tctaacctgg gttatagtga caaatcttcc tccaccaccg cccaagaagg ttatttctat caactctaca cctcccctat tttctctctt atgagatttt taagtatagt tatagagaag gttttatact ccaaactgag ttagtagata tgtggggagc ataatgattt tagatgtgga ttacataact gaagaaggaa aacctgttat taggctattc aaaaaagaga acggaaaatt taagatagag catgatagaa cttttagacc atacatttac gctcttctca gggatgattc aaagattgaa gaagttaaga aaataacggg ggaaaggcat ggaaagattg tgagaattgt tgatgtagag aaggttgaga aaaagtttct cggcaagcct attaccgtgt ggaaacttta tttggaacat ccccaagatg ttcccactat tagagaaaaa gttagagaac atccagcagt tgtggacatc ttcgaatacg atattccatt tgcaaagaga tacctcatcg acaaaggcct aataccaatg gagggggaag aagagctaaa gattcttgcc ttcgatatag aaaccctcta tcacgaagga gaagagtttg gaaaaggccc aattataatg attagttatg cagatgaaaa tgaagcaaag gtgattactt ggaaaaacat agatcttcca tacgttgagg ttgtatcaag cgagagagag atgataaaga gatttctcag gattatcagg gagaaggatc ctgacattat agttacttat aatggagact cattcgactt cccatattta gcgaaaaggg cagaaaaact tgggattaaa ttaaccattg gaagagatgg aagcgagccc aagatgcaga gaataggcga tatgacggct gtagaagtca agggaagaat acatttcgac ttgtatcatg taataacaag gacaataaat ctcccaacat acacactaga ggctgtatat gaagcaattt ttggaaagcc aaaggagaag gtatacgccg acgagatagc aaaagcctgg gaaagtggag agaaccttga gagagttgcc aaatactcga tggaagatgc aaaggcaact tatgaactcg ggaaagaatt FIGURE 17D (Cont.)

ccttccaatg gaaattcagc tttcaagatt agttggacaa cctttatggg atgtttcaag gtcaagcaca gggaaccttg tagagtggtt cttacttagg aaagcctacg aaagaaacga agtagctcca aacaagccaa gtgaagagga gtatcaaaga aggctcaggg agagctacac aggtggattc gttaaagagc cagaaaaggg gttgtgggaa aacatagtat acctagattt tagagcccta tatccctcga ttataattac ccacaatgtt tctcccgata ctctaaatct tgagggatgc aagaactatg atatcgctcc tcaagtaggc cacaagttct gcaaggacat ccctggtttt ataccaagtc tcttgggaca tttgttagag gaaagacaaa agattaagac aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg gaaggagctc gaagaaaagt ttggatttaa agtcctctac attgacactg atggtctcta tgcaactatc ccaggaggag aaagtgagga aataaagaaa aaggctctag aatttgtaaa atacataaat tcaaagctcc ctggactgct agagcttgaa tatgaagggt tttataagag gggattcttc gttacgaaga agaggtatgc agtaatagat gaagaaggaa aagtcattac tcgtggttta gagatagtta ggagagattg gagtgaaatt gcaaaagaaa ctcaagctag agttttggag acaatactaa aacacggaga tgttgaagaa gctgtgagaa tagtaaaaga agtaatacaa aagcttgcca attatgaaat tccaccagag aagctcgcaa tatatgagca gataacaaga ccattacatg agtataaggc gataggtcct cacgtagctg ttgcaaagaa actagctgct aaaggagtta aaataaagcc aggaatggta attggataca tagtacttag aggcgatggt ccaattagca atagggcaat tctagctgag gaatacgatc ccaaaaagca caagtatgac gcagaatatt acattgagaa ccaggttctt ccagcggtac ttaggatatt FIGURE 17D (Cont.)

```
ggagggattt ggatacagaa aggaagacct cagataccaa aagacaagac aagtcggcct

aacttcctgg cttaacatta aaaaatccta gaaaagcgat agatatcaac ttttattctt

tctaaccttt ttctatgaaa gaagaactga gcaggaatta ccagttcttc cgttatttta

tgggtaatta aaaacccatg ctcttgggag aatcttcgaa taaaatccct aacttcaggc

tttgctaagt gaatagaata aacaacatca ctcacttcaa acgccttcgt tagaaatggt

ctatctgcat gcttctctgg ctcggaanng gaggattcat aacaacagta tcaacattct

cagagaattg agaaacatca gaaactttga cttctacaac atttctaact ttgcaactct

tcaagatttt ctaaaagaat tttaacggcc tcctcgtcaa tttcgacgac gtagatcttt

tttgctccaa gcagagccgc tccaatggat aacacccctg ttcccgcacc caagtccgct

acaatttttt ccttgtatct cctaatgtat aagcaagcca aaggagagta gatgctacct

ttccgggagt tttgtattgc tctagccaag gtttgggatt tttgaatcct ttaactctgg

aaagtataat ttcaagctcc ttcttcttca tgacagatga aaaattgttt tgtctctttt

taacttttac agaaataact gtctcaaatt atgacaactc ttgacatttt tacttcatta

ccagggtaat gtttttaagt atgaaatttt tctttcatag aggaggnnnn nngtcctctc

ctcgatttcc ttggttgtgc tccatatgat aagcttccaa agtgggtgtt cagactttta

gacactcaaa taccagacga caatggtgtg ctcactcaag ccccatatgg gttgagaaaa

gtagaagcgg cactactcag atgcttcccc aggaatgagg ttgttgtagc tcntcccnga

aagattgaga tgttcttgg  //

ATG ATG GGA GAA TTA CCA ATT GCC CCA GTT GAC AGA CTT ATA AGA AAG GCT GGT     54
GCT CAG AGA GTT AGC GAG CAA GCA GCT AAG GTA CTT GCA GAG CAC CTT GAG GAA    108
AAA GCT ATT GAG ATC GCA AAA AAG GCA GTA GAT CTT GCA AAG CAC GCA GGT AGA    162
AAG ACC GTT AAG GTC GAA GAC ATT AAG CTC GCA ATT AAG AGC TGA
```

Figure 17E

(HMf-like) - Pfu DNA Polymerase (WT) fusion protein

Nucleotide sequence (SEQ ID NO: 63) //Nucleotide sequence (SEQ ID NO: 61)

```
ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA   162
AAG ACC GTT AAG GTC GAA GAC ATT AAG CTC GCA ATT AAG AGC //

ccctggtcct gggtccacat atatgttctt actcgccttt atgaagaatc ccccagtcgc

tctaacctgg gttatagtga caaatcttcc tccaccaccg cccaagaagg ttatttctat

caactctaca cctcccctat tttctctctt atgagatttt taagtatagt tatagagaag

gttttatact ccaaactgag ttagtagata tgtggggagc ataatgattt tagatgtgga

ttacataact gaagaaggaa aacctgttat taggctattc aaaaaagaga acggaaaatt

taagatagag catgatagaa cttttagacc atacatttac gctcttctca gggatgattc

aaagattgaa gaagttaaga aaataacggg ggaaaggcat ggaaagattg tgagaattgt

tgatgtagag aaggttgaga aaaagtttct cggcaagcct attaccgtgt ggaaacttta

tttggaacat ccccaagatg ttcccactat tagagaaaaa gttagagaac atccagcagt

tgtggacatc ttcgaatacg atattccatt tgcaaagaga tacctcatcg acaaaggcct

aataccaatg gagggggaag aagagctaaa gattcttgcc ttcgatatag aaaccctcta

tcacgaagga gaagagtttg gaaaaggccc aattataatg attagttatg cagatgaaaa

tgaagcaaag gtgattactt ggaaaaacat agatcttcca tacgttgagg ttgtatcaag
```

FIGURE 17E (Cont.)

cgagagagag atgataaaga gatttctcag gattatcagg gagaaggatc ctgacattat
agttacttat aatggagact cattcgactt cccatattta gcgaaaaggg cagaaaaact
tgggattaaa ttaaccattg gaagagatgg aagcgagccc aagatgcaga gaataggcga
tatgacggct gtagaagtca agggaagaat acatttcgac ttgtatcatg taataacaag
gacaataaat ctcccaacat acacactaga ggctgtatat gaagcaattt ttggaaagcc
aaaggagaag gtatacgccg acgagatagc aaaagcctgg gaaagtggag agaaccttga
gagagttgcc aaatactcga tggaagatgc aaaggcaact tatgaactcg ggaaagaatt
ccttccaatg gaaattcagc tttcaagatt agttggacaa cctttatggg atgtttcaag
gtcaagcaca gggaaccttg tagagtggtt cttacttagg aaagcctacg aaagaaacga
agtagctcca aacaagccaa gtgaagagga gtatcaaaga aggctcaggg agagctacac
aggtggattc gttaaagagc cagaaaaggg gttgtgggaa aacatagtat acctagattt
tagagcccta tatccctcga ttataattac ccacaatgtt tctcccgata ctctaaatct
tgagggatgc aagaactatg atatcgctcc tcaagtaggc cacaagttct gcaaggacat
ccctggtttt ataccaagtc tcttgggaca tttgttagag gaaagacaaa agattaagac
aaaaatgaag gaaactcaag atcctataga aaaaatactc cttgactata gacaaaaagc
gataaaactc ttagcaaatt ctttctacgg atattatggc tatgcaaaag caagatggta
ctgtaaggag tgtgctgaga gcgttactgc ctggggaaga aagtacatcg agttagtatg
gaaggagctc gaagaaaagt ttggatttaa agtcctctac attgacactg atggtctcta
tgcaactatc ccaggaggag aaagtgagga aataaagaaa aaggctctag aatttgtaaa
atacataaat tcaaagctcc ctggactgct agagcttgaa tatgaagggt tttataagag
gggattcttc gttacgaaga agaggtatgc agtaatagat gaagaaggaa aagtcattac FIGURE 17E (Cont.)

tcgtggttta gagatagtta ggagagattg gagtgaaatt gcaaaagaaa ctcaagctag
agttttggag acaatactaa aacacggaga tgttgaagaa gctgtgagaa tagtaaaaga
agtaatacaa aagcttgcca attatgaaat tccaccagag aagctcgcaa tatatgagca
gataacaaga ccattacatg agtataaggc gataggtcct cacgtagctg ttgcaaagaa
actagctgct aaaggagtta aaataaagcc aggaatggta attggataca tagtacttag
aggcgatggt ccaattagca atagggcaat tctagctgag gaatacgatc ccaaaaagca
caagtatgac gcagaatatt acattgagaa ccaggttctt ccagcggtac ttaggatatt
ggagggattt ggatacagaa aggaagacct cagataccaa aagacaagac aagtcggcct
aacttcctgg cttaacatta aaaaatccta gaaaagcgat agatatcaac ttttattctt
tctaaccttt ttctatgaaa gaagaactga gcaggaatta ccagttcttc cgttatttta
tgggtaatta aaaacccatg ctcttgggag aatcttcgaa taaaatccct aacttcaggc
tttgctaagt gaatagaata aacaacatca ctcacttcaa acgccttcgt tagaaatggt
ctatctgcat gcttctctgg ctcggaanng gaggattcat aacaacagta tcaacattct
cagagaattg agaaacatca gaaactttga cttctacaac atttctaact ttgcaactct
tcaagatttt ctaaaagaat tttaacggcc tcctcgtcaa tttcgacgac gtagatcttt
tttgctccaa gcagagccgc tccaatggat aacacccctg ttcccgcacc caagtccgct
acaatttttt ccttgtatct cctaatgtat aagcaagcca aaggagagta gatgctacct
ttccgggagt tttgtattgc tctagccaag gtttgggatt tttgaatcct ttaactctgg
aaagtataat ttcaagctcc ttcttcttca tgacagatga aaaattgttt tgtctctttt
taacttttac agaaataact gtctcaaatt atgacaactc ttgacatttt tacttcatta FIGURE 17E (Cont.)

ccagggtaat gtttttaagt atgaaatttt tctttcatag aggaggnnnn nngtcctctc ctcgatttcc ttggttgtgc tccatatgat aagcttccaa agtgggtgtt cagactttta gacactcaaa taccagacga caatggtgtg ctcactcaag ccccatatgg gttgagaaaa gtagaagcgg cactactcag atgcttcccc aggaatgagg ttgttgtagc tcntcccnga aagattgaga tgttcttgg // TGA

Figure 17F

(HMf-like) - PFU DNA POLYMERASE (V93 R OR E) fusion protein

Nucleotide sequence (SEQ ID NO: 63) // Nucleotide sequence (SEQ ID NO: 27)
Nucleotide sequence (SEQ ID NO: 63) //Nucleotide sequence (SEQ ID NO: 28)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT     54
GCT CAG AGA GTT AGC GAG CAA GCA GCT AAG GTA CTT GCA GAG CAC CTT GAG GAA    108
AAA GCT ATT GAG ATC GCA AAA AAG GCA GTA GAT CTT GCA AAG CAC GCA GGT AGA    162
AAG ACC GTT AAG GTC GAA GAC ATT AAG CTC GCA ATT AAG AGC //

//ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
```

FIGURE 17F (Cont.)

```
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //             2328
// TGA
```

Figure 17G

PFU DNA POLYMERASE (V93 R OR E)-(HMf-like) fusion protein

Nucleotide sequence (SEQ ID NO: 27) // Nucleotide sequence (SEQ ID NO: 63)
Nucleotide sequence (SEQ ID NO: 28) // Nucleotide sequence (SEQ ID NO: 63)

FIGURE 17G (Cont.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
```

FIGURE 17G (Cont.)

```
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //              2328

ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA   162
AAG ACC GTT AAG GTC GAA GAC ATT AAG CTC GCA ATT AAG AGC TGA
```

Figure 17H

PFU DNA POLYMERASE (G387P/V93R OR E) -(HMf-like) fusion protein

Nucleotide sequence (SEQ ID NO: 29) // Nucleotide sequence (SEQ ID NO: 63)
Nucleotide sequence (SEQ ID NO: 30) // Nucleotide sequence (SEQ ID NO: 63)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
```

FIGURE 17H (Cont.)

```
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //             2328
```

```
ATG ATG GGA GAA TTA CCA ATT GCC CCA GTT GAC AGA CTT ATA AGA AAG GCT GGT     54
GCT CAG AGA GTT AGC GAG CAA GCA GCT AAG GTA CTT GCA GAG CAC CTT GAG GAA    108
AAA GCT ATT GAG ATC GCA AAA AAG GCA GTA GAT CTT GCA AAG CAC GCA GGT AGA    162
AAG ACC GTT AAG GTC GAA GAC ATT AAG CTC GCA ATT AAG AGC TGA
```

Figure 17I

(HMf-like) - PFU DNA POLYMERASE (G387P/V93R OR E) fusion protein

Nucleotide sequence (SEQ ID NO: 63) // Nucleotide sequence (SEQ ID NO: 29)
Nucleotide sequence (SEQ ID NO: 63) // Nucleotide sequence (SEQ ID NO: 30)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT     54
```

FIGURE 17I (Cont.)

```
GCT CAG AGA GTT AGC GAG CAA GCA GCT AAG GTA CTT GCA GAG CAC CTT GAG GAA    108
AAA GCT ATT GAG ATC GCA AAA AAG GCA GTA GAT CTT GCA AAG CAC GCA GGT AGA    162
AAG ACC GTT AAG GTC GAA GAC ATT AAG CTC GCA ATT AAG AGC //

//ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
```

FIGURE 17I (Cont.)

```
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //TAG          2328
```

Figure 17J

(HMF-LIKE)-PFU DNA POLYMERASE(D141A/E143A/V93R OR E) fusion protein

Nucleotide sequence (SEQ ID NO: 63) // Nucleotide sequence (SEQ ID NO: 31)
Nucleotide sequence (SEQ ID NO: 63) // Nucleotide sequence (SEQ ID NO: 32)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA   162
AAG ACC GTT AAG GTC GAA GAC ATT AAG CTC GCA ATT AAG AGC //

//ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
```

FIGURE 17J (Cont.)

```
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGACGAGTA TCAAAGAAGG 1140
CTCAGGGAGA GCTACACA GGT_GGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //            2328

TGA
```

Figure 17K

PFU DNA POLYMERASE(D141A/E143A/V93R OR E) - (HMF-LIKE) fusion protein

Nucleotide sequence (SEQ ID NO: 31) // Nucleotide sequence (SEQ ID NO: 63)
Nucleotide sequence (SEQ ID NO: 32) // Nucleotide sequence (SEQ ID NO: 63)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
```

FIGURE 17K (Cont.)

```
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACA GGTGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //            2328

ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA   162
AAG ACC GTT AAG GTC GAA GAC ATT AAG CTC GCA ATT AAG AGC TGA
```

Figure 17L

KOD DNA POLYMERASE - (HMf-like) fusion protein

Nucleotide sequence (SEQ ID NO: 33) // Nucleotide sequence (SEQ ID NO: 63)
Nucleotide sequence (SEQ ID NO: 34) // Nucleotide sequence (SEQ ID NO: 63)

```
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)
ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
```

FIGURE 17L (Cont.)

```
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT  2325
//
   ATG ATG GGA GAA TTA CCA ATT GCC CCA GTT GAC AGA CTT ATA AGA AAG GCT GGT     54
   GCT CAG AGA GTT AGC GAG CAA GCA GCT AAG GTA CTT GCA GAG CAC CTT GAG GAA    108
   AAA GCT ATT GAG ATC GCA AAA AAG GCA GTA GAT CTT GCA AAG CAC GCA GGT AGA    162
   AAG ACC GTT AAG GTC GAA GAC ATT AAG CTC GCA ATT AAG AGC TGA
```

Figure 17M

(HMf-like) - KOD DNA POLYMERASE fusion protein

Nucleotide sequence (SEQ ID NO: 63) // Nucleotide sequence (SEQ ID NO: 33)
Nucleotide sequence (SEQ ID NO: 63) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT     54
GCT CAG AGA GTT AGC GAG CAA GCA GCT AAG GTA CTT GCA GAG CAC CTT GAG GAA    108
AAA GCT ATT GAG ATC GCA AAA AAG GCA GTA GAT CTT GCA AAG CAC GCA GGT AGA    162
AAG ACC GTT AAG GTC GAA GAC ATT AAG CTC GCA ATT AAG AGC //

ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
```

FIGURE 17M (Cont.)

```
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT //TAG 2325
```

Figure 17N

(HMf-like)-Vent DNA POLYMERASE FUSION PROTEIN

Nucleotide sequence (SEQ ID NO: 63) // Nucleotide sequence (SEQ ID NO: 35)
Nucleotide sequence (SEQ ID NO: 63) // Nucleotide sequence (SEQ ID NO: 36)

FIGURE 17N (Cont.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA   162
AAG ACC GTT AAG GTC GAA GAC ATT AAG CTC GCA ATT AAG AGC //

ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
```

FIGURE 17N (Cont.)

```
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325
```

Figure 17O

Vent DNA POLYMERASE - (HMf-like) FUSION PROTEIN

Nucleotide sequence (SEQ ID NO: 35) // Nucleotide sequence (SEQ ID NO: 63)
Nucleotide sequence (SEQ ID NO: 36) // Nucleotide sequence (SEQ ID NO: 63)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
```

FIGURE 17O (Cont.)

```
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GG 2325 //

ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA   162
AAG ACC GTT AAG GTC GAA GAC ATT AAG CTC GCA ATT AAG AGC TGA
```

Figure 17P

Deep Vent- (HMf-like) DNA polymerase fusion protein

Nucleotide sequence (SEQ ID NO: 37) // Nucleotide sequence (SEQ ID NO: 63)
Nucleotide sequence (SEQ ID NO: 38) // Nucleotide sequence (SEQ ID NO: 63)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTTG ACGCTGACTA CATCACCGAG GATGGGAAGC CGATTATAAG GATTTTCAAG    60
AAAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
AAGATAGTGA GAATTATAGA TGCCGAAAAG GTAAGGAAGA AGTTCCTGGG GAGGCCGATT   240
GAGGTATGGA GGCTGTACTT TGAACACCCT CAGGACXXXC CCGCAATAAG GGATAAGATA   300
AGAGAGCATT CCGCAGTTAT TGACATCTTT GAGTACGACA TTCCGTTCGC GAAGAGGTAC   360
```

FIGURE 17P (Cont.)

```
CTAATAGACA AAGGCCTAAT TCCAATGGAA GGCGATGAAG AGCTCAAGTT GCTCGCATTT   420
GACATAGAAA CCCTCTATCA CGAAGGGGAG GAGTTCGCGA AGGGGCCCAT TATAATGATA   480
AGCTATGCTG ATGAGGAAGA AGCCAAAGTC ATAACGTGGA AAAAGATCGA TCTCCCGTAC   540
GTCGAGGTAG TTTCCAGCGA GAGGGAGATG ATAAAGCGGT TCCTCAAGGT GATAAGGGAG   600
AAAGATCCCG ATGTTATAAT TACCTACAAC GGCGATTCTT TCGACCTTCC CTATCTAGTT   660
AAGAGGGCCG AAAAGCTCGG GATAAAGCTA CCCCTGGGAA GGGACGGTAG TGAGCCAAAG   720
ATGCAGAGGC TTGGGGATAT GACAGCGGTG GAGATAAAGG GAAGGATACA CTTTGACCTC   780
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG //               2328
```

```
ATG ATG GGA GAA TTA CCA ATT GCC CCA GTT GAC AGA CTT ATA AGA AAG GCT GGT     54
GCT CAG AGA GTT AGC GAG CAA GCA GCT AAG GTA CTT GCA GAG CAC CTT GAG GAA    108
AAA GCT ATT GAG ATC GCA AAA AAG GCA GTA GAT CTT GCA AAG CAC GCA GGT AGA    162
AAG ACC GTT AAG GTC GAA GAC ATT AAG CTC GCA ATT AAG AGC TGA
```

(HMflike) - Deep Vent DNA polymerase fusion protein

Nucleotide sequence (SEQ ID NO: 63) // Nucleotide sequence (SEQ ID NO: 37)
Nucleotide sequence (SEQ ID NO: 63) // Nucleotide sequence (SEQ ID NO: 38)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA   162
AAG ACC GTT AAG GTC GAA GAC ATT AAG CTC GCA ATT AAG AGC TGA
```

```
ATGATACTTG ACGCTGACTA CATCACCGAG GATGGGAAGC CGATTATAAG GATTTTCAAG    60
AAAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
AAGATAGTGA GAATTATAGA TGCCGAAAAG GTAAGGAAGA AGTTCCTGGG GAGGCCGATT   240
GAGGTATGGA GGCTGTACTT TGAACACCCT CAGGACXXXC CCGCAATAAG GGATAAGATA   300
AGAGAGCATT CCGCAGTTAT TGACATCTTT GAGTACGACA TTCCGTTCGC GAAGAGGTAC   360
CTAATAGACA AAGGCCTAAT TCCAATGGAA GGCGATGAAG AGCTCAAGTT GCTCGCATTT   420
GACATAGAAA CCCTCTATCA CGAAGGGGAG GAGTTCGCGA AGGGGCCCAT TATAATGATA   480
AGCTATGCTG ATGAGGAAGA AGCCAAAGTC ATAACGTGGA AAAAGATCGA TCTCCCGTAC   540
GTCGAGGTAG TTTCCAGCGA GAGGGAGATG ATAAAGCGGT TCCTCAAGGT GATAAGGGAG   600
AAAGATCCCG ATGTTATAAT TACCTACAAC GGCGATTCTT TCGACCTTCC CTATCTAGTT   660
AAGAGGGCCG AAAAGCTCGG GATAAAGCTA CCCCTGGGAA GGGACGGTAG TGAGCCAAAG   720
ATGCAGAGGC TTGGGGATAT GACAGCGGTG GAGATAAAGG GAAGGATACA CTTTGACCTC   780
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
```

FIGURE 17Q (Cont.)

```
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG TAA              2328
```

Figure 17R

JDF-3 - (HMf-like) fusion protein

Nucleotide sequence (SEQ ID NO: 39) // Nucleotide sequence (SEQ ID NO: 63)
Nucleotide sequence (SEQ ID NO: 40) // Nucleotide sequence (SEQ ID NO: 63)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTCGG
CAGGTCTGTGGAGGTCTGGGTCCTCTACTTCACGCACCCGCAGGACXXXCCGGCAATCCGCGACAAAATAAGGAAGCACCCCGCGGTCATCGACATCTACGAGTACGACATACCC
TTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGGAA
CCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATTAA
GCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCTTT
ACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCATAA
ACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAGAG
GGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTTCC
CGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGGGCT
ACgcCGGTGGCTACGTCAAGGAGCCGGAGCGGGGACTGTGGGACAATATCGTGTATCTAGACTTTCGTAGTCTCTACCCTTCAATCATAATCACCCACAACGTCTCGCCAGATAC
GCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGG
CAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCT
ATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTCCT
CTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTCTC
GAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCGCG
```

FIGURE 17R (Cont.)

ACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGCAA
GTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAGGT
GTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGATG
CGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGCGC
GTGGCTGAAGCCGAAGGGGAAGAAGAAG//

ATG ATG GGA GAA TTA CCA ATT GCC CCA GTT GAC AGA CTT ATA AGA AAG GCT GGT 54
GCT CAG AGA GTT AGC GAG CAA GCA GCT AAG GTA CTT GCA GAG CAC CTT GAG GAA 108
AAA GCT ATT GAG ATC GCA AAA AAG GCA GTA GAT CTT GCA AAG CAC GCA GGT AGA 162
AAG ACC GTT AAG GTC GAA GAC ATT AAG CTC GCA ATT AAG AGC TGA

Figure 17S

(HMf-like) - JDF-3 fusion protein

Nucleotide sequence (SEQ ID NO: 63) // Nucleotide sequence (SEQ ID NO: 39)
Nucleotide sequence (SEQ ID NO: 63) // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATG ATG GGA GAA TTA CCA ATT GCC CCA GTT GAC AGA CTT ATA AGA AAG GCT GGT 54
GCT CAG AGA GTT AGC GAG CAA GCA GCT AAG GTA CTT GCA GAG CAC CTT GAG GAA 108
AAA GCT ATT GAG ATC GCA AAA AAG GCA GTA GAT CTT GCA AAG CAC GCA GGT AGA 162
AAG ACC GTT AAG GTC GAA GAC ATT AAG CTC GCA ATT AAG AGC //

ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCC
CTACTTCTACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGA
AGAAAAAGTTCCTCGGCAGGTCTGTGGAGGTCTGGGTCCTCTACTTCACGCACCCGCAGGACXXXCCGGCAATCCGCGACAAAATAAGGAAGCACCCCGCGGTCATC
GACATCTACGAGTACGACATACCCTTCGCCAAGCGCTACCTCATAGACAAGGGCCTAATCCCGATGGAAGGTGAGGAAGAGCTTAAACTCATGTCCTTCGACATCGA
GACGCTCTACCACGAGGGAGAAGAGTTTGGAACCGGGCCGATTCTGATGATAAGCTACGCCGATGAAAGCGAGGCGCGCGTGATAACCTGGAAGAAGATCGACCTTC
CTTACGTTGAGGTTGTCTCCACCGAGAAGGAGATGATTAAGCGCTTCTTGAGGGTCGTTAAGGAGAAGGACCCGGACGTGCTGATAACATACAACGGCGACAACTTC
GACTTCGCCTACCTGAAAAAGCGCTGTGAGAAGCTTGGCGTGAGCTTTACCCTCGGGAGGGACGGGAGCGAGCCGAAGATACAGCGCATGGGGGACAGGTTTGCGGT
CGAGGTGAAGGGCAGGGTACACTTCGACCTTTATCCAGTCATAAGGCGCACCATAAACCTCCCGACCTACACCCTTGAGGCTGTATACGAGGCGGTTTTCGGCAAGC
CCAAGGAGAAGGTCTACGCCGAGGAGATAGCCACCGCCTGGGAGACCGGCGAGGGGCTTGAGAGGGTCGCGCGCTACTCGATGGAGGACGCGAGGGTTACCTACGAG
CTTGGCAGGGAGTTCTTCCCGATGGAGGCCCAGCTTTCCAGGCTCATCGGCCAAGGCCTCTGGGACGTTTCCCGCTCCAGCACCGGCAACCTCGTCGAGTGGTTCCT
CCTAAGGAAGGCCTACGAGAGGAACGAACTCGCTCCCAACAAGCCCGACGAGAGGGAGCTGGCGAGGAGAAGGGGGGCTACgcCGGTGGCTACGTCAAGGAGCCGG
AGCGGGGACTGTGGGACAATATCGTGTATCTAGACTTTCGTAGTCTCTACCCTTCAATCATAATCACCCACAACGTCTCGCCAGATACGCTCAACCGCGAGGGGTGT
AGGAGCTACGACGTTGCCCCCGAGGTCGGTCACAAGTTCTGCAAGGACTTCCCCGGCTTCATTCCGAGCCTGCTCGGAAACCTGCTGGAGGAAAGGCAGAAGATAAA

FIGURE 17S (Cont.)

GAGGAAGATGAAGGCAACTCTCGACCCGCTGGAGAAGAATCTCCTCGATTACAGGCAACGCGCCATCAAGATTCTCGCCAACAGCTACTACGGCTACTACGGCTATG
CCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAA
GTCCTCTATGCAGACACAGACGGTCTCCATGCCACCATTCCTGGAGCGGACGCTGAAACAGTCAAGAAAAAGGCAATGGAGTTCTTAAACTATATCAATCCCAAACT
GCCCGGCCTTCTCGAACTCGAATACGAGGGCTTCTACGTCAGGGGCTTCTTCGTCACGAAGAAAAAGTACGCGGTCATCGACGAGGAGGGCAAGATAACCACGCGCG
GGCTTGAGATAGTCAGGCGCGACTGGAGCGAGATAGCGAAGGAGACGCAGGCGAGGGTTTTGGAGGCGATACTCAGGCACGGTGACGTTGAAGAGGCCGTCAGAATT
GTCAGGGAAGTCACCGAAAAGCTGAGCAAGTACGAGGTTCCGCCGGAGAAGCTGGTTATCCACGAGCAGATAACGCGCGAGCTCAAGGACTACAAGGCCACCGGCCC
GCACGTAGCCATAGCGAAgcGTTTGGCCGCCAGAGGTGTTAAAATCCGGCCCGGAACTGTGATAAGCTACATCGTTCTGAAGGGCTCCGGAAGGATAGGCGACAGGG
CGATTCCCTTCGACGAGTTCGACCCGACGAAGCACAAGTACGATGCGGACTACTACATCGAGAACCAGGTTCTGCCGGCAGTTGAGAGAATCCTCAGGGCCTTCGGC
TACCGCAAGGAAGACCTGCGCTACCAGAAGACGAGGCAGGTCGGGCTTGGCGCGTGGCTGA

Figure 17T

Pyrococcus furiosus DSM 3638, Archeael hostone (HMf-1) section 85 of 173 of the complete genome.
ACCESSION No: AE010210 REGION: complement (8333..9082)
/product="pcna sliding clamp (proliferating-cell nuclear antigen)"

Nucleotide sequence (SEQ ID NO: 67)
Amino acid sequence (SEQ ID NO: 68)

```
 M   P   F   E   I   V   F   E   G   A   K   E   F   A   Q   L   I   D     18
ATG CCA TTT GAA ATC GTA TTT GAA GGT GCA AAA GAG TTT GCC CAA CTT ATA GAC    54

 T   A   S   K   L   I   D   E   A   A   F   K   V   T   E   D   G   I     36
ACC GCA AGT AAG TTA ATA GAT GAG GCC GCG TTT AAA GTT ACA GAA GAT GGG ATA   108

 S   M   R   A   M   D   P   S   R   V   V   L   I   D   L   N   L   P     54
AGC ATG AGG GCC ATG GAT CCA AGT AGA GTT GTC CTG ATT GAC CTA AAT CTC CCG   162

 S   S   I   F   S   K   Y   E   V   V   E   P   E   T   I   G   V   N     72
TCA AGC ATA TTT AGC AAA TAT GAA GTT GTT GAA CCA GAA ACA ATT GGA GTT AAC   216

 M   D   H   L   K   K   I   L   K   R   G   K   A   K   D   T   L   I     90
ATG GAC CAC CTA AAG AAG ATC CTA AAG AGA GGT AAA GCA AAG GAC ACC TTA ATA   270

 L   K   K   G   E   E   N   F   L   E   I   T   I   Q   G   T   A   T    108
CTC AAG AAA GGA GAG GAA AAC TTC TTA GAG ATA ACA ATT CAA GGA ACT GCA ACA   324

 R   T   F   R   V   P   L   I   D   V   E   E   M   E   V   D   L   P    126
AGA ACA TTT AGA GTT CCC CTA ATA GAT GTA GAA GAG ATG GAA GTT GAC CTC CCA   378

 E   L   P   F   T   A   K   V   V   V   L   G   E   V   L   K   D   A    144
GAA CTT CCA TTC ACT GCA AAG GTT GTA GTT CTT GGA GAA GTC CTA AAA GAT GCT   432

 V   K   D   A   S   L   V   S   D   S   I   K   F   I   A   R   E   N    162
```

```
GTT AAA GAT GCC TCT CTA GTG AGT GAC AGC ATA AAA TTT ATT GCC AGG GAA AAT    486

 E   F   I   M   K   A   E   G   E   T   Q   E   V   E   I   K   L   T     180
GAA TTT ATA ATG AAG GCA GAG GGA GAA ACC CAG GAA GTT GAG ATA AAG CTA ACT    540

 L   E   D   E   G   L   L   D   I   E   V   Q   E   E   T   K   S   A     198
CTT GAA GAT GAG GGA TTA TTG GAC ATC GAG GTT CAA GAG GAG ACA AAG AGC GCA    594

 Y   G   V   S   Y   L   S   D   M   V   K   G   L   G   K   A   D   E     216
TAT GGA GTC AGC TAT CTC TCC GAC ATG GTT AAA GGA CTT GGA AAG GCC GAT GAA    648

 V   T   I   K   F   G   N   E   M   P   M   Q   M   E   Y   Y   I   R     234
GTT ACA ATA AAG TTT GGA AAT GAA ATG CCC ATG CAA ATG GAG TAT TAC ATT AGA    702

 D   E   G   R   L   T   F   L   L   A   P   R   V   E   E   *             250
GAT GAA GGA AGA CTT ACA TTC CTA CTG GCT CCA AGA GTT GAA GAG TGA            750
```

Figure 17U

<u>(PCNA)-Taq DNA polymerase fusion protein</u>

Nucleotide sequence (SEQ ID NO: 67) // Nucleotide sequence (SEQ ID NO: 65)
Amino acid sequence (SEQ ID NO: 68) // Amino acid sequence (SEQ ID NO: 66)

```
 M   P   F   E   I   V   F   E   G   A   K   E   F   A   Q   L   I   D      18
ATG CCA TTT GAA ATC GTA TTT GAA GGT GCA AAA GAG TTT GCC CAA CTT ATA GAC     54

 T   A   S   K   L   I   D   E   A   A   F   K   V   T   E   D   G   I      36
ACC GCA AGT AAG TTA ATA GAT GAG GCC GCG TTT AAA GTT ACA GAA GAT GGG ATA    108

 S   M   R   A   M   D   P   S   R   V   V   L   I   D   L   N   L   P      54
AGC ATG AGG GCC ATG GAT CCA AGT AGA GTT GTC CTG ATT GAC CTA AAT CTC CCG    162
```

FIGURE 17U (Cont.)

```
 S   S   I   F   S   K   Y   E   V   V   E   P   E   T   I   G   V   N      72
TCA AGC ATA TTT AGC AAA TAT GAA GTT GTT GAA CCA GAA ACA ATT GGA GTT AAC    216

 M   D   H   L   K   K   I   L   K   R   G   K   A   K   D   T   L   I      90
ATG GAC CAC CTA AAG AAG ATC CTA AAG AGA GGT AAA GCA AAG GAC ACC TTA ATA    270

 L   K   K   G   E   E   N   F   L   E   I   T   I   Q   G   T   A   T     108
CTC AAG AAA GGA GAG GAA AAC TTC TTA GAG ATA ACA ATT CAA GGA ACT GCA ACA    324

 R   T   F   R   V   P   L   I   D   V   E   E   M   E   V   D   L   P     126
AGA ACA TTT AGA GTT CCC CTA ATA GAT GTA GAA GAG ATG GAA GTT GAC CTC CCA    378

 E   L   P   F   T   A   K   V   V   V   L   G   E   V   L   K   D   A     144
GAA CTT CCA TTC ACT GCA AAG GTT GTA GTT CTT GGA GAA GTC CTA AAA GAT GCT    432

 V   K   D   A   S   L   V   S   D   S   I   K   F   I   A   R   E   N     162
GTT AAA GAT GCC TCT CTA GTG AGT GAC AGC ATA AAA TTT ATT GCC AGG GAA AAT    486

 E   F   I   M   K   A   E   G   E   T   Q   E   V   E   I   K   L   T     180
GAA TTT ATA ATG AAG GCA GAG GGA GAA ACC CAG GAA GTT GAG ATA AAG CTA ACT    540

 L   E   D   E   G   L   L   D   I   E   V   Q   E   E   T   K   S   A     198
CTT GAA GAT GAG GGA TTA TTG GAC ATC GAG GTT CAA GAG GAG ACA AAG AGC GCA    594

 Y   G   V   S   Y   L   S   D   M   V   K   G   L   G   K   A   D   E     216
TAT GGA GTC AGC TAT CTC TCC GAC ATG GTT AAA GGA CTT GGA AAG GCC GAT GAA    648

 V   T   I   K   F   G   N   E   M   P   M   Q   M   E   Y   Y   I   R     234
GTT ACA ATA AAG TTT GGA AAT GAA ATG CCC ATG CAA ATG GAG TAT TAC ATT AGA    702

 D   E   G   R   L   T   F   L   L   A   P   R   V   E   E                 250
GAT GAA GGA AGA CTT ACA TTC CTA CTG GCT CCA AGA GTT GAA GAG

     G   G   G
// GGC GGC GGT

 V   T   S   G   M   L   P   L   F   E   P   K   G   R   V   L   L   V
```

```
GTC ACT AGT GGG ATG CTG CCC CTC TTT GAG CCC AAG GGC CGG GTC CTC CTG GTG

 D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

 S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

 A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

 S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG
```

FIGURE 17U (Cont.)

```
 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC

 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC

 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC
```

FIGURE 17U (Cont.)

```
 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
```

```
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H   *
CAT CAT TAA
```

Figure 17V

<u>Taq DNA polymerase- (PCNA) fusion protein</u>

FIGURE 17V (Cont.)

Nucleotide sequence (SEQ ID NO: 65) //Nucleotide sequence (SEQ ID NO: 67)
Amino acid sequence (SEQ ID NO: 66) /Amino acid sequence (SEQ ID NO: 68)

```
    G   G   G
// GGC GGC GGT

 V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

 D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

 S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

 A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

 S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG
```

FIGURE 17V (Cont.)

```
A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG

A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC

Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC
```

FIGURE 17V (Cont.)

```
 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
```

```
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H   //
CAT CAT  //
```

FIGURE 17V (Cont.)

```
M   P   F   E   I   V   F   E   G   A   K   E   F   A   Q   L   I   D     18
ATG CCA TTT GAA ATC GTA TTT GAA GGT GCA AAA GAG TTT GCC CAA CTT ATA GAC   54

T   A   S   K   L   I   D   E   A   A   F   K   V   T   E   D   G   I     36
ACC GCA AGT AAG TTA ATA GAT GAG GCC GCG TTT AAA GTT ACA GAA GAT GGG ATA  108

S   M   R   A   M   D   P   S   R   V   V   L   I   D   L   N   L   P     54
AGC ATG AGG GCC ATG GAT CCA AGT AGA GTT GTC CTG ATT GAC CTA AAT CTC CCG  162

S   S   I   F   S   K   Y   E   V   V   E   P   E   T   I   G   V   N     72
TCA AGC ATA TTT AGC AAA TAT GAA GTT GTT GAA CCA GAA ACA ATT GGA GTT AAC  216

M   D   H   L   K   K   I   L   K   R   G   K   A   K   D   T   L   I     90
ATG GAC CAC CTA AAG AAG ATC CTA AAG AGA GGT AAA GCA AAG GAC ACC TTA ATA  270

L   K   K   G   E   E   N   F   L   E   I   T   I   Q   G   T   A   T    108
CTC AAG AAA GGA GAG GAA AAC TTC TTA GAG ATA ACA ATT CAA GGA ACT GCA ACA  324

R   T   F   R   V   P   L   I   D   V   E   E   M   E   V   D   L   P    126
AGA ACA TTT AGA GTT CCC CTA ATA GAT GTA GAA GAG ATG GAA GTT GAC CTC CCA  378

E   L   P   F   T   A   K   V   V   V   L   G   E   V   L   K   D   A    144
GAA CTT CCA TTC ACT GCA AAG GTT GTA GTT CTT GGA GAA GTC CTA AAA GAT GCT  432

V   K   D   A   S   L   V   S   D   S   I   K   F   I   A   R   E   N    162
GTT AAA GAT GCC TCT CTA GTG AGT GAC AGC ATA AAA TTT ATT GCC AGG GAA AAT  486

E   F   I   M   K   A   E   G   E   T   Q   E   V   E   I   K   L   T    180
GAA TTT ATA ATG AAG GCA GAG GGA GAA ACC CAG GAA GTT GAG ATA AAG CTA ACT  540

L   E   D   E   G   L   L   D   I   E   V   Q   E   E   T   K   S   A    198
CTT GAA GAT GAG GGA TTA TTG GAC ATC GAG GTT CAA GAG GAG ACA AAG AGC GCA  594

Y   G   V   S   Y   L   S   D   M   V   K   G   L   G   K   A   D   E    216
TAT GGA GTC AGC TAT CTC TCC GAC ATG GTT AAA GGA CTT GGA AAG GCC GAT GAA  648
```

FIGURE 17V (Cont.)

```
 V   T   I   K   F   G   N   E   M   P   M   Q   M   E   Y   Y   I   R     234
GTT ACA ATA AAG TTT GGA AAT GAA ATG CCC ATG CAA ATG GAG TAT TAC ATT AGA    702

 D   E   G   R   L   T   F   L   L   A   P   R   V   E   E   *             250
GAT GAA GGA AGA CTT ACA TTC CTA CTG GCT CCA AGA GTT GAA GAG TGA
```

Figure 17W

Pfu DNA Polymerase (WT) -(PCNA) fusion protein

Nucleotide sequence (SEQ ID NO: 61) // Nucleotide sequence (SEQ ID NO: 67)

```
ccctggtcct gggtccacat atatgttctt actcgccttt atgaagaatc ccccagtcgc
tctaacctgg gttatagtga caaatcttcc tccaccaccg cccaagaagg ttatttctat
caactctaca cctcccctat tttctctctt atgagatttt taagtatagt tatagagaag
gttttatact ccaaactgag ttagtagata tgtggggagc ataatgattt tagatgtgga
ttacataact gaagaaggaa aacctgttat taggctattc aaaaaagaga acggaaaatt
taagatagag catgatagaa cttttagacc atacatttac gctcttctca gggatgattc
aaagattgaa gaagttaaga aaataacggg ggaaaggcat ggaaagattg tgagaattgt
tgatgtagag aaggttgaga aaaagtttct cggcaagcct attaccgtgt ggaaacttta
tttggaacat ccccaagatg ttcccactat tagagaaaaa gttagagaac atccagcagt
tgtggacatc ttcgaatacg atattccatt tgcaaagaga tacctcatcg acaaaggcct
```

FIGURE 17W (Cont.)

aataccaatg gagggggaag aagagctaaa gattcttgcc ttcgatatag aaaccctcta
tcacgaagga gaagagtttg gaaaaggccc aattataatg attagttatg cagatgaaaa
tgaagcaaag gtgattactt ggaaaaacat agatcttcca tacgttgagg ttgtatcaag
cgagagagag atgataaaga gatttctcag gattatcagg gagaaggatc ctgacattat
agttacttat aatggagact cattcgactt cccatattta gcgaaaaggg cagaaaaact
tgggattaaa ttaaccattg gaagagatgg aagcgagccc aagatgcaga gaataggcga
tatgacggct gtagaagtca agggaagaat acatttcgac ttgtatcatg taataacaag
gacaataaat ctcccaacat acacactaga ggctgtatat gaagcaattt ttggaaagcc
aaaggagaag gtatacgccg acgagatagc aaaagcctgg gaaagtggag agaaccttga
gagagttgcc aaatactcga tggaagatgc aaaggcaact tatgaactcg ggaaagaatt
ccttccaatg gaaattcagc tttcaagatt agttggacaa cctttatggg atgtttcaag
gtcaagcaca gggaaccttg tagagtggtt cttacttagg aaagcctacg aaagaaacga
agtagctcca aacaagccaa gtgaagagga gtatcaaaga aggctcaggg agagctacac
aggtggattc gttaaagagc cagaaaaggg gttgtgggaa aacatagtat acctagattt
tagagcccta tatccctcga ttataattac ccacaatgtt tctcccgata ctctaaatct
tgagggatgc aagaactatg atatcgctcc tcaagtaggc cacaagttct gcaaggacat
ccctggtttt ataccaagtc tcttgggaca tttgttagag gaaagacaaa agattaagac
aaaaatgaag gaaactcaag atcctataga aaaaatactc cttgactata gacaaaaagc
gataaaactc ttagcaaatt ctttctacgg atattatggc tatgcaaaag caagatggta FIGURE 17W (Cont.)

ctgtaaggag tgtgctgaga gcgttactgc ctggggaaga aagtacatcg agttagtatg gaaggagctc gaagaaaagt ttggatttaa agtcctctac attgacactg atggtctcta tgcaactatc ccaggaggag aaagtgagga aataaagaaa aaggctctag aatttgtaaa atacataaat tcaaagctcc ctggactgct agagcttgaa tatgaagggt tttataagag gggattcttc gttacgaaga agaggtatgc agtaatagat gaagaaggaa aagtcattac tcgtggttta gagatagtta ggagagattg gagtgaaatt gcaaaagaaa ctcaagctag agttttggag acaatactaa aacacggaga tgttgaagaa gctgtgagaa tagtaaaaga agtaatacaa aagcttgcca attatgaaat tccaccagag aagctcgcaa tatatgagca gataacaaga ccattacatg agtataaggc gataggtcct cacgtagctg ttgcaaagaa actagctgct aaaggagtta aaataaagcc aggaatggta attggataca tagtacttag aggcgatggt ccaattagca atagggcaat tctagctgag gaatacgatc ccaaaaagca caagtatgac gcagaatatt acattgagaa ccaggttctt ccagcggtac ttaggatatt ggagggattt ggatacagaa aggaagacct cagataccaa aagacaagac aagtcggcct aacttcctgg cttaacatta aaaaatccta gaaaagcgat agatatcaac ttttattctt tctaaccttt ttctatgaaa gaagaactga gcaggaatta ccagttcttc cgttatttta tgggtaatta aaaacccatg ctcttgggag aatcttcgaa taaaatccct aacttcaggc tttgctaagt gaatagaata aacaacatca ctcacttcaa acgccttcgt tagaaatggt ctatctgcat gcttctctgg ctcggaanng gaggattcat aacaacagta tcaacattct cagagaattg agaaacatca gaaactttga cttctacaac atttctaact ttgcaactct FIGURE 17W (Cont.)

tcaagatttt ctaaaagaat tttaacggcc tcctcgtcaa tttcgacgac gtagatcttt tttgctccaa gcagagccgc tccaatggat aacacccctg ttcccgcacc caagtccgct acaatttttt ccttgtatct cctaatgtat aagcaagcca aaggagagta gatgctacct ttccgggagt tttgtattgc tctagccaag gtttgggatt tttgaatcct ttaactctgg aaagtataat ttcaagctcc ttcttcttca tgacagatga aaaattgttt tgtctctttt taacttttac agaaataact gtctcaaatt atgacaactc ttgacatttt tacttcatta ccagggtaat gtttttaagt atgaaatttt tctttcatag aggaggnnnn nngtcctctc ctcgatttcc ttggttgtgc tccatatgat aagcttccaa agtgggtgtt cagactttta gacactcaaa taccagacga caatggtgtg ctcactcaag ccccatatgg gttgagaaaa gtagaagcgg cactactcag atgcttcccc aggaatgagg ttgttgtagc tcntcccnga aagattgaga tgttcttgg //

ATG CCA TTT GAA ATC GTA TTT GAA GGT GCA AAA GAG TTT GCC CAA CTT ATA GAC 54
ACC GCA AGT AAG TTA ATA GAT GAG GCC GCG TTT AAA GTT ACA GAA GAT GGG ATA 108
AGC ATG AGG GCC ATG GAT CCA AGT AGA GTT GTC CTG ATT GAC CTA AAT CTC CCG 162
TCA AGC ATA TTT AGC AAA TAT GAA GTT GTT GAA CCA GAA ACA ATT GGA GTT AAC 216
ATG GAC CAC CTA AAG AAG ATC CTA AAG AGA GGT AAA GCA AAG GAC ACC TTA ATA 270
CTC AAG AAA GGA GAG GAA AAC TTC TTA GAG ATA ACA ATT CAA GGA ACT GCA ACA 324
AGA ACA TTT AGA GTT CCC CTA ATA GAT GTA GAA GAG ATG GAA GTT GAC CTC CCA 378
GAA CTT CCA TTC ACT GCA AAG GTT GTA GTT CTT GGA GAA GTC CTA AAA GAT GCT 432
GTT AAA GAT GCC TCT CTA GTG AGT GAC AGC ATA AAA TTT ATT GCC AGG GAA AAT 486
GAA TTT ATA ATG AAG GCA GAG GGA GAA ACC CAG GAA GTT GAG ATA AAG CTA ACT 540
CTT GAA GAT GAG GGA TTA TTG GAC ATC GAG GTT CAA GAG GAG ACA AAG AGC GCA 594
TAT GGA GTC AGC TAT CTC TCC GAC ATG GTT AAA GGA CTT GGA AAG GCC GAT GAA 648
GTT ACA ATA AAG TTT GGA AAT GAA ATG CCC ATG CAA ATG GAG TAT TAC ATT AGA 702
GAT GAA GGA AGA CTT ACA TTC CTA CTG GCT CCA AGA GTT GAA GAG TGA

Figure 17X

(PCNA) - Pfu DNA Polymerase (WT) fusion protein

Nucleotide sequence (SEQ ID NO: 67) // Nucleotide sequence (SEQ ID NO: 61)

```
ATG CCA TTT GAA ATC GTA TTT GAA GGT GCA AAA GAG TTT GCC CAA CTT ATA GAC     54
ACC GCA AGT AAG TTA ATA GAT GAG GCC GCG TTT AAA GTT ACA GAA GAT GGG ATA    108
AGC ATG AGG GCC ATG GAT CCA AGT AGA GTT GTC CTG ATT GAC CTA AAT CTC CCG    162
TCA AGC ATA TTT AGC AAA TAT GAA GTT GTT GAA CCA GAA ACA ATT GGA GTT AAC    216
ATG GAC CAC CTA AAG AAG ATC CTA AAG AGA GGT AAA GCA AAG GAC ACC TTA ATA    270
CTC AAG AAA GGA GAG GAA AAC TTC TTA GAG ATA ACA ATT CAA GGA ACT GCA ACA    324
AGA ACA TTT AGA GTT CCC CTA ATA GAT GTA GAA GAG ATG GAA GTT GAC CTC CCA    378
GAA CTT CCA TTC ACT GCA AAG GTT GTA GTT CTT GGA GAA GTC CTA AAA GAT GCT    432
GTT AAA GAT GCC TCT CTA GTG AGT GAC AGC ATA AAA TTT ATT GCC AGG GAA AAT    486
GAA TTT ATA ATG AAG GCA GAG GGA GAA ACC CAG GAA GTT GAG ATA AAG CTA ACT    540
CTT GAA GAT GAG GGA TTA TTG GAC ATC GAG GTT CAA GAG GAG ACA AAG AGC GCA    594
TAT GGA GTC AGC TAT CTC TCC GAC ATG GTT AAA GGA CTT GGA AAG GCC GAT GAA    648
GTT ACA ATA AAG TTT GGA AAT GAA ATG CCC ATG CAA ATG GAG TAT TAC ATT AGA    702
GAT GAA GGA AGA CTT ACA TTC CTA CTG GCT CCA AGA GTT GAA GAG
```

```
ccctggtcct gggtccacat atatgttctt actcgccttt atgaagaatc ccccagtcgc

tctaacctgg gttatagtga caaatcttcc tccaccaccg cccaagaagg ttatttctat

caactctaca cctcccctat tttctctctt atgagatttt taagtatagt tatagagaag

gttttatact ccaaactgag ttagtagata tgtggggagc ataatgattt tagatgtgga

ttacataact gaagaaggaa aacctgttat taggctattc aaaaaagaga acggaaaatt
```

FIGURE 17X (Cont.)

taagatagag catgatagaa cttttagacc atacatttac gctcttctca gggatgattc
aaagattgaa gaagttaaga aaataacggg ggaaaggcat ggaaagattg tgagaattgt
tgatgtagag aaggttgaga aaaagtttct cggcaagcct attaccgtgt ggaaacttta
tttggaacat ccccaagatg ttcccactat tagagaaaaa gttagagaac atccagcagt
tgtggacatc ttcgaatacg atattccatt tgcaaagaga tacctcatcg acaaaggcct
aataccaatg gagggggaag aagagctaaa gattcttgcc ttcgatatag aaaccctcta
tcacgaagga gaagagtttg gaaaaggccc aattataatg attagttatg cagatgaaaa
tgaagcaaag gtgattactt ggaaaaacat agatcttcca tacgttgagg ttgtatcaag
cgagagagag atgataaaga gatttctcag gattatcagg gagaaggatc ctgacattat
agttacttat aatggagact cattcgactt cccatattta gcgaaaaggg cagaaaaact
tgggattaaa ttaaccattg gaagagatgg aagcgagccc aagatgcaga gaataggcga
tatgacggct gtagaagtca agggaagaat acatttcgac ttgtatcatg taataacaag
gacaataaat ctcccaacat acacactaga ggctgtatat gaagcaattt ttggaaagcc
aaaggagaag gtatacgccg acgagatagc aaaagcctgg gaaagtggag agaaccttga
gagagttgcc aaatactcga tggaagatgc aaaggcaact tatgaactcg ggaaagaatt
ccttccaatg gaaattcagc tttcaagatt agttggacaa cctttatggg atgtttcaag
gtcaagcaca gggaaccttg tagagtggtt cttacttagg aaagcctacg aaagaaacga
agtagctcca aacaagccaa gtgaagagga gtatcaaaga aggctcaggg agagctacac
aggtggattc gttaaagagc cagaaaaggg gttgtgggaa aacatagtat acctagattt FIGURE 17X (Cont.)

tagagcccta tatccctcga ttataattac ccacaatgtt tctcccgata ctctaaatct tgagggatgc aagaactatg atatcgctcc tcaagtaggc cacaagttct gcaaggacat ccctggtttt ataccaagtc tcttgggaca tttgttagag gaaagacaaa agattaagac aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg gaaggagctc gaagaaaagt ttggatttaa agtcctctac attgacactg atggtctcta tgcaactatc ccaggaggag aaagtgagga aataaagaaa aaggctctag aatttgtaaa atacataaat tcaaagctcc ctggactgct agagcttgaa tatgaagggt tttataagag gggattcttc gttacgaaga agaggtatgc agtaatagat gaagaaggaa aagtcattac tcgtggttta gagatagtta ggagagattg gagtgaaatt gcaaaagaaa ctcaagctag agttttggag acaatactaa aacacggaga tgttgaagaa gctgtgagaa tagtaaaaga agtaatacaa aagcttgcca attatgaaat tccaccagag aagctcgcaa tatatgagca gataacaaga ccattacatg agtataaggc gataggtcct cacgtagctg ttgcaaagaa actagctgct aaaggagtta aaataaagcc aggaatggta attggataca tagtacttag aggcgatggt ccaattagca atagggcaat tctagctgag gaatacgatc ccaaaaagca caagtatgac gcagaatatt acattgagaa ccaggttctt ccagcggtac ttaggatatt ggagggattt ggatacagaa aggaagacct cagataccaa aagacaagac aagtcggcct aacttcctgg cttaacatta aaaaatccta gaaaagcgat agatatcaac ttttattctt FIGURE 17X (Cont.)

tctaaccttt ttctatgaaa gaagaactga gcaggaatta ccagttcttc cgttatttta
tgggtaatta aaaacccatg ctcttgggag aatcttcgaa taaaatccct aacttcaggc
tttgctaagt gaatagaata aacaacatca ctcacttcaa acgccttcgt tagaaatggt
ctatctgcat gcttctctgg ctcggaanng gaggattcat aacaacagta tcaacattct
cagagaattg agaaacatca gaaactttga cttctacaac atttctaact ttgcaactct
tcaagatttt ctaaaagaat tttaacggcc tcctcgtcaa tttcgacgac gtagatcttt
tttgctccaa gcagagccgc tccaatggat aacacccctg ttcccgcacc caagtccgct
acaatttttt ccttgtatct cctaatgtat aagcaagcca aaggagagta gatgctacct
ttccgggagt tttgtattgc tctagccaag gtttgggatt tttgaatcct ttaactctgg
aaagtataat ttcaagctcc ttcttcttca tgacagatga aaaattgttt tgtctctttt
taacttttac agaaataact gtctcaaatt atgacaactc ttgacatttt tacttcatta
ccagggtaat gtttttaagt atgaaatttt tctttcatag aggaggnnnn nngtcctctc
ctcgatttcc ttggttgtgc tccatatgat aagcttccaa agtgggtgtt cagactttta
gacactcaaa taccagacga caatggtgtg ctcactcaag ccccatatgg gttgagaaaa
gtagaagcgg cactactcag atgcttcccc aggaatgagg ttgttgtagc tcntcccnga
aagattgaga tgttcttgg // TGA

(PCNA) - PFU DNA POLYMERASE (V93 R OR E) fusion protein

Nucleotide sequence (SEQ ID NO: 67) // Nucleotide sequence (SEQ ID NO: 27)
Nucleotide sequence (SEQ ID NO: 67) //Nucleotide sequence (SEQ ID NO: 28)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC    54
ACC GCA AGT AAG TTA ATA GAT GAG GCC GCG TTT AAA GTT ACA GAA GAT GGG ATA   108
AGC ATG AGG GCC ATG GAT CCA AGT AGA GTT GTC CTG ATT GAC CTA AAT CTC CCG   162
TCA AGC ATA TTT AGC AAA TAT GAA GTT GTT GAA CCA GAA ACA ATT GGA GTT AAC   216
ATG GAC CAC CTA AAG AAG ATC CTA AAG AGA GGT AAA GCA AAG GAC ACC TTA ATA   270
CTC AAG AAA GGA GAG GAA AAC TTC TTA GAG ATA ACA ATT CAA GGA ACT GCA ACA   324
AGA ACA TTT AGA GTT CCC CTA ATA GAT GTA GAA GAG ATG GAA GTT GAC CTC CCA   378
GAA CTT CCA TTC ACT GCA AAG GTT GTA GTT CTT GGA GAA GTC CTA AAA GAT GCT   432
GTT AAA GAT GCC TCT CTA GTG AGT GAC AGC ATA AAA TTT ATT GCC AGG GAA AAT   486
GAA TTT ATA ATG AAG GCA GAG GGA GAA ACC CAG GAA GTT GAG ATA AAG CTA ACT   540
CTT GAA GAT GAG GGA TTA TTG GAC ATC GAG GTT CAA GAG GAG ACA AAG AGC GCA   594
TAT GGA GTC AGC TAT CTC TCC GAC ATG GTT AAA GGA CTT GGA AAG GCC GAT GAA   648
GTT ACA ATA AAG TTT GGA AAT GAA ATG CCC ATG CAA ATG GAG TAT TAC ATT AGA   702
GAT GAA GGA AGA CTT ACA TTC CTA CTG GCT CCA AGA GTT GAA GAG //
```

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
```

FIGURE 17Y (Cont.)

```
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAACGGGTT GTGGAAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //             2328
// TGA
```

Figure 17Z

PFU DNA POLYMERASE (V93 R OR E)-(PCNA) fusion protein

FIGURE 17Z (Cont.)

Nucleotide sequence (SEQ ID NO: 27) // Nucleotide sequence (SEQ ID NO: 67)
Nucleotide sequence (SEQ ID NO: 28) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
```

FIGURE 17Z (Cont.)

```
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //             2328

ATG CCA TTT GAA ATC GTA TTT GAA GGT GCA AAA GAG TTT GCC CAA CTT ATA GAC     54
ACC GCA AGT AAG TTA ATA GAT GAG GCC GCG TTT AAA GTT ACA GAA GAT GGG ATA    108
AGC ATG AGG GCC ATG GAT CCA AGT AGA GTT GTC CTG ATT GAC CTA AAT CTC CCG    162
TCA AGC ATA TTT AGC AAA TAT GAA GTT GTT GAA CCA GAA ACA ATT GGA GTT AAC    216
ATG GAC CAC CTA AAG AAG ATC CTA AAG AGA GGT AAA GCA AAG GAC ACC TTA ATA    270
CTC AAG AAA GGA GAG GAA AAC TTC TTA GAG ATA ACA ATT CAA GGA ACT GCA ACA    324
AGA ACA TTT AGA GTT CCC CTA ATA GAT GTA GAA GAG ATG GAA GTT GAC CTC CCA    378
GAA CTT CCA TTC ACT GCA AAG GTT GTA GTT CTT GGA GAA GTC CTA AAA GAT GCT    432
GTT AAA GAT GCC TCT CTA GTG AGT GAC AGC ATA AAA TTT ATT GCC AGG GAA AAT    486
GAA TTT ATA ATG AAG GCA GAG GGA GAA ACC CAG GAA GTT GAG ATA AAG CTA ACT    540
CTT GAA GAT GAG GGA TTA TTG GAC ATC GAG GTT CAA GAG GAG ACA AAG AGC GCA    594
TAT GGA GTC AGC TAT CTC TCC GAC ATG GTT AAA GGA CTT GGA AAG GCC GAT GAA    648
GTT ACA ATA AAG TTT GGA AAT GAA ATG CCC ATG CAA ATG GAG TAT TAC ATT AGA    702
GAT GAA GGA AGA CTT ACA TTC CTA CTG GCT CCA AGA GTT GAA GAG TGA
```

Figure 17AA

PFU DNA POLYMERASE (G387P/V93R OR E)-(PCNA) fusion protein

Nucleotide sequence (SEQ ID NO: 29) // Nucleotide sequence (SEQ ID NO: 67)
Nucleotide sequence (SEQ ID NO: 30) // Nucleotide sequence (SEQ ID NO: 67)

FIGURE 17AA (Cont.)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
```

FIGURE 17AA (Cont.)

```
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //             2328

ATG CCA TTT GAA ATC GTA TTT GAA GGT GCA AAA GAG TTT GCC CAA CTT ATA GAC    54
ACC GCA AGT AAG TTA ATA GAT GAG GCC GCG TTT AAA GTT ACA GAA GAT GGG ATA   108
AGC ATG AGG GCC ATG GAT CCA AGT AGA GTT GTC CTG ATT GAC CTA AAT CTC CCG   162
TCA AGC ATA TTT AGC AAA TAT GAA GTT GTT GAA CCA GAA ACA ATT GGA GTT AAC   216
ATG GAC CAC CTA AAG AAG ATC CTA AAG AGA GGT AAA GCA AAG GAC ACC TTA ATA   270
CTC AAG AAA GGA GAG GAA AAC TTC TTA GAG ATA ACA ATT CAA GGA ACT GCA ACA   324
AGA ACA TTT AGA GTT CCC CTA ATA GAT GTA GAA GAG ATG GAA GTT GAC CTC CCA   378
GAA CTT CCA TTC ACT GCA AAG GTT GTA GTT CTT GGA GAA GTC CTA AAA GAT GCT   432
GTT AAA GAT GCC TCT CTA GTG AGT GAC AGC ATA AAA TTT ATT GCC AGG GAA AAT   486
GAA TTT ATA ATG AAG GCA GAG GGA GAA ACC CAG GAA GTT GAG ATA AAG CTA ACT   540
CTT GAA GAT GAG GGA TTA TTG GAC ATC GAG GTT CAA GAG GAG ACA AAG AGC GCA   594
TAT GGA GTC AGC TAT CTC TCC GAC ATG GTT AAA GGA CTT GGA AAG GCC GAT GAA   648
GTT ACA ATA AAG TTT GGA AAT GAA ATG CCC ATG CAA ATG GAG TAT TAC ATT AGA   702
GAT GAA GGA AGA CTT ACA TTC CTA CTG GCT CCA AGA GTT GAA GAG TGA
```

Figure 17BB

(PCNA) - PFU DNA POLYMERASE (G387P/V93R OR E) fusion protein

Nucleotide sequence (SEQ ID NO: 67) // Nucleotide sequence (SEQ ID NO: 29)
Nucleotide sequence (SEQ ID NO: 67) // Nucleotide sequence (SEQ ID NO: 30)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

FIGURE 17BB (Cont.)

```
ATG CCA TTT GAA ATC GTA TTT GAA GGT GCA AAA GAG TTT GCC CAA CTT ATA GAC     54
ACC GCA AGT AAG TTA ATA GAT GAG GCC GCG TTT AAA GTT ACA GAA GAT GGG ATA    108
AGC ATG AGG GCC ATG GAT CCA AGT AGA GTT GTC CTG ATT GAC CTA AAT CTC CCG    162
TCA AGC ATA TTT AGC AAA TAT GAA GTT GTT GAA CCA GAA ACA ATT GGA GTT AAC    216
ATG GAC CAC CTA AAG AAG ATC CTA AAG AGA GGT AAA GCA AAG GAC ACC TTA ATA    270
CTC AAG AAA GGA GAG GAA AAC TTC TTA GAG ATA ACA ATT CAA GGA ACT GCA ACA    324
AGA ACA TTT AGA GTT CCC CTA ATA GAT GTA GAA GAG ATG GAA GTT GAC CTC CCA    378
GAA CTT CCA TTC ACT GCA AAG GTT GTA GTT CTT GGA GAA GTC CTA AAA GAT GCT    432
GTT AAA GAT GCC TCT CTA GTG AGT GAC AGC ATA AAA TTT ATT GCC AGG GAA AAT    486
GAA TTT ATA ATG AAG GCA GAG GGA GAA ACC CAG GAA GTT GAG ATA AAG CTA ACT    540
CTT GAA GAT GAG GGA TTA TTG GAC ATC GAG GTT CAA GAG GAG ACA AAG AGC GCA    594
TAT GGA GTC AGC TAT CTC TCC GAC ATG GTT AAA GGA CTT GGA AAG GCC GAT GAA    648
GTT ACA ATA AAG TTT GGA AAT GAA ATG CCC ATG CAA ATG GAG TAT TAC ATT AGA    702
GAT GAA GGA AGA CTT ACA TTC CTA CTG GCT CCA AGA GTT GAA GAG //

ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
```

FIGURE 17BB (Cont.)

```
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //TAG         2328
```

Figure 17CC

(PCNA)-PFU DNA POLYMERASE(D141A/E143A/V93R OR E) fusion protein

Nucleotide sequence (SEQ ID NO: 67) // Nucleotide sequence (SEQ ID NO: 31)
Nucleotide sequence (SEQ ID NO: 67) // Nucleotide sequence (SEQ ID NO: 32)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC    54
ACC GCA AGT AAG TTA ATA GAT GAG GCC GCG TTT AAA GTT ACA GAA GAT GGG ATA   108
AGC ATG AGG GCC ATG GAT CCA AGT AGA GTT GTC CTG ATT GAC CTA AAT CTC CCG   162
TCA AGC ATA TTT AGC AAA TAT GAA GTT GTT GAA CCA GAA ACA ATT GGA GTT AAC   216
```

FIGURE 17CC (Cont.)

ATG GAC CAC CTA AAG AAG ATC CTA AAG AGA GGT AAA GCA AAG GAC ACC TTA ATA 270
CTC AAG AAA GGA GAG GAA AAC TTC TTA GAG ATA ACA ATT CAA GGA ACT GCA ACA 324
AGA ACA TTT AGA GTT CCC CTA ATA GAT GTA GAA GAG ATG GAA GTT GAC CTC CCA 378
GAA CTT CCA TTC ACT GCA AAG GTT GTA GTT CTT GGA GAA GTC CTA AAA GAT GCT 432
GTT AAA GAT GCC TCT CTA GTG AGT GAC AGC ATA AAA TTT ATT GCC AGG GAA AAT 486
GAA TTT ATA ATG AAG GCA GAG GGA GAA ACC CAG GAA GTT GAG ATA AAG CTA ACT 540
CTT GAA GAT GAG GGA TTA TTG GAC ATC GAG GTT CAA GAG GAG ACA AAG AGC GCA 594
TAT GGA GTC AGC TAT CTC TCC GAC ATG GTT AAA GGA CTT GGA AAG GCC GAT GAA 648
GTT ACA ATA AAG TTT GGA AAT GAA ATG CCC ATG CAA ATG GAG TAT TAC ATT AGA 702
GAT GAA GGA AGA CTT ACA TTC CTA CTG GCT CCA AGA GTT GAA GAG //

//ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACA GTT_GGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620

FIGURE 17CC (Cont.)

```
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //            2328
TGA
```

Figure 17DD

PFU DNA POLYMERASE(D141A/E143A/V93R OR E) - (PCNA) fusion protein

Nucleotide sequence (SEQ ID NO: 31) // Nucleotide sequence (SEQ ID NO: 67)
Nucleotide sequence (SEQ ID NO: 32) // Nucleotide sequence (SEQ ID NO: 67)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAACAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA GAGTTTGGAA AAGGCCCAAT TATAATGATT 480
```

FIGURE 17DD (Cont.)

```
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACA GTT_GGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //             2328

ATG CCA TTT GAA ATC GTA TTT GAA GGT GCA AAA GAG TTT GCC CAA CTT ATA GAC     54
ACC GCA AGT AAG TTA ATA GAT GAG GCC GCG TTT AAA GTT ACA GAA GAT GGG ATA    108
AGC ATG AGG GCC ATG GAT CCA AGT AGA GTT GTC CTG ATT GAC CTA AAT CTC CCG    162
TCA AGC ATA TTT AGC AAA TAT GAA GTT GTT GAA CCA GAA ACA ATT GGA GTT AAC    216
ATG GAC CAC CTA AAG AAG ATC CTA AAG AGA GGT AAA GCA AAG GAC ACC TTA ATA    270
CTC AAG AAA GGA GAG GAA AAC TTC TTA GAG ATA ACA ATT CAA GGA ACT GCA ACA    324
```

FIGURE 17DD (Cont.)

```
AGA ACA TTT AGA GTT CCC CTA ATA GAT GTA GAA GAG ATG GAA GTT GAC CTC CCA    378
GAA CTT CCA TTC ACT GCA AAG GTT GTA GTT CTT GGA GAA GTC CTA AAA GAT GCT    432
GTT AAA GAT GCC TCT CTA GTG AGT GAC AGC ATA AAA TTT ATT GCC AGG GAA AAT    486
GAA TTT ATA ATG AAG GCA GAG GGA GAA ACC CAG GAA GTT GAG ATA AAG CTA ACT    540
CTT GAA GAT GAG GGA TTA TTG GAC ATC GAG GTT CAA GAG GAG ACA AAG AGC GCA    594
TAT GGA GTC AGC TAT CTC TCC GAC ATG GTT AAA GGA CTT GGA AAG GCC GAT GAA    648
GTT ACA ATA AAG TTT GGA AAT GAA ATG CCC ATG CAA ATG GAG TAT TAC ATT AGA    702
GAT GAA GGA AGA CTT ACA TTC CTA CTG GCT CCA AGA GTT GAA GAG TGA
```

Figure 17EE

KOD DNA POLYMERASE - (PCNA) fusion protein

Nucleotide sequence (SEQ ID NO: 33) // Nucleotide sequence (SEQ ID NO: 67)
Nucleotide sequence (SEQ ID NO: 34) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
```

FIGURE 17EE (Cont.)

```
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT  2325

ATG CCA TTT GAA ATC GTA TTT GAA GGT GCA AAA GAG TTT GCC CAA CTT ATA GAC     54
ACC GCA AGT AAG TTA ATA GAT GAG GCC GCG TTT AAA GTT ACA GAA GAT GGG ATA    108
AGC ATG AGG GCC ATG GAT CCA AGT AGA GTT GTC CTG ATT GAC CTA AAT CTC CCG    162
TCA AGC ATA TTT AGC AAA TAT GAA GTT GTT GAA CCA GAA ACA ATT GGA GTT AAC    216
ATG GAC CAC CTA AAG AAG ATC CTA AAG AGA GGT AAA GCA AAG GAC ACC TTA ATA    270
CTC AAG AAA GGA GAG GAA AAC TTC TTA GAG ATA ACA ATT CAA GGA ACT GCA ACA    324
AGA ACA TTT AGA GTT CCC CTA ATA GAT GTA GAA GAG ATG GAA GTT GAC CTC CCA    378
GAA CTT CCA TTC ACT GCA AAG GTT GTA GTT CTT GGA GAA GTC CTA AAA GAT GCT    432
GTT AAA GAT GCC TCT CTA GTG AGT GAC AGC ATA AAA TTT ATT GCC AGG GAA AAT    486
GAA TTT ATA ATG AAG GCA GAG GGA GAA ACC CAG GAA GTT GAG ATA AAG CTA ACT    540
CTT GAA GAT GAG GGA TTA TTG GAC ATC GAG GTT CAA GAG GAG ACA AAG AGC GCA    594
TAT GGA GTC AGC TAT CTC TCC GAC ATG GTT AAA GGA CTT GGA AAG GCC GAT GAA    648
GTT ACA ATA AAG TTT GGA AAT GAA ATG CCC ATG CAA ATG GAG TAT TAC ATT AGA    702
GAT GAA GGA AGA CTT ACA TTC CTA CTG GCT CCA AGA GTT GAA GAG TGA
```

Figure 17FF

(PCNA) - KOD DNA POLYMERASE fusion protein

Nucleotide sequence (SEQ ID NO: 67) // Nucleotide sequence (SEQ ID NO: 33)
Nucleotide sequence (SEQ ID NO: 67) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC    54
ACC GCA AGT AAG TTA ATA GAT GAG GCC GCG TTT AAA GTT ACA GAA GAT GGG ATA   108
AGC ATG AGG GCC ATG GAT CCA AGT AGA GTT GTC CTG ATT GAC CTA AAT CTC CCG   162
TCA AGC ATA TTT AGC AAA TAT GAA GTT GTT GAA CCA GAA ACA ATT GGA GTT AAC   216
ATG GAC CAC CTA AAG AAG ATC CTA AAG AGA GGT AAA GCA AAG GAC ACC TTA ATA   270
CTC AAG AAA GGA GAG GAA AAC TTC TTA GAG ATA ACA ATT CAA GGA ACT GCA ACA   324
AGA ACA TTT AGA GTT CCC CTA ATA GAT GTA GAA GAG ATG GAA GTT GAC CTC CCA   378
GAA CTT CCA TTC ACT GCA AAG GTT GTA GTT CTT GGA GAA GTC CTA AAA GAT GCT   432
GTT AAA GAT GCC TCT CTA GTG AGT GAC AGC ATA AAA TTT ATT GCC AGG GAA AAT   486
GAA TTT ATA ATG AAG GCA GAG GGA GAA ACC CAG GAA GTT GAG ATA AAG CTA ACT   540
CTT GAA GAT GAG GGA TTA TTG GAC ATC GAG GTT CAA GAG GAG ACA AAG AGC GCA   594
TAT GGA GTC AGC TAT CTC TCC GAC ATG GTT AAA GGA CTT GGA AAG GCC GAT GAA   648
GTT ACA ATA AAG TTT GGA AAT GAA ATG CCC ATG CAA ATG GAG TAT TAC ATT AGA   702
GAT GAA GGA AGA CTT ACA TTC CTA CTG GCT CCA AGA GTT GAA GAG //
```

```
ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
```

FIGURE 17FF (Cont.)

```
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT //TAG 2325
```

(PCNA)-Vent DNA POLYMERASE FUSION PROTEIN

Nucleotide sequence (SEQ ID NO: 67) // Nucleotide sequence (SEQ ID NO: 35)
Nucleotide sequence (SEQ ID NO: 67) // Nucleotide sequence (SEQ ID NO: 36)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC     54
ACC GCA AGT AAG TTA ATA GAT GAG GCC GCG TTT AAA GTT ACA GAA GAT GGG ATA    108
AGC ATG AGG GCC ATG GAT CCA AGT AGA GTT GTC CTG ATT GAC CTA AAT CTC CCG    162
TCA AGC ATA TTT AGC AAA TAT GAA GTT GTT GAA CCA GAA ACA ATT GGA GTT AAC    216
ATG GAC CAC CTA AAG AAG ATC CTA AAG AGA GGT AAA GCA AAG GAC ACC TTA ATA    270
CTC AAG AAA GGA GAG GAA AAC TTC TTA GAG ATA ACA ATT CAA GGA ACT GCA ACA    324
AGA ACA TTT AGA GTT CCC CTA ATA GAT GTA GAA GAG ATG GAA GTT GAC CTC CCA    378
GAA CTT CCA TTC ACT GCA AAG GTT GTA GTT CTT GGA GAA GTC CTA AAA GAT GCT    432
GTT AAA GAT GCC TCT CTA GTG AGT GAC AGC ATA AAA TTT ATT GCC AGG GAA AAT    486
GAA TTT ATA ATG AAG GCA GAG GGA GAA ACC CAG GAA GTT GAG ATA AAG CTA ACT    540
CTT GAA GAT GAG GGA TTA TTG GAC ATC GAG GTT CAA GAG GAG ACA AAG AGC GCA    594
TAT GGA GTC AGC TAT CTC TCC GAC ATG GTT AAA GGA CTT GGA AAG GCC GAT GAA    648
GTT ACA ATA AAG TTT GGA AAT GAA ATG CCC ATG CAA ATG GAG TAT TAC ATT AGA    702
GAT GAA GGA AGA CTT ACA TTC CTA CTG GCT CCA AGA GTT GAA GAG //

ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
```

FIGURE 17GG (Cont.)

```
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325
```

Figure 17HH

Vent DNA POLYMERASE - (PCNA) FUSION PROTEIN

FIGURE 17HH (Cont.)

Nucleotide sequence (SEQ ID NO: 35) // Nucleotide sequence (SEQ ID NO: 67)
Nucleotide sequence (SEQ ID NO: 36) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
```

FIGURE 17HH (Cont.)

```
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GG 2325 //
```

```
ATG CCA TTT GAA ATC GTA TTT GAA GGT GCA AAA GAG TTT GCC CAA CTT ATA GAC    54
ACC GCA AGT AAG TTA ATA GAT GAG GCC GCG TTT AAA GTT ACA GAA GAT GGG ATA   108
AGC ATG AGG GCC ATG GAT CCA AGT AGA GTT GTC CTG ATT GAC CTA AAT CTC CCG   162
TCA AGC ATA TTT AGC AAA TAT GAA GTT GTT GAA CCA GAA ACA ATT GGA GTT AAC   216
ATG GAC CAC CTA AAG AAG ATC CTA AAG AGA GGT AAA GCA AAG GAC ACC TTA ATA   270
CTC AAG AAA GGA GAG GAA AAC TTC TTA GAG ATA ACA ATT CAA GGA ACT GCA ACA   324
AGA ACA TTT AGA GTT CCC CTA ATA GAT GTA GAA GAG ATG GAA GTT GAC CTC CCA   378
GAA CTT CCA TTC ACT GCA AAG GTT GTA GTT CTT GGA GAA GTC CTA AAA GAT GCT   432
GTT AAA GAT GCC TCT CTA GTG AGT GAC AGC ATA AAA TTT ATT GCC AGG GAA AAT   486
GAA TTT ATA ATG AAG GCA GAG GGA GAA ACC CAG GAA GTT GAG ATA AAG CTA ACT   540
CTT GAA GAT GAG GGA TTA TTG GAC ATC GAG GTT CAA GAG GAG ACA AAG AGC GCA   594
TAT GGA GTC AGC TAT CTC TCC GAC ATG GTT AAA GGA CTT GGA AAG GCC GAT GAA   648
GTT ACA ATA AAG TTT GGA AAT GAA ATG CCC ATG CAA ATG GAG TAT TAC ATT AGA   702
GAT GAA GGA AGA CTT ACA TTC CTA CTG GCT CCA AGA GTT GAA GAG TGA
```

Figure 17II

Deep Vent- (PCNA) DNA polymerase fusion protein

FIGURE 17II (Cont.)

Nucleotide sequence (SEQ ID NO: 37) // Nucleotide sequence (SEQ ID NO: 67)
Nucleotide sequence (SEQ ID NO: 38) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTTG ACGCTGACTA CATCACCGAG GATGGGAAGC CGATTATAAG GATTTTCAAG   60
AAAGAAAACG GCGAGTTTAA GGTTGAGTAC GACAGAAACT TTAGACCTTA CATTTACGCT  120
CTCCTCAAAG ATGACTCGCA GATTGATGAG GTTAGGAAGA TAACCGCCGA GAGGCATGGG  180
AAGATAGTGA GAATTATAGA TGCCGAAAAG GTAAGGAAGA AGTTCCTGGG GAGGCCGATT  240
GAGGTATGGA GGCTGTACTT TGAACACCCT CAGGACXXXC CCGCAATAAG GGATAAGATA  300
AGAGAGCATT CCGCAGTTAT TGACATCTTT GAGTACGACA TTCCGTTCGC GAAGAGGTAC  360
CTAATAGACA AAGGCCTAAT TCCAATGGAA GGCGATGAAG AGCTCAAGTT GCTCGCATTT  420
GACATAGAAA CCCTCTATCA CGAAGGGGAG GAGTTCGCGA AGGGGCCCAT TATAATGATA  480
AGCTATGCTG ATGAGGAAGA AGCCAAAGTC ATAACGTGGA AAAAGATCGA TCTCCCGTAC  540
GTCGAGGTAG TTTCCAGCGA GAGGGAGATG ATAAAGCGGT TCCTCAAGGT GATAAGGGAG  600
AAAGATCCCG ATGTTATAAT TACCTACAAC GGCGATTCTT TCGACCTTCC CTATCTAGTT  660
AAGAGGGCCG AAAAGCTCGG GATAAAGCTA CCCCTGGGAA GGGACGGTAG TGAGCCAAAG  720
ATGCAGAGGC TTGGGGATAT GACAGCGGTG GAGATAAAGG GAAGGATACA CTTTGACCTC  780
TACCACGTGA TTAGGAGAAC GATAAACCTC CCAACATACA CCCTCGAGGC AGTTTATGAG  840
GCAATCTTCG GAAAGCCAAA GGAGAAAGTT TACGCTCACG AGATAGCTGA GGCCTGGGAG  900
ACTGGAAAGG GACTGGAGAG AGTTGCAAAG TATTCAATGG AGGATGCAAA GGTAACGTAC  960
GAGCTCGGTA GGGAGTTCTT CCCAATGGAG GCCCAGCTTT CAAGGTTAGT CGGCCAGCCC 1020
CTGTGGGATG TTTCTAGGTC TTCAACTGGC AACTTGGTGG AGTGGTACCT CCTCAGGAAG 1080
GCCTACGAGA GGAATGAATT GGCTCCAAAC AAGCCGGATG AGAGGGAGTA CGAGAGAAGG 1140
CTAAGGGAGA GCTACGCTGG GGGATACGTT AAGGAGCCGG AGAAAGGGCT CTGGGAGGGG 1200
TTAGTTTCCC TAGATTTCAG GAGCCTGTAC CCCTCGATAA TAATCACCCA TAACGTCTCA 1260
CCGGATACGC TGAACAGGGA AGGGTGTAGG GAATACGATG TCGCCCCAGA GGTTGGGCAC 1320
AAGTTCTGCA AGGACTTCCC GGGGTTTATC CCCAGCCTGC TCAAGAGGTT ATTGGATGAA 1380
AGGCAAGAAA TAAAAAGGAA GATGAAAGCT TCTAAAGACC CAATCGAGAA GAAGATGCTT 1440
GATTACAGGC AACGGGCAAT CAAAATCCTG GCAAACAGCT ATTATGGGTA TTATGGGTAC 1500
GCAAAAGCCC GTTGGTACTG TAAGGAGTGC GCAGAGAGCG TTACGGCCTG GGGGAGGGAA 1560
TATATAGAGT TCGTAAGGAA GGAACTGGAG GAAAAGTTCG GGTTCAAAGT CTTATACATA 1620
GACACAGATG GACTCTACGC CACAATTCCT GGGGCAAAAC CCGAGGAGAT AAAGAAGAAA 1680
GCCCTAGAGT TCGTAGATTA TATAAACGCC AAGCTCCCAG GGCTGTTGGA GCTTGAGTAC 1740
GAGGGCTTCT ACGTGAGAGG GTTCTTCGTG ACGAAGAAGA AGTATGCGTT GATAGATGAG 1800
GAAGGGAAGA TAATCACTAG GGGGCTTGAA ATAGTCAGGA GGGACTGGAG CGAAATAGCC 1860
```

FIGURE 17II (Cont.)

```
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG //               2328

ATG CCA TTT GAA ATC GTA TTT GAA GGT GCA AAA GAG TTT GCC CAA CTT ATA GAC    54
ACC GCA AGT AAG TTA ATA GAT GAG GCC GCG TTT AAA GTT ACA GAA GAT GGG ATA   108
AGC ATG AGG GCC ATG GAT CCA AGT AGA GTT GTC CTG ATT GAC CTA AAT CTC CCG   162
TCA AGC ATA TTT AGC AAA TAT GAA GTT GTT GAA CCA GAA ACA ATT GGA GTT AAC   216
ATG GAC CAC CTA AAG AAG ATC CTA AAG AGA GGT AAA GCA AAG GAC ACC TTA ATA   270
CTC AAG AAA GGA GAG GAA AAC TTC TTA GAG ATA ACA ATT CAA GGA ACT GCA ACA   324
AGA ACA TTT AGA GTT CCC CTA ATA GAT GTA GAA GAG ATG GAA GTT GAC CTC CCA   378
GAA CTT CCA TTC ACT GCA AAG GTT GTA GTT CTT GGA GAA GTC CTA AAA GAT GCT   432
GTT AAA GAT GCC TCT CTA GTG AGT GAC AGC ATA AAA TTT ATT GCC AGG GAA AAT   486
GAA TTT ATA ATG AAG GCA GAG GGA GAA ACC CAG GAA GTT GAG ATA AAG CTA ACT   540
CTT GAA GAT GAG GGA TTA TTG GAC ATC GAG GTT CAA GAG GAG ACA AAG AGC GCA   594
TAT GGA GTC AGC TAT CTC TCC GAC ATG GTT AAA GGA CTT GGA AAG GCC GAT GAA   648
GTT ACA ATA AAG TTT GGA AAT GAA ATG CCC ATG CAA ATG GAG TAT TAC ATT AGA   702
GAT GAA GGA AGA CTT ACA TTC CTA CTG GCT CCA AGA GTT GAA GAG TGA
```

Figure 17JJ

<u>(PCNA) - Deep Vent DNA polymerase fusion protein</u>

Nucleotide sequence (SEQ ID NO: 67) // Nucleotide sequence (SEQ ID NO: 37)
Nucleotide sequence (SEQ ID NO: 67) // Nucleotide sequence (SEQ ID NO: 38)

FIGURE 17JJ (Cont.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC    54
ACC GCA AGT AAG TTA ATA GAT GAG GCC GCG TTT AAA GTT ACA GAA GAT GGG ATA   108
AGC ATG AGG GCC ATG GAT CCA AGT AGA GTT GTC CTG ATT GAC CTA AAT CTC CCG   162
TCA AGC ATA TTT AGC AAA TAT GAA GTT GTT GAA CCA GAA ACA ATT GGA GTT AAC   216
ATG GAC CAC CTA AAG AAG ATC CTA AAG AGA GGT AAA GCA AAG GAC ACC TTA ATA   270
CTC AAG AAA GGA GAG GAA AAC TTC TTA GAG ATA ACA ATT CAA GGA ACT GCA ACA   324
AGA ACA TTT AGA GTT CCC CTA ATA GAT GTA GAA GAG ATG GAA GTT GAC CTC CCA   378
GAA CTT CCA TTC ACT GCA AAG GTT GTA GTT CTT GGA GAA GTC CTA AAA GAT GCT   432
GTT AAA GAT GCC TCT CTA GTG AGT GAC AGC ATA AAA TTT ATT GCC AGG GAA AAT   486
GAA TTT ATA ATG AAG GCA GAG GGA GAA ACC CAG GAA GTT GAG ATA AAG CTA ACT   540
CTT GAA GAT GAG GGA TTA TTG GAC ATC GAG GTT CAA GAG GAG ACA AAG AGC GCA   594
TAT GGA GTC AGC TAT CTC TCC GAC ATG GTT AAA GGA CTT GGA AAG GCC GAT GAA   648
GTT ACA ATA AAG TTT GGA AAT GAA ATG CCC ATG CAA ATG GAG TAT TAC ATT AGA   702
GAT GAA GGA AGA CTT ACA TTC CTA CTG GCT CCA AGA GTT GAA GAG //
```

```
ATGATACTTG ACGCTGACTA CATCACCGAG GATGGGAAGC CGATTATAAG GATTTTCAAG    60
AAAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
AAGATAGTGA GAATTATAGA TGCCGAAAAG GTAAGGAAGA AGTTCCTGGG GAGGCCGATT   240
GAGGTATGGA GGCTGTACTT TGAACACCCT CAGGACXXXC CCGCAATAAG GGATAAGATA   300
AGAGAGCATT CCGCAGTTAT TGACATCTTT GAGTACGACA TTCCGTTCGC GAAGAGGTAC   360
CTAATAGACA AAGGCCTAAT TCCAATGGAA GGCGATGAAG AGCTCAAGTT GCTCGCATTT   420
GACATAGAAA CCCTCTATCA CGAAGGGGAG GAGTTCGCGA AGGGGCCCAT TATAATGATA   480
AGCTATGCTG ATGAGGAAGA AGCCAAAGTC ATAACGTGGA AAAAGATCGA TCTCCCGTAC   540
GTCGAGGTAG TTTCCAGCGA GAGGGAGATG ATAAAGCGGT TCCTCAAGGT GATAAGGGAG   600
AAAGATCCCG ATGTTATAAT TACCTACAAC GGCGATTCTT TCGACCTTCC CTATCTAGTT   660
AAGAGGGCCG AAAAGCTCGG GATAAAGCTA CCCCTGGGAA GGGACGGTAG TGAGCCAAAG   720
ATGCAGAGGC TTGGGGATAT GACAGCGGTG GAGATAAAGG GAAGGATACA CTTTGACCTC   780
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
```

FIGURE 17JJ (Cont.)

```
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG TAA              2328
```

Figure 17KK

JDF-3 - (PCNA) fusion protein

Nucleotide sequence (SEQ ID NO: 39) // Nucleotide sequence (SEQ ID NO: 67)
Nucleotide sequence (SEQ ID NO: 40) // Nucleotide sequence (SEQ ID NO: 67)

FIGURE 17KK (Cont.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTCGG
CAGGTCTGTGGAGGTCTGGGTCCTCTACTTCACGCACCCGCAGGACXXXCCGGCAATCCGCGACAAAATAAGGAAGCACCCCGCGGTCATCGACATCTACGAGTACGACATACCC
TTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGGAA
CCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATTAA
GCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCTTT
ACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCATAA
ACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAGAG
GGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTTCC
CGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGGGCT
ACgcCGGTGGCTACGTCAAGGAGCCGGAGCGGGGACTGTGGACAATATCGTGTATCTAGACTTTCGTAGTCTCTACCCTTCAATCATAATCACCCACAACGTCTCGCCAGATAC
GCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGG
CAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCT
ATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTCCT
CTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTCTC
GAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCGCG
ACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGCAA
GTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAGGT
GTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGATG
CGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGCGC
GTGGCTGAAGCCGAAGGGGAAGAAGAAG//

ATG CCA TTT GAA ATC GTA TTT GAA GGT GCA AAA GAG TTT GCC CAA CTT ATA GAC 54
ACC GCA AGT AAG TTA ATA GAT GAG GCC GCG TTT AAA GTT ACA GAA GAT GGG ATA 108
AGC ATG AGG GCC ATG GAT CCA AGT AGA GTT GTC CTG ATT GAC CTA AAT CTC CCG 162
TCA AGC ATA TTT AGC AAA TAT GAA GTT GTT GAA CCA GAA ACA ATT GGA GTT AAC 216
ATG GAC CAC CTA AAG AAG ATC CTA AAG AGA GGT AAA GCA AAG GAC ACC TTA ATA 270
CTC AAG AAA GGA GAG GAA AAC TTC TTA GAG ATA ACA ATT CAA GGA ACT GCA ACA 324
AGA ACA TTT AGA GTT CCC CTA ATA GAT GTA GAA GAG ATG GAA GTT GAC CTC CCA 378
GAA CTT CCA TTC ACT GCA AAG GTT GTA GTT CTT GGA GAA GTC CTA AAA GAT GCT 432
GTT AAA GAT GCC TCT CTA GTG AGT GAC AGC ATA AAA TTT ATT GCC AGG GAA AAT 486
GAA TTT ATA ATG AAG GCA GAG GGA GAA ACC CAG GAA GTT GAG ATA AAG CTA ACT 540
CTT GAA GAT GAG GGA TTA TTG GAC ATC GAG GTT CAA GAG GAG ACA AAG AGC GCA 594
TAT GGA GTC AGC TAT CTC TCC GAC ATG GTT AAA GGA CTT GGA AAG GCC GAT GAA 648

FIGURE 17KK (Cont.)

```
GTT ACA ATA AAG TTT GGA AAT GAA ATG CCC ATG CAA ATG GAG TAT TAC ATT AGA    702
GAT GAA GGA AGA CTT ACA TTC CTA CTG GCT CCA AGA GTT GAA GAG TGA
```

Figure 17LL

(PCNA) - JDF-3 fusion protein

Nucleotide sequence (SEQ ID NO: 67) // Nucleotide sequence (SEQ ID NO: 39)
Nucleotide sequence (SEQ ID NO: 67) // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC     54
ACC GCA AGT AAG TTA ATA GAT GAG GCC GCG TTT AAA GTT ACA GAA GAT GGG ATA    108
AGC ATG AGG GCC ATG GAT CCA AGT AGA GTT GTC CTG ATT GAC CTA AAT CTC CCG    162
TCA AGC ATA TTT AGC AAA TAT GAA GTT GTT GAA CCA GAA ACA ATT GGA GTT AAC    216
ATG GAC CAC CTA AAG AAG ATC CTA AAG AGA GGT AAA GCA AAG GAC ACC TTA ATA    270
CTC AAG AAA GGA GAG GAA AAC TTC TTA GAG ATA ACA ATT CAA GGA ACT GCA ACA    324
AGA ACA TTT AGA GTT CCC CTA ATA GAT GTA GAA GAG ATG GAA GTT GAC CTC CCA    378
GAA CTT CCA TTC ACT GCA AAG GTT GTA GTT CTT GGA GAA GTC CTA AAA GAT GCT    432
GTT AAA GAT GCC TCT CTA GTG AGT GAC AGC ATA AAA TTT ATT GCC AGG GAA AAT    486
GAA TTT ATA ATG AAG GCA GAG GGA GAA ACC CAG GAA GTT GAG ATA AAG CTA ACT    540
CTT GAA GAT GAG GGA TTA TTG GAC ATC GAG GTT CAA GAG GAG ACA AAG AGC GCA    594
TAT GGA GTC AGC TAT CTC TCC GAC ATG GTT AAA GGA CTT GGA AAG GCC GAT GAA    648
GTT ACA ATA AAG TTT GGA AAT GAA ATG CCC ATG CAA ATG GAG TAT TAC ATT AGA    702
GAT GAA GGA AGA CTT ACA TTC CTA CTG GCT CCA AGA GTT GAA GAG //
```

```
ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCC
CTACTTCTACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGA
AGAAAAAGTTCCTCGGCAGGTCTGTGGAGGTCTGGGTCCTCTACTTCACGCACCCGCAGGACXXXCCGGCAATCCGCGACAAAATAAGGAAGCACCCCGCGGTCATC
GACATCTACGAGTACGACATACCCTTCGCCAAGCGCTACCTCATAGACAAGGGCCTAATCCCGATGGAAGGTGAGGAAGAGCTTAAACTCATGTCCTTCGACATCGA
GACGCTCTACCACGAGGGAGAAGAGTTTGGAACCGGGCCGATTCTGATGATAAGCTACGCCGATGAAAGCGAGGCGCGCGTGATAACCTGGAAGAAGATCGACCTTC
```

FIGURE 17LL (Cont.)

CTTACGTTGAGGTTGTCTCCACCGAGAAGGAGATGATTAAGCGCTTCTTGAGGGTCGTTAAGGAGAAGGACCCGGACGTGCTGATAACATACAACGGCGACAACTTC
GACTTCGCCTACCTGAAAAAGCGCTGTGAGAAGCTTGGCGTGAGCTTTACCCTCGGGAGGGACGGGAGCGAGCCGAAGATACAGCGCATGGGGGACAGGTTTGCGGT
CGAGGTGAAGGGCAGGGTACACTTCGACCTTTATCCAGTCATAAGGCGCACCATAAACCTCCCGACCTACACCCTTGAGGCTGTATACGAGGCGGTTTTCGGCAAGC
CCAAGGAGAAGGTCTACGCCGAGGAGATAGCCACCGCCTGGGAGACCGGCGAGGGGCTTGAGAGGGTCGCGCGCTACTCGATGGAGGACGCGAGGGTTACCTACGAG
CTTGGCAGGGAGTTCTTCCCGATGGAGGCCCAGCTTTCCAGGCTCATCGGCCAAGGCCTCTGGGACGTTTCCCGCTCCAGCACCGGCAACCTCGTCGAGTGGTTCCT
CCTAAGGAAGGCCTACGAGAGGAACGAACTCGCTCCCAACAAGCCCGACGAGAGGGAGCTGGCGAGGAGAAGGGGGGGCTACgcCGGTGGCTACGTCAAGGAGCCGG
AGCGGGGACTGTGGGACAATATCGTGTATCTAGACTTTCGTAGTCTCTACCCTTCAATCATAATCACCCACAACGTCTCGCCAGATACGCTCAACCGCGAGGGGTGT
AGGAGCTACGACGTTGCCCCCGAGGTCGGTCACAAGTTCTGCAAGGACTTCCCCGGCTTCATTCCGAGCCTGCTCGGAAACCTGCTGGAGGAAAGGCAGAAGATAAA
GAGGAAGATGAAGGCAACTCTCGACCCGCTGGAGAAGAATCTCCTCGATTACAGGCAACGCGCCATCAAGATTCTCGCCAACAGCTACTACGGCTACTACGGCTATG
CCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAA
GTCCTCTATGCAGACACAGACGGTCTCCATGCCACCATTCCTGGAGCGGACGCTGAAACAGTCAAGAAAAAGGCAATGGAGTTCTTAAACTATATCAATCCCAAACT
GCCCGGCCTTCTCGAACTCGAATACGAGGGCTTCTACGTCAGGGGCTTCTTCGTCACGAAGAAAAAGTACGCGGTCATCGACGAGGAGGGCAAGATAACCACGCGCG
GGCTTGAGATAGTCAGGCGCGACTGGAGCGAGATAGCGAAGGAGACGCAGGCGAGGGTTTTGGAGGCGATACTCAGGCACGGTGACGTTGAAGAGGCCGTCAGAATT
GTCAGGGAAGTCACCGAAAAGCTGAGCAAGTACGAGGTTCCGCCGGAGAAGCTGGTTATCCACGAGCAGATAACGCGCGAGCTCAAGGACTACAAGGCCACCGGCCC
GCACGTAGCCATAGCGAAgcGTTTGGCCGCCAGAGGTGTTAAAATCCGGCCCGGAACTGTGATAAGCTACATCGTTCTGAAGGGCTCCGGAAGGATAGGCGACAGGG
CGATTCCCTTCGACGAGTTCGACCCGACGAAGCACAAGTACGATGCGGACTACTACATCGAGAACCAGGTTCTGCCGGCAGTTGAGAGAATCCTCAGGGCCTTCGGC
TACCGCAAGGAAGACCTGCGCTACCAGAAGACGAGGCAGGTCGGGCTTGGCGCGTGGCTGA

Figure 17MM

Sac7d gene (ACCESSION No: M87569)

Nucleotide sequence (SEQ ID NO: 69)
Amino acid sequence (SEQ ID NO: 70)

```
 M   V   K   V   K   F   K   Y   K   G   E   E   K   E   V   D   T   S     18
ATG GTG AAG GTA AAG TTC AAG TAT AAG GGT GAA GAG AAA GAA GTA GAC ACT TCA    54

 K   I   K   K   V   W   R   V   G   K   M   V   S   F   T   Y   D   D     36
AAG ATA AAG AAG GTT TGG AGA GTA GGC AAA ATG GTG TCC TTT ACC TAT GAC GAC   108

 N   G   K   T   G   R   G   A   V   S   E   K   D   A   P   K   E   L     54
AAT GGT AAG ACA GGT AGA GGA GCT GTA AGC GAG AAA GAT GCT CCA AAA GAA TTA   162

 L   D   M   L   A   R   A   E   R   E   K   K   *                         67
TTA GAC ATG TTA GCA AGA GCA GAA AGA GAG AAG AAA TAA                       201
```

Figure 17NN

Sac7d-Taq DNA polymerase fusion protein

Nucleotide sequence (SEQ ID NO: 69) // Nucleotide sequence (SEQ ID NO: 65)
Amino acid sequence (SEQ ID NO: 70) // Amino acid sequence (SEQ ID NO: 66)

```
 M   V   K   V   K   F   K   Y   K   G   E   E   K   E   V   D   T   S
ATG GTG AAG GTA AAG TTC AAG TAT AAG GGT GAA GAG AAA GAA GTA GAC ACT TCA

 K   I   K   K   V   W   R   V   G   K   M   V   S   F   T   Y   D   D
AAG ATA AAG AAG GTT TGG AGA GTA GGC AAA ATG GTG TCC TTT ACC TAT GAC GAC

 N   G   K   T   G   R   G   A   V   S   E   K   D   A   P   K   E   L
AAT GGT AAG ACA GGT AGA GGA GCT GTA AGC GAG AAA GAT GCT CCA AAA GAA TTA
```

FIGURE 17NN (Cont.)

```
 L   D   M   L   A   R   A   E   R   E   K   K  //
TTA GAC ATG TTA GCA AGA GCA GAA AGA GAG AAG AAA //

    G   G   G
// GGC GGC GGT

 V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

 D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

 S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

 A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

 S   F   R   H   E  .A   Y   G   G   Y   K   A   G   R   A   P   T   P
TCC TTC CGC CAC GAG GCC TAC GGG GGG TAC AAG GCG GGC CGG GCC CCC ACG CCA

 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
```

```
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG

 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC

 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC
```

FIGURE 17NN (Cont.)

```
 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC
```

FIGURE 17NN (Cont.)

```
 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H   *
CAT CAT TAA
```

Figure 17OO

Taq DNA polymerase- Sac7d fusion protein

Nucleotide sequence (SEQ ID NO: 65) //Nucleotide sequence (SEQ ID NO: 69)
Amino acid sequence (SEQ ID NO: 66) /Amino acid sequence (SEQ ID NO: 70)

```
    G   G   G
 // GGC GGC GGT

 V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

 D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

 S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

 A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

 S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA
```

FIGURE 1700 (Cont.)

```
 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG

 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC
```

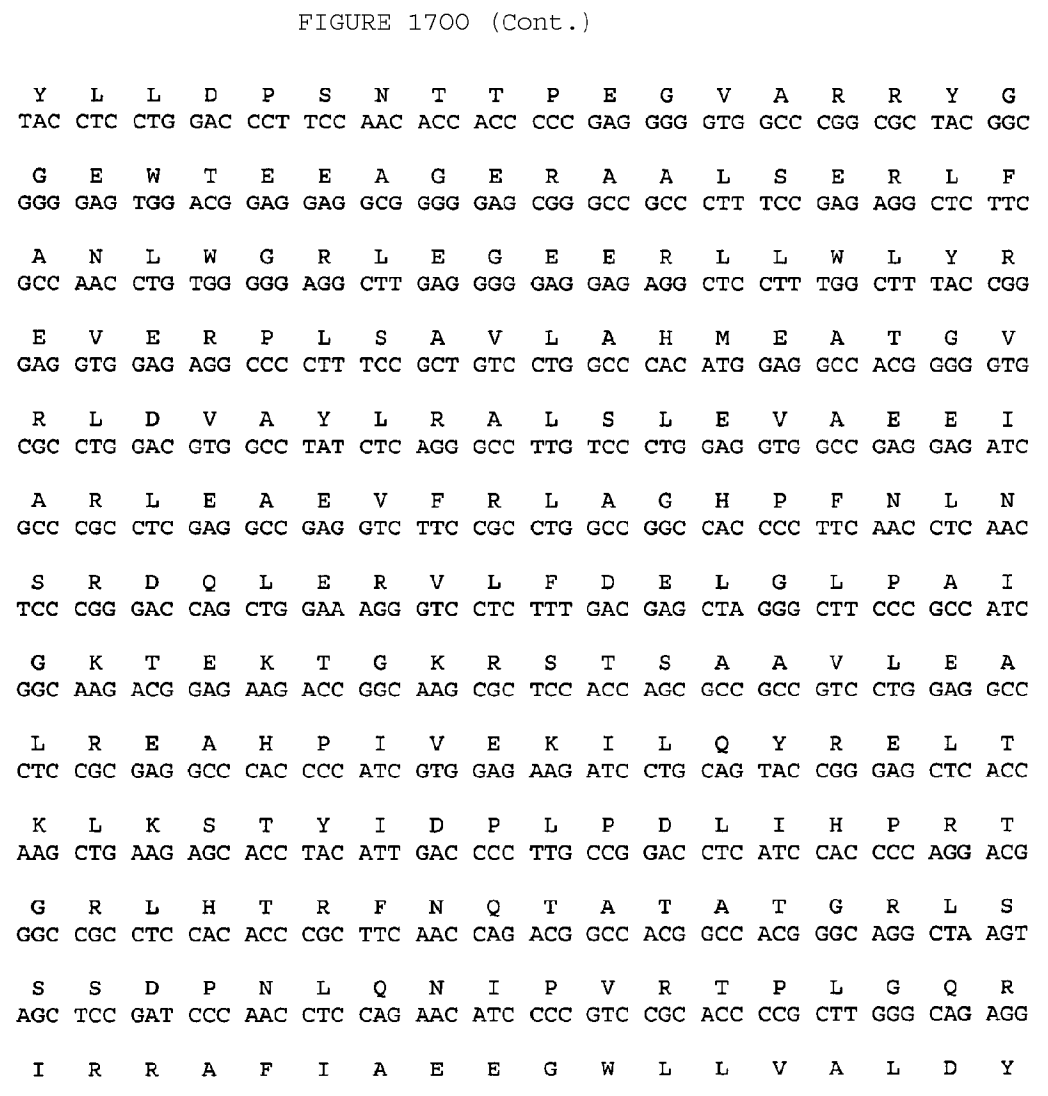

FIGURE 1700 (Cont.)

```
 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC

 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
```

```
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG
```

FIGURE 17OO (Cont.)

```
 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H  //
CAT CAT //

 M   V   K   V   K   F   K   Y   K   G   E   E   K   E   V   D   T   S
ATG GTG AAG GTA AAG TTC AAG TAT AAG GGT GAA GAG AAA GAA GTA GAC ACT TCA

 K   I   K   K   V   W   R   V   G   K   M   V   S   F   T   Y   D   D
AAG ATA AAG AAG GTT TGG AGA GTA GGC AAA ATG GTG TCC TTT ACC TAT GAC GAC

 N   G   K   T   G   R   G   A   V   S   E   K   D   A   P   K   E   L
AAT GGT AAG ACA GGT AGA GGA GCT GTA AGC GAG AAA GAT GCT CCA AAA GAA TTA

 L   D   M   L   A   R   A   E   R   E   K   K  //   *
TTA GAC ATG TTA GCA AGA GCA GAA AGA GAG AAG AAA //  TAG
```

Figure 17PP

Pfu DNA Polymerase (WT) -Sac7d fusion protein

Nucleotide sequence (SEQ ID NO: 61) // Nucleotide sequence (SEQ ID NO: 69)

```
//
ccctggtcct gggtccacat atatgttctt actcgccttt atgaagaatc ccccagtcgc

tctaacctgg gttatagtga caaatcttcc tccaccaccg cccaagaagg ttatttctat

caactctaca cctcccctat tttctctctt atgagatttt taagtatagt tatagagaag

gttttatact ccaaactgag ttagtagata tgtggggagc ataatgattt tagatgtgga
```

FIGURE 17PP (Cont.)

ttacataact gaagaaggaa aacctgttat taggctattc aaaaaagaga acggaaaatt taagatagag catgatagaa cttttagacc atacatttac gctcttctca gggatgattc aaagattgaa gaagttaaga aaataacggg ggaaaggcat ggaaagattg tgagaattgt tgatgtagag aaggttgaga aaaagtttct cggcaagcct attaccgtgt ggaaacttta tttggaacat ccccaagatg ttcccactat tagagaaaaa gttagagaac atccagcagt tgtggacatc ttcgaatacg atattccatt tgcaaagaga tacctcatcg acaaaggcct aataccaatg gagggggaag aagagctaaa gattcttgcc ttcgatatag aaaccctcta tcacgaagga gaagagtttg gaaaaggccc aattataatg attagttatg cagatgaaaa tgaagcaaag gtgattactt ggaaaaacat agatcttcca tacgttgagg ttgtatcaag cgagagagag atgataaaga gatttctcag gattatcagg gagaaggatc ctgacattat agttacttat aatggagact cattcgactt cccatattta gcgaaaaggg cagaaaaact tgggattaaa ttaaccattg gaagagatgg aagcgagccc aagatgcaga gaataggcga tatgacggct gtagaagtca agggaagaat acatttcgac ttgtatcatg taataacaag gacaataaat ctcccaacat acacactaga ggctgtatat gaagcaattt ttggaaagcc aaaggagaag gtatacgccg acgagatagc aaaagcctgg gaaagtggag agaaccttga gagagttgcc aaatactcga tggaagatgc aaaggcaact tatgaactcg ggaaagaatt ccttccaatg gaaattcagc tttcaagatt agttggacaa cctttatggg atgtttcaag gtcaagcaca gggaaccttg tagagtggtt cttacttagg aaagcctacg aaagaaacga agtagctcca aacaagccaa gtgaagagga gtatcaaaga aggctcaggg agagctacac FIGURE 17PP (Cont.)

aggtggattc gttaaagagc cagaaaaggg gttgtgggaa aacatagtat acctagattt tagagcccta tatccctcga ttataattac ccacaatgtt tctcccgata ctctaaatct tgagggatgc aagaactatg atatcgctcc tcaagtaggc cacaagttct gcaaggacat ccctggtttt ataccaagtc tcttgggaca tttgttagag gaaagacaaa agattaagac aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg gaaggagctc gaagaaaagt ttggatttaa agtcctctac attgacactg atggtctcta tgcaactatc ccaggaggag aaagtgagga aataaagaaa aaggctctag aatttgtaaa atacataaat tcaaagctcc ctggactgct agagcttgaa tatgaagggt tttataagag gggattcttc gttacgaaga agaggtatgc agtaatagat gaagaaggaa aagtcattac tcgtggttta gagatagtta ggagagattg gagtgaaatt gcaaaagaaa ctcaagctag agttttggag acaatactaa aacacggaga tgttgaagaa gctgtgagaa tagtaaaaga agtaatacaa aagcttgcca attatgaaat tccaccagag aagctcgcaa tatatgagca gataacaaga ccattacatg agtataaggc gataggtcct cacgtagctg ttgcaaagaa actagctgct aaaggagtta aaataaagcc aggaatggta attggataca tagtacttag aggcgatggt ccaattagca atagggcaat tctagctgag gaatacgatc ccaaaaagca caagtatgac gcagaatatt acattgagaa ccaggttctt ccagcggtac ttaggatatt ggagggattt ggatacagaa aggaagacct cagataccaa aagacaagac aagtcggcct FIGURE 17PP (Cont.)

aacttcctgg cttaacatta aaaaatccta gaaaagcgat agatatcaac ttttattctt tctaaccttt ttctatgaaa gaagaactga gcaggaatta ccagttcttc cgttatttta tgggtaatta aaaacccatg ctcttgggag aatcttcgaa taaaatccct aacttcaggc tttgctaagt gaatagaata aacaacatca ctcacttcaa acgccttcgt tagaaatggt ctatctgcat gcttctctgg ctcggaanng gaggattcat aacaacagta tcaacattct cagagaattg agaaacatca gaaactttga cttctacaac atttctaact ttgcaactct tcaagatttt ctaaaagaat tttaacggcc tcctcgtcaa tttcgacgac gtagatcttt tttgctccaa gcagagccgc tccaatggat aacacccctg ttcccgcacc caagtccgct acaatttttt ccttgtatct cctaatgtat aagcaagcca aaggagagta gatgctacct ttccgggagt tttgtattgc tctagccaag gtttgggatt tttgaatcct ttaactctgg aaagtataat ttcaagctcc ttcttcttca tgacagatga aaaattgttt tgtctctttt taacttttac agaaataact gtctcaaatt atgacaactc ttgacatttt tacttcatta ccagggtaat gtttttaagt atgaaatttt tctttcatag aggaggnnnn nngtcctctc ctcgatttcc ttggttgtgc tccatatgat aagcttccaa agtgggtgtt cagactttta gacactcaaa taccagacga caatggtgtg ctcactcaag ccccatatgg gttgagaaaa gtagaagcgg cactactcag atgcttcccc aggaatgagg ttgttgtagc tcntcccnga aagattgaga tgttcttgg //

// ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA

FIGURE 17PP (Cont.)

TTA GAC ATG TTA GCA AGA GCA GAA AGA GAG AAG AAA //TGA

Figure 17QQ

Sac7d - Pfu DNA Polymerase (WT) fusion protein

Nucleotide sequence (SEQ ID NO: 69) // Nucleotide sequence (SEQ ID NO: 61)

```
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //
//
ccctggtcct gggtccacat atatgttctt actcgccttt atgaagaatc ccccagtcgc

tctaacctgg gttatagtga caaatcttcc tccaccaccg cccaagaagg ttatttctat

caactctaca cctcccctat tttctctctt atgagatttt taagtatagt tatagagaag

gttttatact ccaaactgag ttagtagata tgtggggagc ataatgattt tagatgtgga

ttacataact gaagaaggaa aacctgttat taggctattc aaaaaagaga acggaaaatt

taagatagag catgatagaa cttttagacc atacatttac gctcttctca gggatgattc

aaagattgaa gaagttaaga aaataacggg ggaaaggcat ggaaagattg tgagaattgt

tgatgtagag aaggttgaga aaaagtttct cggcaagcct attaccgtgt ggaaacttta

tttggaacat ccccaagatg ttcccactat tagagaaaaa gttagagaac atccagcagt

tgtggacatc ttcgaatacg atattccatt tgcaaagaga tacctcatcg acaaaggcct

aataccaatg gagggggaag aagagctaaa gattcttgcc ttcgatatag aaaccctcta
```

FIGURE 17QQ (Cont.)

tcacgaagga gaagagtttg gaaaaggccc aattataatg attagttatg cagatgaaaa tgaagcaaag gtgattactt ggaaaaacat agatcttcca tacgttgagg ttgtatcaag cgagagagag atgataaaga gatttctcag gattatcagg gagaaggatc ctgacattat agttacttat aatggagact cattcgactt cccatattta gcgaaaaggg cagaaaaact tgggattaaa ttaaccattg gaagagatgg aagcgagccc aagatgcaga gaataggcga tatgacggct gtagaagtca agggaagaat acatttcgac ttgtatcatg taataacaag gacaataaat ctcccaacat acacactaga ggctgtatat gaagcaattt ttggaaagcc aaaggagaag gtatacgccg acgagatagc aaaagcctgg gaaagtggag agaaccttga gagagttgcc aaatactcga tggaagatgc aaaggcaact tatgaactcg ggaaagaatt ccttccaatg gaaattcagc tttcaagatt agttggacaa cctttatggg atgtttcaag gtcaagcaca gggaaccttg tagagtggtt cttacttagg aaagcctacg aaagaaacga agtagctcca aacaagccaa gtgaagagga gtatcaaaga aggctcaggg agagctacac aggtggattc gttaaagagc cagaaaaggg gttgtgggaa aacatagtat acctagattt tagagcccta tatccctcga ttataattac ccacaatgtt tctcccgata ctctaaatct tgagggatgc aagaactatg atatcgctcc tcaagtaggc cacaagttct gcaaggacat ccctggtttt ataccaagtc tcttgggaca tttgttagag gaaagacaaa agattaagac aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg FIGURE 17QQ (Cont.)

gaaggagctc gaagaaaagt ttggatttaa agtcctctac attgacactg atggtctcta
tgcaactatc ccaggaggag aaagtgagga aataaagaaa aaggctctag aatttgtaaa
atacataaat tcaaagctcc ctggactgct agagcttgaa tatgaagggt tttataagag
gggattcttc gttacgaaga agaggtatgc agtaatagat gaagaaggaa aagtcattac
tcgtggttta gagatagtta ggagagattg gagtgaaatt gcaaaagaaa ctcaagctag
agttttggag acaatactaa aacacggaga tgttgaagaa gctgtgagaa tagtaaaaga
agtaatacaa aagcttgcca attatgaaat tccaccagag aagctcgcaa tatatgagca
gataacaaga ccattacatg agtataaggc gataggtcct cacgtagctg ttgcaaagaa
actagctgct aaaggagtta aaataaagcc aggaatggta attggataca tagtacttag
aggcgatggt ccaattagca atagggcaat tctagctgag gaatacgatc ccaaaaagca
caagtatgac gcagaatatt acattgagaa ccaggttctt ccagcggtac ttaggatatt
ggagggattt ggatacagaa aggaagacct cagataccaa aagacaagac aagtcggcct
aacttcctgg cttaacatta aaaaatccta gaaaagcgat agatatcaac ttttattctt
tctaaccttt ttctatgaaa gaagaactga gcaggaatta ccagttcttc cgttatttta
tgggtaatta aaaacccatg ctcttgggag aatcttcgaa taaaatccct aacttcaggc
tttgctaagt gaatagaata aacaacatca ctcacttcaa acgccttcgt tagaaatggt
ctatctgcat gcttctctgg ctcggaanng gaggattcat aacaacagta tcaacattct
cagagaattg agaaacatca gaaactttga cttctacaac atttctaact ttgcaactct
tcaagatttt ctaaaagaat tttaacggcc tcctcgtcaa tttcgacgac gtagatcttt FIGURE 17QQ (Cont.)

```
tttgctccaa gcagagccgc tccaatggat aacacccctg ttcccgcacc caagtccgct
acaatttttt ccttgtatct cctaatgtat aagcaagcca aaggagagta gatgctacct
ttccgggagt tttgtattgc tctagccaag gtttgggatt tttgaatcct ttaactctgg
aaagtataat ttcaagctcc ttcttcttca tgacagatga aaaattgttt tgtctctttt
taacttttac agaaataact gtctcaaatt atgacaactc ttgacatttt tacttcatta
ccagggtaat gtttttaagt atgaaatttt tctttcatag aggaggnnnn nngtcctctc
ctcgatttcc ttggttgtgc tccatatgat aagcttccaa agtgggtgtt cagactttta
gacactcaaa taccagacga caatggtgtg ctcactcaag ccccatatgg gttgagaaaa
gtagaagcgg cactactcag atgcttcccc aggaatgagg ttgttgtagc tcntcccnga
aagattgaga tgttcttgg  //   TGA
```

Figure 17RR

Sac7d - PFU DNA POLYMERASE (V93 R OR E) fusion protein

Nucleotide sequence (SEQ ID NO: 69) // Nucleotide sequence (SEQ ID NO: 27)
Nucleotide sequence (SEQ ID NO: 69) //Nucleotide sequence (SEQ ID NO: 28)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

FIGURE 17RR (Cont.)

ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA GCA GAA AGA GAG AAG AAA //

ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980

FIGURE 17RR (Cont.)

```
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //             2328
// TGA
```

Figure 17SS

<u>PFU DNA POLYMERASE (V93 R OR E)</u> - <u>Sac7d fusion protein</u>

Nucleotide sequence (SEQ ID NO: 27) // Nucleotide sequence (SEQ ID NO: 69)
Nucleotide sequence (SEQ ID NO: 28) // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
```

FIGURE 17SS (Cont.)

```
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //             2328

// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //  TGA
```

Figure 17TT

PFU DNA POLYMERASE (G387P/V93R OR E)-Sac7d fusion protein

Nucleotide sequence (SEQ ID NO: 29) // Nucleotide sequence (SEQ ID NO: 69)
Nucleotide sequence (SEQ ID NO: 30) // Nucleotide sequence (SEQ ID NO: 69)

FIGURE 17TT (Cont.)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040

FIGURE 17TT (Cont.)

```
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //             2328

// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //  TGA
```

Figure 17UU

<u>PFU DNA POLYMERASE (G387P/V93R OR E) -Sac7d fusion protein</u>

Nucleotide sequence (SEQ ID NO: 29) // Nucleotide sequence (SEQ ID NO: 69)
Nucleotide sequence (SEQ ID NO: 30) // Nucleotide sequence (SEQ ID NO: 69)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
```

FIGURE 17UU (Cont.)

```
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGTTGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //            2328

// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //  TGA
```

Figure 17VV

SAC7D-PFU DNA POLYMERASE(D141A/E143A/V93R OR E) fusion protein

Nucleotide sequence (SEQ ID NO: 69) // Nucleotide sequence (SEQ ID NO: 31)
Nucleotide sequence (SEQ ID NO: 69) // Nucleotide sequence (SEQ ID NO: 32)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //

//ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
```

FIGURE 17VV (Cont.)

```
CTCAGGGAGA GCTACACAGTTGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //             2328

TGA
```

Figure 17WW

KOD DNA POLYMERASE - Sac7d fusion protein

Nucleotide sequence (SEQ ID NO: 33) // Nucleotide sequence (SEQ ID NO: 69)
Nucleotide sequence (SEQ ID NO: 34) // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
```

FIGURE 17WW (Cont.)

```
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT  2325
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //  TGA
```

Figure 17XX

Sac7d - KOD DNA POLYMERASE fusion protein

Nucleotide sequence (SEQ ID NO: 69) // Nucleotide sequence (SEQ ID NO: 33)
Nucleotide sequence (SEQ ID NO: 69) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
// ATG GTG AAG GTA AAG TTC AAG TAT AAG GGT GAA GAG AAA GAA GTA GAC ACT TCA
 AAG ATA AAG AAG GTT TGG AGA GTA GGC AAA ATG GTG TCC TTT ACC TAT GAC GAC
 AAT GGT AAG ACA GGT AGA GGA GCT GTA AGC GAG AAA GAT GCT CCA AAA GAA TTA
 TTA GAC ATG TTA GCA AGA GCA GAA AGA GAG AAG AAA //

//ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTAGATC CCTGTACCCC TCAATCATCA TCACCCACAA CGTCTCGCCG 1260
```

FIGURE 17XX (Cont.)

```
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT //TAG 2325
```

Figure 17YY

Sac7d-Vent DNA POLYMERASE FUSION PROTEIN

Nucleotide sequence (SEQ ID NO: 69) // Nucleotide sequence (SEQ ID NO: 35)
Nucleotide sequence (SEQ ID NO: 69) // Nucleotide sequence (SEQ ID NO: 36)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
// ATG GTG AAG GTA AAG TTC AAG TAT AAG GGT GAA GAG AAA GAA GTA GAC ACT TCA
 AAG ATA AAG AAG GTT TGG AGA GTA GGC AAA ATG GTG TCC TTT ACC TAT GAC GAC
 AAT GGT AAG ACA GGT AGA GGA GCT GTA AGC GAG AAA GAT GCT CCA AAA GAA TTA
 TTA GAC ATG TTA GCA AGA GCA GAA AGA GAG AAG AAA //

ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
```

FIGURE 17YY (Cont.)

```
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325
```

Figure 17ZZ

Vent DNA POLYMERASE - Sac7d FUSION PROTEIN

Nucleotide sequence (SEQ ID NO: 35) // Nucleotide sequence (SEQ ID NO: 69)
Nucleotide sequence (SEQ ID NO: 36) // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
```

FIGURE 17ZZ (Cont.)

```
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GG 2325 //

// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //  TGA
```

Figure 17AAA

Deep Vent- Sac7d DNA polymerase fusion protein

Nucleotide sequence (SEQ ID NO: 37) // Nucleotide sequence (SEQ ID NO: 69)
Nucleotide sequence (SEQ ID NO: 38) // Nucleotide sequence (SEQ ID NO: 69)

FIGURE 17AAA (Cont.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTTG ACGCTGACTA CATCACCGAG GATGGGAAGC CGATTATAAG GATTTTCAAG    60
AAAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
AAGATAGTGA GAATTATAGA TGCCGAAAAG GTAAGGAAGA AGTTCCTGGG GAGGCCGATT   240
GAGGTATGGA GGCTGTACTT TGAACACCCT CAGGACXXXC CCGCAATAAG GGATAAGATA   300
AGAGAGCATT CCGCAGTTAT TGACATCTTT GAGTACGACA TTCCGTTCGC GAAGAGGTAC   360
CTAATAGACA AAGGCCTAAT TCCAATGGAA GGCGATGAAG AGCTCAAGTT GCTCGCATTT   420
GACATAGAAA CCCTCTATCA CGAAGGGGAG GAGTTCGCGA AGGGGCCCAT TATAATGATA   480
AGCTATGCTG ATGAGGAAGA AGCCAAAGTC ATAACGTGGA AAAAGATCGA TCTCCCGTAC   540
GTCGAGGTAG TTTCCAGCGA GAGGGAGATG ATAAAGCGGT TCCTCAAGGT GATAAGGGAG   600
AAAGATCCCG ATGTTATAAT TACCTACAAC GGCGATTCTT TCGACCTTCC CTATCTAGTT   660
AAGAGGGCCG AAAAGCTCGG GATAAAGCTA CCCCTGGGAA GGGACGGTAG TGAGCCAAAG   720
ATGCAGAGGC TTGGGGATAT GACAGCGGTG GAGATAAAGG GAAGGATACA CTTTGACCTC   780
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
```

FIGURE 17AAA (Cont.)

```
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG //               2328

// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //  TGA
```

Figure 17BBB

Sac7d - Deep Vent DNA polymerase fusion protein

Nucleotide sequence (SEQ ID NO: 69) // Nucleotide sequence (SEQ ID NO: 37)
Nucleotide sequence (SEQ ID NO: 69) // Nucleotide sequence (SEQ ID NO: 38)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //

//ATGATACTTG ACGCTGACTA CATCACCGAG GATGGGAAGC CGATTATAAG GATTTTCAAG   60
AAAGAAAACG GCGAGTTTAA GGTTGAGTAC GACAGAAACT TTAGACCTTA CATTTACGCT  120
CTCCTCAAAG ATGACTCGCA GATTGATGAG GTTAGGAAGA TAACCGCCGA GAGGCATGGG  180
AAGATAGTGA GAATTATAGA TGCCGAAAAG GTAAGGAAGA AGTTCCTGGG GAGGCCGATT  240
GAGGTATGGA GGCTGTACTT TGAACACCCT CAGGACXXXC CCGCAATAAG GGATAAGATA  300
AGAGAGCATT CCGCAGTTAT TGACATCTTT GAGTACGACA TTCCGTTCGC GAAGAGGTAC  360
CTAATAGACA AAGGCCTAAT TCCAATGGAA GGCGATGAAG AGCTCAAGTT GCTCGCATTT  420
GACATAGAAA CCCTCTATCA CGAAGGGGAG GAGTTCGCGA AGGGGCCCAT TATAATGATA  480
AGCTATGCTG ATGAGGAAGA AGCCAAAGTC ATAACGTGGA AAAAGATCGA TCTCCCGTAC  540
GTCGAGGTAG TTTCCAGCGA GAGGGAGATG ATAAAGCGGT TCCTCAAGGT GATAAGGGAG  600
AAAGATCCCG ATGTTATAAT TACCTACAAC GGCGATTCTT TCGACCTTCC CTATCTAGTT  660
AAGAGGGCCG AAAAGCTCGG GATAAAGCTA CCCCTGGGAA GGGACGGTAG TGAGCCAAAG  720
ATGCAGAGGC TTGGGGATAT GACAGCGGTG GAGATAAAGG GAAGGATACA CTTTGACCTC  780
TACCACGTGA TTAGGAGAAC GATAAACCTC CCAACATACA CCCTCGAGGC AGTTTATGAG  840
GCAATCTTCG GAAAGCCAAA GGAGAAAGTT TACGCTCACG AGATAGCTGA GGCCTGGGAG  900
ACTGGAAAGG GACTGGAGAG AGTTGCAAAG TATTCAATGG AGGATGCAAA GGTAACGTAC  960
GAGCTCGGTA GGGAGTTCTT CCCAATGGAG GCCCAGCTTT CAAGGTTAGT CGGCCAGCCC 1020
CTGTGGGATG TTTCTAGGTC TTCAACTGGC AACTTGGTGG AGTGGTACCT CCTCAGGAAG 1080
GCCTACGAGA GGAATGAATT GGCTCCAAAC AAGCCGGATG AGAGGGAGTA CGAGAGAAGG 1140
CTAAGGGAGA GCTACGCTGG GGGATACGTT AAGGAGCCGG AGAAAGGGCT CTGGGAGGGG 1200
TTAGTTTCCC TAGATTTCAG GAGCCTGTAC CCCTCGATAA TAATCACCCA TAACGTCTCA 1260
CCGGATACGC TGAACAGGGA AGGGTGTAGG GAATACGATG TCGCCCCAGA GGTTGGGCAC 1320
```

FIGURE 17BBB (Cont.)

| | | | | | | |
|---|---|---|---|---|---|---|
| AAGTTCTGCA | AGGACTTCCC | GGGGTTTATC | CCCAGCCTGC | TCAAGAGGTT | ATTGGATGAA | 1380 |
| AGGCAAGAAA | TAAAAAGGAA | GATGAAAGCT | TCTAAAGACC | CAATCGAGAA | GAAGATGCTT | 1440 |
| GATTACAGGC | AACGGGCAAT | CAAAATCCTG | GCAAACAGCT | ATTATGGGTA | TTATGGGTAC | 1500 |
| GCAAAAGCCC | GTTGGTACTG | TAAGGAGTGC | GCAGAGAGCG | TTACGGCCTG | GGGGAGGGAA | 1560 |
| TATATAGAGT | TCGTAAGGAA | GGAACTGGAG | GAAAAGTTCG | GGTTCAAAGT | CTTATACATA | 1620 |
| GACACAGATG | GACTCTACGC | CACAATTCCT | GGGGCAAAAC | CCGAGGAGAT | AAAGAAGAAA | 1680 |
| GCCCTAGAGT | TCGTAGATTA | TATAAACGCC | AAGCTCCCAG | GGCTGTTGGA | GCTTGAGTAC | 1740 |
| GAGGGCTTCT | ACGTGAGAGG | GTTCTTCGTG | ACGAAGAAGA | AGTATGCGTT | GATAGATGAG | 1800 |
| GAAGGGAAGA | TAATCACTAG | GGGGCTTGAA | ATAGTCAGGA | GGGACTGGAG | CGAAATAGCC | 1860 |
| AAAGAAACCC | AAGCAAAAGT | CCTAGAGGCT | ATCCTAAAGC | ATGGCAACGT | TGAGGAGGCA | 1920 |
| GTAAAGATAG | TTAAGGAGGT | AACTGAAAAG | CTGAGCAAGT | ACGAAATACC | TCCAGAAAAG | 1980 |
| CTAGTTATTT | ACGAGCAGAT | CACGAGGCCC | CTTCACGAGT | ACAAGGCTAT | AGGTCCGCAC | 2040 |
| GTTGCCGTGG | CAAAAAGGTT | AGCCGCTAGA | GGAGTAAAGG | TGAGGCCTGG | CATGGTGATA | 2100 |
| GGGTACATAG | TGCTGAGGGG | AGACGGGCCA | ATAAGCAAGA | GGGCTATCCT | TGCAGAGGAG | 2160 |
| TTCGATCTCA | GGAAGCATAA | GTATGACGCT | GAGTATTACA | TAGAAAATCA | GGTTTTACCT | 2220 |
| GCCGTTCTTA | GAATATTAGA | GGCCTTTGGG | TACAGGAAAG | AAGACCTCAG | GTGGCAGAAG | 2280 |
| ACTAAACAGA | CAGGTCTTAC | GGCATGGCTT | AACATCAAGA | AGAAG TAA | | 2328 |

Figure 17CCC

<u>JDF-3 - Sac7d fusion protein</u>

Nucleotide sequence (SEQ ID NO: 39) // Nucleotide sequence (SEQ ID NO: 69)
Nucleotide sequence (SEQ ID NO: 40) // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTCGG
CAGGTCTGTGGAGGTCTGGGTCCTCTACTTCACGCACCCGCAGGAC<u>XXX</u>CCGGCAATCCGCGACAAAATAAGGAAGCACCCCGCGGTCATCGACATCTACGAGTACGACATACCC
TTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGGAA
CCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATTAA
GCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCTTT
ACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCATAA
ACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAGAG

FIGURE 17CCC (Cont.)

```
GGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTTCC
CGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGGCT
ACgcCGGTGGCTACGTCAAGGAGCCGGAGCGGGGACTGTGGGACAATATCGTGTATCTAGACTTTCGTAGTCTCTACCCTTCAATCATAATCACCCACAACGTCTCGCCAGATAC
GCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGG
CAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCT
ATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTCCT
CTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTCTC
GAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCGCG
ACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGCAA
GTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAGGT
GTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGATG
CGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGCGC
GTGGCTGAAGCCGAAGGGGAAGAAGAAG//
```

```
//ATG GTG AAG GTA AAG TTC AAG TAT AAG GGT GAA GAG AAA GAA GTA GAC ACT TCA
  AAG ATA AAG AAG GTT TGG AGA GTA GGC AAA ATG GTG TCC TTT ACC TAT GAC GAC
  AAT GGT AAG ACA GGT AGA GGA GCT GTA AGC GAG AAA GAT GCT CCA AAA GAA TTA
  TTA GAC ATG TTA GCA AGA GCA GAA AGA GAG AAG AAA // TAG
```

Figure 17DDD

Sac7d - JDF-3 fusion protein

Nucleotide sequence (SEQ ID NO: 69) // Nucleotide sequence (SEQ ID NO: 39)
Nucleotide sequence (SEQ ID NO: 69) // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//ATG GTG AAG GTA AAG TTC AAG TAT AAG GGT GAA GAG AAA GAA GTA GAC ACT TCA
  AAG ATA AAG AAG GTT TGG AGA GTA GGC AAA ATG GTG TCC TTT ACC TAT GAC GAC
  AAT GGT AAG ACA GGT AGA GGA GCT GTA AGC GAG AAA GAT GCT CCA AAA GAA TTA
  TTA GAC ATG TTA GCA AGA GCA GAA AGA GAG AAG AAA //
```

FIGURE 17DDD (Cont.)

//ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTT
CTACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTC
GGCAGGTCTGTGGAGGTCTGGGTCCTCTACTTCACGCACCCGCAGGACXXXCCGGCAATCCGCGACAAAATAAGGAAGCACCCCGCGGTCATCGACATCTACGAGTACGACATAC
CCTTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGG
AACCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATT
AAGCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCT
TTACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCAT
AAACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAG
AGGGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTT
CCCGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGG
CTACgcCGGTGGCTACGTCAAGGAGCCGGAGCGGGGACTGTGGGACAATATCGTGTATCTAGACTTTCGTAGTCTCTACCCTTCAATCATAATCACCCACAACGTCTCGCCAGAT
ACGCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAA
GGCAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGG
CTATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTC
CTCTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTC
TCGAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCG
CGACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGC
AAGTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAG
GTGTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGA
TGCGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGC
GCGTGGCTGAAGCCGAAGGGGAAGAAGAAGTGA

Figure 17EEE

Synthetic Sso7d gene:

Nucleotide sequence (SEQ ID NO: 71)
Amino acid sequence (SEQ ID NO: 72)

```
 A   T   V   K   F   K   Y   K   G   E   E   K   E   V   D   I   S   K
GCA ACC GTA AAG TTC AAG TAC AAA GGC GAA GAA AAA GAG GTA GAC ATC TCC AAG

 I   K   K   V   W   R   V   G   K   M   I   S   F   T   Y   D   E   G
ATC AAG AAA GTA TGG CGT GTG GGC AAG ATG ATC TCC TTC ACC TAC GAC GAG GGC

 G   G   K   T   G   R   G   A   V   S   E   K   D   A   P   K   E   L
GGT GGC AAG ACC GGC CGT GGT GCG GTA AGC GAA AAG GAC GCG CCG AAG GAG CTG

 L   Q   M   L   E   K   Q   K   K
CTG CAG ATG CTG GAG AAG CAG AAA AAG
```

Figure 17FFF

Sso7d-Taq DNA polymerase fusion protein

Nucleotide sequence (SEQ ID NO: 71) // Nucleotide sequence (SEQ ID NO: 65)
Amino acid sequence (SEQ ID NO: 72) // Amino acid sequence (SEQ ID NO: 66)

```
 // A   T   V   K   F   K   Y   K   G   E   E   K   E   V   D   I   S   K
// GCA ACC GTA AAG TTC AAG TAC AAA GGC GAA GAA AAA GAG GTA GAC ATC TCC AAG

 I   K   K   V   W   R   V   G   K   M   I   S   F   T   Y   D   E   G
ATC AAG AAA GTA TGG CGT GTG GGC AAG ATG ATC TCC TTC ACC TAC GAC GAG GGC

 G   G   K   T   G   R   G   A   V   S   E   K   D   A   P   K   E   L
GGT GGC AAG ACC GGC CGT GGT GCG GTA AGC GAA AAG GAC GCG CCG AAG GAG CTG

 L   Q   M   L   E   K   Q   K   K    //   G   G   G
CTG CAG ATG CTG GAG AAG CAG AAA AAG   //   GGC GGC GGT
```

FIGURE 17FFF (Cont.)

```
V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG

A   H   M   D   D   L   K   L   S   W   D   L   A   K   V   R   T   D
```

```
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC

 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC

 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC
```

FIGURE 17FFF (Cont.)

```
 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG
```

FIGURE 17FFF (Cont.)

```
K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

H   H   *
CAT CAT TAA
```

Figure 17GGG

Pfu DNA Polymerase (WT) -Sso7d fusion protein

Nucleotide sequence (SEQ ID NO: 61) // Nucleotide sequence (SEQ ID NO: 71)

//

```
ccctggtcct gggtccacat atatgttctt actcgccttt atgaagaatc ccccagtcgc

tctaacctgg gttatagtga caaatcttcc tccaccaccg cccaagaagg ttatttctat

caactctaca cctcccctat tttctctctt atgagatttt taagtatagt tatagagaag

gttttatact ccaaactgag ttagtagata tgtggggagc ataatgattt tagatgtgga
```

FIGURE 17GGG (Cont.)

ttacataact gaagaaggaa aacctgttat taggctattc aaaaaagaga acggaaaatt taagatagag catgatagaa cttttagacc atacatttac gctcttctca gggatgattc aaagattgaa gaagttaaga aaataacggg ggaaaggcat ggaaagattg tgagaattgt tgatgtagag aaggttgaga aaaagtttct cggcaagcct attaccgtgt ggaaacttta tttggaacat ccccaagatg ttcccactat tagagaaaaa gttagagaac atccagcagt tgtggacatc ttcgaatacg atattccatt tgcaaagaga tacctcatcg acaaaggcct aataccaatg gagggggaag aagagctaaa gattcttgcc ttcgatatag aaaccctcta tcacgaagga gaagagtttg gaaaaggccc aattataatg attagttatg cagatgaaaa tgaagcaaag gtgattactt ggaaaaacat agatcttcca tacgttgagg ttgtatcaag cgagagagag atgataaaga gatttctcag gattatcagg gagaaggatc ctgacattat agttacttat aatggagact cattcgactt cccatattta gcgaaaaggg cagaaaaact tgggattaaa ttaaccattg gaagagatgg aagcgagccc aagatgcaga gaataggcga tatgacggct gtagaagtca agggaagaat acatttcgac ttgtatcatg taataacaag gacaataaat ctcccaacat acacactaga ggctgtatat gaagcaattt ttggaaagcc aaaggagaag gtatacgccg acgagatagc aaaagcctgg gaaagtggag agaaccttga gagagttgcc aaatactcga tggaagatgc aaaggcaact tatgaactcg ggaaagaatt ccttccaatg gaaattcagc tttcaagatt agttggacaa cctttatggg atgtttcaag gtcaagcaca gggaaccttg tagagtggtt cttacttagg aaagcctacg aaagaaacga agtagctcca aacaagccaa gtgaagagga gtatcaaaga aggctcaggg agagctacac aggtggattc gttaaagagc cagaaaaggg gttgtgggaa aacatagtat acctagattt tagagcccta tatccctcga ttataattac ccacaatgtt tctcccgata ctctaaatct FIGURE 17GGG (Cont.)

tgagggatgc aagaactatg atatcgctcc tcaagtaggc cacaagttct gcaaggacat ccctggtttt ataccaagtc tcttgggaca tttgttagag gaaagacaaa agattaagac aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg gaaggagctc gaagaaaagt ttggatttaa agtcctctac attgacactg atggtctcta tgcaactatc ccaggaggag aaagtgagga aataaagaaa aaggctctag aatttgtaaa atacataaat tcaaagctcc ctggactgct agagcttgaa tatgaagggt tttataagag gggattcttc gttacgaaga agaggtatgc agtaatagat gaagaaggaa aagtcattac tcgtggttta gagatagtta ggagagattg gagtgaaatt gcaaaagaaa ctcaagctag agttttggag acaatactaa aacacggaga tgttgaagaa gctgtgagaa tagtaaaaga agtaatacaa aagcttgcca attatgaaat tccaccagag aagctcgcaa tatatgagca gataacaaga ccattacatg agtataaggc gataggtcct cacgtagctg ttgcaaagaa actagctgct aaaggagtta aaataaagcc aggaatggta attggataca tagtacttag aggcgatggt ccaattagca atagggcaat tctagctgag gaatacgatc ccaaaaagca caagtatgac gcagaatatt acattgagaa ccaggttctt ccagcggtac ttaggatatt ggagggattt ggatacagaa aggaagacct cagataccaa aagacaagac aagtcggcct aacttcctgg cttaacatta aaaaatccta gaaaagcgat agatatcaac ttttattctt tctaaccttt ttctatgaaa gaagaactga gcaggaatta ccagttcttc cgttatttta tgggtaatta aaaacccatg ctcttgggag aatcttcgaa taaaatccct aacttcaggc FIGURE 17GGG (Cont.)

tttgctaagt gaatagaata aacaacatca ctcacttcaa acgccttcgt tagaaatggt ctatctgcat gcttctctgg ctcggaanng gaggattcat aacaacagta tcaacattct cagagaattg agaaacatca gaaactttga cttctacaac atttctaact ttgcaactct tcaagatttt ctaaaagaat tttaacggcc tcctcgtcaa tttcgacgac gtagatcttt tttgctccaa gcagagccgc tccaatggat aacacccctg ttcccgcacc caagtccgct acaatttttt ccttgtatct cctaatgtat aagcaagcca aaggagagta gatgctacct ttccgggagt tttgtattgc tctagccaag gtttgggatt tttgaatcct ttaactctgg aaagtataat ttcaagctcc ttcttcttca tgacagatga aaaattgttt tgtctctttt taacttttac agaaataact gtctcaaatt atgacaactc ttgacatttt tacttcatta ccagggtaat gtttttaagt atgaaatttt tctttcatag aggaggnnnn nngtcctctc ctcgatttcc ttggttgtgc tccatatgat aagcttccaa agtgggtgtt cagactttta gacactcaaa taccagacga caatggtgtg ctcactcaag ccccatatgg gttgagaaaa gtagaagcgg cactactcag atgcttcccc aggaatgagg ttgttgtagc tcntcccnga aagattgaga tgttcttgg //

// GCA ACC GTA AAG TTC AAG TAC AAA GGC GAA GAA AAA GAG GTA GAC ATC TCC AAG

ATC AAG AAA GTA TGG CGT GTG GGC AAG ATG ATC TCC TTC ACC TAC GAC GAG GGC

GGT GGC AAG ACC GGC CGT GGT GCG GTA AGC GAA AAG GAC GCG CCG AAG GAG CTG

CTG CAG ATG CTG GAG AAG CAG AAA AAG // TGA

Figure 17HHH

PFU DNA POLYMERASE (V93 R OR E)-Sso7d fusion protein

Nucleotide sequence (SEQ ID NO: 27) // Nucleotide sequence (SEQ ID NO: 71)
Nucleotide sequence (SEQ ID NO: 28) // Nucleotide sequence (SEQ ID NO: 71)

```
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
```

FIGURE 17HHH (Cont.)

```
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC 2328
// GCA ACC GTA AAG TTC AAG TAC AAA GGC GAA GAA AAA GAG GTA GAC ATC TCC AAG
   ATC AAG AAA GTA TGG CGT GTG GGC AAG ATG ATC TCC TTC ACC TAC GAC GAG GGC
   GGT GGC AAG ACC GGC CGT GGT GCG GTA AGC GAA AAG GAC GCG CCG AAG GAG CTG
   CTG CAG ATG CTG GAG AAG CAG AAA AAG   //  TGA
```

Figure 17III

PFU DNA POLYMERASE (G387P/V93R OR E)-Sso7d fusion protein

Nucleotide sequence (SEQ ID NO: 29) // Nucleotide sequence (SEQ ID NO: 71)
Nucleotide sequence (SEQ ID NO: 30) // Nucleotide sequence (SEQ ID NO: 71)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
```

FIGURE 17III (Cont.)

```
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //            2328
```

```
// GCA ACC GTA AAG TTC AAG TAC AAA GGC GAA GAA AAA GAG GTA GAC ATC TCC AAG
   ATC AAG AAA GTA TGG CGT GTG GGC AAG ATG ATC TCC TTC ACC TAC GAC GAG GGC
   GGT GGC AAG ACC GGC CGT GGT GCG GTA AGC GAA AAG GAC GCG CCG AAG GAG CTG
   CTG CAG ATG CTG GAG AAG CAG AAA AAG   //  TGA
```

Figure 17JJJ

PFU DNA POLYMERASE(D141A/E143A/V93R OR E)-Sso7d fusion protein

Nucleotide sequence (SEQ ID NO: 31) // Nucleotide sequence (SEQ ID NO: 71)

FIGURE 17JJJ (Cont.)

Nucleotide sequence (SEQ ID NO: 32) // Nucleotide sequence (SEQ ID NO: 71)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACA GTTGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
```

FIGURE 17JJJ (Cont.)

```
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //             2328

// GCA ACC GTA AAG TTC AAG TAC AAA GGC GAA GAA AAA GAG GTA GAC ATC TCC AAG
   ATC AAG AAA GTA TGG CGT GTG GGC AAG ATG ATC TCC TTC ACC TAC GAC GAG GGC
   GGT GGC AAG ACC GGC CGT GGT GCG GTA AGC GAA AAG GAC GCG CCG AAG GAG CTG
   CTG CAG ATG CTG GAG AAG CAG AAA AAG   //   TGA
```

Figure 17KKK

KOD DNA POLYMERASE - Sso7d fusion protein

Nucleotide sequence (SEQ ID NO: 33) // Nucleotide sequence (SEQ ID NO: 71)
Nucleotide sequence (SEQ ID NO: 34) // Nucleotide sequence (SEQ ID NO: 71)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
```

FIGURE 17KKK (Cont.)

```
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT  2325

// GCA ACC GTA AAG TTC AAG TAC AAA GGC GAA GAA AAA GAG GTA GAC ATC TCC AAG
   ATC AAG AAA GTA TGG CGT GTG GGC AAG ATG ATC TCC TTC ACC TAC GAC GAG GGC
   GGT GGC AAG ACC GGC CGT GGT GCG GTA AGC GAA AAG GAC GCG CCG AAG GAG CTG
   CTG CAG ATG CTG GAG AAG CAG AAA AAG //  TGA
```

Figure 17LLL

Sso7d - KOD DNA POLYMERASE fusion protein

Nucleotide sequence (SEQ ID NO: 71) // Nucleotide sequence (SEQ ID NO: 33)
Nucleotide sequence (SEQ ID NO: 71) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//GCA ACC GTA AAG TTC AAG TAC AAA GGC GAA GAA AAA GAG GTA GAC ATC TCC AAG
  ATC AAG AAA GTA TGG CGT GTG GGC AAG ATG ATC TCC TTC ACC TAC GAC GAG GGC
  GGT GGC AAG ACC GGC CGT GGT GCG GTA AGC GAA AAG GAC GCG CCG AAG GAG CTG
  CTG CAG ATG CTG GAG AAG CAG AAA AAG   //
```

FIGURE 17LLL (Cont.)

```
//ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT //TAG 2325
```

Figure 17MMM

Sso7d-Vent DNA POLYMERASE FUSION PROTEIN

Nucleotide sequence (SEQ ID NO: 71) // Nucleotide sequence (SEQ ID NO: 35)
Nucleotide sequence (SEQ ID NO: 71) // Nucleotide sequence (SEQ ID NO: 36)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//GCA ACC GTA AAG TTC AAG TAC AAA GGC GAA GAA AAA GAG GTA GAC ATC TCC AAG
  ATC AAG AAA GTA TGG CGT GTG GGC AAG ATG ATC TCC TTC ACC TAC GAC GAG GGC
  GGT GGC AAG ACC GGC CGT GGT GCG GTA AGC GAA AAG GAC GCG CCG AAG GAG CTG
  CTG CAG ATG CTG GAG AAG CAG AAA AAG  //

ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
```

FIGURE 17MMM (Cont.)

GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGCTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325

Figure 17NNN

Vent DNA POLYMERASE - Sso7d FUSION PROTEIN

Nucleotide sequence (SEQ ID NO: 35) // Nucleotide sequence (SEQ ID NO: 71)
Nucleotide sequence (SEQ ID NO: 36) // Nucleotide sequence (SEQ ID NO: 71)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720

FIGURE 17NNN (Cont.)

```
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GG 2325 //

// GCA ACC GTA AAG TTC AAG TAC AAA GGC GAA GAA AAA GAG GTA GAC ATC TCC AAG
   ATC AAG AAA GTA TGG CGT GTG GGC AAG ATG ATC TCC TTC ACC TAC GAC GAG GGC
   GGT GGC AAG ACC GGC CGT GGT GCG GTA AGC GAA AAG GAC GCG CCG AAG GAG CTG
   CTG CAG ATG CTG GAG AAG CAG AAA AAG //  TGA
```

Figure 17OOO

Deep Vent- Ssod7 DNA polymerase fusion protein

Nucleotide sequence (SEQ ID NO: 37) // Nucleotide sequence (SEQ ID NO: 71)
Nucleotide sequence (SEQ ID NO: 38) // Nucleotide sequence (SEQ ID NO: 71)

FIGURE 17000 (Cont.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTTG ACGCTGACTA CATCACCGAG GATGGGAAGC CGATTATAAG GATTTTCAAG   60
AAAGAAAACG GCGAGTTTAA GGTTGAGTAC GACAGAAACT TTAGACCTTA CATTTACGCT  120
CTCCTCAAAG ATGACTCGCA GATTGATGAG GTTAGGAAGA TAACCGCCGA GAGGCATGGG  180
AAGATAGTGA GAATTATAGA TGCCGAAAAG GTAAGGAAGA AGTTCCTGGG GAGGCCGATT  240
GAGGTATGGA GGCTGTACTT TGAACACCCT CAGGACXXXC CCGCAATAAG GGATAAGATA  300
AGAGAGCATT CCGCAGTTAT TGACATCTTT GAGTACGACA TTCCGTTCGC GAAGAGGTAC  360
CTAATAGACA AAGGCCTAAT TCCAATGGAA GGCGATGAAG AGCTCAAGTT GCTCGCATTT  420
GACATAGAAA CCCTCTATCA CGAAGGGGAG GAGTTCGCGA AGGGGCCCAT TATAATGATA  480
AGCTATGCTG ATGAGGAAGA AGCCAAAGTC ATAACGTGGA AAAAGATCGA TCTCCCGTAC  540
GTCGAGGTAG TTTCCAGCGA GAGGGAGATG ATAAAGCGGT TCCTCAAGGT GATAAGGGAG  600
AAAGATCCCG ATGTTATAAT TACCTACAAC GGCGATTCTT TCGACCTTCC CTATCTAGTT  660
AAGAGGGCCG AAAAGCTCGG GATAAAGCTA CCCCTGGGAA GGGACGGTAG TGAGCCAAAG  720
ATGCAGAGGC TTGGGGATAT GACAGCGGTG GAGATAAAGG GAAGGATACA CTTTGACCTC  780
TACCACGTGA TTAGGAGAAC GATAAACCTC CCAACATACA CCCTCGAGGC AGTTTATGAG  840
GCAATCTTCG GAAAGCCAAA GGAGAAAGTT TACGCTCACG AGATAGCTGA GGCCTGGGAG  900
ACTGGAAAGG GACTGGAGAG AGTTGCAAAG TATTCAATGG AGGATGCAAA GGTAACGTAC  960
GAGCTCGGTA GGGAGTTCTT CCCAATGGAG GCCCAGCTTT CAAGGTTAGT CGGCCAGCCC 1020
CTGTGGGATG TTTCTAGGTC TTCAACTGGC AACTTGGTGG AGTGGTACCT CCTCAGGAAG 1080
GCCTACGAGA GGAATGAATT GGCTCCAAAC AAGCCGGATG AGAGGGAGTA CGAGAGAAGG 1140
CTAAGGGAGA GCTACGCTGG GGGATACGTT AAGGAGCCGG AGAAAGGGCT CTGGGAGGGG 1200
TTAGTTTCCC TAGATTTCAG GAGCCTGTAC CCCTCGATAA TAATCACCCA TAACGTCTCA 1260
CCGGATACGC TGAACAGGGA AGGGTGTAGG GAATACGATG TCGCCCCAGA GGTTGGGCAC 1320
AAGTTCTGCA AGGACTTCCC GGGGTTTATC CCCAGCCTGC TCAAGAGGTT ATTGGATGAA 1380
AGGCAAGAAA TAAAAAGGAA GATGAAAGCT TCTAAAGACC CAATCGAGAA GAAGATGCTT 1440
GATTACAGGC AACGGGCAAT CAAAATCCTG GCAAACAGCT ATTATGGGTA TTATGGGTAC 1500
GCAAAAGCCC GTTGGTACTG TAAGGAGTGC GCAGAGAGCG TTACGGCCTG GGGGAGGGAA 1560
TATATAGAGT TCGTAAGGAA GGAACTGGAG GAAAAGTTCG GGTTCAAAGT CTTATACATA 1620
GACACAGATG GACTCTACGC CACAATTCCT GGGGCAAAAC CCGAGGAGAT AAAGAAGAAA 1680
GCCCTAGAGT TCGTAGATTA TATAAACGCC AAGCTCCCAG GGCTGTTGGA GCTTGAGTAC 1740
GAGGGCTTCT ACGTGAGAGG GTTCTTCGTG ACGAAGAAGA AGTATGCGTT GATAGATCAG 1800
GAAGGGAAGA TAATCACTAG GGGGCTTGAA ATAGTCAGGA GGGACTGGAG CGAAATAGCC 1860
AAAGAAACCC AAGCAAAAGT CCTAGAGGCT ATCCTAAAGC ATGGCAACGT TGAGGAGGCA 1920
GTAAAGATAG TTAAGGAGGT AACTGAAAAG CTGAGCAAGT ACGAAATACC TCCAGAAAAG 1980
CTAGTTATTT ACGAGCAGAT CACGAGGCCC CTTCACGAGT ACAAGGCTAT AGGTCCGCAC 2040
GTTGCCGTGG CAAAAAGGTT AGCCGCTAGA GGAGTAAAGG TGAGGCCTGG CATGGTGATA 2100
GGGTACATAG TGCTGAGGGG AGACGGGCCA ATAAGCAAGA GGGCTATCCT TGCAGAGGAG 2160
TTCGATCTCA GGAAGCATAA GTATGACGCT GAGTATTACA TAGAAAATCA GGTTTTACCT 2220
GCCGTTCTTA GAATATTAGA GGCCTTTGGG TACAGGAAAG AAGACCTCAG GTGGCAGAAG 2280
ACTAAACAGA CAGGTCTTAC GGCATGGCTT AACATCAAGA AGAAG                2328
```

FIGURE 17OOO (Cont.)

```
// GCA ACC GTA AAG TTC AAG TAC AAA GGC GAA GAA AAA GAG GTA GAC ATC TCC AAG
   ATC AAG AAA GTA TGG CGT GTG GGC AAG ATG ATC TCC TTC ACC TAC GAC GAG GGC
   GGT GGC AAG ACC GGC CGT GGT GCG GTA AGC GAA AAG GAC GCG CCG AAG GAG CTG
   CTG CAG ATG CTG GAG AAG CAG AAA AAG //  TGA
```

Figure 17PPP

Ssod7 - Deep Vent DNA polymerase fusion protein

Nucleotide sequence (SEQ ID NO: 71) // Nucleotide sequence (SEQ ID NO: 37)
Nucleotide sequence (SEQ ID NO: 71) // Nucleotide sequence (SEQ ID NO: 38)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
 //GCA ACC GTA AAG TTC AAG TAC AAA GGC GAA GAA AAA GAG GTA GAC ATC TCC AAG
   ATC AAG AAA GTA TGG CGT GTG GGC AAG ATG ATC TCC TTC ACC TAC GAC GAG GGC
   GGT GGC AAG ACC GGC CGT GGT GCG GTA AGC GAA AAG GAC GCG CCG AAG GAG CTG
   CTG CAG ATG CTG GAG AAG CAG AAA AAG  //

ATGATACTTG ACGCTGACTA CATCACCGAG GATGGGAAGC CGATTATAAG GATTTTCAAG   60
AAAGAAAACG GCGAGTTTAA GGTTGAGTAC GACAGAAACT TTAGACCTTA CATTTACGCT  120
CTCCTCAAAG ATGACTCGCA GATTGATGAG GTTAGGAAGA TAACCGCCGA GAGGCATGGG  180
AAGATAGTGA GAATTATAGA TGCCGAAAAG GTAAGGAAGA AGTTCCTGGG GAGGCCGATT  240
GAGGTATGGA GGCTGTACTT TGAACACCCT CAGGACXXXC CCGCAATAAG GGATAAGATA  300
AGAGAGCATT CCGCAGTTAT TGACATCTTT GAGTACGACA TTCCGTTCGC GAAGAGGTAC  360
CTAATAGACA AAGGCCTAAT TCCAATGGAA GGCGATGAAG AGCTCAAGTT GCTCGCATTT  420
GACATAGAAA CCCTCTATCA CGAAGGGGAG GAGTTCGCGA AGGGGCCCAT TATAATGATA  480
AGCTATGCTG ATGAGGAAGA AGCCAAAGTC ATAACGTGGA AAAAGATCGA TCTCCCGTAC  540
GTCGAGGTAG TTTCCAGCGA GAGGGAGATG ATAAAGCGGT TCCTCAAGGT GATAAGGGAG  600
AAAGATCCCG ATGTTATAAT TACCTACAAC GGCGATTCTT TCGACCTTCC CTATCTAGTT  660
AAGAGGGCCG AAAAGCTCGG GATAAAGCTA CCCCTGGGAA GGGACGGTAG TGAGCCAAAG  720
ATGCAGAGGC TTGGGGATAT GACAGCGGTG GAGATAAAGG GAAGGATACA CTTTGACCTC  780
```

FIGURE 17PPP (Cont.)

```
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG TAA              2328
```

Figure 17QQQ

JDF-3 - Sso7d fusion protein

Nucleotide sequence (SEQ ID NO: 39) // Nucleotide sequence (SEQ ID NO: 71)
Nucleotide sequence (SEQ ID NO: 40) // Nucleotide sequence (SEQ ID NO: 71)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTCGG
CAGGTCTGTGGAGGTCTGGGTCCTCTACTTCACGCACCCGCAGGACXXXCCGGCAATCCGCGACAAAATAAGGAAGCACCCCGCGGTCATCGACATCTACGAGTACGACATACCC
```

FIGURE 17QQQ (Cont.)

TTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGGAA
CCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATTAA
GCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCTTT
ACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCATAA
ACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAGAG
GGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTTCC
CGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGGCT
ACgcCGGTGGCTACGTCAAGGAGCCGGAGCGGGGACTGTGGGACAATATCGTGTATCTAGACTTTCGTAGTCTCTACCCTTCAATCATAATCACCCACAACGTCTCGCCAGATAC
GCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGG
CAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCT
ATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTCCT
CTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTCTC
GAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCGCG
ACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGCAA
GTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAGGT
GTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGATG
CGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGCGC
GTGGCTGAAGCCGAAGGGGAAGAAGAAG//

//GCA ACC GTA AAG TTC AAG TAC AAA GGC GAA GAA AAA GAG GTA GAC ATC TCC AAG
ATC AAG AAA GTA TGG CGT GTG GGC AAG ATG ATC TCC TTC ACC TAC GAC GAG GGC
GGT GGC AAG ACC GGC CGT GGT GCG GTA AGC GAA AAG GAC GCG CCG AAG GAG CTG
CTG CAG ATG CTG GAG AAG CAG AAA AAG // TAG

Figure 17RRR

Sso7d - JDF-3 fusion protein

Nucleotide sequence (SEQ ID NO: 71) // Nucleotide sequence (SEQ ID NO: 39)
Nucleotide sequence (SEQ ID NO: 71) // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

//GCA ACC GTA AAG TTC AAG TAC AAA GGC GAA GAA AAA GAG GTA GAC ATC TCC AAG
ATC AAG AAA GTA TGG CGT GTG GGC AAG ATG ATC TCC TTC ACC TAC GAC GAG GGC
GGT GGC AAG ACC GGC CGT GGT GCG GTA AGC GAA AAG GAC GCG CCG AAG GAG CTG
CTG CAG ATG CTG GAG AAG CAG AAA AAG //

FIGURE 17RRR (Cont.)

ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTCGG
CAGGTCTGTGGAGGTCTGGGTCCTCTACTTCACGCACCCGCAGGACXXXCCGGCAATCCGCGACAAAATAAGGAAGCACCCCGCGGTCATCGACATCTACGAGTACGACATACCC
TTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGGAA
CCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATTAA
GCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCTTT
ACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCATAA
ACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAGAG
GGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTTCC
CGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGGGCT
ACgcCGGTGGCTACGTCAAGGAGCCGGAGCGGGGACTGTGGGACAATATCGTGTATCTAGACTTTCGTAGTCTCTACCCTTCAATCATAATCACCCACAACGTCTCGCCAGATAC
GCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGG
CAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCT
ATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTCCT
CTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTCTC
GAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCGCG
ACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGCAA
GTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAGGT
GTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGATG
CGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGCGC
GTGGCTGAAGCCGAAGGGGAAGAAGAAGTGA

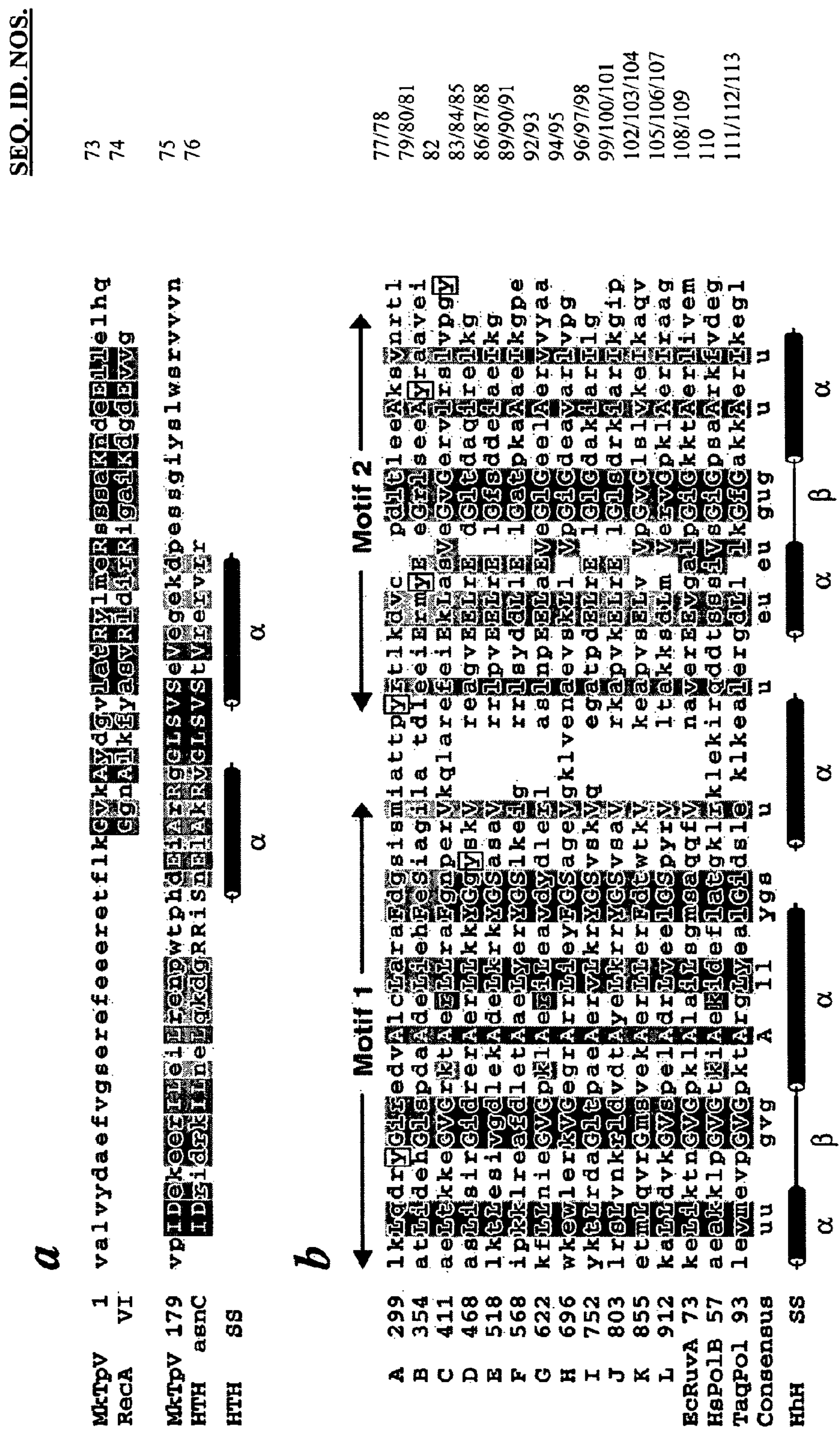
FIGURE 18 (cited from Belova et al. (2001) Proc. Natl. Acad. Sci 98: 6015-6020)

FIGURE 19

SEQ ID NO: 120 Synthetic Sso7d gene

GCAACCGTAAAGTTCAAGTACAAAGGCGAAGAAAAAGAGGTAGACATCTCCAA
GATCAAGAAAGTATGGCGTGTGGGCAAGATGATCTCCTTCACCTACGACGAGGG
CGGTGGCAAGACCGGCCGTGGTGCGGTAAGCGAAAAGGACGCGCCGAAGGAGC
TGCTGCAGATGCTGGAGAAG CAGAAAAAG

SEQ ID NO: 121 The amino acid sequence of Sso7d.

ATVKFKYKGEEKEVDISKIKKVWRVGKMISFTYDEGGGKTGRGAVSEKDAPKELLQ
MLEKQKK

SEQ ID NO: 122 The DNA sequence encoding the Sso7d-ΔTaq fusion protein

ATGATTACGAATTCGAGCGCAACCGTAAAGTTCAAGTACAAAGGCGAAGAAAAA
GAGGTAGACATCTCCAAGATCAAGAAAGTATGGCGTGTGGGCAAGATGATCTCC
TTCACCTACGACGAGGGCGGTGGCAAGACCGGCCGTGGTGCGGTAAGCGAAAAG
GACGCGCCGAAGGAGCTGCTGCAGATGCTGGAGAAGCAGAAAAAGGGCGGCGG
TGTCACTAGTCCCAAGGCcCTGGAGGAGGCCCCCTGGCCCCCGCCGGAAGGGGCC
TTCGTGGGCTTTGTGCTTTCCCGCAAGGAGCCCATGTGGGCCGATCTTCTGGCCCT
GGCCGCCGCCAGGGGGGGCCGGGTCCACCGGGCCCCCGAGCCTTATAAAGCCCT
CAGGGACCTGAAGGAGGCGCGGGGGCTTCTCGCCAAAGACCTGAGCGTTCTGGC
CCTGAGGGAAGGCCTTGGCCTCCCGCCCGGCGACGACCCCATGCTCCTCGCCTAC
CTCCTGGACCCTTCCAACACCACCCCCGAGGGGGTGGCCCGGCGCTACGGCGGG
GAGTGGACGGAGGAGGCGGGGGAGCGGGCCGCCCTTTCCGAGAGGCTCTTCGCC
AACCTGTGGGGGAGGCTTGAGGGGGAGGAGAGGCTCCTTTGGCTTTACCGGGAG
GTGGAGAGGCCCCTTTCCGCTGTCCTGGCCCACATGGAGGCCACGGGGGTGCGC
CTGGACGTGGCCTATCTCAGGGCCTTGTCCCTGGAGGTGGCCGAGGAGATCGCCC
GCCTCGAGGCCGAGGTCTTCCGCCTGGCCGGCCACCCCTTCAACCTCAACTCCCG
GGACCAGCTGGAAAGGGTCCTCTTTGACGAGCTAGGGCTTCCCGCCATCGGCAA
GACGGAGAAGACCGGCAAGCGCTCCACCAGCGCCGCCGTCCTGGAGGCCCTCCG
CGAGGCCCACCCCATCGTGGAGAAGATCCTGCAGTACCGGGAGCTCACCAAGCT
GAAGAGCACCTACATTGACCCCTTGCCGGACCTCATCCACCCCAGGACGGGCCG
CCTCCACACCCGCTTCAACCAGACGGCCACGGCCACGGGCAGGCTAAGTAGCTC
CGATCCCAACCTCCAGAACATCCCCGTCCGCACCCCGCTTGGGCAGAGGATCCGC
CGGGCCTTCATCGCCGAGGAGGGGTGGCTATTGGTGGCCCTGGACTATAGCCAG
ATAGAGCTCAGGGTGCTGGCCCACCTCTCCGGCGACGAGAACCTGATCCGGGTCT
TCCAGGAGGGGCGGGACATCCACACGGAGACCGCCAGCTGGATGTTCGGCGTCC
CCCGGGAGGCCGTGGACCCCCTGATGCGCCGGGCGGCCAAGACCATCAACTTCG
GGGTCCTCTACGGCATGTCGGCCCACCGCCTCTCCCAGGAGCTAGCCATCCCTTA
CGAGGAGGCCCAGGCCTTCATTGAGCGCTACTTTCAGAGCTTCCCCAAGGTGCGG
GCCTGGATTGAGAAGACCCTGGAGGAGGGCAGGAGGCGGGGGTACGTGGAGAC
CCTCTTCGGCCGCCGCCGCTACGTGCCAGACCTAGAGGCCCGGGTGAAGAGCGT
GCGGGAGGCGGCCGAGCGCATGGCCTTCAACATGCCCGTCCAGGGCACCGCCGC
CGACCTCATGAAGCTGGCTATGGTGAAGCTCTTCCCCAGGCTGGAGGAAATGGG
GGCCAGGATGCTCCTTCAGGTCCACGACGAGCTGGTCCTCGAGGCCCCAAAAGA
GAGGGCGGAGGCCGTGGCCCGGCTGGCCAAGGAGGTCATGGAGGGGGTGTATCC
CCTGGCCGTGCCCCTGGAGGTGGAGGTGGGGATAGGGGAGGACTGGCTCTCCGC
CAAGGAGGGCATTGATGGCCGCGGCGGAGGCGGGCATCATCATCATCATCATTA A

SEQ ID NO: 123 The amino acid sequence of Sso7d-ΔTaq fusion protein

MITNSSATVKFKYKGEEKEVDISKIKKVWRVGKMISFTYDEGGGKTGRGAVSEKDA
PKELLQMLEKQKKGGGVTSPKALEEAPWPPPEGAFVGFVLSRKEPMWADLLALAA

FIGURE 19 (Cont.)

ARGGRVHRAPEPYKALRDLKEARGLLAKDLSVLALREGLGLPPGDDPMLLAYLLDP
SNTTPEGVARRYGGEWTEEAGERAALSERLFANLWGRLEGEERLLWLYREVERPLS
AVLAHMEATGVRLDVAYLRALSLEVAEEIARLEAEVFRLAGHPFNLNSRDQLERVLF
DELGLPAIGKTEKTGKRSTSAAVLEALREAHPIVEKILQYRELTKLKSTYIDPLPDLIH
PRTGRLHTRFNQTATATGRLSSSDPNLQNIPVRTPLGQRIRRAFIAEEGWLLVALDYS
QIELRVLAHLSGDENLIRVFQEGRDIHTETASWMFGVPREAVDPLMRRAAKTINFGV
LYGMSAHRLSQELAIPYEEAQAFIERYFQSFPKVRAWIEKTLEEGRRRGYVETLFGRR
RYVPDLEARVKSVREAAERMAFNMPVQGTAADLMKLAMVKLFPRLEEMGARMLL
QVHDELVLEAPKERAEAVARLAKEVMEGVYPLAVPLEVEVGIGEDWLSAKEGIDGR
GGGGHHHHHH

SEQ ID NO: 124 The DNA sequence encoding the Sso7d-Taq fusion protein

ATGATTACGAATTCGAGCGCAACCGTAAAGTTCAAGTACAAAGGCGAAGAAAAA
GAGGTAGACATCTCCAAGATCAAGAAAGTATGGCGTGTGGGCAAGATGATCTCC
TTCACCTACGACGAGGGCGGTGGCAAGACCGGCCGTGGTGCGGTAAGCGAAAAG
GACGCGCCGAAGGAGCTGCTGCAGATGCTGGAGAAGCAGAAAAAGGGCGGCGG
TGTCACTAGTGGGATGCTGCCCCTCTTTGAGCCCAAGGGCCGGGTCCTCCTGGTG
GACGGCCACCACCTGGCCTACCGCACCTTCCACGCCCTGAAGGGCCTCACCACCA
GCCGGGGGGAGCCGGTGCAGGCGGTCTACGGCTTCGCCAAGAGCCTCCTCAAGG
CCCTCAAGGAGGACGGGGACGCGGTGATCGTGGTCTTTGACGCCAAGGCCCCCT
CCTTCCGCCACGAGGCCTACGGGGGGTACAAGGCGGGCCGGGCCCCCACGCCAG
AGGACTTTCCCCGGCAACTCGCCCTCATCAAGGAGCTGGTGGACCTCCTGGGGCT
GGCGCGCCTCGAGGTCCCGGGCTACGAGGCGGACGACGTCCTGGCCAGCCTGGC
CAAGAAGGCGGAAAAGGAGGGCTACGAGGTCCGCATCCTCACCGCCGACAAAG
ACCTTTACCAGCTCCTTTCCGACCGCATCCACGTCCTCCACCCCGAGGGGTACCT
CATCACCCCGGCCTGGCTTTGGGAAAAGTACGGCCTGAGGCCCGACCAGTGGGC
CGACTACCGGGCCCTGACCGGGGACGAGTCCGACAACCTTCCCGGGGTCAAGGG
CATCGGGGAGAAGACGGCGAGGAAGCTTCTGGAGGAGTGGGGGAGCCTGGAAG
CCCTCCTCAAGAACCTGGACCGGCTGAAGCCCGCCATCCGGGAGAAGATCCTGG
CCCACATGGACGATCTGAAGCTCTCCTGGGACCTGGCCAAGGTGCGCACCGACCT
GCCCCTGGAGGTGGACTTCGCCAAAAGGCGGGAGCCCGACCGGGAGAGGCTTAG
GGCCTTTCTGGAGAGGCTTGAGTTTGGCAGCCTCCTCCACGAGTTCGGCCTTCTG
GAAAGCCCCAAGGCcCTGGAGGAGGCCCCCTGGCCCCCGCCGGAAGGGGCCTTC
GTGGGCTTTGTGCTTTCCCGCAAGGAGCCCATGTGGGCCGATCTTCTGGCCCTGG
CCGCCGCCAGGGGGGGCCGGGTCCACCGGGCCCCCGAGCCTTATAAAGCCCTCA
GGGACCTGAAGGAGGCGCGGGGGCTTCTCGCCAAAGACCTGAGCGTTCTGGCCC
TGAGGGAAGGCCTTGGCCTCCCGCCCGGCGACGACCCCATGCTCCTCGCCTACCT
CCTGGACCCTTCCAACACCACCCCCGAGGGGGTGGCCCGGCGCTACGGCGGGGA
GTGGACGGAGGAGGCGGGGGAGCGGGCCGCCCTTTCCGAGAGGCTCTTCGCCAA
CCTGTGGGGGAGGCTTGAGGGGGAGGAGAGGCTCCTTTGGCTTTACCGGGAGGT
GGAGAGGCCCCTTTCCGCTGTCCTGGCCCACATGGAGGCCACGGGGGTGCGCCT
GGACGTGGCCTATCTCAGGGCCTTGTCCCTGGAGGTGGCCGAGGAGATCGCCCG
CCTCGAGGCCGAGGTCTTCCGCCTGGCCGGCCACCCCTTCAACCTCAACTCCCGG
GACCAGCTGGAAAGGGTCCTCTTTGACGAGCTAGGGCTTCCCGCCATCGGCAAG
ACGGAGAAGACCGGCAAGCGCTCCACCAGCGCCGCCGTCCTGGAGGCCCTCCGC
GAGGCCCACCCCATCGTGGAGAAGATCCTGCAGTACCGGGAGCTCACCAAGCTG
AAGAGCACCTACATTGACCCCTTGCCGGACCTCATCCACCCCAGGACGGGCCGCC
TCCACACCCGCTTCAACCAGACGGCCACGGCCACGGGCAGGCTAAGTAGCTCCG
ATCCCAACCTCCAGA. ACATCCCCGTCCGCACCCCGCTTGGGCAGAGGATCCGCCG
GGCCTTCATCGCCGAGGAGGGGTGGCTATTGGTGGCCCTGGACTATAGCCAGAT
AGAGCTCAGGGTGCTGGCCCACCTCTCCGGCGACGAGAACCTGATCCGGGTCTTC
CAGGAGGGGCGGGACATCCACACGGAGACCGCCAGCTGGATGTTCGGCGTCCCC
CGGGAGGCCGTGGACCCCCTGATGCGCCGGGCGGCCAAGACCATCAACTTCGGG
GTCCTCTACGGCATGTCGGCCCACCGCCTCTCCCAGGAGCTAGCCATCCCTTACG
AGGAGGCCCAGGCCTTCATTGAGCGCTACTTTCAGAGCTTCCCCAAGGTGCGGGC

FIGURE 19 (Cont.)

CTGGATTGAGAAGACCCTGGAGGAGGGCAGGAGGCGGGGGTACGTGGAGACCC
TCTTCGGCCGCCGCCGCTACGTGCCAGACCTAGAGGCCCGGGTGAAGAGCGTGC
GGGAGGCGGCCGAGCGCATGGCCTTCAACATGCCCGTCCAGGGCACCGCCGCCG
ACCTCATGAAGCTGGCTATGGTGAAGCTCTTCCCCAGGCTGGAGGAAATGGGGG
CCAGGATGCTCCTTCAGGTCCACGACGAGCTGGTCCTCGAGGCCCCAAAAGAGA
GGGCGGAGGCCGTGGCCCGGCTGGCCAAGGAGGTCATGGAGGGGGTGTATCCCC
TGGCCGTGCCCCTGGAGGTGGAGGTGGGGATAGGGGAGGACTGGCTCTCCGCCA
AGGAGGGCATTGATGGCCGCGGCGGAGGCGGGCATCATCATCATCATCATTAA

SEQ ID NO: 125 The amino acid sequence of Sso7d-Taq fusion protein.

MITNSSATVKFKYKGEEKEVDISKIKKVWRVGKMISFTYDEGGGKTGRGAVSEKDA
PKELLQMLEKQKKGGGVTSGMLPLFEPKGRVLLVDGHHLAYRTFHALKGLTTSRGE
PVQAVYGFAKSLLKALKEDGDAVIVVFDAKAPSFRHEAYGGYKAGRAPTPEDFPRQ
LALIKELVDLLGLARLEVPGYEADDVLASLAKKAEKEGYEVRILTADKDLYQLLSDR
IHVLHPEGYLITPAWLWEKYGLR. PDQWADYRALTGDESDNLPGVKGIGEKTARKLL
EEWGSLEALLKNLDRLKPAIREKILAHMDDLKLSWDLAKVRTDLPLEVDFAKRREP
DRERLRAFLERLEFGSLLHEFGLLESPKALEEAPWPPPEGAFVGFVLSRKEPMWADL
LALAAARGGRVHRAPEPYKALRDLKEARGLLAKDLSVLALREGLGLPPGDDPMLLA
YLLDPSNTTPEGVARRYGGEWTEEAGERAALSERLFANLWGRLEGEERLLWLYREV
ERPLSAVLAHMEATGVRLDVAYLRALSLEVAEEIARLEAEVFRLAGHPFNLNSRDQL
ERVLFDELGLPAIGKTEKTGKRSTSAAVLEALREAHPIVEKILQYRELTKLKSTYIDPL
PDLIHPRTGRLHTRFNQTATATGRLSSSDPNLQNIPVRTPLGQIRJRRAFIAEEGWLLVA
LDYSQIELRVLAHLSGDENLIRVFQEGRDIHTETASWMFGVPREAVDPLMRRAAKTI
NFGVLYGMSAHRLSQELAIPYEEAQAFIERYFQSFPKVRAWIEKTLEEGRRRGYVETL
FGRRRYVPDLEARVKSVREAAERMAFNMPVQGTAADLMKLAMVKLFPRLEEMGA
RMLLQVHDELVLEAPKERAEAVARLAKEVMEGVYPLAVPLEVEVGIGEDWLSAKE
GIDGRGGGGHHHHHH

SEQ ID NO: 126 The DNA sequence encoding the Pfu-Sso7d fusion protein

ATGATTTTAGATGTGGATTACATAACTGAAGAAGGAAAACCTGTTATTAGGCTAT
TCAAAAAAGAGAACGGAAAATTTAAGATAGAGCATGATAGAACTTTTAGACCAT
ACATTTACGCTCTTCTCAGGGATGATTCAAAGATTGAAGAAGTTAAGAAAATAAC
GGGGGAAAGGCATGGAAAGATTGTGAGAATTGTTGATGTAGAGAAGGTTGAGAA
AAAGTTTCTCGGCAAGCCTATTACCGTGTGGAAACTTTATTTGGAACATCCCCAA
GATGTTCCCACTATTAGAGAAAAAGTTAGAGAACATCCAGCAGTTGTGGACATCT
TCGAATACGATATTCCATTTGCAAAGAGATACCTCATCGACAAAGGCCTAATACC
AATGGAGGGGGAAGAAGAGCTAAAGATTCTTGCCTTCGATATAGAAACCCTCTA
TCACGAAGGAGAAGAGTTTGGAAAAGGCCCAATTATAATGATTAGTTATGCAGA
TGAAAATGAAGCAAAGGTGATTACTTGGAAAAACATAGATCTTCCATACGTTGA
GGTTGTATCAAGCGAGAGAGAGATGATAAAGAGATTTCTCAGGATTATCAGGGA
GAAGGATCCTGACATTATAGTTACTTATAATGGAGACTCATTCGACTTCCCATAT
TTAGCGAAAAGGGCAGAAAAACTTGGGATTAAATTAACCATTGGAAGAGATGGA
AGCGAGCCCAAGATGCAGAGAATAGGCGATATGACGGCTGTAGAAGTCAAGGG
AAGAATACATTTCGACTTGTATCATGTAATAACAAGGACAATAAATCTCCCAACA
TACACACTAGAGGCTGTATATGAAGCAATTTTTGGAAAGCCAAAGGAGAAGGTA
TACGCCGACGAGATAGCAAAAGCCTGGGAAAGTGGAGAGAACCTTGAGAGAGTT
GCCAAATACTCGATGGAAGATGCAAAGGCAACTTATGAACTCGGGAAAGAATTC
CTTCCAATGGAAATTCAGCTTTCAAGATTAGTTGGACAACCTTTATGGGATGTTT
CAAGGTCAAGCACAGGGAACCTTGTAGAGTGGTTCTTACTTAGGAAAGCCTACG
AAAGAAACGAAGTAGCTCCAAACAAGCCAAGTGAAGAGGAGTATCAAAGAAGG
CTCAGGGAGAGCTACACAGGTGGATTCGTTAAAGAGCCAGAAAAGGGGTTGTGG
GAAAACATAGTATACCTAGATTTTAGAGCCCTATATCCCTCGATTATAATTACCC
ACAATGTTTCTCCCGATACTCTAAATCTTGAGGGATGCAAGAACTATGATATCGC
TCCTCAAGTAGGCCACAAGTTCTGCAAGGACATCCCTGGTTTTATACCAAGTCTC

FIGURE 19 (Cont.)

TTGGGACATTTGTTAGAGGAAAGACAAAAGATTAAGACAAAAATGAAGGAAACT
TTAGCAAATTCTTTCTACGGATATTATGGCTATGCAAAAGCAAGATGGTACTGTA
AGGAGTGTGCTGAGAGCGTTACTGCCTGGGGAAGAAAGTACATCGAGTTAGTAT
GGAAGGAGCTCGAAGAAAAGTTTGGATTTAAAGTCCTCTACATTGACACTGATG
GTCTCTATGCAACTATCCCAGGAGGAGAAAGTGAGGAAATAAAGAAAAAGGCTC
TAGAATTTGTAAAATACATAAATTCAAAGCTCCCTGGACTGCTAGAGCTTGAATA
TGAAGGGTTTTATAAGAGGGGATTCTTCGTTACGAAGAAGAGGTATGCAGTAAT
AGATGAAGAAGGAAAAGTCATTACTCGTGGTTTAGAGATAGTTAGGAGAGATTG
GAGTGAAATTGCAAAAGAAACTCAAGCTAGAGTTTTGGAGACAATACTAAAACA
CGGAGATGTTGAAGAAGCTGTGAGAATAGTAAAAGAAGTAATACAAAAGCTTGC
CAATTATGAAATTCCACCAGAGAAGCTCGCAATATATGAGCAGATAACAAGACC
ATTACATGAGTATAAGGCGATAGGTCCTCACGTAGCTGTTGCAAAGAAACTAGCT
GCTAAAGGAGTTAAAATAAAGCCAGGAATGGTAATTGGATACATAGTACTTAGA
GGCGATGGTCCAATTAGCAATAGGGCAATTCTAGCTGAGGAATACGATCCCAAA
AAGCACAAGTATGACGCAGAATATTACATTGAGAACCAGGTTCTTCCAGCGGTA
CTTAGGATATTGGAGGGATTTGGATACAGAAAGGAAGACCTCAGATACCAAAAG
ACAAGACAAGTCGGCCTAACTTCCTGGCTTAACATTAAAAAATCCGGTACCGGC
GGTGGCGGTGCAACCGTAAAGTTCAAGTACAAAGGCGAAGAAAAAGAGGTAGA
CATCTCCAAGATCAAGAAAGTATGGCGTGTGGGCAAGATGATCTCCTTCACCTAC
GACGAGGGCGGTGGCAAGACCGGCCGTGGTGCGGTAAGCGAAAAGGACGCGCC
GAAGGAGCTGCTGCAGATGCTGGAGAAGCAGAAAAAGTGA

SEQ ID NO: 127 The amino acid sequence of the Pfu-Sso7d fusion protein

MILDVDYITEEGKPVIRLFKKENGKFKIEHDRTFRPYIYALLRDDSKIEEVKKITGERH
GKIVRIVDVEKVEKKFLGKPITVWKLYLEHPQDVPTIREKVREHPAVVDIFEYDIPFA
KRYLIDKGLIPMEGEEELKILAFDIETLYHEGEEFGKGPIIMISYADENEAKVITWKNID
LPYVEVVSSEREMIKRFLRIIREKDPDIIVTYNGDSFDFPYLAKRAEKLGIKLTIGRDGS
EPKMQRIGDMTAVEVKGRIHFDLYHVITRTINLPTYTLEAVYEAIFGKPKEKVYADEI
AKAWESGENLERVAKYSMEDAKATYELGKEFLPMEIQLSRLVGQPLWDVSRSSTGN
LVEWFLLRKAYERNEVAPNKPSEEEYQRRLRESYTGGFVKEPEKGLWENIVYLDFR
ALYPSIIITHNVSPDTLNLEGCKNYDIAPQVGHKFCKDIPGFIPSLLGHLLEERQKIKTK
MKETQDPIEKILLDYRQKAIKLLANSFYGYYGYAKARWYCKECAESVTAWGRKYIE
LVWKELEEKFGFKVLYIDTDGLYATIPGGESEEIKKKALEFVKYINSKLPGLLELEYE
GFYKRGFFVTKKRYAVIDEEGKVITRGLEIVRRDWSEIAKETQARVLETILKHGDVEE
AVRIVKEVIQKLANYEIPPEKLAIYEQITRPLHEYKAIGPHVAVAKKLAAKGVKIKPG
MVIGYIVLRGDGPISNRAILAEEYDPKKHKYDAEYYIENQVLPAVLRILEGFGYRKED
LRYQKTRQVGLTSWLNIKKSGTGGGGATVKFKYKGEEKEVDISKIKKVWRVGKMIS
FTYDEGGGKTGRGAVSEKDAPKELLQMLEKQKK

SEQ ID NO: 128 The DNA sequence encoding the Sac7d-ΔTaq fusion protein

```
atgattacga attcgacggt gaaggtaaag ttcaagtata agggtgaaga gaaagaagta
gacacttcaa agataaagaa ggtttggaga gtaggcaaaa tggtgtcctt tacctatgac
gacaatggta agacaggtag aggagctgta agcgagaaag atgctccaaa agaattatta
gacatgttag caagagcaga aagagagaag aaaggcggcg gtgtcactag ccccaaggcc
ctggaggagg cccccctggcc cccgccggaa ggggccttcg tgggctttgt gctttcccgc
aaggagccca tgtgggccga tcttctggcc ctggccgccg ccaggggggg ccgggtccac
cgggcccccg agccttataa agccctcagg gacctgaagg aggcgcgggg gcttctcgcc
aaagacctga gcgttctggc cctgagggaa ggccttggcc tcccgcccgg cgacgacccc
atgctcctcg cctacctcct ggacccttcc aacaccaccc ccgagggggt ggcccggcgc
tacggcgggg agtggacgga ggaggcgggg gagcgggccg ccctttccga gaggctcttc
gccaacctgt gggggaggct tgagggggag gagaggctcc tttggcttta ccgggaggtg
gagaggcccc tttccgctgt cctggcccac atggaggcca cgggggtgcg cctggacgtg
gcctatctca gggccttgtc cctggaggtg gccgaggaga tcgcccgcct cgaggccgag
gtcttccgcc tggccggcca ccccttcaac ctcaactccc gggaccagct ggaaagggtc
ctctttgacg agctagggct tcccgccatc ggcaagacgg agaagaccgg caagcgctcc
accagcgccg ccgtcctgga ggccctccgc gaggcccacc ccatcgtgga gaagatcctg
cagtaccggg agctcaccaa gctgaagagc acctacattg accccttgcc ggacctcatc
```

FIGURE 19 (Cont.)

caccccagga cgggccgcct ccacacccgc ttcaaccaga cggccacggc cacgggcagg
ctaagtagct ccgatcccaa cctccagaac atccccgtcc gcaccccgct tgggcagagg
atccgccggg ccttcatcgc cgaggagggg tggctattgg tggccctgga ctatagccag
atagagctca gggtgctggc ccacctctcc ggcgacgaga acctgatccg ggtcttccag
gaggggcggg acatccacac ggagaccgcc agctggatgt tcggcgtccc ccgggaggcc
gtggaccccc tgatgcgccg ggcggccaag accatcaact tcggggtcct ctacggcatg
tcggcccacc gcctctccca ggagctagcc atcccttacg aggaggccca ggccttcatt
gagcgctact ttcagagctt ccccaaggtg cgggcctgga ttgagaagac cctggaggag
ggcaggaggc gggggtacgt ggagaccctc ttcggccgcc gccgctacgt gccagaccta
gaggcccggg tgaagagcgt gcgggaggcg gccgagcgca tggccttcaa catgcccgtc
cagggcaccg ccgccgacct catgaagctg gctatggtga agctcttccc caggctggag
gaaatggggg ccaggatgct ccttcaggtc cacgacgagc tggtcctcga ggcccccaaa
gagagggcgg aggccgtggc ccggctggcc aaggaggtca tggagggggt gtatcccctg
gccgtgcccc tggaggtgga ggtggggata ggggaggact ggctctccgc caaggagggc
attgatggcc gcggcggagg cgggcatcat catcatcatc attaa SEQ ID NO: 129 The amino acid sequence of the Sac7d-ΔTaq fusion protein

MITNSTVKVKFKYKGEEKEVDTSKIKKVWRVGKMVSFTYDDNGKTGRGAVSEKDA
PKELLDMLARAEREKKGGGVTSPKALEEAPWPPPEGAFVGFVLSRKEPMWADLLAL
AAARGGRVHRAPEPYKALRDLKEARGLLAKDLSVLALREGLGLPPGDDPMLLAYLL
DPSNTTPEGVARRYGGEWTEEAGERAALSERLFANLWGRLEGEERLLWLYREVERP
LSAVLAHMEATGVRLDVAYLRALSLEVAEEIARLEAEVFRLAGHPFNLNSRDQLERV
LFDELGLPAIGKTEKTGKRSTSAAVLEALREAHPIVEKILQYRELTKLKSTYIDPLPDLI
HPRTGRLHTRFNQTATATGRLSSSDPNLQNIPVRTPLGQRIRRAFIAEEGWLLVALDY
SQIELRVLAHLSGDENLIRVFQEGRDIHTETASWMFGVPREAVDPLMRRAAKTINFG
VLYGMSAHRLSQELAIPYEEAQAFIERYFQSFPKVRAWIEKTLEEGRRRGYVETLFGR
RRYVPDLEARVKSVREAAERMAFNMPVQGTAADLMKLAMVKLFPRLEEMGARML
LQVHDELVLEAPKERAEAVARLAKEVMEGVYPLAVPLEVEVGIGEDWLSAKEGIDG
RGGGGHHHHHH

SEQ ID NO: 130 The DNA sequence encoding the PL-ΔTaq fusion protein

ATGATTACGAATTCGAAGAAAAAGAAAAAGAAAAAGCGTAAGAAACGCAAAAA
GAAAAAGAAAGGCGGCGGTGTCACTAGTGGCGCAACCGTAAAGTTCAAGTACAA
AGGCGAAGAAAAAGAGGTAGACATCTCCAAGATCAAGAAAGTATGGCGTGTGG
GCAAGATGATCTCCTTCACCTACGACGAGGGCGGTGGCAAGACCGGCCGTGGTG
CGGTAAGCGAAAAGGACGCGCCGAAGGAGCTGCTGCAGATGCTGGAGAAGCAG
AAAAAGGGCGGCGGTGTCACCAGTCCCAAGGCCCTGGAGGAGGCCCCCTGGCCC
CCGCCGGAAGGGGCCTTCGTGGGCTTTGTGCTTTCCCGCAAGGAGCCCATGTGGG
CCGATCTTCTGGCCCTGGCCGCCGCCAGGGGGGGCCGGGTCCACCGGGCCCCCG
AGCCTTATAAAGCCCTCAGGGACCTGAAGGAGGCGCGGGGGCTTCTCGCCAAAG
ACCTGAGCGTTCTGGCCCTGAGGGAAGGCCTTGGCCTCCCGCCCGGCGACGACCC
CATGCTCCTCGCCTACCTCCTGGACCCTTCCAACACCACCCCCGAGGGGGTGGCC
CGGCGCTACGGCGGGGAGTGGACGGAGGAGGCGGGGGAGCGGGCCGCCCTTTCC
GAGAGGCTCTTCGCCAACCTGTGGGGGAGGCTTGAGGGGGAGGAGAGGCTCCTT
TGGCTTTACCGGGAGGTGGAGAGGCCCCTTTCCGCTGTCCTGGCCCACATGGAGG
CCACGGGGGTGCGCCTGGACGTGGCCTATCTCAGGGCCTTGTCCCTGGAGGTGGC
CGAGGAGATCGCCCGCCTCGAGGCCGAGGTCTTCCGCCTGGCCGGCCACCCCTTC
AACCTCAACTCCCGGGACCAGCTGGAAAGGGTCCTCTTTGACGAGCTAGGGCTTC
CCGCCATCGGCAAGACGGAGAAGACCGGCAAGCGCTCCACCAGCGCCGCCGTCC
TGGAGGCCCTCCGCGAGGCCCACCCCATCGTGGAGAAGATCCTGCAGTACCGGG
AGCTCACCAAGCTGAAGAGCACCTACATTGACCCCTTGCCGGACCTCATCCACCC
CAGGACGGGCCGCCTCCACACCCGCTTCAACCAGACGGCCACGGCCACGGGCAG
GCTAAGTAGCTCCGATCCCAACCTCCAGAACATCCCCGTCCGCACCCCGCTTGGG
CAGAGGATCCGCCGGGCCTTCATCGCCGAGGAGGGGTGGCTATTGGTGGCCCTG
GACTATAGCCAGATAGAGCTCAGGGTGCTGGCCCACCTCTCCGGCGACGAGAAC
CTGATCCGGGTCTTCCAGGAGGGGCGGGACATCCACACGGAGACCGCCAGCTGG

FIGURE 19 (Cont.)

ATGTTCGGCGTCCCCCGGGAGGCCGTGGACCCCCTGATGCGCCGGGCGGCCAAG
ACCATCAACTTCGGGGTCCTCTACGGCATGTCGGCCCACCGCCTCTCCCAGGAGC
TAGCCATCCCTTACGAGGAGGCCCAGGCCTTCATTGAGCGCTACTTTCAGAGCTT
CCCCAAGGTGCGGGCCTGGATTGAGAAGACCCTGGAGGAGGGCAGGAGGCGGG
GGTACGTGGAGACCCTCTTCGGCCGCCGCCGCTACGTGCCAGACCTAGAGGCCC
GGGTGAAGAGCGTGCGGGAGGCGGCCGAGCGCATGGCCTTCAACATGCCCGTCC
AGGGCACCGCCGCCGACCTCATGAAGCTGGCTATGGTGAAGCTCTTCCCCAGGCT
GGAGGAAATGGGGGCCAGGATGCTCCTTCAGGTCCACGACGAGCTGGTCCTCGA
GGCCCCAAAAGAGAGGGCGGAGGCCGTGGCCCGGCTGGCCAAGGAGGTCATGG
AGGGGGTGTATCCCCTGGCCGTGCCCCTGGAGGTGGAGGTGGGGATAGGGGAGG
ACTGGCTCTCCGCCAAGGAGGGCATTGATGGCCGCGGCGGAGGCGGGCATCATC
ATCATCATCATTAA

SEQ ID NO: 131 The amino acid sequence of PL- ΔTaq fusion protein

MITNSKKKKKKKRKKRKKKKKGGGVTSGATVKFKYKGEEKEVDISKIKKVWRVGK
MISFTYDEGGGKTGRGAVSEKDAPKELLQMLEKQKKGGGVTSPKALEEAPWPPPEG
AFVGFVLSRKEPMWADLLALAAARGGRVHRAPEPYKALRDLKEARGLLAKDLSVL
ALREGLGLPPGDDPMLLAYLLDPSNTTPEGVARRYGGEWTEEAGERAALSERLFAN
LWGRLEGEERLLWLYREVERPLSAVLAHMEATGVRLDVAYLRALSLEVAEEIARLE
AEVFRLAGHPFNLNSRDQLERVLFDELGLPAIGKTEKTGKRSTSAAVLEALREAHPIV
EKILQYRELTKLKSTYIDPLPDLIHPRTGRLHTRFNQTATATGRLSSSDPNLQNIPVRTP
LGQRIRRAFIAEEGWLLVALDYSQIELRVLAHLSGDENLIRVFQEGRDIHTETASWMF
GVPREAVDPLMRRAAKTINFGVLYGMSAHRLSQELAIPYEEAQAFIERYFQSFPKVR
AWIEKTLEEGRRRGYVETLFGRRRYVPDLEARVKSVREAAERMAFNMPVQGTAAD
LMKLAMVKLFPRLEEMGARMLLQVHDELVLEAPKERAEAVARLAKEVMEGVYPL
AVPLEVEVGIGEDWLSAKEGIDGRGGGGHHHHHH

SEQ ID NO: 132 PRIMER L71F 5'-CCTGCTCTGCCGCTTCACGC-3'

SEQIDNO: 133 PRIMER L71R 5'-GCACAGCGGCTGGCTGAGGA-3'

SEQ ID NO: 134 PRIMER L18015F 15 5'-TGACGGAGGATAACGCCAGCAG-3'

SEQ ID NO: 135 PRIMER L23474R 5'-GAAAGACGA TGGGTCGCTAATACGC-3'

SEQ ID NO: 136 PRIMER L18015F 5'-TGACGGAGGATAAC GCCAGCAG-3'

SEQ ID NO: 137 PRIMER L29930R 5'-GGGGTTGGAGGTCAATGGGTTC-3'

SEQ ID NO: 138 PRIMER L3035OF 5'-CCTGCTCTGCCGCTTCACGC-3'

SEQ ID NO: 139 PRIMER L35121R 30 5'- CACATGGTACAGCAAGCCTGGC-3'

SEQ ID NO: 140 PRIMER L2089F 5'-CCCGTATCTGCTGGGA TACTGGC-3'

SEQ IUD NO: 141 PRIMER L7112R 5'-CAGCGGTGCTGACTGAATCATGG-3'

SEQ ID NO: 142 PRIMER L3035OF 5 5'-CCTGCCTGCCGCTTCACGC-3'

SEQ ID NO: 143 PRIMER L40547R 5'-CCAATACCCGTTTCA TCGCGGC-3'

SEQ ID NO: 144 PRIMER H-Amelo-Y 5'-CCACCTCATCCTGG GCACC-3'

SEQ ID NO: 145 PRIMER H-Amelo-YR 5'-GCTTGAGGCCAACCATCAGAGC-3'

FIGURE 19 (Cont.)

SEQ ID NO: 146 Human beta-globin primer 536F 5'-GGTTGGCCAATCTACTCCCAGG-3'

SEQ ID NO: 147 Human beta-globin primer 536R 5'-GCTCACTCAGTGTGGCAAAG-3'

SEQ ID NO: 148 Human beta-globin primer 1408R 5'-GATTAGCAAAAGGGCCTAGCTTGG- 3'

Figure 20

PURIFIED THERMOSTABLE PYROCOCCUS FURIOSUS DNA POLYMERASE I

AMINO ACID SEQUENCE (SEQ ID NO: 62)

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270
```

FIGURE 20 (Cont.)

```
Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575
```

FIGURE 20 (Cont.)

```
Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775
```

PURIFIED THERMOSTABLE PYROCOCCUS FURIOSUS DNA POLYMERASE I

NUCLEOTIDE SEQUENCE (SEQ ID NO: 61)

```
ccctggtcct gggtccacat atatgttctt actcgccttt atgaagaatc ccccagtcgc     60

tctaacctgg gttatagtga caaatcttcc tccaccaccg cccaagaagg ttatttctat    120

caactctaca cctcccctat tttctctctt atgagatttt taagtatagt tatagagaag    180

gttttatact ccaaactgag ttagtagata tgtggggagc ataatgattt tagatgtgga    240

ttacataact gaagaaggaa aacctgttat taggctattc aaaaaagaga acggaaaatt    300

taagatagag catgatagaa cttttagacc atacatttac gctcttctca gggatgattc    360

aaagattgaa gaagttaaga aaataacggg ggaaaggcat ggaaagattg tgagaattgt    420
```

FIGURE 20 (Cont.)

```
tgatgtagag aaggttgaga aaaagtttct cggcaagcct attaccgtgt ggaaacttta    480
tttggaacat ccccaagatg ttcccactat tagagaaaaa gttagagaac atccagcagt    540
tgtggacatc ttcgaatacg atattccatt tgcaaagaga tacctcatcg acaaaggcct    600
aataccaatg gagggggaag aagagctaaa gattcttgcc ttcgatatag aaaccctcta    660
tcacgaagga gaagagtttg gaaaaggccc aattataatg attagttatg cagatgaaaa    720
tgaagcaaag gtgattactt ggaaaaacat agatcttcca tacgttgagg ttgtatcaag    780
cgagagagag atgataaaga gatttctcag gattatcagg gagaaggatc ctgacattat    840
agttacttat aatggagact cattcgactt cccatattta gcgaaaaggg cagaaaaact    900
tgggattaaa ttaaccattg gaagagatgg aagcgagccc aagatgcaga gaataggcga    960
tatgacggct gtagaagtca agggaagaat acatttcgac ttgtatcatg taataacaag   1020
gacaataaat ctcccaacat acacactaga ggctgtatat gaagcaattt ttggaaagcc   1080
aaaggagaag gtatacgccg acgagatagc aaaagcctgg gaaagtggag agaaccttga   1140
gagagttgcc aaatactcga tggaagatgc aaaggcaact tatgaactcg ggaaagaatt   1200
ccttccaatg gaaattcagc tttcaagatt agttggacaa cctttatggg atgtttcaag   1260
gtcaagcaca gggaaccttg tagagtggtt cttacttagg aaagcctacg aaagaaacga   1320
agtagctcca aacaagccaa gtgaagagga gtatcaaaga aggctcaggg agagctacac   1380
aggtggattc gttaaagagc cagaaaaggg gttgtgggaa aacatagtat acctagattt   1440
tagagcccta tatccctcga ttataattac ccacaatgtt tctcccgata ctctaaatct   1500
tgagggatgc aagaactatg atatcgctcc tcaagtaggc cacaagttct gcaaggacat   1560
ccctggtttt ataccaagtc tcttgggaca tttgttagag gaaagacaaa agattaagac   1620
aaaaatgaag gaaactcaag atcctataga aaaaatactc cttgactata gacaaaaagc   1680
gataaaactc ttagcaaatt ctttctacgg atattatggc tatgcaaaag caagatggta   1740
ctgtaaggag tgtgctgaga gcgttactgc ctggggaaga aagtacatcg agttagtatg   1800
gaaggagctc gaagaaaagt ttggatttaa agtcctctac attgacactg atggtctcta   1860
tgcaactatc ccaggaggag aaagtgagga aataaagaaa aaggctctag aatttgtaaa   1920
atacataaat tcaaagctcc ctggactgct agagcttgaa tatgaagggt tttataagag   1980
gggattcttc gttacgaaga agaggtatgc agtaatagat gaagaaggaa aagtcattac   2040
tcgtggttta gagatagtta ggagagattg gagtgaaatt gcaaaagaaa ctcaagctag   2100
agttttggag acaatactaa aacacggaga tgttgaagaa gctgtgagaa tagtaaaaga   2160
```

FIGURE 20 (Cont.)

```
agtaatacaa aagcttgcca attatgaaat tccaccagag aagctcgcaa tatatgagca   2220
gataacaaga ccattacatg agtataaggc gataggtcct cacgtagctg ttgcaaagaa   2280
actagctgct aaaggagtta aaataaagcc aggaatggta attggataca tagtacttag   2340
aggcgatggt ccaattagca atagggcaat tctagctgag gaatacgatc ccaaaaagca   2400
caagtatgac gcagaatatt acattgagaa ccaggttctt ccagcggtac ttaggatatt   2460
ggagggattt ggatacagaa aggaagacct cagataccaa aagacaagac aagtcggcct   2520
aacttcctgg cttaacatta aaaaatccta gaaaagcgat agatatcaac ttttattctt   2580
tctaaccttt ttctatgaaa gaagaactga gcaggaatta ccagttcttc cgttatttta   2640
tgggtaatta aaaacccatg ctcttgggag aatcttcgaa taaaatccct aacttcaggc   2700
tttgctaagt gaatagaata aacaacatca ctcacttcaa acgccttcgt tagaaatggt   2760
ctatctgcat gcttctctgg ctcggaanng gaggattcat aacaacagta tcaacattct   2820
cagagaattg agaaacatca gaaactttga cttctacaac atttctaact ttgcaactct   2880
tcaagatttt ctaaaagaat tttaacggcc tcctcgtcaa tttcgacgac gtagatcttt   2940
tttgctccaa gcagagccgc tccaatggat aacacccctg ttcccgcacc caagtccgct   3000
acaatttttt ccttgtatct cctaatgtat aagcaagcca aaggagagta gatgctacct   3060
ttccgggagt tttgtattgc tctagccaag gtttgggatt tttgaatcct ttaactctgg   3120
aaagtataat ttcaagctcc ttcttcttca tgacagatga aaaattgttt tgtctctttt   3180
taacttttac agaaataact gtctcaaatt atgacaactc ttgacatttt tacttcatta   3240
ccagggtaat gtttttaagt atgaaatttt tctttcatag aggaggnnnn nngtcctctc   3300
ctcgatttcc ttggttgtgc tccatatgat aagcttccaa agtgggtgtt cagactttta   3360
gacactcaaa taccagacga caatggtgtg ctcactcaag ccccatatgg gttgagaaaa   3420
gtagaagcgg cactactcag atgcttcccc aggaatgagg ttgttgtagc tcntcccnga   3480
aagattgaga tgttcttgg
```

DNA POLYMERASE FUSIONS AND USES THEREOF

RELATED APPLICATIONS

This application is a divisional of U.S. application Ser. No. 11/606,865 filed Nov. 29, 2006 now U.S. Pat. No. 7,659,100, which is a divisional of U.S. application Ser. No. 10/805,650 filed Mar. 19, 2004, now U.S. Pat. No. 7,704,712, which claims the benefit of U.S. Provisional Application No. 60/457,426, filed Mar. 25, 2003. The entire teachings of the above application are incorporated herein by reference.

FIELD OF THE INVENTION

The present invention relates to blends of chimeric and non chimeric DNA polymerases, methods for their synthesis, and methods for their use. The DNA polymerase blends disclosed herein are useful for many recombinant DNA techniques, especially nucleic acid sequencing, nucleic acid amplification by the polymerase chain reaction (PCR) or mutagenesis.

BACKGROUND

Thermostable DNA polymerases which catalyze the template-directed polymerization of deoxyribonucleoside triphosphates (dNTPs) to form DNA, are used in a variety of in vitro DNA synthesis applications, such as DNA sequencing, DNA amplification and mutagenesis. However, thermostable DNA polymerases and their associated activities (reviewed in Abramson, 1995, in PCR Strategies, (Innis et al. ed., Academic Press, Inc.)) are not always optimal for a given application (reviewed in WO 01/61015, hereby incorporated by reference in its entirety). Because of the diversity of properties and characteristics potentially exhibited by nucleic acid polymerases generally, practitioners in the art have sought to modify, to alter, or to recombine various features of nucleic acid polymerases in an effort to develop new and useful variants of the enzyme.

One approach has been directed to the discovery and isolation of new thermophilic nucleic acid polymerases, which may possess a unique and/or improved collection of catalytic properties. As a result, thermostable nucleic acid polymerases have been isolated from a variety of biological sources, including, but not limited to, species of the taxonomic genera, *Thermus, Thermococcus, Thermotoga, Pyrococcus*, and *Sulfolobus*.

Some of these naturally occurring thermostable DNA polymerases possess enzymatically active 3'-5' exonuclease domains, providing a natural proofreading capability and, thus, exhibiting higher fidelity than Taq DNA polymerase. However, these DNA polymerases also show slower DNA extension rates and an overall lower processivity when compared to Taq DNA polymerase, thus rendering these naturally occurring thermostable DNA polymerases less desirable for PCR, despite their higher fidelity.

In an effort to compensate for the deficiencies of individual thermostable polymerases, a second approach has been to develop multiple enzyme assemblages, combining, for example, Taq polymerase and a proofreading enzyme, such as Pfu polymerase or Vent® (New England BioLabs, Inc., Beverly, Mass.) DNA polymerase. These multiple-enzyme mixtures exhibit higher PCR efficiency and reduced error rates when compared to Taq polymerase alone (Barnes, Proc. Natl. Acad. Sci USA 91:2216-2220 (1994).).

Another approach has been to develop new and useful variants of Taq polymerase through deletion/truncation techniques. The Stoffel fragment, for example, is a 544 amino acid C-terminal truncation of Taq DNA polymerase, possessing an enzymatically active 5' 3' polymerase domain but lacking 3'-exonuclease and 5'-3' exonuclease activity. Other commercially available thermostable polymerase deletions include Vent® (exo-) and Deep Vent® (exo-) (New England BioLabs, Beverly, Mass.). Deletion mutations serve only to remove functional domains of a nucleic acid polymerase, however, and do not add any novel features or enzymatic properties.

Polymerase mutagenesis is yet another approach that has been attempted to develop new and useful nucleic acid polymerase variants. For example, naturally occurring DNA polymerases strongly discriminate against the incorporation of nucleotide analogues. This property contributes to the fidelity of DNA replication and repair. However, the incorporation of nucleotide analogues is useful for many DNA synthesis applications, especially DNA sequencing. Hence, a DNA polymerase that lacks associated exonucleolytic activity, either 5'-nuclease activity or 3' to 5' exonuclease activity, is preferred for DNA sequencing. In order to generate thermostable DNA polymerases with reduced nucleotide discrimination, site-directed mutagenesis studies were initiated and resulted in the identification of mutant forms of a number of thermostable DNA polymerases with the requisite activities suitable for DNA sequencing (U.S. Pat. No. 5,466,591, incorporated herein by reference).

Yet another approach to modifying the property of a DNA polymerase is to generate DNA polymerase fusions in which one or more protein domains having the requisite activity are combined with a DNA polymerase. DNA polymerase has been fused in frame to the helix-hairpin-helix DNA binding motifs from DNA topoisomerase V and shown to increase processivity, salt resistance and thermostability of the chimeric DNA polymerase as described in Pavlov et al., 2002, Proc. Natl. Acad. Sci. USA, 99:13510-13515. Fusion of the thioredoxin binding domain to T7 DNA polymerase enhances the processivity of the DNA polymerase fusion in the presence of thioredoxin as described in WO 97/29209, U.S. Pat. No. 5,972,603 and Bedford et al. Proc. Natl. Acad. Sci. USA 94: 479-484 (1997). Fusion of the archaeal PCNA binding domain to Tag DNA polymerase results in a DNA polymerase fusion that has enhanced processivity and produces higher yields of PCR amplified DNA in the presence of PCNA (Motz, M., et al., J. Biol. Chem. 2002 May 3; 277 (18); 16179-88). Also, fusion of the sequence non-specific DNA binding protein Sso7d or Sac7d from *Sulfolobus sulfataricus* to a DNA polymerase, such as Pfu or Tag DNA polymerase, was shown to greatly increase the processivity of these DNA polymerases as disclosed in WO 01/92501 A1 which is hereby incorporated by reference in its entirety. Domain substitution of all or a portion of a DNA polymerase with the corresponding domain of a different DNA polymerase have also been described (U.S. 2002/0119461).

Despite these intense research efforts, there remains a need in the art to develop conditions, which are more suitable for supporting the nucleic acid synthesis, sequencing, and amplification activity of DNA polymerases.

SUMMARY OF THE INVENTION

The invention relates to methods of using a DNA polymerase fusion at high pH for DNA synthesis, DNA sequencing, cloning of a DNA synthesis product or linear or exponential PCR amplification.

One of skill in the art will understand that the DNA polymerase fusions useful according to the invention possess one or more DNA polymerase functions which are active at high pH. DNA polymerase functions are well known in the art (Ausubel et. al. *Short Protocols in Molecular Biology* (1995) 3rd Ed. John Wiley & Sons, Inc.; (Sambrook et al., (1989) in: Molecular Cloning, A Laboratory Manual (2nd Ed.), Cold Spring Harbor Laboratory Press, Cold Spring Harbor, N.Y.); Stratagene Catalog). Thus, the invention specifically encompasses a method of using the DNA polymerase fusions of the invention at high pH for a DNA polymerase fusion that is now known or becomes available in the art.

As used herein, "DNA polymerase function" refers to the activity of a DNA polymerase, described herein. Activities of the DNA polymerase include, but are not limited to, processivity, salt-resistance, DNA binding, strand displacement activity, polymerase activity, nucleotide binding and recognition, 3'-5' or 5'-3' exonuclease activities, proofreading, fidelity and/or decreased DNA polymerization at room temperature, as defined hereinbelow. DNA polymerase activities are well known in the art (Ausubel et. al. Short *Protocols in Molecular Biology* (1995) 3rd Ed. John Wiley & Sons, Inc.; (Sambrook et al., (1989) in: Molecular Cloning, A Laboratory Manual (2nd Ed.), Cold Spring Harbor Laboratory Press, Cold Spring Harbor, N.Y., see additional references incorporated by reference in their entirety herein); Stratagene Catalog). Thus, the invention specifically encompasses a method of using a DNA polymerase fusions according to the invention at high pH for a DNA polymerase activity that is now known or becomes available in the art.

DNA polymerase "function" also includes an activity of a "mutant" DNA polymerase, as defined herein. The invention encompasses but is not limited to the following activities of a "mutant" according to the invention: base analog detection activities, DNA polymerization activity, reverse transcriptase activity, processivity, salt resistance, DNA binding, strand displacement activity, nucleotide binding and recognition, 3'-5' or 5'-3' exonuclease activities, proofreading, fidelity, efficiency, specificity, thermostability and intrinsic hot start capability or decreased DNA polymerization at room temperature, decreased amplification slippage on templates with tri-nucleotide repeat stretches, decreased amplification cycles, decreased extension times, and a decrease in the amount of polymerase needed for the applications described herein. In one embodiment, the "mutant" polymerase of the invention refers to a DNA polymerase containing one or more mutations that reduce one or more base analog detection activities of the DNA polymerase. In one embodiment, a "mutant" refers to a polymerase that has a mutation that confers an improved polymerization rate or fidelity on the polymerase. In a preferred embodiment, the "mutant" polymerase of the invention has a reduced uracil detection activity. In a preferred embodiment, the "mutant" polymerase of the invention has a reduced inosine detection activity. In another preferred embodiment, the "mutant" polymerase of the invention has a reduced uracil and inosine detection activity. In another preferred embodiment, the "mutant" polymerase of the invention has a reduced DNA polymerization activity. Any of the "mutants", for example, a mutant with reduced uracil activity, may also possess improved polymerization rate and/or fidelity, as compared to a wild-type polymerase.

The invention provides for a method for DNA synthesis at high pH, comprising: a) providing a DNA polymerase fusion; and b) contacting the fusion with a nucleic acid template, wherein the fusion permits DNA synthesis.

The invention also provides for a method for cloning of a DNA synthesis product at high pH comprising: a) providing a DNA polymerase fusion; b) contacting the fusion with a nucleic acid template, wherein the fusion permits DNA synthesis to generate a synthesized DNA product; and c) inserting the synthesized DNA product into a cloning vector.

The invention also provides for a method for sequencing DNA at high pH, comprising the steps of (a) contacting a template DNA strand with a sequencing DNA primer; (b) contacting the DNA of step (a) with a DNA polymerase fusion, deoxyribonucleoside triphosphates, and a chain-terminating nucleotide analog; (c) incubating the mixture of step (b) under conditions sufficient to synthesize a random population of DNA molecules complementary to the first DNA molecule, wherein the synthesized DNA molecules are shorter in length than the first DNA molecule and wherein the synthesized DNA molecules comprise a terminator nucleotide at their 5' termini; and (d) separating the synthesized DNA molecules by size so that at least a part of the nucleotide sequence of the first DNA molecule can be determined.

The invention also provides a method of linear or exponential PCR amplification at high pH for site-directed or random mutagenesis comprising the steps of: incubating a reaction mixture comprising a nucleic acid template, at least two PCR primers, and a DNA polymerase fusion under conditions which permit amplification of the nucleic acid template by the fusion to produce a mutated amplified product.

The invention also provides a method of reverse transcriptase PCR at high pH comprising the steps of incubating a reaction mixture comprising a nucleic acid template, at least one PCR primer, and a DNA polymerase fusion under conditions which permit amplification of the nucleic acid template by said fusion to produce an amplified product.

The invention provides for a composition for any one of DNA synthesis, cloning of a DNA synthesis product at high pH, sequencing DNA, linear or exponential PCR amplification for site directed or random mutagenesis, wherein the composition comprises a DNA polymerase fusion and a high pH buffer. In addition to the high pH buffer and polymerase fusion, the other components of a reaction mix may be present in the composition, e.g., template, primer, nucleotides, labels, labeled nucleotides, etc.

The invention provides for a composition for DNA synthesis, wherein the composition comprises a DNA polymerase fusion and a high pH DNA synthesis buffer. The invention contemplates a high pH DNA synthesis buffer, wherein the composition of the DNA synthesis buffer is that of a DNA synthesis buffer known in the art and described herein in the section entitled, "Applications of the Subject Invention", and wherein the DNA synthesis buffer is a "high pH" buffer, as defined herein.

The invention provides for a composition for cloning of a DNA synthesis product, wherein the composition comprises a DNA polymerase fusion and a high pH DNA cloning buffer. The invention contemplates a high pH DNA cloning buffer, wherein the composition of the DNA cloning buffer is that of a DNA cloning buffer known in the art and described herein in the section entitled, "Applications of the Subject Invention", and wherein the DNA cloning buffer is a "high pH" buffer, as defined herein.

The invention provides for a composition for sequencing DNA, wherein the composition comprises a DNA polymerase fusion and a high pH DNA sequencing buffer. The invention contemplates a high pH DNA sequencing buffer, wherein the composition of the DNA sequencing buffer is that of a DNA sequencing buffer known in the art and described herein in the section entitled, "Applications of the Subject Invention", and wherein the DNA sequencing buffer is a "high pH" buffer, as defined herein.

The invention provides for a composition for linear or exponential PCR amplification for site directed or random mutagenesis, wherein the composition comprises a DNA polymerase fusion and a high pH PCR reaction buffer. The invention contemplates a high pH PCR reaction buffer, wherein the composition of the PCR reaction buffer is that of a PCR reaction buffer known in the art and described herein in the section entitled, "Applications of the Subject Invention", and wherein the PCR reaction buffer is a "high pH" buffer, as defined herein.

In one embodiment, the methods and compositions of the invention further comprise a PCR enhancing factor and/or an additive.

In another embodiment, the DNA polymerase fusion used in the methods of the invention has reduced DNA polymerization activity.

In another embodiment, the DNA polymerase fusion comprises a Glycine to Proline substitution at amino acid position 387 (G387P) and has reduced DNA polymerization activity.

In another embodiment, the DNA polymerase fusion comprises reduced base analog detection activity.

In another embodiment, the DNA polymerase fusion comprises reduced base analog detection activity and a mutation at position V93, wherein the mutation is a Valine to Arginine substitution, a Valine to Glutamic acid substitution, a Valine to Lysine substitution, a Valine to Aspartic acid substitution or a Valine to Asparagine substitution.

In another embodiment, the DNA polymerase fusion has reduced base analog detection activity.

In another embodiment, the DNA polymerase fusion comprises reduced base analog detection activity.

In another embodiment, the DNA polymerase fusion further comprises a mutation at position V93, wherein the mutation is a Valine to Arginine substitution, a Valine to Glutamic acid substitution, a Valine to Lysine substitution, a Valine to Aspartic acid substitution or a Valine to Asparagine substitution that confers a reduced base analog detection activity phenotype to the chimeric DNA polymerase.

In another embodiment, the DNA polymerase fusion further comprises a reduced DNA polymerization activity.

In another embodiment, the DNA polymerase fusion further comprises a Glycine to Proline substitution at amino acid position 387 (G387P) that confers a reduced DNA polymerization phenotype to said chimeric DNA polymerase.

In another embodiment, the DNA polymerase fusion further comprises an Aspartate to alanine substitution at amino acid 141 (D141A) and a Glutamic acid to Alanine substitution at amino acid position 143 (D141A/E143A) that renders the chimeric DNA polymerase 3'-5' exonuclease deficient.

In another embodiment, the DNA polymerase fusion with reduced base analog detection activity further comprises an Aspartate to alanine substitution at amino acid 141 (D141A) and a Glutamic acid to Alanine substitution at amino acid position 143 (D141A/E143A) that renders the chimeric DNA polymerase 3'-5' exonuclease deficient.

In another embodiment, the DNA polymerase fusion comprises a wild type, mutant or chemically modified DNA polymerase.

In another embodiment, the DNA polymerase fusion is a proofreading polymerase.

In another embodiment, the proofreading polymerase is selected from the group consisting of Pfu, KOD, Tgo, Vent® and Deep Vent®.

In another embodiment, the DNA polymerase fusion further comprises a polypeptide with an increase in an activity selected from the group consisting of: processivity, proofreading, fidelity, DNA binding activity, strand displacement activity, polymerase activity, nucleotide binding and recognition, efficiency, template length amplification capability, GC-rich target amplification efficiency, specificity, thermostability, intrinsic hot start capability, or salt resistance.

In another embodiment, the DNA polymerase fusion further comprises a polypeptide with a reduced activity selected from the group consisting of: DNA polymerase activity at room temperature, amplification slippage on templates with tri-nucleotide repeat stretches, extension time in a PCR reaction or amplification cycles in a PCR reaction.

In another, embodiment, the DNA polymerase fusion consists of a protein domain selected from the group of: thioredoxin processivity factor binding domain of bacteriophage T7, archaeal PCNA binding domain, PCNA, the helix-hairpin-helix DNA binding motifs from DNA topoisomerase V or the DNA binding protein Sso7d or Sac7d.

The invention also provides for a kit for performing at high pH a method selected from the group consisting of DNA synthesis; cloning of a DNA synthesis product; sequencing DNA; and linear or exponential PCR amplification, or any additional polymerase function encompassed herein, comprising a DNA polymerase fusion and packaging materials.

The kit of the invention may further comprise a high pH buffer, or a PCR enhancing factor and/or an additive.

DEFINITIONS

A "fusion" as defined herein, is a first amino acid sequence (protein) comprising a wild type or mutant DNA polymerase of the invention, joined to a second amino acid sequence defining a polypeptide that modulates one or more activities of the DNA polymerase including, but not limited to, processivity, salt-resistance, DNA binding, strand displacement activity, polymerase activity, nucleotide binding and recognition, 3'-5' or 5'-3' exonuclease activities, proofreading, fidelity and/or decreased DNA polymerization at room temperature, wherein the first and second amino acids are not found in the same relationship in nature. A "fusion" according to the invention contains two or more amino acid sequences (for example a sequence encoding a wild type or mutant DNA polymerase and a polypeptide that increases processivity and/or salt resistance) from unrelated proteins, joined to form a new functional protein. In one embodiment a "fusion" according to the invention comprises a first amino acid sequence derived from a first polymerase species (e.g. Pfu N-terminus) and a second amino acid sequence derived from a second polymerase species (e.g. KOD C-terminus. In one embodiment, a "fusion" of the invention comprises a first amino acid sequence derived from a first polymerase and a second amino acid sequence derived from a polypeptide that is not a polymerase. In one embodiment, the amino acid sequence derived from a polypeptide that is not a polymerase is not enzymatically active.

As used herein, "enzymatically active" means catalyzing a specific enzymatic reaction.

A fusion of the invention may present a foreign polypeptide which is found (albeit in a different protein) in an organism which also expresses the first protein, or it may be an "interspecies", "intergenic", etc. fusion of protein structures expressed by different kinds of organisms. The invention encompasses fusions wherein the polypeptide that increases processivity and/or salt resistance is joined N-terminally or C-terminally to, or is inserted at any internal position of a wild-type DNA polymerase or any of the mutant DNA polymerases described herein or known in the art.

In one embodiment, the fusion of the invention is a fusion DNA polymerase comprising a wild type or mutated thermostable DNA polymerase with or without 3'-5' exonuclease activity including but not limited to Pfu or Taq. The chimeric component added to the Pfu or Taq DNA polymerase is a basic or non-basic, protein or protein domain fused to the Pfu or Taq DNA polymerase at the N- or C-terminus or at any internal position such that the chimeric component and the polymerase are in a relationship that does not exist in nature. The chimeric contribution to the activity of the Pfu or Taq DNA polymerase increases or enhances processivity, DNA binding, strand displacement activity, polymerase activity, nucleotide binding and recognition, proofreading, fidelity, and salt resistance and/or decrease DNA polymerase activity at room temperature.

A DNA polymerase fusion of the invention has a >10% increase in one or more of the following activities (using the assays described hereinbelow) as compared to a DNA polymerase that is not a fusion using a genomic and/or plasmid template: processivity, efficiency, template length amplification capability, GC-rich target amplification efficiency, specificity, thermostability; intrinsic hot start capability, proofreading activity, fidelity, DNA binding activity, strand displacement activity, nucleotide binding and recognition, and salt resistance. A DNA polymerase fusion of the invention will also have a >10% decrease as compared to a DNA polymerase that is not a fusion using a genomic and/or plasmid template in one or more of the following activities (assayed as described hereinbelow): amplification slippage on templates with tri-nucleotide repeat stretches or DNA polymerase activity at room temperature. In one embodiment, a "fusion" of the invention has an extension time in a PCR reaction that is decreased by 5 sec, preferably 15 sec and more preferably 45 sec or more, as compared to the extension time observed in the presence of a DNA polymerase that is not a fusion alone. In another embodiment, a "fusion" of the invention has a decrease in the number of amplification cycles for PCR of 1, 1-5 or 5 or more cycles, as compared to a DNA polymerase that is not a fusion alone. In another embodiment, fewer units (0.001, 0.01, 0.1 or 1 or more) of a "fusion" of the invention are useful in an application of the invention as compared to a DNA polymerase that is not a fusion. In all cases where the activity of a "fusion" is compared to the activity of a DNA polymerase that is not a fusion, the DNA polymerase that is not a fusion is identical to the polymerase domain of the fusion, and only differs from the fusion by the absence of the second amino acid sequence of the fusion, as defined herein.

As used herein, a "genomic template" means a template comprising the nucleic acid material constituting the genome of a cell or an organism.

As used herein, "fused" or "joined" refers to any method known in the art for functionally connecting polypeptide domains, including without limitation recombinant fusion with or without intervening domains, intein-mediated fusion, non-covalent association, and covalent bonding, including disulfide bonding, hydrogen bonding, electrostatic bonding, and conformational bonding.

"Domain" refers to a unit of a protein or protein complex, comprising a polypeptide subsequence, a complete polypeptide sequence, or a plurality of peptide sequences.

As used herein, the term "modulate" refers to an increase or decrease of 2 fold, preferably 5 fold, preferably 20 fold, preferably 100 fold, more preferably 500 fold or more in an activity of a DNA polymerase fusion of the invention as compared to a DNA polymerase that is not a fusion. In one embodiment, the DNA polymerase domain of the fusion comprises one or more mutations, as described herein. In this embodiment, the term "modulate" refers to an increase or decrease of 2 fold, preferably 5 fold, preferably 20 fold, preferably 100 fold, more preferably 500 fold or more in an activity of a DNA polymerase fusion of the invention as compared to a DNA polymerase that is not a fusion, wherein the DNA polymerase that is not a fusion is identical to the mutant DNA polymerase domain of the fusion but lacks the second amino acid sequence of the fusion as described herein.

A DNA polymerase fusion be used in combination with a PCR enhancing factor and/or an additive, as described herein.

As used herein, "high pH" refers to a pH that is greater than 9. A "high pH" is preferably 10 or more, for example 10, 11, 12, 13 or 14. A "high pH" includes any pH greater than 9 and up to a pH of 14, for example a pH of 9.1, 9.5, 9.8, 10, 10.5, 11, 11.5, 12, 12.5, 13, 13.5, or 14 is a "high pH" according to the invention.

As used herein, "polypeptide that increases processivity and/or salt resistance" refers to a domain that is a protein or a region of a protein or a protein complex, comprising a polypeptide sequence, or a plurality of peptide sequences wherein that region increases processivity, as defined herein, or increases salt resistance, as defined herein. A "polypeptide that increases processivity and/or salt resistance useful according to the invention includes but is not limited to any of the domains included in Pavlov et al., supra or WO 01/92501, for example Sso7d, Sac7d, HMF-like proteins, PCNA homologs, helix-hairpin-helix domains, for example derived from Topoisomerase V, or the thioredoxin binding domain of T7 DNA polymerase as described in WO 97/29209, U.S. Pat. No. 5,972,603 and Bedford et al. Proc. Natl. Acad. Sci. USA 94: 479-484 (1997).

As used herein, "processivity" refers to the ability of a nucleic acid modifying enzyme, for example a polymerase, to remain attached to the template or substrate and perform multiple modification reactions. "Modification reactions" include but are not limited to polymerization, and exonucleolytic cleavage. "Processivity" also refers to the ability of a nucleic acid modifying enzyme, for example a polymerase, to modify relatively long (for example 0.5-1 kb, 1-5 kb or 5 kb or more) tracts of nucleotides. "Processivity" also refers to the ability of a nucleic, acid modifying enzyme, for example a DNA polymerase, to perform a sequence of polymerization steps without intervening dissociation of the enzyme from the growing DNA chains. "Processivity" can depend on the nature of the polymerase, the sequence of a DNA template, and reaction conditions, for example, salt concentration, temperature or the presence of specific proteins.

As used herein, "increased processivity" refers to an increase of 5-10%, preferably 10-50%, more preferably 50-100% or more, as compared to a wild type or mutant archael DNA polymerase that lacks a polypeptide that increases processivity and/or salt resistance as defined herein. Processivity and increased processivity can be measured according to the methods defined herein and in Pavlov et al., supra and WO 01/92501 A1. A polymerase with increased processivity that is a chimera comprising a polypeptide that increases processivity, as defined herein, is described in Pavlov et al. supra and WO 01/92501 A1.

As used herein, "increased salt resistance" refers to a polymerase that exhibits >50% activity at a salt concentration that is know to be greater than the maximum salt concentration at which the wild-type polymerase is active. The maximum salt concentration differs for each polymerase and is known in the art, or can be experimentally determined according to methods in the art. For example, Pfu is inhibited at 30 mM salt (in a PCR reaction) so a Pfu enzyme with increased salt resistance would have significant activity (>50%) at salt concentrations above 30 mM. A polymerase with increased salt resistance that is a fusion comprising a polypeptide that increases salt resistance, as defined herein, is described in Pavlov et al. supra and WO 01/92501 A1.

As used herein, "fidelity" refers to the accuracy of polymerization, or the ability of the polymerase to discriminate correct from incorrect substrates, (e.g., nucleotides) when synthesizing nucleic acid molecules (e.g. RNA or DNA) which are complementary to a template. The higher the fidelity of a polymerase, the less the polymerase misincorporates nucleotides in the growing strand during nucleic acid synthesis; that is, an increase or enhancement in fidelity results in a more faithful polymerase having a decreased error rate (decreased misincorporation rate).

The term "fidelity" as used herein also refers to the accuracy of DNA polymerization by a template-dependent DNA polymerase. The fidelity of a DNA polymerase is measured by the error rate (the frequency of incorporating an inaccurate nucleotide, i.e., a nucleotide that is not incorporated in a template-dependent manner). The accuracy or fidelity of DNA polymerization is maintained by both the polymerase activity and the 3'-5' exonuclease activity of a DNA polymerase. The term "high fidelity" refers to an error rate of $5\times10^{-6}$ per base pair or lower. The fidelity or error rate of a DNA polymerase may be measured using assays known in the art. For example, the error rates of DNA polymerase mutants can be tested using the lad PCR fidelity assay described in Cline, J., Braman, J. C., and Hogrefe, H. H. (96) NAR 24:3546-3551. Briefly, a 1.9 kb fragment encoding the lacIOlacZα target gene is amplified from pPRIAZ plasmid DNA using 2.5 U DNA polymerase (i.e. amount of enzyme necessary to incorporate 25 nmoles of total dNTPs in 30 min. at 72° C.) in the appropriate PCR buffer. The lacI-containing PCR products are then cloned into lambda GT10 arms, and the percentage of lad mutants (MF, mutation frequency) is determined in a color screening assay, as described (Lundberg, K. S., Shoemaker, D. D., Adams, M. W. W., Short, J. M., Sorge, J. A., and Mathur, E. J. (1991) Gene 180:1-8). Error rates are expressed as mutation frequency per by per duplication (MF/bp/d), where by is the number of detectable sites in the lacI gene sequence (349) and d is the number of effective target doublings. For each DNA polymerase mutant, at least two independent PCR amplifications are performed.

A DNA polymerase having increased/enhanced/higher fidelity is defined as a polymerase having about 2 to about 10,000 fold, about 2 to about 5,000 fold, or about 2 to about 2,000 fold (preferably greater than about 5 fold, more preferably greater than about 10 fold, still more preferably greater than about 50 fold, still more preferably greater than about 100 fold, still more preferably greater than about 500 fold and most preferably greater than about 1000 fold) reduction in the number of misincorporated nucleotides during synthesis of any given nucleic acid molecule of a given length. For example, a mutated polymerase may misincorporate one nucleotide in the synthesis of 1000 bases compared to an unmutated polymerase misincorporating 10 nucleotides. Such a mutant polymerase would be said to have an increase of fidelity of 10 fold.

A DNA polymerase having reduced misincorporation is defined herein as either a mutated or modified DNA polymerase that has about or less than 50%, or preferably about or less than 25%, more preferably about or less than 10% and most preferably about or less than 1% of relative misincorporation compared to the corresponding unmutated, unmodified or wild type enzyme. A DNA polymerase of lower fidelity may also initiate DNA synthesis with an incorrect nucleotide incorporation (Perrion & Loeb, 1989, J. Biol. Chem. 264:2898-2905).

The fidelity or misincorporation rate of a polymerase can be determined in a sequencing reaction by other methods known in the art (Eckert & Kunkel, Nucl. Acids Res. 3739-3744 (1990)). In one example, the sequence of a DNA molecule synthesized by the unmutated and mutated polymerase can be compared to the expected (known) sequence. In this way, the number of errors (misincorporation) can be determined for each enzyme and compared.

DNA binding and assays for detecting DNA binding are described in: PCT/US01/17492.

Strand displacement refers to the activity described in Hogrefe et al Methods of Enzymology (2001) 334:91-116 and Kong et al (93) J. Biol. Chem. 268:1965. Assays for measuring strand displacement activity are described in Hogrefe et al Methods of Enzymology (2001) 334:91-116 and Kong et al (93) J. Biol. Chem. 268:1965.

DNA polymerase activity at room temperature is as described in The Methods of Enzymology (2001) 334:91-116. Assays for measuring DNA polymerase activity at room temperature are described in The Methods of Enzymology (2001) 334:91-116 and in Nielson et al (1997) Strategies 10:40-43 Newsletter articles.

As used herein, "GC—rich target amplification efficiency" refers to the amplification efficiency of DNA templates that have greater than 50% GC content and are more difficult to melt during PCR. These targets frequently form secondary structure when the temperature cycles to the annealing temperature making PCR amplification difficult. "GC-rich target amplification" is assayed by performing PCR amplification on a target with greater than 50% GC content and comparing the yield of amplicon generated on a gel (see Biotechniques 2002 April; 32(4):866, 868, 870-2, 874).

A polymerase with "intrinsic hot start capability" refers to a thermostable DNA polymerase that has very low)(<25° DNA polymerase activity at non-stringent primer annealing temperatures (≤45°. These polymerases and assays for their detection are described in Nielson et al (1997) Strategies 10:40-43.

"DNA slippage" or "amplification slippage on templates with tri-nucleotide repeat stretches" and assays for detection of this activity is as described in J Mol Biol 2001 Sep. 14; 312(2):323-33, J Biol Chem 1999 Sep. 24; 274(39):27481-90, EMBO J. 2001 May 15; 20(10):2587-95, Biochemistry 1996 Jan. 23; 35(3):1046-53.

A DNA polymerase fusion that exhibits decreased DNA polymerase activity at room temperature preferably exhibits a shift in the activity vs. temperature profile such that reduced polymerase activity is observed at a suboptimal temperature (for example a non-specific primer annealing/extension temperature) and wild type polymerase activity is observed at stringent primer annealing/extension temperature. Such fusions are expected to exhibit improved specificity in PCR.

Methods of measuring the efficiency of a DNA polymerase are described in PCR Primer: A Laboratory Manual, 1995, CSHL Press, Cha and Thilly, pp. 37-51.

Methods of measuring template length amplification capability are described in Proc Natl. Acad. Sci. USA, 2002, 99:596-601 and J. Biotechnol., 2001, 88:141-149.

Methods of measuring specificity of a DNA polymerase are described in J. Biochem. (Tokyo), 1999, 126:762-8.

Methods of measuring thermostability of a DNA polymerase are described in FEMS Microbiol. Lett, 2002, 217: 89-94.

Methods of measuring nucleotide binding and recognition are described in J. Mol. Biol., 2002, 322:719-729 and Nucleic Acids Res., 2002, 30:605-13.

A "domain" useful according to the invention includes any double stranded or single stranded DNA binding domain known in the art or that becomes known in the art.

As used herein, "polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed toward the 5' end of the template strand. A "DNA polymerase" catalyzes the polymerization of deoxynucleotides. In a preferred embodiment, the DNA polymerase according to the invention is thermostable. In another preferred embodiment, the DNA polymerase according to the invention is an archaeal DNA polymerase.

As used herein in reference to a DNA polymerase, the term DNA polymerase includes a "functional fragment thereof". A "functional fragment thereof" refers to any portion of a wild-type or mutant DNA polymerase that encompasses less than the entire amino acid sequence of the polymerase and which retains the ability, under at least one set of conditions, to catalyze the polymerization of a polynucleotide. Such a functional fragment may exist as a separate entity, or it may be a constituent of a larger polypeptide, such as a fusion protein.

The nucleic acid polymerases used in the present invention may be mesophilic or thermophilic, and are preferably thermophilic. Preferred mesophilic DNA polymerases include T7 DNA polymerase, T5 DNA polymerase, T4 DNA polymerase, Klenow fragment DNA polymerase, DNA polymerase III and the like. Preferred thermostable DNA polymerases that may be used in the methods of the invention include Taq, Tne, Tma, Pfu, Tfl, Tth, Stoffel fragment, VENTT™ and DEEPVENT™ DNA polymerases, KOD, Tgo, JDF3, and mutants, variants and derivatives thereof (U.S. Pat. No. 5,436,149; U.S. Pat. No. 4,889,818; U.S. Pat. No. 4,965,185; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., Gene 112:29-35 (1992); Lawyer, F. C., et al., PCR Meth. Appl. 2:275-287 (1993); Flaman, J.-M, et al., Nuc. Acids Res. 22(15):3259-3260 (1994)). For amplification of long nucleic acid molecules (e.g, nucleic acid molecules longer than about 3-5 Kb in length), at least two DNA polymerases (one substantially lacking 3' exonuclease activity and the other having 3' exonuclease activity) are typically used. See U.S. Pat. No. 5,436,149; U.S. Pat. No. 5,512,462; Frames, W. M., Gene 112:29-35 (1992); and copending U.S. patent application Ser. No. 09/741,664, filed Dec. 21, 2000, the disclosures of which are incorporated herein in their entireties. Examples of DNA polymerases substantially lacking in 3' exonuclease activity include, but are not limited to, Taq, Tne(exo-), Tma(exo-), Pfu(exo-), Pwo(exo-), exo-KOD and Tth DNA polymerases, and mutants, variants and derivatives thereof.

As used herein, "archaeal" DNA polymerase refers to DNA polymerases that belong to either the Family B/pol I-type group (e.g., Pfu, KOD, Pfx; Vent®, Deep Vent®, Tgo, Pwo) or the pol II group (e.g., *Pyrococcus furiosus* DP1/DP2 2-subunit DNA polymerase). In one embodiment, "archaeal" DNA polymerase refers to thermostable archaeal DNA polymerases (PCR-able) and include, but arenot limited to, DNA polymerses isolated from *Pyrococcus* species (furiosus, species GB-D, woesii, abysii, *horikoshii*), *Thermococcus* species (kodakaraensis KOD1, litoralis, species 9 degrees North-7, species JDF-3, gorgonarius), *Pyrodictium occultum*, and *Archaeoglobus fulgidus*. It is estimated that suitable archaea would exhibit maximal growth temperatures of >80-85° C. or optimal growth temperatures of >70-80° C. Appropriate PCR enzymes from the archaeal pol I DNA polymerase group are commercially available, including Pfu (Stratagene), KOD (Toyobo), Pfx (Life Technologies, Inc.), Vent® (New England BioLabs), Deep Vent® (New England BioLabs), Tgo (Roche), and Pwo (Roche). Additional archaea related to those listed above are described in the following references: Archaea: A Laboratory Manual (Robb, F. T. and Place, A. R., eds.), Cold Spring Harbor Laboratory Press, Cold Spring Harbor, N.Y., 1995.

As used herein, "mutant" polymerase refers to a DNA polymerase, as defined herein, comprising one or more mutations that modulate, as defined herein, one or more activities of the DNA polymerase including, but not limited to, base analog detection activities, DNA polymerization activity, reverse transcriptase activity, processivity, salt resistance, DNA binding, strand displacement activity, nucleotide binding and recognition, 3'-5' or 5'-3' exonuclease activities, proofreading, fidelity, efficiency, specificity, thermostability and intrinsic hot start capability or decreased DNA polymerization at room temperature, decreased amplification slippage on templates with tri-nucleotide repeat stretches, decreased amplification cycles, decreased extension times, and a decrease in the amount of polymerase needed for the applications described herein. In one embodiment, the "mutant" polymerase of the invention refers to a DNA polymerase containing one or more mutations that reduce one or more base analog detection activities of the DNA polymerase. In one embodiment, a "mutant" refers to a polymerase that has a mutation that confers an improved polymerization rate or fidelity on the polymerase. In a preferred embodiment, the "mutant" polymerase of the invention has a reduced uracil detection activity. In a preferred embodiment, the "mutant" polymerase of the invention has a reduced inosine detection activity. In another preferred embodiment, the "mutant" polymerase of the invention has a reduced uracil and inosine detection activity. In another preferred embodiment, the "mutant" polymerase of the invention has a reduced DNA polymerization activity. Any of the "mutants" for example a mutant with reduced uracil activity, may also possess improved polymerization rate and/or fidelity, as compared to a wild-type polymerase. A "mutant" polymerase as defined herein, includes a polymerase comprising one or more amino acid substitutions, one or more amino acid insertions, a truncation or an internal deletion. A "mutant" polymerase as defined herein includes non-fusion and fusion polymerases as defined herein.

A "mutant" polymerase as defined herein also includes a fusion polymerase wherein any of the single, double or triple mutant DNA polymerases described herein, any mutant DNA polymerase comprising an insertion, described herein, or any of the truncated, or deleted mutant DNA polymerases described herein, occur in combination with a polypeptide that modulates one or more activities of the DNA polymerase including, but not limited to, DNA polymerization activity, base analog detection activities, DNA polymerization activity, reverse transcriptase activity, processivity, salt resistance, DNA binding, strand displacement activity, nucleotide or nucleotide analog binding and recognition, sensitivity to uracil, 3'-5' or 5'-3' exonuclease activities, proofreading, fidelity efficiency, specificity, thermostability and intrinsic hot start capability or decreased DNA polymerization at room temperature, decreased amplification slippage on templates with tri-nucleotide repeat stretches, decreased amplification cycles, decreased extension times, and a decrease in the amount of polymerase needed for the applications described herein, thereby forming a fusion, as defined herein. For example, a polypeptide that increases processivity and or salt resistance is described in WO 01/92501 A1 and Pavlov et al., 2002, Proc. Natl. Acad. Sci. USA, 99:13510-13515, herein incorporated by reference in their entirety. Other specific examples of commercially useful mutations include, but are not limited to, V93R,K,E,D in Pfu, which confer uracil insensitivity and D141A/E143A in Pfu, which eliminates 3'-5' exonuclease activity. A commercially useful truncation includes, but is not limited to the N-terminal truncation in Taq (KlenTaq) which eliminates 5'-3' exonulease activity.

As used herein, “mutation” refers to a change introduced into a parental or wild type DNA sequence that changes the amino acid sequence encoded by the DNA, including, but not limited to, substitutions, insertions, deletions or truncations. The consequences of a mutation include, but are not limited to, the creation of a new character, property, function, or trait not found in the protein encoded by the parental DNA, including, but not limited to, N terminal truncation, C terminal truncation or chemical modification. A “mutant” DNA polymerase as used herein, refers to a DNA polymerase comprising a mutation as defined herein. A “mutant” DNA polymerase of the invention can encompass a DNA polymerase “fusion” of the invention.

As used herein, a DNA polymerase with a “reduced DNA polymerization activity” is a DNA polymerase mutant comprising a DNA polymerization activity which is lower than that of the wild-type enzyme, e.g., comprising less than 10% DNA (e.g., 19.9%, 9%, 8%, 6%, 4%, 2% or less than 1%) polymerization activity of that of the wild-type enzyme or less than that of a DNA polymerase that is not a fusion. Methods used to generate and characterize Pfu DNA polymerases with reduced DNA polymerization activity are disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety. The invention contemplates a DNA polymerase fusion with reduced DNA polymerization activity.

As used herein, “proofreading” activity refers to 3' to 5' exonuclease activity of a DNA polymerase.

A “non-proofreading” enyzme refers to a DNA polymerase that is “3' to 5' exonuclease deficient” or “3' to 5' exo-”.

As used herein, “3' to 5' exonuclease deficient” or “3' to 5' exo-” refers to an enzyme that substantially lacks the ability to remove incorporated nucleotides from the 3' end of a DNA polymer. DNA polymerase exonuclease activities, such as the 3' to 5' exonuclease activity exemplified by members of the Family B polymerases, can be lost through mutation, yielding an exonuclease-deficient polymerase. As used herein, a DNA polymerase that is deficient in 3' to 5' exonuclease activity substantially lacks 3' to 5' exonuclease activity. “Substantially lacks” encompasses a complete lack of activity, for example, 0.03%, 0.05%, 0.1%, 1%, 5%, 10%, 20% or even up to 50% of the exonuclease activity relative to the parental enzyme. Methods used to generate and characterize 3'-5' exonuclease DNA polymerases including the D141A and E143A mutations as well as other mutations that reduce or eliminate 3'-5' exonuclease activity are disclosed in the pending U.S. patent application Ser. No. 09/698,341 (Sorge et al; filed Oct. 27, 2000). Additional mutations that reduce or eliminate 3' to 5' exonuclease activity are known in the art and contemplated herein.

As used herein, “synthesis” refers to any in vitro method for making a new strand of polynucleotide or elongating existing polynucleotide (i.e., DNA or RNA) in a template dependent manner. Synthesis, according to the invention, includes amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules.

“DNA synthesis”, according to the invention, includes, but is not limited to, PCR, the labelling of polynucleotide (i.e., for probes and oligonucleotide primers), and polynucleotide sequencing. The invention contemplates mutant DNA polymerases, and fusions thereof, that exhibit reduced base analog detection (for example, reduced detection of a particular base analog such as uracil or inosine or reduced detection of at least two base analogs).

As used herein, “base analogs” refer to bases that have undergone a chemical modification as a result of the elevated temperatures required for PCR reactions. In a preferred embodiment, “base analog” refers to uracil that is generated by deamination of cytosine. In another preferred embodiment, “base analog” refers to inosine that is generated by deamination of adenine.

As used herein, “thermostable” refers to an enzyme which is stable and active at temperatures as great as preferably between about 90-100° C. and more preferably between about 70-980 C. to heat as compared, for example, to a non-thermostable form of an enzyme with a similar activity. For example, a thermostable nucleic acid polymerase derived from thermophilic organisms such as *P. furiosus, M. jannaschii, A. fulgidus* or *P. horikoshii* are more stable and active at elevated temperatures as compared to a nucleic acid polymerase from *E. coli*. A representative thermostable nucleic acid polymerase isolated from *P. furiosus* (Pfu) is described in Lundberg et al., 1991, Gene, 108:1-6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima*, or from thermophilic archaea *Thermococcus litoralis*, and *Methanothermus fervidus*.

Temperature stable polymerases are preferred in a thermocycling process wherein double stranded nucleic acids are denatured by exposure to a high temperature (about 95° C.) during the PCR cycle.

As used herein, the term “template DNA molecule” refers to that strand of a nucleic acid from which a complementary nucleic acid strand is synthesized by a DNA polymerase, for example, in a primer extension reaction.

As used herein, the term “template dependent manner” is intended to refer to a process that involves the template dependent extension of a primer molecule (e.g., DNA synthesis by DNA polymerase). The term “template dependent manner” refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene*, 4th Ed., W. A. Benjamin, Inc., Menlo Park, Calif. (1987)).

As used herein, an “amplified product” refers to the double stranded polynucleotide population at the end of a PCR amplification reaction. The amplified product contains the original polynucleotide template and polynucleotide synthesized by DNA polymerase using the polynucleotide template during the PCR reaction.

As used herein, "polynucleotide template" or "target polynucleotide template" or "template" refers to a polynucleotide containing an amplified region. The "amplified region," as used herein, is a region of a polynucleotide that is to be, for example, synthesized by polymerase chain, reaction (PCR). For example, an amplified region of a polynucleotide template resides between two sequences, to which two PCR primers are complementary.

As used herein, the term "primer" refers to a single stranded DNA or RNA molecule that can hybridize to a polynucleotide template and prime enzymatic synthesis of a second polynucleotide strand. A primer useful according to the invention is between 10 to 100 nucleotides in length, preferably 17-50 nucleotides in length and more preferably 17-45 nucleotides in length.

"Complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

The term "wild-type" refers to a gene or gene product which has the characteristics of that gene or gene product when isolated from a naturally occurring source. In contrast, the term "modified" or "mutant" refers to a gene or gene product which displays altered characteristics when compared to the wild-type gene or gene product. For example, a mutant DNA polymerase in the present invention is a DNA polymerase which exhibits a reduced uracil detection activity.

As used herein, "reduced base analog detection" refers to a DNA polymerase, with a reduced ability to recognize a base analog, for example, uracil or inosine, present in a DNA template. In this context, mutant DNA polymerase with "reduced" base analog detection activity is a DNA polymerase mutant having a base analog detection activity which is lower than that of the wild-type enzyme. In the case of a mutant DNA polymerase fusion the activity of a mutant DNA polymerase may be compared to the corresponding non-fusion DNA polymerase, i.e., having less than 10% (e.g., 9.9%, 9%, 8%, 6%, 4%, 2% or less than 1%) of the base analog detection activity of that of the wild-type enzyme. Base analog detection activity may be determined according to the assays similar to those described for the detection of DNA polymerases having a reduced uracil detection activity as described in Greagg et al. (1999) Proc. Natl. Acad. Sci. 96, 9045-9050. Alternatively, "reduced" base analog detection refers to a mutant DNA polymerase with a reduced ability to recognize a base analog, the "reduced" recognition of a base analog being evident by an increase in the amount of >10 Kb PCR of at least 10%, preferably 50%, more preferably 90%, most preferably 99% or more, as compared to a wild type DNA polymerase without a reduced base analog detection activity. The amount of a >10 Kb PCR product is measured either by spectorophotometer-absorbance assays of gel eluted >10 Kb PCR DNA product or by fluorometric analysis of >10 Kb PCR products in an ethidium bromide stained agarose electrophoresis gel using, for example, a Molecular Dynamics (MD) FluorImager™ (Amersham Biosciences, catalogue #63-0007-79).

As used herein, "reduced uracil detection" refers to a DNA polymerase with a reduced ability to recognize a uracil base present in a DNA template. In this context, mutant DNA polymerase with "reduced" uracil detection activity is a DNA polymerase mutant having a uracil detection activity which is lower than that of the wild-type enzyme, i.e., having less than 10% (e.g., 9.9%1, 9%, 8%, 6%, 4%, 2% or less than 1%) of the uracil detection activity of that of the wild-type enzyme. Uracil detection activity may be determined according to the assays described in Greagg et al. (1999) Proc. Natl. Acad. Sci. 96, 9045-9050. Alternatively, "reduced" uracil detection refers to a mutant DNA polymerase with a reduced ability to recognize uracil, the "reduced" recognition of uracil being evident by an increase in the amount of >10 Kb PCR of at least 10%, preferably 50%, more preferably 90%, most preferably 99% or more, as compared to a wild type DNA polymerase without a reduced uracil detection activity. The amount of a >10 Kb PCR product is measured either by spectorophotometer-absorbance assays of gel eluted >10 Kb PCR DNA product or by fluorometric analysis of >10 Kb PCR products in an ethidium bromide stained agarose electrophoresis gel using, for example, a Molecular Dynamics (MD) FluorImager™ (Amersham Biosciences, catalogue #63-0007-79).

As used herein, "chemically modified" refers to a nucleic acid that is chemically or biochemically modified or contains non-natural or derivatized nucleotide bases. Such modifications include, for example, labels, methylation, substitution of one or more of the naturally occurring nucleotides with an analog, internucleotide modifications such as uncharged linkages (e.g. methyl phosphonates, phosphorodithioates, etc.), pendent moieties (e.g., polypeptides), intercalators, (e.g. acridine, psoralen, etc.) chelators, alkylators, and modified linkages (e.g. alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

As used herein, a "PCR enhancing factor" or, a "Polymerase Enhancing Factor" (PEF) refers to a complex or protein possessing polynucleotide polymerase enhancing activity including, but not limited to, PEF, dUTPase, ssbPCNA, RFC, helicases etc (Hogrefe et al., 1997, Strategies 10:93-96; and U.S. Pat. No. 6,183,997, both of which are hereby incorporated by reference). A "PCR enhancing factor" also includes non-protein factors, for example DMSO and betaine.

The invention also contemplates mutant archael DNA polymerases in combination with accessory factors, for example as described in U.S. Pat. No. 6,333,158, and WO 01/09347 A2, hereby incorporated by reference in their entirety.

As used herein, "additive" refers to a PCR enhancing additive, including but not limited to, Pfu dUTPase (PEF), PCNA, RPA, ssb, antibodies, DMSO, betaine, or 3'-5' exonuclease (e.g., Pfu G387P).

The invention also provides for kits for performing at high pH a method selected from the group consisting of: DNA synthesis; cloning of a DNA synthesis product; sequencing DNA; and linear or exponential PCR amplification comprising a DNA polymerase fusion and packaging materials therefore. The kits of the invention may include a high pH buffer and/or a PCR enhancing factor and/or an additive.

As used herein, a high pH buffer refers to a buffer that has a pH greater than 9. As used herein, "high pH" refers to a pH that is greater than 9. A "high pH" is preferably 10 or more, for example 11, 12, 13 or 14. A "high pH" includes any pH greater than 9 and up to a pH of 14, for example a pH of 9.1, 9.5, 9.8, 10, 10.5, 11, 11.5, 12, 12.5, 13, 13.5, or 14 is a "high pH" according to the invention.

In a preferred embodiment the high pH buffer is a standard PCR reaction buffer, for example cloned Pfu reaction buffer described in Example 3, but wherein the buffering component is at a high pH (i.e., 9.1-14). For example, a buffering component of the invention is 30 mM Tris [Tris(hydroxymethyl) aminomethane] at a pH of 10.0 or 11.8. The pH of the buffering component in standard PCR reaction buffers is from 8.3-8.8. The buffering component is used at a concentration from 1 mM to 1M in the final PCR reaction and is at a pH from 9.1-14. The highly alkaline buffer for PCR reactions is used with the fusion DNA polymerases or fusion DNA polymerase blends of the invention. A buffering component of the present invention includes, but is not limited to, Tris, Tricine, bicine, Bis-Tris, CAPS, EPPS, HEPES, MES, MOPS, PIPES, TAPS and TES.

As used herein "FEN-1 nuclease" refers to thermostable FEN-1 endonucleases useful according to the invention and includes, but is not limited to, FEN-1 endonuclease purified from the "hyperthermophiles", e.g., from *M. jannaschii, P. furiosus* and *P. woesei*. See U.S. Pat. No. 5,843,669, hereby incorporated by reference.

According to the methods of the present invention, the addition of FEN-1 in the amplification reaction dramatically increases the efficiency of the multi-site mutagenesis. 400 ng to 4000 ng of FEN-1 may be used in each amplification reaction. Preferably 400-1000 ng, more preferably, 400-600 ng of FEN-1 is used in the amplification reaction. In a preferred embodiment of the invention, 400 ng FEN-1 is used.

As used herein, "*Thermus* DNA ligase" refers to a thermostable DNA ligase that is used in the multi-site mutagenesis amplification reaction to ligate the mutant fragments synthesized by extending each mutagenic primer so as to form a circular mutant strand. Tth and Taq DNA ligase require NAD as a cofactor.

Preferably, 1-20 U DNA ligase is used in each amplification reaction, more preferably, 2-15 U DNA ligase is used in each amplification reaction.

In a preferred embodiment, 15 U Taq DNA ligase is used in an amplification reaction. Taq DNA ligase cofactor NAD is used at a concentration of 0-1 mM, preferably between 0.02-0.2 mM, more preferably at 0.1 mM.

As used herein, a "blend" refers to a combination of two or more DNA polymerases comprising at least one DNA polymerase fusion and at least one non-fusion DNA polymerase (see Example 2). The invention contemplates a "blend" wherein at least one of said fusion or non-fusion DNA polymerase is thermostable, is an archael or eubacterial DNA polymerase and/or is a Pfu DNA polymerase. The ratio of DNA polymerase enzymes in a "blend" comprising one fusion and one non-fusion polymerase is in the range of 1:1-1:5-5:1, or 1:1-1:10-10:1, or 1:1-1:25-25:1 or 1:1-1:100-100:1. For embodiments wherein a "blend" comprises one fusion DNA polymerase and two non-fusion polymerases the ratio of the first non-fusion DNA polymerase to the second non-fusion DNA polymerase is in the range of 1:1-1:5-5:1, or 1:1-1:10-10:1, or 1:1-1:25-25:1 or 1:1-1:100-100:1. A "blend" of the invention has a >10% increase in one or more of the following activities (using the assays described hereinbelow) as compared to the non-fusion component of the blend using a genomic and/or plasmid template: processivity, efficiency, template length amplification capability, GC-rich target amplification efficiency, specificity, thermostability; intrinsic hot start capability, proofreading activity, fidelity, DNA binding activity, strand displacement activity, nucleotide binding and recognition, and salt resistance. A blend of the invention will also have a >10% decrease as compared to the non-fusion blends using genomic and/or plasmid template in one or more of the following activities (assayed as described hereinbelow): amplification slippage on templates with tri-nucleotide repeat stretches or DNA polymerase activity at room temperature. In one embodiment, a "blend" of the invention has an extension time in a PCR reaction that is decreased by 5 sec, preferably 15 sec and more preferably 45 sec or more, as compared to the extension time observed in the presence of the non-fusion component of the blend alone. In another embodiment, a "blend" of the invention has a decrease in the number of amplification cycles for PCR of 1, 1-5 or 5 or more cycles; as compared to the non-chimeric component of the blend alone. In another embodiment, fewer units (0.001, 0.01, 0.1 or 1 or more) of a "blend" of the invention are useful in an application of the invention as compared to the non-fusion component of the blend.

A blend may also include a PCR enhancing factor and/or an additive, as described herein.

The invention also relates to compositions made for carrying out the methods of the invention and compositions made while carrying out the methods of the invention. Such compositions may comprise one or more components selected from the group consisting of one or more polymerases of the invention, one or more nucleotides, one or more templates, one or more reaction buffers or buffering salts, one or more primers, one or more nucleic acid products made by the methods of the invention and the like.

BRIEF DESCRIPTION OF THE DRAWINGS

FIG. 10: Oligonucleotide Primers for QuickChange Mutagenesis (SEQ ID Nos: 6-14)

FIG. 11: (a) dUTP incorporation of V93E and V93R mutants compared to wild type Pfu DNA polymerase.

(b) PCR Amplification of Pfu V93R mutant extract in the presence of 100% dUTP.

Figure 12:
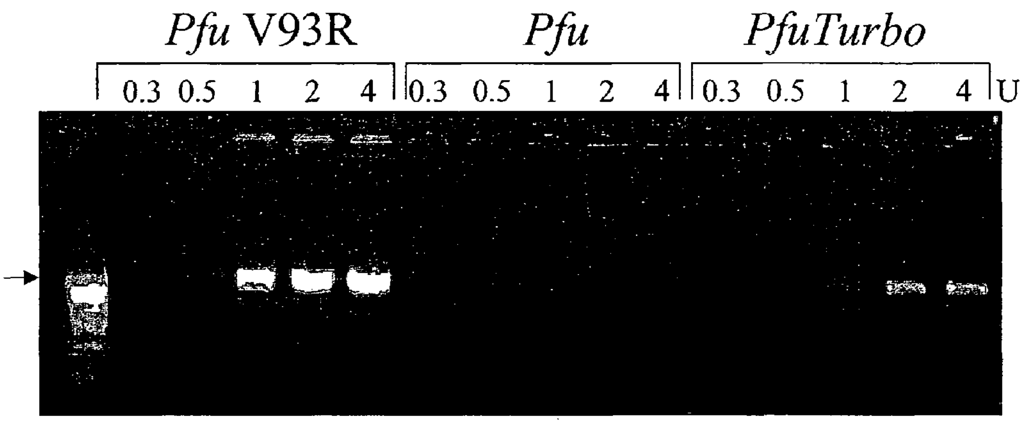

FIG. 12: Comparison of the efficacy of "long" PCR amplification of Pfu DNA polymerase mutants and wt enzyme.

FIG. 13: 13A. DNA sequence of mutant archeael DNA polymerases

13B. Amino acid sequence of mutant archeael DNA polymerases

FIG. 14: DNA and Amino acid sequence of mutant Tgo DNA polymerase DNA

Figure 15:
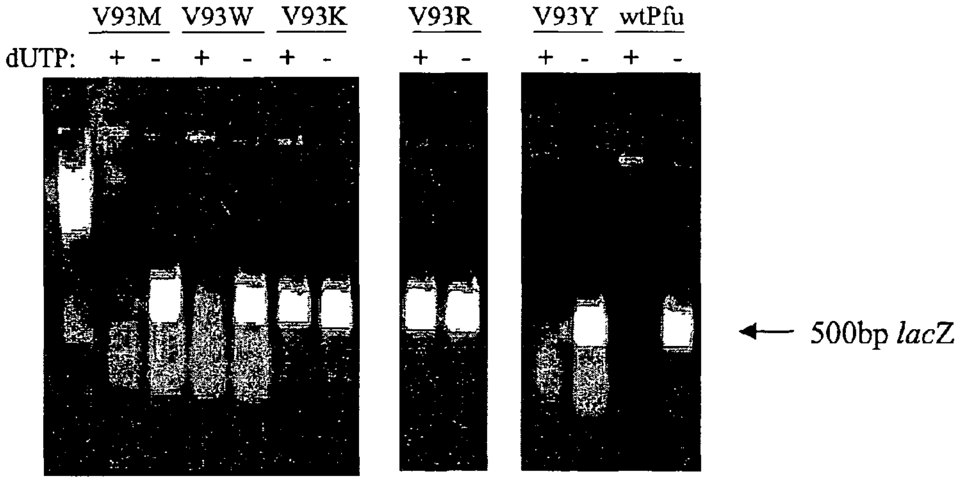
Figure 15:
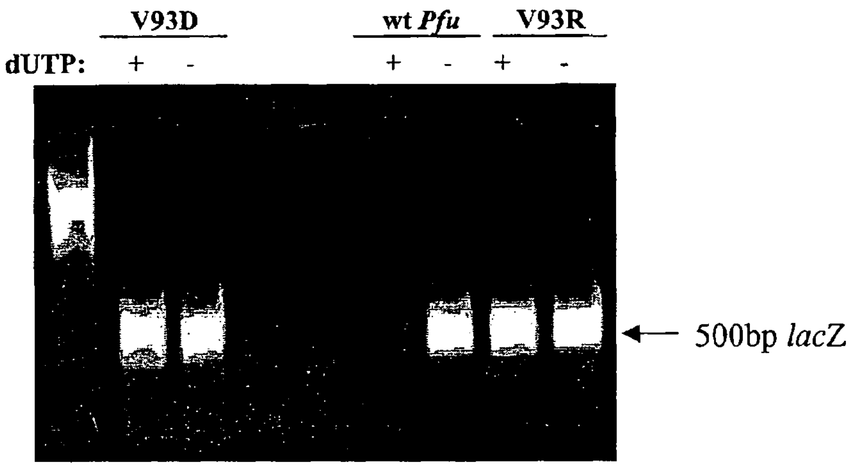
Figure 15:
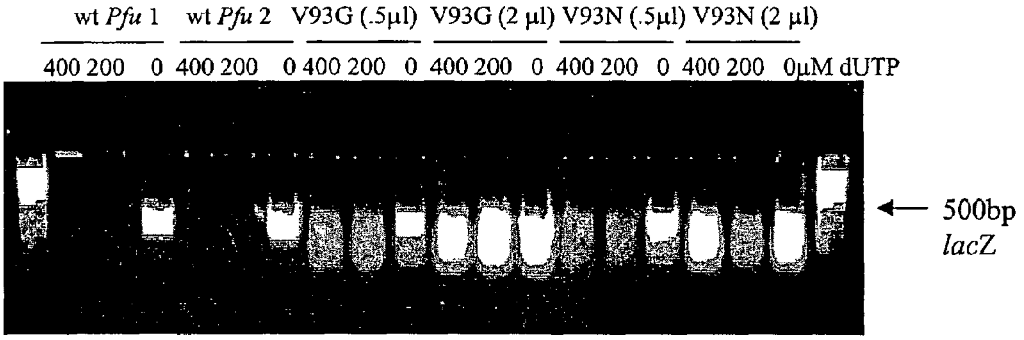

FIG. 15: dUTP incorporation of Pfu mutants compared to wild type Pfu DNA polymerase

15A. dUTP incorporation of Pfu mutants V93W, V93Y, V93M, V93K and V93R compared to wild type Pfu DNA polymerase

15B. dUTP incorporation of the Pfu V93D and V93R mutants compared to wild type Pfu DNA polymerase.

15C. dUTP incorporation of the Pfu V93N and V93G mutant compared to wild type Pfu DNA polymerase FIG. 16: DNA polymerase activity of N-terminal Pfu DNA polymerase truncation mutants.

FIG. 17: shows the sequence of

A. HMf-like protein
B. HMf-like protein-Taq fusion
C. HMf-like protein-Taq fusion
D. Pfu WT-HMf like protein fusion
E. Pfu WT-HMf like protein fusion
F. Pfu-V93 R or E-HMf-like protein fusion
G. Pfu-V93 R or E-HMf-like protein fusion
H. Pfu-G387P/V93 R or E-HMf-like protein fusion
I. Pfu-G387PN93 R or E-HMf-like protein fusion
J. Pfu-D141A/E143A/V93 R or E-HMf-like protein fusion
K. Pfu-D141A/E143A/V93 R or E-HMf-like protein fusion
L. KOD-HMf-like protein fusion
M. KOD-HMf-like protein fusion
N. HMf-like protein-Vent fusion
O. HMf-like protein-Vent fusion
P. HMf-like protein-DeepVent fusion
Q. HMf-like protein-DeepVent fusion
R. HMf-like protein-JDF3 fusion
S. HMf-like protein-JDF3 fusion
T. PCNA
U. PCNA-Taq fusion
V. PCNA-Taq fusion
W. PCNA-PfuWT fusion
X. PCNA-PfuWT fusion
Y. Pfu-V93 R or E-PCNA fusion
Z. Pfu-V93 R or E-PCNA fusion
AA. Pfu-G387P/V93 R or E-PCNA fusion
BB. Pfu-G387P/V93 R or E-PCNA fusion
CC. Pfu-D141A/E143A/V93 R or E-PCNA fusion
DD. Pfu-D141A/E143A/V93 R or E-PCNA fusion
EE. KOD-PCNA fusion
FF. KOD-PCNA protein fusion
GG. PCNA-Vent fusion
HH. PCNA-Vent fusion
II. PCNA-DeepVent fusion
JJ. PCNA-DeepVent fusion
KK. PCNA-JDF3 fusion
LL. PCNA-JDF3 fusion
MM. Sac7d
NN. Sac7d-Taq fusion
OO. Sac7d-Taq fusion
PP. Sac7d-PfuWT fusion
QQ. Sac7d-PfuWT fusion
RR. Pfu-V93 R or E-Sac7d-like protein fusion
SS. Pfu-V93 R or E-Sac7d fusion
TT. Pfu-G387P/V93 R or E-Sac7d fusion UU. Pfu-G387P/V93 R or E-Sac7d fusion
VV. Pfu-D141A/E143A/V93 R or E-Sac7d fusion
WW. KOD-Sac7d fusion
XX. KOD-Sac7d protein fusion
YY. Sac7d-Vent fusion
ZZ. Sac7d-Vent fusion
AAA. Sac7d-DeepVent fusion
BBB. Sac7d-DeepVent fusion
CCC. Sac7d-JDF3 fusion
DDD. Sac7d-JDF3 fusion
EEE. Sso7D
FFF. Sso7D-Taq fusion
GGG. Sso7D-PfuWT fusion
HHH. Pfu-G387P/V93 R or E-Sso7D fusion
III. Pfu-G387P/V93 R or E-Sso7D fusion
JJJ. Pfu-D141A/E143A/V93 R or E-Sso7D fusion
KKK. KOD-Sso7D fusion
LLL. KOD-Sso7D fusion
MMM. Sso7D-Vent fusion
NNN. Sso7D-Vent fusion
OOO. Sso7D-DeepVent fusion
PPP. Sso7D-DeepVent fusion
QQQ. Sso7D-JDF3 fusion
RRR. Sso7D-JDF3 fusion FIG. 18: HhH motif Sequences (a) Motifs conserved between topo V, RecA, and leucine-responsive regulator signature sequences. Topo V amino acid region 236-298 made no hits in databases and is not shown. A short region between positions 677-695 connecting repeats G and H and the 19-aa residues at the end of the sequence is not shown for simplicity. Invariant residues are shown on blue backgrounds with white lettering. Conservative positions are highlighted on the yellow background. (b) Structure of topo V HhH motifs. Backgrounds of Lys-68 and Lys-72 of -pol and corresponding positions in C and G repeats of topo V are colored cyan and magenta, respectively. Secondary structures in a and b were predicted by using JPRED. Cylinders represent-helices, and lines between them (b) represent-hairpins. MkTpV, *M. kandleri* topo V; HTH asnC, the three-element fingerprint that provides a signature for the HTH motif of the asnC bacterial regulatory proteins; HTH SS, secondary structure of the HTH motif; A-L, topo V's HhH repeats; EcRuvA, *E. coli* RuvA protein, HsPolB, human polymerase; TaqPol, *T. aquaticus* polymerase I; HhH SS, secondary structure of HhH motifs. ALSCRIPT (Pargellis et al. (1988) J. Biol. Chem. 263, 7678-7685) was used to illustrate the alignments. Cited from Belova et al., 2001, Proc. Natl. Acad. Sci. USA, 98:6015).

FIG. 19: Additional sequences of the invention

FIG. 20: DNA and Amino acid sequence of wild type Pfu DNA polymerase

DETAILED DESCRIPTION

The present invention discloses DNA polymerase fusions for use in PCR, DNA sequencing and mutagenesis protocols at high pH. The invention allows for PCR reactions with shorter extension times that will facilitate PCR amplification of genomic DNA templates and improve the efficacy of long PCR.

I. DNA Polymerases According to the Invention

The invention provides for a DNA polymerase fusion. The DNA polymerase fusions, useful according to the invention, can be with or without 3'-5' exonuclease activity, i.e., proofreading or non-proofreading, and are preferably thermostable. The invention provides for DNA polymerase fusions that harbor one or more mutations that modify one or more activities normally found in the wild-type DNA polymerase that is not a fusion, as defined herein.

Additional nucleic acid polymerases useful according to the invention are listed below.

A. Bacteriophage DNA Polymerases (Useful for 37° C. Assays):

Bacteriophage DNA polymerases are devoid of 5' to 3' exonuclease activity, as this activity is encoded by a separate polypeptide. Examples of suitable DNA polymerases are T4, T7, and ϕ29 DNA polymerase. The enzymes available commercially are: T4 (available from many sources e.g., Epicentre) and T7 (available from many sources, e.g. Epicentre for unmodified and USB for 3' to 5' exo T7 "Sequenase" DNA polymerase).

B. Archaeal DNA Polymerases:

There are 2 different classes of DNA polymerases which have been identified in archaea: 1. Family B/pol I type (homologs of Pfu from *Pyrococcus furiosus*) and 2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol I or pol II) can be derived from archaea with optimal growth temperatures that are similar to the desired assay temperatures.

Thermostable archaeal DNA polymerases are isolated from *Pyrococcus* species (furiosus, species GB-D, woesii, abysii, horikoshii), *Thermococcus* species (kodakaraensis KOD1, litoralis, species 9 degrees North-7, species JDF-3, gorgonarius), *Pyrodictium occultum*, and *Archaeoglobus fulgidus*. It is estimated that suitable archaea would exhibit maximal growth temperatures of >80-85° C. or optimal growth temperatures of >70-80° C. Appropriate PCR enzymes from the archaeal pol I DNA polymerase group are commercially available, including Pfu (Stratagene), KOD (Toyobo), Pfx (Life Technologies, Inc.), Vent (New England BioLabs), Deep Vent (New England BioLabs), Tgo (Roche), and Pwo (Roche).

Additional archaea DNA polymerases related to those listed above are described in the following references: Archaea: A Laboratory Manual (Robb, F. T. and Place, A. R., eds.), Cold Spring Harbor Laboratory Press, Cold Spring Harbor, N.Y., 1995 and *Thermophilic Bacteria* (Kristjansson, J. K., ed.) CRC Press, Inc., Boca Raton, Fla., 1992.

The invention therefore provides for thermostable archaeal DNA polymerases of either Family B/pol I type or pol II type as well as mutants or derivatives thereof.

TABLE 1

| ACCESSION INFORMATION FOR CLONED FAMILY B POLYMERASES | |
|---|---|
| Vent *Thermococcus litoralis* | |
| ACCESSION | AAA72101 |
| PID | g348689 |
| VERSION | AAA72101.1 GI: 348689 |
| DBSOURCE | locus THCVDPE accession M74198.1 |
| THEST *THERMOCOCCUS* SP. (STRAIN TY) | |
| ACCESSION | O33845 |
| PID | g3913524 |
| VERSION | O33845 GI: 3913524 |
| DBSOURCE | swissprot: locus DPOL_THEST, accession O33845 |
| Pab *Pyrococcus abyssi* | |
| ACCESSION | P77916 |
| PID | g3913529 |
| VERSION | P77916 GI: 3913529 |
| DBSOURCE | swissprot: locus DPOL_PYRAB, accession P77916 |

TABLE 1-continued

| ACCESSION INFORMATION FOR CLONED FAMILY B POLYMERASES | |
|---|---|
| PYRHO *Pyrococcus horikoshii* | |
| ACCESSION | O59610 |
| PID | g3913526 |
| VERSION | O59610 GI: 3913526 |
| DBSOURCE | swissprot: locus DPOL__PYRHO, accession O59610 |
| PYRSE *PYROCOCCUS* SP. (STRAIN GE23) | |
| ACCESSION | P77932 |
| PID | g3913530 |
| VERSION | P77932 GI: 3913530 |
| DBSOURCE | swissprot: locus DPOL__PYRSE, accession P77932 |
| DeepVent *Pyrococcus* sp. | |
| ACCESSION | AAA67131 |
| PID | g436495 |
| VERSION | AAA67131.1 GI: 436495 |
| DBSOURCE | locus PSU00707 accession U00707.1 |
| Pfu *Pyrococcus furiosus* | |
| ACCESSION | P80061 |
| PID | g399403 |
| VERSION | P80061 GI: 399403 |
| DBSOURCE | swissprot: locus DPOL__PYRFU, accession P80061 |
| JDF-3 *Thermococcus* sp. Unpublished Baross gi\|2097756\|pat\|US\|5602011\|12 Sequence 12 from patent U.S. Pat. No. 5,602,011 | |
| 9degN *THERMOCOCCUS* SP. (STRAIN 9ON-7). | |
| ACCESSION | Q56366 |
| PID | g3913540 |
| VERSION | Q56366 GI: 3913540 |
| DBSOURCE | swissprot: locus DPOL__THES9, accession Q56366 |
| KOD *Pyrococcus* sp. | |
| ACCESSION | BAA06142 |
| PID | g1620911 |
| VERSION | BAA06142.1 GI: 1620911 |
| DBSOURCE | locus PYWKODPOL accession D29671.1 |
| Tgo *Thermococcus gorgonarius*. | |
| ACCESSION | 4699806 |
| PID | g4699806 |
| VERSION | GI: 4699806 |
| DBSOURCE | pdb: chain 65, release Feb. 23, 1999 |
| THEFM *Thermococcus fumicolans* | |
| ACCESSION | P74918 |
| PID | g3913528 |
| VERSION | P74918 GI: 3913528 |
| DBSOURCE | swissprot: locus DPOL__THEFM, accession P74918 |
| METTH *Methanobacterium thermoautotrophicum* | |
| ACCESSION | O27276 |
| PID | g3913522 |
| VERSION | O27276 GI: 3913522 |
| DBSOURCE | swissprot: locus DPOL__METTH, accession O27276 |
| Metja *Methanococcus jannaschii* | |
| ACCESSION | Q58295 |
| PID | g3915679 |
| VERSION | Q58295 GI: 3915679 |
| DBSOURCE | swissprot: locus DPOL__METJA, accession Q58295 |
| POC *Pyrodictium occultum* | |
| ACCESSION | B56277 |
| PID | g1363344 |
| VERSION | B56277 GI: 1363344 |
| DBSOURCE | pir: locus B56277 |
| ApeI *Aeropyrum permix* | |
| ACCESSION | BAA81109 |
| PID | g5105797 |
| VERSION | BAA81109.1 GI: 5105797 |
| DBSOURCE | locus AP000063 accession AP000063.1 |

TABLE 1-continued

| ACCESSION INFORMATION FOR CLONED FAMILY B POLYMERASES | |
|---|---|
| ARCFU *Archaeoglobus fulgidus* | |
| ACCESSION | O29753 |
| PID | g3122019 |
| VERSION | O29753 GI: 3122019 |
| DBSOURCE | swissprot: locus DPOL__ARCFU, accession O29753 |
| *Desulfurococcus* sp. Tok. | |
| ACCESSION | 6435708 |
| PID | g64357089 |
| VERSION | GT: 6435708 |
| DBSOURCE | pdb. chain 65, release Jun. 2, 1999 |

C. Eubacterial DNA Polymerases:

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol III catalytic subunit lacks 5' to 3' exonuclease activity, but in some cases 3' to 5' exonuclease activity is located in the same polypeptide.

There are no commercial sources of eubacterial pol II and pol III DNA polymerases.

There are a variety of commercially available Pol I DNA polymerases, some of which have been modified to reduce or abolish 5' to 3' exonuclease activity.

Suitable thermostable pol I DNA polymerases can be isolated from a variety of thermophilic eubacteria, including *Thermus* species and *Thermotoga maritima* such as *Thermus aquaticus* (Taq), *Thermus thermophilus* (Tth) and *Thermotoga maritima* (Tma UlTma).

Additional eubacteria related to those listed above are described in *Thermophilic Bacteria* (Kristjansson, J. K., ed.) CRC Press, Inc., Boca Raton, Fla., 1992.

The invention further provides for chimeric or non-chimeric DNA polymerases that are chemically modified according to methods disclosed in U.S. Pat. Nos. 5,677,152, 6,479,264 and 6,183,998, the contents of which are hereby incorporated by reference in their entirety.

II. Preparing Mutant DNA Polymerases

According to the invention, DNA polymerases can be generated from any DNA polymerase either wild-type or modified to contain one or more mutations, including but not limited to, one or more point mutations, N- and/or C-truncations, internal deletion or insertion that would cause the DNA polymerase to behave differently than the wild-type polymerase. DNA polymerase mutations useful to the invention include, but are not limited to, mutations that confer base analog or uracil insensitivity, increase fidelity, eliminate 3'-5' exonuclease activity or eliminate 5'-3' exonuclease activity or reduce polymerase activity. Specific examples of useful mutations or truncations include but are not limited to, V93R, K,E,D in Pfu DNA polymerase, which confer uracil insensitivity, D141A/E143A in Pfu DNA polymerase, which eliminates 3'-5' exonuclease activity, and the N-terminal truncation of Taq DNA polymerase to eliminate 5'-3' exonuclease activity(KlenTaq). Methods for generating DNA polymerase mutants are described below and other methods are known in the art.

Genetic Modifications—Mutagenesis

Direct comparison of DNA polymerases from diverse organisms indicates that the domain structure of these enzymes is highly conserved and in many instances, it is possible to assign a particular function to a well-defined domain of the enzyme. For example, the six most conserved C-terminal regions, spanning approximately 340 amino acids, are located in the same linear arrangement and contain highly conserved motifs that form the metal and dNTP binding sites and the cleft for holding the DNA template and are therefore essential for the polymerization function. In another example, the three amino acid regions containing the critical residues in the *E. coli* DNA polymerase I involved in metal binding, single-stranded DNA binding, and catalysis of the 3'-5' exonuclease reaction are located in the amino-terminal half and in the same linear arrangement in several prokaryotic and eukaryotic DNA polymerases. The location of these conserved regions provides a useful model to direct genetic modifications for preparing mutant DNA polymerase with modified activities whilst conserving essential functions e.g. DNA polymerization and proofreading activity.

For example, a mutant DNA polymerase can be generated by genetic modification (e.g., by modifying the DNA sequence of a wild-type DNA polymerase). A number of methods are known in the art that permit the random as well as targeted mutation of DNA sequences (see for example, Ausubel et. al. *Short Protocols in Molecular Biology* (1995) 3rd Ed. John Wiley & Sons, Inc.). In addition, there are a number of commercially available kits for site-directed mutagenesis, including both conventional and PCR-based methods. Examples include the EXSITE™ PCR-Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

In addition mutant DNA polymerases may be generated by insertional mutation or truncation (N-terminal, internal or C-terminal) according to methodology known to a person skilled in the art.

Older methods of site-directed mutagenesis known in the art rely on sub-cloning of the sequence to be mutated into a vector, such as an M13 bacteriophage vector, that allows the isolation of single-stranded DNA template. In these methods, one anneals a mutagenic primer (i.e., a primer capable of annealing to the site to be mutated but bearing one or more mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease Dpn I (recognition target sequence: 5-Gm6ATC-3, where the A residue is methylated) is used to select against parental DNA, since most common strains of *E. coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

A non-limiting example for the isolation of non-chimeric mutant DNA polymerases is described in detail as follows:

Plasmid template DNA (approximately 0.5 pmole) is added to a PCR cocktail containing: 1× mutagenesis buffer (20 mM Tris HCl, pH 7.5; 8 mM $MgCl_2$; 40 μg/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 μM each dNTP, 2.5 U Taq DNA polymerase, and 2.5 U of Taq Extender (Available from Stratagene; See Nielson et al. (1994) Strategies 7: 27, and U.S. Pat. No. 5,556,772). Primers can be prepared using the triester method of Matteucci et al., 1981, J. Am. Chem. Soc. 103:3185-3191, incorporated herein by reference. Alternatively automated synthesis may be preferred, for example, on a Biosearch 8700 DNA Synthesizer using cyanoethyl phosphoramidite chemistry.

The PCR cycling is performed as follows: 1 cycle of 4 min at 94° C., 2 min at 50° C. and 2 min at 72° C.; followed by 5-10 cycles of 1 min at 94° C., 2 min at 54° C. and 1 min at 72° C. The parental template DNA and the linear, PCR-generated DNA incorporating the mutagenic primer are treated with DpnI (10 U) and Pfu DNA polymerase (2.5 U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 mM. Mutagenesis buffer (115 ul of 1×) containing 0.5 mM ATP is added to the DpnI-digested, Pfu DNA polymerase-polished PCR products. The solution is mixed and 10 ul are removed to a new microfuge tube and T4 DNA ligase (2-4 U) is added. The ligation is incubated for greater than 60 min at 37° C. Finally, the treated solution is transformed into competent *E. coli* according to standard methods.

Methods of random mutagenesis, which will result in a panel of mutants bearing one or more randomly situated mutations, exist in the art. Such a panel of mutants may then be screened for improved activity such as those exhibiting properties including but not limited to reduced DNA polymerization activity, 3'-5' exonuclease deficiency, and/or reduced uracil detection activity relative to the wild-type polymerase (e.g., by measuring the incorporation of 10 nmoles of dNTPs into polymeric form in 30 minutes in the presence of 200 μM dUTP and at the optimal temperature for a given DNA polymerase). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Genes for desired mutant DNA polymerases generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

In one embodiment, the invention provides for blends of two or more DNA polymerases comprising one or more DNA polymerase fusions of the invention with or without an additive as described herein.

In a preferred embodiment, the invention provides for blends of two or more DNA polymerases comprising one or more DNA polymerase fusions and one or more mutant DNA polymerases, at least one of which is derived from Pfu DNA polymerase.

In another preferred embodiment, the invention provides for blends of two or more DNA polymerases comprising one or more DNA polymerase fusions and one or more non-chimeric DNA polymerases, at least one of which is derived from TaqDNA polymerase.

In another preferred embodiment, the invention provides for a high pH buffer used in PCR amplification reactions with a fusion DNA polymerase or with a blend of a fusion DNA polymerase and a wild type, mutant, or chemically modified DNA polymerase and/or a wild type, mutant, or chemically modified DNA polymerase formulation (see Example 2). As used herein, a "DNA polymerase" formulation is a blend of two or more DNA polymerases, for example, 2, 3, 4, 5 or more, with or without an additive as defined herein.

A person of average skill in the art having the benefit of this disclosure will recognize that DNA polymerases derived from other exo+ DNA polymerases including Vent DNA polymerase, JDF-3 DNA polymerase, Tgo DNA polymerase, KOD DNA polymerase and the like may be suitably used in the subject compositions.

The amino acid and DNA coding sequence of a wild-type Pfu DNA polymerase are shown in FIG. 20 (Genbank Accession # P80061). A detailed description of the structure and function of Pfu DNA polymerase can be found, among other places in U.S. Pat. Nos. 5,948,663; 5,866,395; 5,545,552; 5,556,772, all of which are hereby incorporated in their entirety by reference.

The enzyme of the subject composition may comprise DNA polymerases that have not yet been isolated.

The invention provides for blends of two or more DNA polymerases comprising one or more DNA polymerase fusion and one or more mutant or wild type DNA polymerase that is not a fusion.

The invention provides for blends of two or more DNA polymerases comprising one or more DNA polymerase fusions and one or more non-fusion mutant Pfu DNA polymerases containing one or more mutations that reduce base analog detection activity as disclosed in the pending U.S. patent application Ser. No. 10/280,962 (Sorge et al.; filed: Oct. 25, 2002) and the pending U.S. patent application Ser. No. 10/298,680 (Sorge et al.; filed Nov. 18, 2002), the contents of which are hereby incorporated in their entirety.

In a preferred embodiment, the blend of two or more DNA polymerases comprises one or more DNA polymerase fusion and one or more non-fusion mutant Pfu DNA polymerase of the invention containing a Valine to Arginine, Valine to Glutamic acid, Valine to Lysine, Valine to Aspartic Acid or Valine to Asparagine substitution at amino acid position 93.

The invention further provides for a blend of two or more DNA polymerases comprising one or more DNA polymerase fusions and one or more non-fusion mutant archaeal DNA polymerases with reduced base analog detection activity that contain a Valine to Arginine, Valine to Glutamic acid, Valine to Lysine, Valine to Aspartic Acid or Valine to Asparagine substitution at amino acid position 93.

A Pfu DNA polymerase mutant with Reduced Uracil Detection can be prepared as follows. Mutations are introduced into Pfu DNA polymerase that are likely to reduce uracil detection, while having minimal effects on polymerase or proofreading activity. The DNA template used for mutagenesis contains the Pfu pol gene, cloned into pBluescript (pF72 clone described in U.S. Pat. No. 5,489,523). Point mutations are introduced using the QuikChange or the QuikChange Multi Site-Directed Mutagenesis Kit (Stratagene). With the QuikChange kit, point mutations are introduced using a pair of mutagenic primers (V93E, H, K, R, and N). With the QuikChange Multi kit, specific point mutations are introduced by incorporating one phosphorylated mutagenic primer or by selecting random mutants from a library of Pfu V93 variants, created by incorporating a degenerate codon (V93G and L). Clones are sequenced to identify the incorporated mutations.

Valine 93 in Pfu DNA polymerase was substituted with Glycine (G), asparagine (N), arginine [R], glutamic acid (E), histidine (H), and leucine (L) using the QuikChange primer sequences listed in FIG. 10.

Assessment of the activity of a mutant chimeric or non-chimeric Pfu DNA polymerase is determined as follows.

Partially-purified Pfu mutant preparations (heat-treated bacterial extracts) were assayed for dUTP incorporation during PCR. In this example, a 2.3 kb fragment containing the Pfu pol gene was from plasmid DNA using PCR primers: (FPfuLIC) 5'-gACgACgACAAgATgATTTTAgATgTggAT-3' (SEQ ID NO: 1) and (RPfuLIC) 5'-ggAACAAgAC-CCgTCTAggATTTTTTAATg-3' (SEQ ID NO: 2). Amplification reactions consisted of 1× cloned Pfu PCR buffer, 7 ng plasmid DNA, 100 ng of each primer, 2.5 U of Pfu mutant (or wild type Pfu), and 200 μM each dGTP, dCTP, and dATP. To assess relative dUTP incorporation, various amounts of dUTP (0-400 μM) and/or TTP (0-200 μM) were added to the PCR reaction cocktail. The amplification reactions were cycled as described in example 6.

Cycling Conditions and primer sequences:

| Target size (kb) | Target gene | Cycling Parameters |
|---|---|---|
| 0.9 | Hα1AT | (1 cycle) 95° C. 2 min<br>(30 cycles) 95° C. 5 sec, 58° C. 5 sec, 72° C. 1 sec or 5 sec.<br>(1 cycle) 72° C. 2 min |
| 2.6 | Hα1AT | (1 cycle) 95° C. 2 min<br>(30 cycles) 95° C. 20 sec, 58° C. 20 sec, 72° C. 5 sec or 1 min 30 sec.<br>(1 cycle) 72° C. 3 min |
| 6 | β globin | (1 cycle) 95° C. 2 min<br>(30 cycles) 95° C. 30 sec, 58° C. 30 sec, 72° C. 1 min or 1 min 30 sec.<br>(1 cycle) 72° C. 5 min |
| 19 | β globin | (1 cycle) 92° C. 2 min<br>(10 cycles) 92° C. 10 sec, 63° C. 30 sec, 68° C. 9.5 min<br>(20 cycles) 92° C. 10 sec, 63° C. 30 sec, 68° C. 9.5 min (plus 10 sec/cycle)<br>(one cycle) 68° C. 7 min |

| Primer size (bp) | Target | Primer sequence |
|---|---|---|
| 30 | Hα1AT<br>0.9 kb | F-5'-AGA.GCT.TGA.GGA.GAG.CAG.GAA.AGG.TGG.AAC-3'<br>(SEQ ID NO. 3) |
| 30 | Hα1AT<br>0.9 kb | R-5'-GGG.AGG.GGA.GGT.ACA.GGG.TTG.AGG.CTA.GTG-3'<br>(SEQ ID NO. 4) |
| 30 | Hα1AT<br>2.6 kb | F-5'-AGA.GCT.TGA.GGA.GAG.CAG.GAA.AGG.TGG.AAC-3'<br>(SEQ ID NO. 114) |
| 24 | Hα1AT<br>2.6 kb | R-5'-TGC.AGA.GCG.ATT.ATT.CAG.GAA.TGC-3'<br>(SEQ ID NO. 115) |
| 30 | β globin<br>6.0 kb | F-5'-ACA.AGG.GCT.ACT.GGT.TGC.CGA.TTT.TTA.TTG-3'<br>(SEQ ID NO. 116) |
| 27 | β globin<br>6.0 kb | R-5'-GGG.ACT.GGC.CTC.AGA.GGA.AAC.TTC.AGG-3'<br>(SEQ ID NO. 117) |
| 30 | β globin<br>19 kb | F-5'-ACA.AGG.GCT.ACT.GGT.TGC.CGA.TTT.TTA.TTG-3'<br>(SEQ ID NO. 118) |
| 28 | β globin<br>19 kb | R-5'-CCT.GCA.TTT.GTG.GGG.TGA.ATT.CCT.TGC.C-3'<br>(SEQ ID NO. 119) |

The invention further provides for a blend of two or more DNA polymerases comprising one or more DNA polymerase fusion and one or more non-fusion mutant archaeal DNA polymerases with a G387P mutant archaeal DNA polymerase with reduced DNA polymerization activity.

The invention further provides for a blend of two or more DNA polymerases comprising one or more DNA polymerase fusions and one or more non-fusion V93 mutant Pfu DNA polymerases with reduced uracil detection activity that contain one or more additional mutations that modulates one or more additional activities of V93 Pfu DNA polymerases, e.g., DNA polymerization activity or 3'-5' exonuclease activity. In one embodiment, the non-fusion V93 mutant Pfu DNA polymerase according to the invention contains one or more mutations that renders the DNA polymerase 3'-5' exonuclease deficient. In another embodiment, the non-fusion V93 mutant Pfu DNA polymerase according to the invention contains one or more mutations that reduce the DNA polymerization activity of the non-fusion V93 Pfu DNA polymerase.

The invention further provides for a blend of two or more DNA polymerases comprising one or more DNA polymerase fusions and one or more non-fusion V93 mutant Pfu DNA polymerases with reduced uracil detection activity that contain one or mutations that reduce DNA polymerization as disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety.

In one embodiment, the invention provides for a V93R/G387P, V93E/G387P, V93D/G387P, V93K/G387P or V93N/G387P double mutant Pfu DNA polymerase with reduced DNA polymerization activity and reduced uracil detection activity.

The invention further provides for V93R, V93E, V93D, V93K or V93N mutant Pfu DNA polymerases with reduced uracil detection activity containing one or more mutations that reduce or eliminate 3'-5' exonuclease activity as disclosed in the pending U.S. patent application Ser. No. 09/698,341 (Sorge et al; filed Oct. 27, 2000).

In one embodiment, the invention provides for a non-fusion V93R/D141A/E143A triple mutant Pfu DNA polymerase with reduced 3'-5' exonuclease activity and reduced uracil detection activity.

The invention further provides for one or more Pfu DNA polymerases of the invention comprising any combination of one or more mutations that may increase or eliminate base analog detection activity of an archaeal DNA polymerase.

DNA polymerases containing additional mutations are generated by site directed mutagenesis using the DNA polymerases of the invention as a template DNA molecule, for example, the Pfu DNA polymerase or Pfu V93R cDNA, according to methods that are well known in the art and are described herein.

The invention contemplates DNA polymerase fusions wherein the DNA polymerase domain of the fusion comprises any of the mutations described herein and known in the art.

Methods used to generate Pfu DNA polymerases with reduced DNA polymerization activity of the invention are disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002); and the pending U.S. patent application Ser. No. 10/324,846 (Borns et al.; filed Dec. 20, 2002), the contents of which are hereby incorporated in their entirety.

Methods used to generate 3'-5' exonuclease deficient JDF-3 DNA polymerases including the D141A and E143A mutations are disclosed in the pending U.S. patent application Ser. No. 09/698,341 (Sorge et al; filed Oct. 27, 2000). A person skilled in the art in possession of the teachings of the pending U.S. patent application Ser. No. 09/698,341 (Sorge et al; filed Oct. 27, 2000) would have no difficulty introducing both the corresponding D141A and E143A mutations or other 3'-5' exonuclease mutations into a DNA polymerase of the invention including for example, the non-chimeric V93 Pfu DNA polymerase cDNA, as disclosed in the pending U.S. patent application Ser. No. 09/698,341, using established site-directed mutagenesis methodology.

Three 3' to 5' exonuclease motifs have been identified, and mutations in these regions have also been shown to abolish 3' to 5' exonuclease activity in Klenow, 429, T4, T7, and Vent DNA polymerases, yeast Pol α, Pol β, and Pol γ, and *Bacillus subtilis* Pol III (reviewed in Derbeyshire et al., 1995, Methods. Enzymol. 262:363). Methods for preparing additional DNA polymerase mutants, with reduced or abolished 3' to 5' exonuclease activity, are well known in the art.

Commercially-available enzymes that lack both 5' to 3' and 3' to 5' exonuclease activities include Sequenase (exo$^-$ T7; USB), Pfu exo$^-$ (Stratagene), exo$^-$ Vent (New England BioLabs), exo$^-$ DeepVent (New England BioLabs), exo$^-$ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffman-LaRoche), any one of which may be used as the non chimeric DNA polymerase component in the blend of the invention disclosed herein.

In accordance with the invention, in addition to the mutations described above, one or more additional mutations or modifications (or combinations thereof) may be made to the polymerases of interest. Mutations or modifications of particular interest include those modifications of mutations which (1) eliminate or reduce 5' to 3' exonuclease activity; and (2) reduce discrimination of dideoxynucleotides (that is, increase incorporation of dideoxynucleotides). The 5'-3' exonuclease activity of the polymerases can be reduced or eliminated by mutating the polymerase gene or by deleting the 5' to 3' exonuclease domain. Such mutations include point mutations, frame shift mutations, deletions, and insertions. Preferably, the region of the gene encoding an DNA polymerase activity is deleted using techniques well known in the art. For example, any one of six conserved amino acids that are associated with the 5'-3' exonuclease activity can be mutated. Examples of these conserved amino acids with respect to Ta DNA polymerase include $Asp^{18}$, $Glu^{117}$, $Asp^{119}$, $Asp^{120}$, $Asp^{142}$, and $Asp^{144}$.

Polymerase mutants can also be made to render the polymerase non-discriminating against non-natural nucleotides such as dideoxynucleotides (see U.S. Pat. No. 5,614,365). Changes within the O-helix, such as other point mutations, deletions, and insertions, can be made to render the polymerase non-discriminating. By way of example, one Tne DNA polymerase mutant having this property substitutes a non-natural amino acid such as Tyr for Phe730 in the O-helix.

Typically, the 5'-3' exonuclease activity, 3' to 5' exonuclease activity, discriminatory activity and fidelity can be affected by substitution of amino acids typically which have different properties. For example, an acidic amino acid such as Asp may be changed to a basic, neutral or polar but uncharged amino acid such as Lys, Arg, His (basic); Ala, Val, Leu, Ile, Pro, Met, Phe, Trp (neutral); or Gly, Ser, Thr, Cys, Tyr, Asn or Gln (polar but uncharged) Glu may be changed to Asp, Ala, Val Leu, Ile, Pro, Met, Phe, Trp, Gly, Ser, Thr, Cys, Tyr, Asn or Gln.

Preferably, oligonucleotide directed mutagenesis is used to create the mutant polymerases which allows for all possible classes of base pair changes at any determined site along the encoding DNA molecule. In general, this technique involves annealing a oligonucleotide complementary (except for one or more mismatches) to a single stranded nucleotide sequence coding for the DNA polymerase of interest. The mismatched oligonucleotide is then extended by DNA polymerase, generating a double stranded DNA molecule which contains the desired change in sequence on one strand. The changes in sequence can of course result in the deletion, substitution, or insertion of an amino acid. The double stranded polynucleotide can then be inserted into an appropriate expression vector, and a mutant polypeptide can thus be produced. The above-described oligonucleotide directed mutagenesis can of course be carried out via PCR.

In one embodiment, the non-chimeric mutant Pfu DNA polymerases are expressed and purified as described in U.S. Pat. No. 5,489,523, hereby incorporated by reference in its entirety.

III. Preparing DNA Polymerase Fusions

The DNA polymerase fusion of the invention has at least two polypeptides covalently linked, in which one polypeptide comes from one protein sequence or domain and the other polypeptide comes from another protein sequence or domain. According to the invention, at least one of the domains of the DNA polymerase fusion originates from a wild type or mutant DNA polymerase of the invention. The polypeptides can be linked either directly or via a covalent linker, e.g., an amino acid linker, such as a polyglycine linker, or another type of chemical linker, e.g., a carbohydrate linker, a lipid linker, a fatty acid linker, a polyether linker, e.g., PEG, etc. (See, e.g., Hermanson, Bioconjugate techniques (1996)). The polypeptides forming the fusion polypeptide are typically linked C-terminus to N-terminus, although they can also be linked C-terminus to C-terminus, N-terminus to N-terminus, or N-terminus to C-terminus. One or more polypeptide domains may be inserted at an internal location within a DNA polymerase of the invention. The polypeptides of the fusion protein can be in any order. The term "fusion polypeptide" or "chimera" also refers to conservatively modified variants, polymorphic variants, alleles, mutant, subsequences and interspecies homologues of the polypeptides that make up the fusion protein. Fusion proteins may be produced by covalently linking a chain of amino acids from one protein sequence to a chain of amino acids from another protein sequence, e.g., by preparing a recombinant polynucleotide contiguously encoding the fusion protein. Fusion proteins can comprise 2, 3, 4 or more different chains of amino acids from the same or different species. The different chains of amino acids in a fusion protein may be directly spliced together or may be indirectly spliced together via a chemical linking group or an amino acid linking group, which can be about 200 amino acids or more in length, with 1 to 100 amino acids being typical. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

In a preferred embodiment, the DNA polymerase fusion, useful according to the invention, is a thermostable DNA polymerase with reduced DNA polymerization activity or with reduced uracil detection activity. In addition, the DNA polymerase fusion of the invention may or may not have 3'-5' exonuclease activity.

In one embodiment, the component fused to the DNA polymerase is any non-native protein or protein domain fused to the DNA polymerase at the N- or C-terminus or at any internal position. The contribution to the activity of the DNA polymerase from the DNA polymerase fusion partner (that is the second amino acid sequence of the fusion as described herein) includes, but is not limited to, an increase in one or more of the following DNA polymerase activities: processivity, DNA binding, strand displacement activity, polymerase activity, nucleotide binding and recognition, proofreading, fidelity, and salt resistance and/or decreased DNA polymerase activity at room temperature.

A DNA polymerase fusion can be prepared by molecular biology techniques for preparing fusion proteins well known in the art.

Using techniques well known in the art (Sambrook et al., (1989) in: Molecular Cloning, A Laboratory Manual (2nd Ed.), Cold Spring Harbor Laboratory Press, Cold Spring Harbor, N.Y.), a protein domain of a DNA polymerase can be substituted with a domain from another polymerase which has the desired activity. Methods of preparing a DNA polymerase fusions of the invention are also described in WO 01/92501 A1 and Pavlov et al., 2002, Proc. Natl. Acad. Sci. USA, 99:13510-13515, which are herein incorporated in its entirety.

In one embodiment, the DNA polymerase fusion of the invention comprises a protein domain of one wild type DNA polymerase of the invention that is fused to a protein domain of a different DNA polymerase of the invention containing one or more mutations.

In another preferred embodiment, the DNA polymerase fusion of the invention comprises all of or a part of Pfu or Taq DNA polymerase.

In one embodiment, the DNA polymerase fusion of the invention comprises a Pfu DNA polymerase, or part thereof, having reduced DNA polymerization as disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated by reference in their entirety.

In one embodiment, the DNA polymerase fusion of the invention comprises a Pfu DNA polymerase, or part thereof, having one or mutations that reduce base analog detection activity as disclosed in the pending U.S. patent application Ser. No. 10/280,962 (Hogrefe, et al.; filed: Oct. 25, 2002) and the pending U.S. patent application Ser. No. 10/298,680 (Hogrefe et al.; filed Nov. 18, 2002) and the pending U.S. patent application Ser. No. 10/324,846 (Borns et al.; filed Dec. 20, 2002), the contents of which are hereby incorporated by reference in their entirety.

In one embodiment, the DNA polymerase fusion of the invention comprises a protein domain of one mutant DNA polymerase of the invention that is fused to a protein domain of a different DNA polymerase of the invention containing one or more mutations.

In one embodiment, the DNA polymerase fusion of the invention comprises a protein domain of one DNA polymerase that replaces an analogous protein domain within another DNA polymerase of the invention. As used herein, two protein domains are said to be "analogous" if they share in common a domain that confers at least one DNA polymerase activity such as processivity, DNA binding, strand displacement activity, nucleotide binding and recognition, proofreading, e.g. 3'-5' exonuclease activity, fidelity, e.g. 5'-3' exonuclease activity, or salt resistance.

In one embodiment, the DNA polymerase fusion of the invention comprises the helix-hairpin-helix DNA binding motifs from DNA topoisomerase V that increases processivity, salt resistance and thermostability as described in Pavlov et al., 2002, Proc. Natl. Acad. Sci. USA, 99:13510-13515.

In another embodiment, the DNA polymerase fusion of the invention comprises the thioredoxin binding domain that enhances the processivity of the DNA polymerase fusion as described in WO 97/29209.

In another embodiment, the DNA polymerase fusion of the invention comprises the archaeal PCNA binding domain fused to Taq DNA polymerase or a related eubacterial DNA polymerase. Addition of PCNA to the PCR reaction containing the PCNA binding domain-Taq DNA polymerase chimera results in enhanced processivity of the DNA polymerase fusion and higher yields of PCR amplified DNA (Motz, M., et al., J. Biol. Chem. 2002 May 3; 277 (18); 16179-88).

In another embodiment, the DNA polymerase fusion of the invention comprises the sequence non-specific DNA binding protein Sso7d or Sac7d from (for example, from *Sulfolobus sulfataricus* fused to a DNA polymerase of the invention. The fusion of the DNA binding protein Sso7d or Sac7d to DNA polymerase fusions of the invention, such as Pfu or Taq DNA polymerase, greatly enhances the processivity of these DNA polymerases as disclosed in WO 01/92501 A1 which is hereby incorporated by reference in its entirety.

The invention contemplates DNA polymerase fusions wherein any of the HhH domains known in the art (see Belova et al., 2001, Proc. Natl. Acad. Sci. USA, 98:6015 and FIG. 18) are fused to any of the wildtype or mutant DNA polymerases included herein. The HhH can be fused directly to the N or C terminus or at any internal site of any of the wildtype or mutant DNA polymerases included herein. One of more (for example the H-L or E-L) HhH domains can be used to create a DNA polymerase fusion.

In another embodiment, the DNA polymerase fusion of the invention comprises a Pfu DNA polymerase, or part thereof, having reduced 3'-5' exonuclease activity. Methods used to generate 3'-5' exonuclease deficient JDF-3 DNA polymerases including the D141A and E143A mutations are disclosed in the pending U.S. patent application Ser. No. 09/698,341 (Sorge et al; filed Oct. 27, 2000), the contents of which are hereby incorporated by reference in their entirety. A person skilled in the art in possession of the teachings of the pending U.S. patent application Ser. No. 09/698,341 (Sorge et al; filed Oct. 27, 2000) would have no difficulty introducing both the corresponding D141A and E143A mutations or other 3'-5' exonuclease mutations into any one of the DNA polymerase fusions of the invention i.e. a DNA polymerase fusion with reduced base analog detection activity or reduced DNA polymerization activity as disclosed herein.

In another embodiment, the DNA polymerase fusion of the invention comprises a DNA polymerase, or part thereof, that lacks both 5' to 3' and 3' to 5' exonuclease activities including, but not limited to, Sequenase ($exo^-$ T7; USB), Pfu $exo^-$ (Stratagene), $exo^-$ Vent (New England BioLabs), $exo^-$ DeepVent (New England BioLabs), $exo^-$ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffman-LaRoche), any one of which may be used as the chimeric DNA polymerase fusion of the invention disclosed herein.

In another embodiment, the DNA polymerase fusion of the invention comprises a thermostable DNA polymerase, or part thereof, that has enhanced 3' to 5' exonuclease activity that confers enhanced fidelity to the DNA polymerase fusion of the invention as disclosed in U.S. Pat. No. 5,795,762, the contents of which are hereby incorporated by reference in their entirety.

IV. Expression of Wild-Type or Mutant Enzymes According to the Invention

Methods known in the art may be applied to express and isolate DNA polymerases of the invention. Many bacterial expression vectors contain sequence elements or combinations of sequence elements allowing high level inducible expression of the protein encoded by a foreign sequence. For example, as mentioned above, bacteria expressing an integrated inducible form of the T7 RNA polymerase gene may be transformed with an expression vector bearing a mutated DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the mutated gene from the T7 promoter.

Appropriate host strains of bacteria may be selected from those available in the art by one of skill in the art. As a non-limiting example, *E. coli* strain BL-21 is commonly used for expression of exogenous proteins since it is protease deficient relative to other strains of *E. coli*. BL-21 strains bearing an inducible T7 RNA polymerase gene include WJ56 and ER2566 (Gardner & Jack, 1999, supra). For situations in which codon usage for the particular polymerase gene differs from that normally seen in *E. coli* genes, there are strains of BL-21 that are modified to carry tRNA genes encoding tRNAs with rarer anticodons (for example, argU, ileY, leuW, and proL tRNA genes), allowing high efficiency expression of cloned protein genes, for example, cloned archaeal enzyme genes (several BL21-CODON PLUSTM cell strains carrying rare-codon tRNAs are available from Stratagene, for example).

There are many methods known to those of skill in the art that are suitable for the purification of a DNA polymerase of the invention. For example, the method of Lawyer et al. (1993, *PCR Meth. & App.* 2: 275) is well suited for the isolation of DNA polymerases expressed in *E. coli*, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure DNA polymerase. Further, DNA polymerases may be isolated by an ammonium sulfate fractionation, followed by Q Sepharose and DNA cellulose columns, or by adsorption of contaminants on a HiTrap Q column, followed by gradient elution from a HiTrap heparin column.

V. Blends of Fusion and Non-Fusion DNA Polymerases

A DNA polymerase fusion blend formulation, according to the invention, can include at least one DNA polymerase fusion and: (1) a proofreading or a non-proofreading non-chimeric DNA polymerase; or (2) a proofreading plus non-proofreading, non-proofreading plus non-proofreading or a proofreading plus proofreading non-fusion DNA polymerase blend, e.g., Pfu, Taq, Pfu/Taq, Pfu/exo-Pfu, Taq/exo-Pfu, Pfu/JDF3, or any of these combinations with pol-Pfu (Pfu G387P). The ratio of DNA polymerase enzymes in a "blend" comprising one fusion and one non-fusion polymerase is in the range of 1:1-1:5-5:1, or 1:1-1:10-10:1, or 1:1-1:25-25:1 or 1:1-1:100-100:1. For embodiments wherein a "blend" comprises one DNA polymerase fusion and two non-fusion polymerases the ratio of the first non-fusion DNA polymerase to the second non-fusion DNA polymerase is in the range of 1:1-1:5-5:1, or 1:1-1:10-10:1, or 1:1-1:25-25:1 or 1:1-1:100-100:1. The formulation of the invention has no limitations on the ratios of the individual components.

In one embodiment, the blend formulation of the invention is 2.5 U Pfu/0.25 U chimeric Pfu.

The wild type DNA polymerase that is blended with the DNA polymerase fusion can be any native or cloned DNA polymerase having native levels of polymerase activity and proofreading activity and preferably is thermostable such as Pfu or Taq. The DNA polymerase fusion and wild type DNA polymerase are blended in the ratio range described above and can be mixed with any replication accessory factor or PCR enhancing additives, e.g., Pfu dUTPase (PEF), PCNA, RPA, ssb, antibodies, DMSO, betaine, or 3'-5' exonuclease (e.g., Pfu G387P).

The mutant DNA polymerase that is blended with the DNA polymerase fusion of the invention is any DNA polymerase having introduced mutations and/or truncations that generates a DNA polymerase with an activity that is distinct from a wild type DNA polymerase. The mutant could have any amount of polymerase and/or proofreading activity. Specific examples of useful mutations or truncations include, but are not limited to, V93R,K,E, or D in Pfu DNA polymerase, which confer uracil insensitivity, D141A/E143A in Pfu DNA polymerase, which eliminates 3'-5' exonuclease activity, and the N-terminal truncation of Taq that eliminates 5'-3' exonuclease activity (KlenTaq).

The invention further provides for mutant V93R, V93E, V93D, V93K or V93N non-fusion Pfu DNA polymerases that contain one or more additional mutations with improved reverse transcriptase activity.

The invention provides for a blend wherein the ratio of DNA polymerase fusion to non-fusion DNA polymerase is in the ratio range of 1:1-1:5-5:1, or 1:1-1:10-10:1, or 1:1-1:25-25:1 or 1:1-1:100-100:1. The invention contemplates a blend comprising a mixture of a DNA polymerase fusion and more than one non-fusion DNA polymerase. For a blend comprising a DNA polymerase fusion in combination with two non-fusion DNA polymerases, the ratio range of the first non-fusion DNA polymerases to the second non-fusion DNA polymerase is 1:1-1:5-5:1, or 1:1-1:10-10:1, or 1:1-1:25-25:1 or 1:1-1:100-100:1.

VI. Applications of the Subject Invention

The invention provides for methods of using polymerase fusions of the invention at high pH as defined herein.

A high pH buffer useful according to the invention includes but is not limited to a standard PCR reaction buffer like cloned Pfu reaction buffer (described in Example 3) wherein the buffering component is at a high pH (i.e. 9.3-14). The buffering component used in the following examples is 30 mM Tris [Tris(hydroxymethyl) aminomethane] at a pH of 10.0 or 11.8. The pH of the buffering component in standard PCR reaction buffers is from 8.3-8.8. The buffering component is used at a concentration from 1 mM to 1M in the final PCR reaction and may be any pH from 9.5-14. The buffering component of the present invention includes, but is not limited to, Tris, Tricine, bicine, Bis-Tris, CAPS, EPPS, HEPES, MES, MOPS, PIPES, TAPS and TES.

In one aspect, the invention provides a method for DNA synthesis using the compositions of the subject invention. Typically, synthesis of a polynucleotide requires a synthesis primer, a synthesis template, polynucleotide precursors for incorporation into the newly synthesized polynucleotide, (e.g. dATP, dCTP, dGTP, dTTP), and the like. Detailed methods for carrying out polynucleotide synthesis are well known to the person of ordinary skill in the art and can be found, for example, in *Molecular Cloning second edition*, Sambrook et al., Cold Spring Harbor Laboratory Press, Cold Spring Harbor, N.Y. (1989).

A. Application in Amplification Reactions

"Polymerase chain reaction" or "PCR" refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

For ease of understanding the advantages provided by the present invention, a summary of PCR is provided. The PCR reaction involves a repetitive series of temperature cycles and is typically performed in a volume of 50-100 μl. The reaction mix comprises dNTPs (each of the four deoxynucleotides dATP, dCTP, dGTP, and dTTP), primers, buffers, DNA polymerase, and polynucleotide template. PCR requires two primers that hybridize with the double-stranded target polynucleotide sequence to be amplified. In PCR, this double-stranded target sequence is denatured and one primer is annealed to each strand of the denatured target. The primers anneal to the target polynucleotide at sites removed from one another and in orientations such that the extension product of one primer, when separated from its complement, can hybridize to the other primer. Once a given primer hybridizes to the target sequence, the primer is extended by the action of a DNA polymerase. The extension product is then denatured from the target sequence, and the process is repeated.

In successive cycles of this process, the extension products produced in earlier cycles serve as templates for DNA synthesis. Beginning in the second cycle, the product of amplification begins to accumulate at a logarithmic rate. The amplification product is a discrete double-stranded DNA molecule comprising: a first strand which contains the sequence of the first primer, eventually followed by the sequence complementary to the second primer, and a second strand which is complementary to the first strand.

Due to the enormous amplification possible with the PCR process, small levels of DNA carryover from samples with high DNA levels, positive control templates or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, Nature, 339:237-238 and Kwok, and Orrego, in: Innis et al. eds., 1990, *PCR Protocols: A Guide to Methods and Applications*, Academic Press, Inc., San Diego, Calif., which are incorporated herein by reference.

The enzymes provided herein are also useful for dUTP/UNG cleanup methods that require PCR enzymes that incorporate dUTP (Longo et al., Supra).

1. Thermostable Enzymes

For PCR amplifications, the enzymes used in the invention are preferably thermostable. As used herein, "thermostable" refers to an enzyme which is stable to heat, is heat resistant, and functions at high temperatures, e.g., 50 to 90° C. The thermostable enzyme according to the present invention must satisfy a single criterion to be effective for the amplification reaction, i.e., the enzyme must not become irreversibly denatured (inactivated) when subjected to the elevated temperatures for the time necessary to effect denaturation of double-stranded polynucleotides. By "irreversible denaturation" as used in this connection, is meant a process bringing a permanent and complete loss of enzymatic activity. The heating conditions necessary for denaturation will depend, e.g., on the buffer salt concentration and the length and nucleotide composition of the polynucleotides being denatured, but typically range from 85° C., for shorter polynucleotides, to 105° C. for a time depending mainly on the temperature and the polynucleotide length, typically from 0.25 minutes for shorter polynucleotides, to 4.0 minutes for longer pieces of DNA. Higher temperatures may be tolerated as the buffer salt concentration and/or GC composition of the polynucleotide is increased. Preferably, the enzyme will not become irreversibly denatured at 90 to 100° C. An enzyme that does not become irreversibly denatured, according to the invention, retains at least 10%, or at least 25%, or at least 50% or more function or activity during the amplification reaction.

2. PCR Reaction Mixture

In addition to the subject enzyme mixture, one of average skill in the art may also employ other PCR parameters to increase the fidelity of synthesis/amplification reaction. It has been reported that PCR fidelity may be affected by factors such as changes in dNTP concentration, units of enzyme used per reaction, pH, and the ratio of $Mg^{2+}$ to dNTPs present in the reaction (Mattila et al., 1991, supra).

$Mg^{2+}$ concentration affects the annealing of the oligonucleotide primers to the template DNA by stabilizing the primer-template interaction, it also stabilizes the replication complex of polymerase with template-primer. It can therefore also increase non-specific annealing and produce undesirable PCR products (gives multiple bands in gel). When non-specific amplification occurs, the $Mg^{2+}$ concentration may need to be lowered or EDTA can be added to chelate $Mg^{2+}$ to increase the accuracy and specificity of the amplification.

Other divalent cations such as $Mn^{2+}$, or $Co^{2+}$ can also affect DNA polymerization. Suitable cations for each DNA polymerase are known in the art (e.g., in *DNA Replication 2^nd^* edition, supra). Divalent cation is supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer are for $MnCl_2$ from 0.5 to 7 mM, preferably, between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM.

Monovalent cation required by DNA polymerase may be supplied by the potassium, sodium, ammonium, or lithium salts of either chloride or acetate. For KCl, the concentration is between 1 and 200 mM, preferably the concentration is between 40 and 100 mM, although the optimum concentration may vary depending on the polymerase used in the reaction.

Deoxyribonucleotide triphosphates (dNTPs) are added as solutions of the salts of dATP, dCTP, dGTP, dUTP, and dTTP, such as disodium or lithium salts. In the present methods, a final concentration in the range of 1 μM to 2 mM each is suitable, and 100-600 μM is preferable, although the optimal concentration of the nucleotides may vary in the PCR reaction depending on the total dNTP and divalent metal ion concentration, and on the buffer, salts, particular primers, and template. For longer products, i.e., greater than 1500 bp, 500 μM each dNTP may be preferred when using a Tris-HCl buffer.

dNTPs chelate divalent cations, therefore amount of divalent cations used may need to be changed according to the dNTP concentration in the reaction. Excessive amount of dNTPs (e.g., larger than 1.5 mM) can increase the error rate and possibly inhibit DNA polymerases. Lowering the dNTP (e.g., to 10-50 μM) may therefore reduce error rate. PCR reaction for amplifying larger size template may need more dNTPs.

The PCR reaction buffer is a standard PCR reaction buffer like cloned Pfu reaction buffer but with a buffering component at a high pH (i.e. 9.1-14). One suitable buffering component is 30 mM Tris [Tris(hydroxymethyl) aminomethane] at a pH of 10.0 or 11.8. The pH of the buffering component in standard PCR reaction buffers is from 8.3-8.8. The buffering component is used at a concentration from 1 mM to 1M in the final PCR reaction at a pH from 9.1-14. A buffering component useful in this invention includes, but is not limited to, Tris, Tricine, bicine, Bis-Tris, CAPS, EPPS, HEPES, MES, MOPS, PIPES, TAPS and TES.

PCR is a very powerful tool for DNA amplification and therefore very little template DNA is needed. However, in some embodiments, to reduce the likelihood of error, a higher DNA concentration may be used, though too many templates may increase the amount of contaminants and reduce efficiency.

Usually, up to 3 μM of primers may be used, but high primer to template ratio can result in non-specific amplification and primer-dimer formation. Therefore it is usually necessary to check primer sequences to avoid primer-dimer formation.

The invention provides for Pfu V93R, V93E, V93K, V93D, or V93N fusion or non-fusion DNA polymerases with reduced uracil detection activity that enhance PCR of GC rich DNA templates by minimizing the effect of cytosine deamination in the template and by allowing the use of higher denaturation times and denaturation temperatures.

3. Cycling Parameters

Denaturation time may be increased if template GC content is high. Higher annealing temperature may be needed for primers with high GC content or longer primers. Gradient PCR is a useful way of determining the annealing temperature. Extension time should be extended for larger PCR product amplifications. However, extension time may need to be reduced whenever possible to limit damage to enzyme.

The number of cycles can be increased if the number of template DNA is very low, and decreased if high amount of template DNA is used.

4. PCR Enhancing Factors and Additives

PCR enhancing factors may also be used to improve efficiency of the amplification. As used herein, a "PCR enhancing factor" or a "Polymerase Enhancing Factor" (PEF) refers to a complex or protein possessing polynucleotide polymerase enhancing activity (Hogrefe et al., 1997, Strategies 10:93-96; and U.S. Pat. No. 6,183,997, both of which are hereby incorporated by references). For Pfu DNA polymerase, PEF comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of an isolated or purified naturally occurring polymerase enhancing protein obtained from an archeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). The PCR enhancing activity of PEF is defined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and PPi. The amount of PPi formed is quantitated using a coupled enzymatic assay system that is commercially available from Sigma (#P7275). One unit of activity is functionally defined as 4.0 nmole of PPi formed per hour (at 85° C.).

Other PCR additives may also affect the accuracy and specificity of PCR reactions. EDTA less than 0.5 mM may be present in the amplification reaction mix. Detergents such as Tween-20™ and Nonidet™ P-40 are present in the enzyme dilution buffers. A final concentration of non-ionic detergent approximately 0.1% or less is appropriate, however, 0.01-0.05% is preferred and will not interfere with polymerase activity. Similarly, glycerol is often present in enzyme preparations and is generally diluted to a concentration of 1-20% in the reaction mix. Glycerol (5-10%), formamide (1-5%) or DMSO (2-10%) can be added in PCR for template DNA with high GC content or long length (e.g., >1 kb). These additives change the Tm (melting temperature) of primer-template hybridization reaction and the thermostability of polymerase enzyme. BSA (up to 0.8 μg/μl) can improve efficiency of PCR reaction. Betaine (0.5-2M) is also useful for PCR over high GC content and long fragments of DNA. Tetramethylammonium chloride (TMAC, >50 mM), Tetraethylammonium chloride (TEAC), and Trimethlamine N-oxide (TMANO) may also be used. Test PCR reactions may be performed to determine optimum concentrations of each additive mentioned above.

The invention provides for additives including, but not limited to antibodies (for hot start PCR) and ssb (single strand DNA binding protein; higher specificity). The invention also contemplates mutant archael DNA polymerases in combination with accessory factors, for example as described in U.S. Pat. No. 6,333,158, and WO 01/09347 A2, hereby incorporated by reference in its entirety.

Various specific PCR amplification applications are available in the art (for reviews, see for example, Erlich, 1999, *Rev Immunogenet.*, 1:127-34; Prediger 2001, *Methods Mol. Biol.* 160:49-63; Jurecic et al., 2000, *Curr. Opin. Microbiol.* 3:316-21; Triglia, 2000, *Methods Mol. Biol.* 130:79-83; MaClelland et al., 1994, *PCR Methods Appl.* 4:S66-81; Abramson and Myers, 1993, *Current Opinion in Biotechnology* 4:41-47; each of which is incorporated herein by references).

The subject invention can be used in PCR applications including, but not limited to, i) hot-start PCR which reduces non-specific amplification; ii) touch-down PCR which starts at high annealing temperature, then decreases annealing temperature in steps to reduce non-specific PCR product; iii) nested PCR which synthesizes more reliable product using an outer set of primers and an inner set of primers; iv) PCR for amplification of regions flanking a known sequence; (in this method, DNA is digested, the desired fragment is circularized by ligation, then PCR using primer complementary to the known sequence extending outwards; v) AP-PCR (arbitrary primed)/RAPD (random amplified polymorphic DNA); these methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cell. It may also be used to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. First step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be used as a control to verify the quality of PCR; x) Q/C-PCR (Quantitative comparative) which uses an internal control DNA sequence (but of a different size) which competes with the target DNA (competitive PCR) for the same set of primers; xi) Recusive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis.

It should be understood that this invention is not limited to any particular amplification system. As other systems are developed, those systems may benefit by practice of this invention.

B. Application in Direct Cloning of PCR Amplified Product

It is understood that the amplified product produced using the subject enzyme can be cloned by any method known in the art. In one embodiment, the invention provides a composition which allows direct cloning of PCR amplified product.

The most common method for cloning PCR products involves incorporation of flanking restriction sites onto the ends of primer molecules. The PCR cycling is carried out and the amplified DNA is then purified, restricted with an appropriate endonuclease(s) and ligated to a compatible vector preparation.

A method for directly cloning PCR products eliminates the need for preparing primers having restriction recognition sequences and it would eliminate the need for a restriction step to prepare the PCR product for cloning. Additionally, such method would preferably allow cloning PCR products directly without an intervening purification step.

U.S. Pat. Nos. 5,827,657 and 5,487,993 (hereby incorporated by their entirety) disclose methods for direct cloning of PCR products using a DNA polymerase which takes advantage of the single 3'-deoxy-adenosine monophosphate (dAMP) residues attached to the 3' termini of PCR generated nucleic acids. Vectors are prepared with recognition sequences that afford single 3'-terminal deoxy-thymidine monophosphate (dTMP) residues upon reaction with a suitable restriction enzyme. Thus, PCR generated copies of genes can be directly cloned into the vectors without a need for preparing primers having suitable restriction sites therein.

Taq DNA polymerase exhibits terminal transferase activity that adds a single dATP to the 3' ends of PCR products in the absence of template. This activity is the basis for the TA cloning method in which PCR products amplified with Taq are directly ligated into vectors containing single 3' dT overhangs. Pfu DNA polymerase, on the other hand, lacks terminal transferase activity, and thus produces blunt-ended PCR products that are efficiently cloned into blunt-ended vectors. The invention also encompasses an Easy A composition that contains of a blend of Taq (5 U/ul), recombinant PEF (4 U/up, and Pfu G387P(40 ng/ul) as disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety. With cloned archaeal DNA polymerase with reduced base analog detection activity at 2.5 U/ul i.e. ~20-50 ng per ul, the ratio of Taq:Pfu is preferably 1:1 or more preferably 2:1 or more.

In one embodiment, the invention provides for a PCR product, generated in the presence of a DNA polymerase fusion at high pH, that is subsequently incubated with Taq DNA polymerase in the presence of dATP at 72° C. for 15-30 minutes. Addition of 3'-dAMP to the ends of the amplified DNA product then permits cloning into TA cloning vectors according to methods that are well known to a person skilled in the art.

C. Application in DNA Sequencing

The invention further provides for dideoxynucleotide DNA sequencing methods using thermostable DNA polymerase fusions to catalyze the primer extension reactions at high pH. Methods for dideoxynucleotide DNA sequencing are well known in the art and are disclosed in U.S. Pat. Nos. 5,075,216, 4,795,699 and 5,885,813, the contents of which are hereby incorporated in their entirety. The invention encompasses DNA polymerase fusions comprising exo-Pfu (for example D141A/E143A double mutant) or the JDF3 P410L/A485T mutant with reduced ddNTP discrimination.

D. Application in Mutagenesis

The DNA polymerase fusions of the invention also provide enhanced efficacy for PCR-based or linear amplification-based mutagenesis. The invention therefore provides for DNA polymerase fusions for site-directed mutagenesis at high pH and their incorporation into commercially available kits, for example, QuikChange Site-directed Mutagenesis, QuikChange Multi-Site-Directed Mutagenesis (Stratagene). Site-directed mutagenesis methods and reagents are disclosed in the pending U.S. patent application Ser. No. 10/198,449 (Hogrefe et al.; filed Jul. 18, 2002), the contents of which are hereby incorporated in its entirety. The invention also encompasses Mutazyme (exo$^-$ Pfu in combination with PEF, GeneMorph Kit). The GeneMorph kits are disclosed in the pending U.S. patent application Ser. No. 10/154,206 (filed May 23, 2002), the contents of which are hereby incorporated in its entirety.

The DNA polymerase fusions described herein are used in the same way as conventional DNA polymerase/DNA polymerase formulations and can be used at high pH in any primer extension application, including PCR, to produce high product yields with shortened extension times. Amplification of genomic targets, in particular, which typically require extension times of 1-2 min./kb and take hours to amplify, is greatly facilitated by the disclosed invention because extension times are reduced to 5-30 sec./kb, or shorter, with the DNA polymerase fusions described herein (see Example 3).

Other applications of the present invention include RT-PCR, site-directed mutagenesis and random mutagenesis. The DNA polymerase fusions of the invention used in all of these applications increase length capability, shorten reaction times and greatly improve overall performance in all standard protocols (see Example 3).

A DNA polymerase fusion with proofreading activity (3'-5' exonuclease activity) is useful for high fidelity PCR: A DNA polymerase fusion that is useful for high fidelity PCR will demonstrate an increase of >10% 3'-5' exonuclease activity and PCR fidelity, and accuracy of incorporation as compared to a corresponding non-fusion polymerase (with 3'-5' exonuclease activity) alone using a complex genomic and/or plasmid template.

A DNA polymerase fusion with higher misinsertion and/or mispair extension frequency is useful for PCR random mutagenesis. A DNA polymerase fusion that is useful for PCR random mutagenesis preferably demonstrates an increase of ≥10% of the mutagenic properties or changes in mutational spectra as compared to a corresponding non-fusion polymerase for plasmid template.

By "mutagenic properties" is meant mutation rate and the overall number of mutation instances per kb of amplicon.

By "mutational spectra" is meant the number of transition and transversion mutations. "Mutational spectra" also encompasses the ratio of transitions to transversions. Preferably the ratio of transitions to transversion is 1:1.

All of the DNA polymerase fusions contemplated herein are useful for PCR and RT-PCR:

DNA polymerase fusions with proofreading activity that are used for PCR amplification and linear amplification are useful for Site Directed Mutagenesis.

DNA polymerase fusions that lack 3'-5' exonuclease activity are useful for sequencing applications. A DNA polymerase fusion useful for sequencing will demonstrate one or more of shorter extension times, higher efficiency, higher specificity, higher fidelity (more accurate incorporation), and higher processivity (an increase of ≥10% above the non-chimeric component of the blend for sequencing template). DNA polymerase fusions that lack 3'-5' exonuclease activity are also useful for random mutagenesis.

Kits

The invention herein also contemplates a kit format which comprises a package unit having one or more containers of the subject composition and in some embodiments including containers of various reagents used for polynucleotide synthesis, including synthesis in PCR. The kit may also contain one or more of the following items: polynucleotide precursors, primers, buffers (preferably a high pH buffer), instructions, and controls. Kits may include containers of reagents mixed together in suitable proportions for performing the methods in accordance with the invention. Reagent containers preferably contain reagents in unit quantities that obviate measuring steps when performing the subject methods.

The invention contemplates a kit comprising a DNA polymerase fusion and a high pH buffer according to the invention, PCR enhancing reagents and reagents for PCR amplification, DNA sequencing or mutagenesis.

A kit for sequencing DNA will comprise a number of container means. A first container means may, for example, comprise a substantially purified sample of the polymerases of the invention. A second container means may comprise one or a number of types of nucleotides needed to synthesize a DNA molecule complementary to DNA template. A third container means may comprise one or a number of different types of terminators (such as dideoxynucleoside triphosphates). A fourth container means may comprise pyrophosphatase. In addition to the above container means, additional container means may be included in the kit which comprise one or a number of primers and/or a suitable sequencing buffer, preferably a high pH buffer.

A kit used for amplifying or synthesis of nucleic acids will comprise, for example, a first container means comprising a substantially pure polymerase fusion of the invention and one or a number of additional container means which comprise a single type of nucleotide or mixtures of nucleotides, and/or a high pH buffer.

Various primers may be included in a kit as well as a suitable amplification or synthesis buffers.

When desired, the kit of the present invention may also include container means which comprise detectably labeled nucleotides which may be used during the synthesis or sequencing of a nucleic acid molecule. One of a number of labels may be used to detect such nucleotides. Illustrative labels include, but are not limited to, radioactive isotopes, fluorescent labels, chemiluminescent labels, bioluminescent labels and enzyme labels.

Having now generally described the invention, the same will be more readily understood through reference to the following Examples which are provided by way of illustration, and are not intended to be limiting of the present invention, unless specified.

EXAMPLES

Example 1

Construction of DNA Polymerase Fusions

A chimera is made by combining the domains of different DNA polymerases, for example, the insertion of the thioredoxin processivity factor binding domain of bacteriophage T7 DNA polymerase into the homologous site in *E. coli* DNA polymerase I. This facilitates a substantial increase in the processivity of the chimeric *E. coli* DNA polymerase I in the presence of thioredoxin. (Bedford, E., et al., PNAS, USA vol. 94, pp. 479-484, January 1997 Biochem.). Another illustration of this strategy is the addition of an archaeal PCNA binding domain to Taq DNA polymerase. PCNA is then added to the PCR reaction with the Taq chimera to enhance processivity and generate higher yields (Motz, M., et al., J. Biol. Chem. 2002 May 3; 277 (18); 16179-88).

A chimeric DNA polymerase is also generated by combining elements (protein or domain) of a double stranded DNA binding protein with a DNA polymerase. The helix-hairpin-helix DNA binding motifs from DNA topoisomerase V have been added to the NH(2) terminus or COOH terminus of Taq DNA polymerase, Stoffel fragment of Taq DNA polymerase or Pfu DNA polymerase. The resulting chimeras have increased processivity, salt tolerance, and thermostability (Pavlov, A. R., et al. PNAS USA 2002, October 15; 99 (21); 13510-5). Another example is the fusion of DNA polymerase with the sequence non-specific DNA binding protein Sso7d or Sac7d from *Sulfolobus sulfataricus*, or an archaeal PCNA DNA binding domain. This strategy is used to enhance the processivity of Pfu or Taq DNA polymerase (WO 01/92501 A1).

DNA polymerases of the invention including but not limited to Pfu fusion proteins are purified as described in PCT/US01 17492 or Pavlov et al., supra.

Example 2

Chimeric DNA Polymerase Blend Formulations

A chimeric DNA polymerase blend formulation is comprised of a chimeric DNA polymerase and: (1) a proofreading or a non-proofreading DNA polymerase; or (2) a proofreading plus non-proofreading, non-proofreading plus non-proofreading or a proofreading plus proofreading DNA polymerase blend, e.g., Pfu, Taq, Pfu/Taq, Pfu/exo-Pfu, Taq/exo-Pfu, Pfu/JDF3, or any of these combinations with pol-Pfu (Pfu G387P). A specific non limiting example of a blend formulation is 2.5 U Pfu/0.25 U chimeric Pfu. A chimeric DNA blend comprises a chimeric DNA polymerase in combination with at least one wild type and/or at least one mutant DNA polymerase (as defined herein).

The wild type DNA polymerase that is blended with the DNA polymerase chimera is any native or cloned DNA polymerase having native levels of polymerase activity, proofreading activity and is preferably thermostable like Pfu or Taq. The chimeric DNA polymerase and wt DNA polymerase are blended (for example in any ratio described herein) and mixed with any replication accessory factor (a protein that enhances DNA synthesis) or PCR enhancing additives, e.g., Pfu dUTPase (PEF), PCNA, RPA, ssb, antibodies, DMSO, betaine, or 3'-5' exonuclease (e.g., Pfu G387P). Specific non-limiting examples of commercially useful mutations or truncations are V93R,K,E,D in Pfu, which confer uracil insensitivity, D141A/E143A in Pfu, which eliminates 3'-5' exonuclease activity, and the N-terminal truncation of Taq to eliminate 5'-3' exonuclease activity(KlenTaq). The chimeric DNA polymerase and mutant DNA polymerase are blended in any ratio and mixed with any replication accessory factor or PCR additives. The DNA polymerase formulation is any mixture of wt, wt and mutant, mutant and mutant DNA polymerases. The chimeric DNA polymerase and DNA polymerase formulation are blended in any ratio and mixed with any replication accessory factor or PCR additives.

High pH PCR Reaction Buffer.

A high pH PCR reaction buffer is formulated at a 10× concentration and used in PCR reactions at a final 1× concentration, which is standard for most commercially produced PCR reaction buffers. A 10× buffer formulation useful according to the invention is: 300 mM Tris pH 10.0 or pH 11.8; 100 mM KCl; 100 mM Ammonium Sulfate; 20 mM Magnesium Sulfate; 1% Trition X-100; 1 mg/ml nuclease-free bovine serum albumin (BSA). This formulation is in no way a limitation of the components or concentrations of components used for the invention. The components of the buffer, other than the buffering component, are varied depending on the requirements for the maximal activity of a specific DNA polymerase or DNA polymerase blend.

Example 3

PCR Amplification with a Chimeric Pfu DNA Polymerase or with DNA Polymerase Blends Containing a Chimeric Pfu DNA Polymerase PCR Reaction Conditions PCR reactions were conducted under standard conditions in 1× cloned Pfu PCR buffer (10 mM KCl, 10 mM $(NH_4)_2SO_4$, 2 mM Mg $SO_4$, 0.1% Triton X-100, and 100 μg/ml BSA) except that 1). The Tris component was at pH 10.0 or 11.8 and at a final concentration of 30 mM and 2). The mixture contained 0.25-1.3 U Pfu-Sso7d chimeric DNA polymerase (sequence provided herein and 10 01/92501, incorporated by reference in its entirety) or chimeric DNA polymerase blends composed of 0.25 U Pfu-Sso7d and either 2.5 U or 5.0 U Pfu DNA polymerase. All PCR reactions contained 2 U/50 μl cloned *Pyrococcus furiosus* dUTPase (PEF). For all genomic targets 0.9-6.0 kb in length, PCR reactions contained 100 ng of human genomic DNA, 300 μM each dNTP, and 100 ng of each primer. For the 19 kb genomic target, PCR reactions contained 250 ng of human genomic DNA, 500 μM each dNTP, and 200 ng of each primer.

Effect of Buffer pH on PCR Amplification

Figure 1:
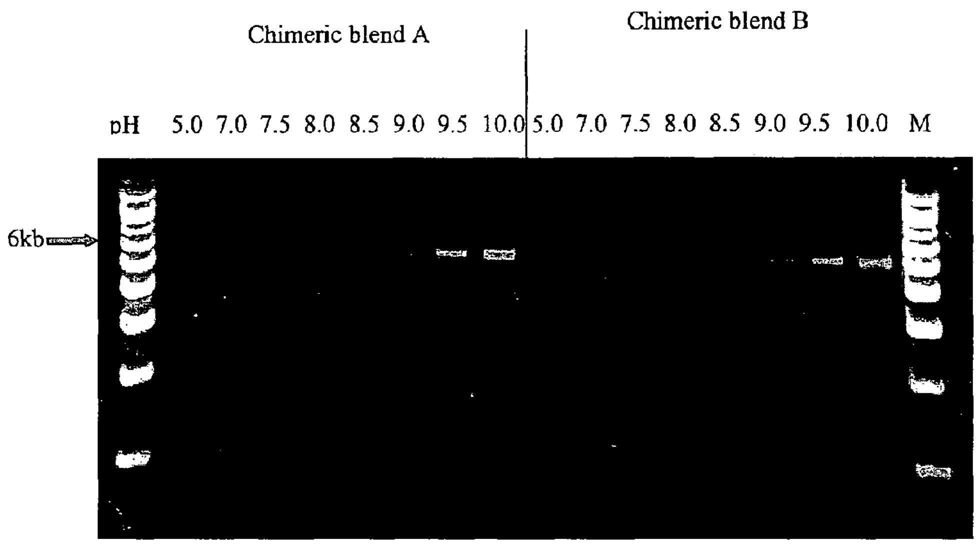
FIG. 1: 6 kb human βeta globin genomic DNA target amplified with a 15 second per kb extension time (1 minute 30 second total extension time). The PCR reaction buffer consisted of 1× cloned Pfu buffer using a 30 mM Tris pH gradient from 5.0 to 10.0. The chimeric DNA polymerase blend was composed of A; 0.25 U chimeric Pfu DNA polymerase and 2.5 U Pfu Turbo for a total of 2.75 U/reaction and B; 0.25 U chimeric Pfu DNA polymerase and 5.0 U Pfu Turbo for a total of 5.25 U/reaction. M is 1 kb DNA marker (Stratagene).
Figure 2:
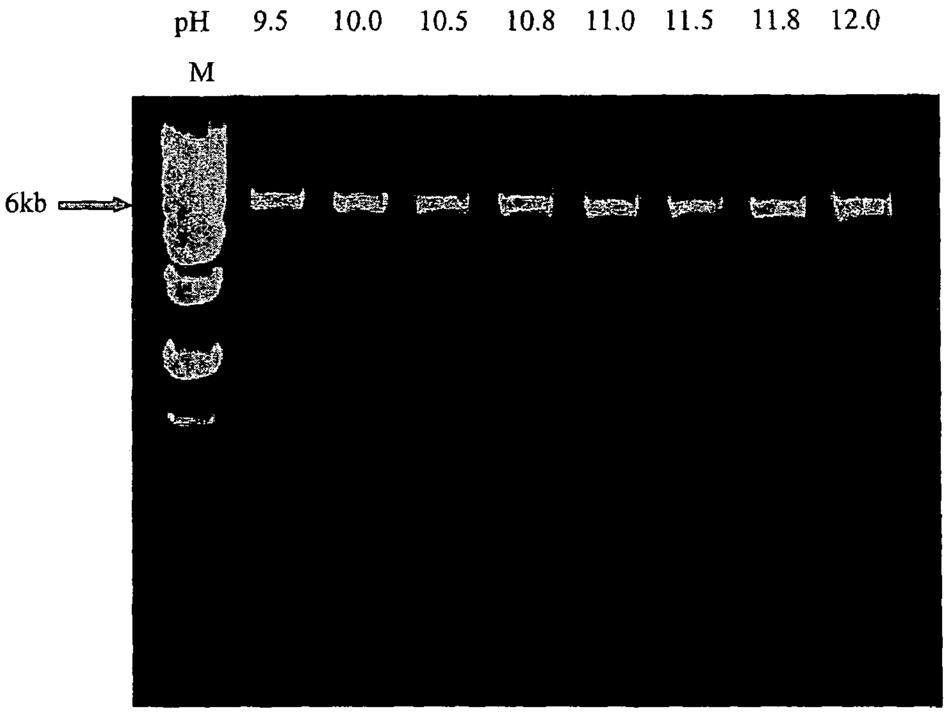
FIG. 2: 6 kb human Geta globin genomic DNA target amplified with a 15 second per kb extension time (1 minute 30 second total extension time). The PCR reaction buffer consisted of 1× cloned Pfu buffer using a 30 mM Tris pH gradient from 9.5 to 12.0. The chimeric DNA polymerase blend was composed of 0.25 U chimeric Pfu DNA polymerase and 2.5 U Pfu Turbo for a total of 2.75 U/reaction. M is 1 kb DNA marker (Stratagene).

To demonstrate the effect of pH on PCR reactions with chimeric Pfu-Sso7d DNA polymerase, PCR reactions were prepared using 1× Pfu reaction buffer wherein the pH of the Tris component was titrated from pH 5.0-12.0 (FIGS. #1 & 2). Pfu-Sso7d/Pfu Turbo blends (0.25 U Pfu-Sso7d+2.5 U or 5.0 U Pfu Turbo) were used to amplify a 6 kb human beta globin genomic target with an extension time of 15 seconds per kb. Pfu Turbo alone cannot amplify this target at 15 seconds per kb. Amplification is only achieved with the contribution of the more processive Pfu-Sso7d. Amplification appears at pH 8.5 and is strongest between pH 10.0-12.0, demonstrating the enhancing effect of high pH on the chimeric Pfu-Sso7d DNA polymerase (FIGS. 1 & 2).

Figure 3:
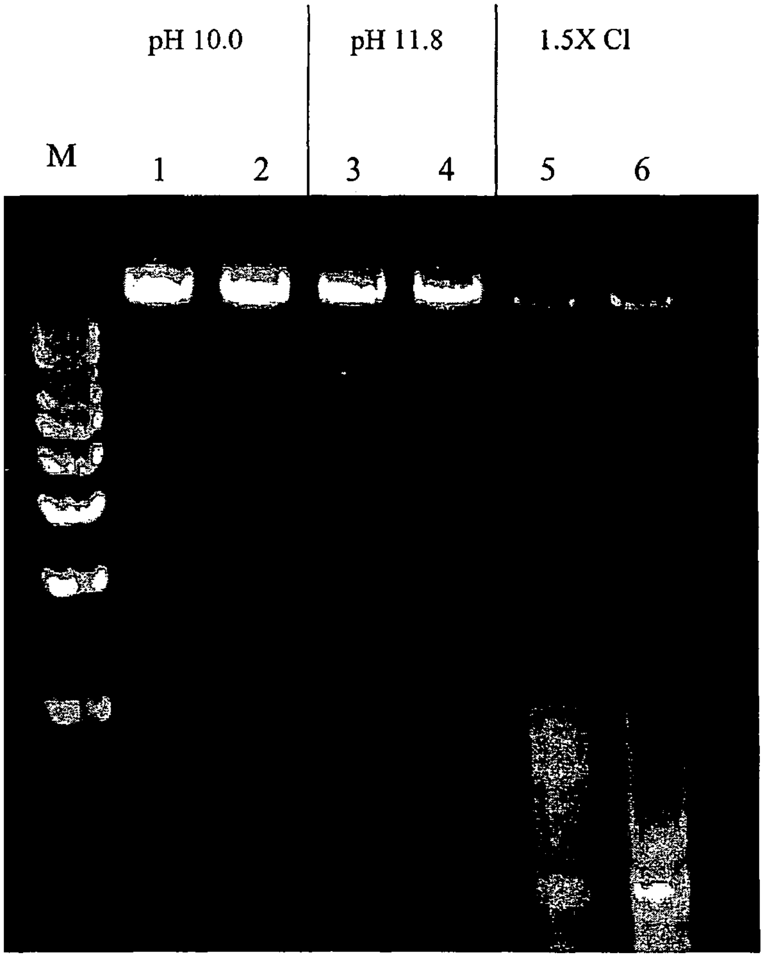
FIG. 3: Comparison of high pH reaction buffers and 1.5× cloned Pfu reaction buffer for the 19 kb beta globin genomic target. Lanes 1 and 2 are with the pH 10 buffer. Lanes 3 and 4 are with the pH 11 buffer. Lanes 5 and 6 are with 1.5× cloned Pfu reaction buffer. Lanes 1, 3 and 5 were amplified with the chimeric DNA polymerase blend that was composed of 0.25 U chimeric Pfu DNA polymerase and 2.5 U Pfu Turbo for a total of 2.75 U/reaction. Lanes 2, 4, & 6 were amplified with the chimeric DNA polymerase blend that was composed of 0.25 U chimeric Pfu DNA polymerase and 5.0 U Pfu Turbo for a total of 5.25 U/reaction. M is 1 kb DNA marker (Stratagene). A 30 second per kb extension time was used.

To demonstrate the enhancing effect of a high pH PCR reaction buffer for the PCR amplification of long genomic targets, a 19 kb fragment of human beta globin was amplified using Pfu-Sso7d/Pfu Turbo blend with an extension time of 30 seconds per kb. Amplification of this target with an extension time of 30 seconds per kb can only be achieved with the contribution of the more processive Pfu-Sso7d chimeric DNA polymerase component of the blend. PCR amplification in the pH 10.0 and pH 11.8 reaction buffers was compared to amplification in 1.5× cloned Pfu reaction buffer, which is the optimal PCR reaction buffer condition for Pfu Turbo (Strategies: Vol. 12, #4; "High fidelity PCR of genomic targets up to 19 kb"). PCR reactions using the high pH 10.0 and 11.8 reaction buffers were dramatically superior to the 1.5× cloned Pfu buffer, further demonstrating the enhancing effects of high pH for PCR amplification with Pfu-Sso7d (FIG. 3).

Figure 4:
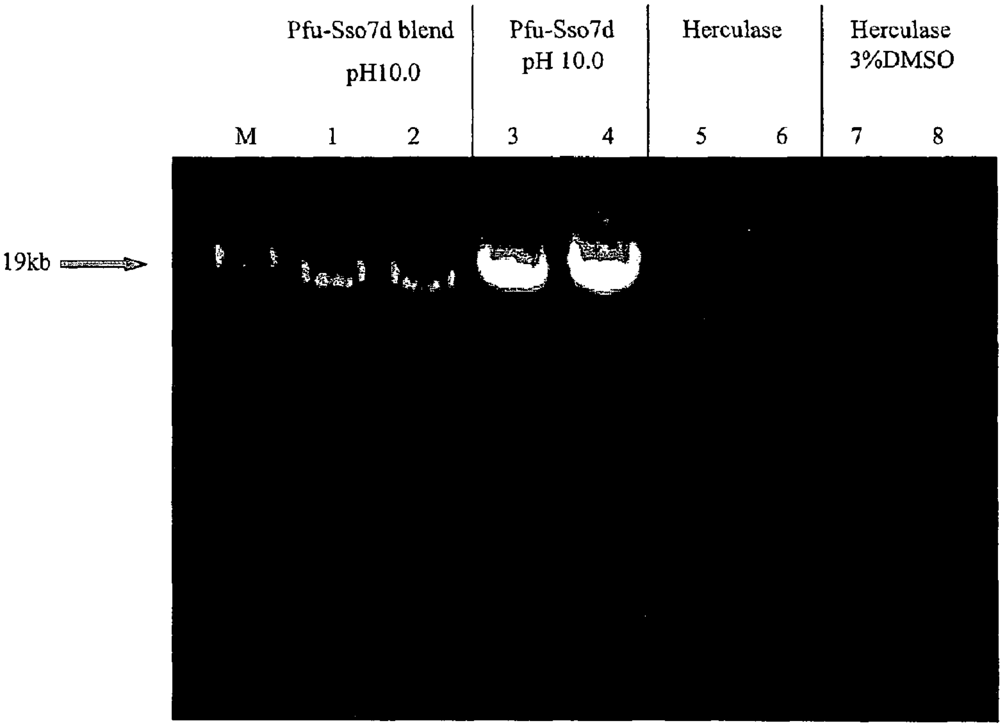
FIG. 4: Comparison of the chimeric Pfu DNA polymerase/Pfu Turbo DNA polymerase blend and the chimeric Pfu. DNA polymerase in the high pH PCR reaction buffer and Herculase DNA polymerase in Herculase PCR reaction buffer for the PCR amplification of the 19 kb beta globin genomic target. Lanes 1 to 4 used the pH 10 PCR reaction buffer. Lanes 5 to 8 used Herculase PCR reaction buffer. Lane 1 was amplified with the chimeric DNA polymerase blend that was composed of 0.25 U chimeric Pfu DNA polymerase and 2.5 U Pfu Turbo for a total of 2.75 U/reaction. Lane 2 was amplified with the chimeric DNA polymerase blend that was composed of 0.25 U chimeric Pfu DNA polymerase and 5.0 U Pfu Turbo for a total of 5.25 U/reaction. Lane 3 was amplified with 0.83 U of the Pfu chimeric DNA polymerase. Lane 4 was amplified with 1.3 U of the chimeric DNA polymerase. Lanes 5 and 6 were amplified with 5.0 U of Herculase DNA polymerase with out DMSO. Lanes 7 and 8 were amplified with 5.0 U of Herculase DNA polymerase with 3% DMSO. A 30 second per kb extension time was used. M is the Lambda/Hind III DNA marker (Stratagene).

To further demonstrate the enhancing effects of high pH on PCR amplification with the chimeric Pfu-Sso7d DNA polymerase, amplification of the 19 kb human beta globin genomic target was compared using the Pfu-Sso7d/Pfu Turbo blends (0.25 U Pfu-Sso7d+2.5 U or 5.0 U Pfu Turbo) and 0.83 U and 1.3 U of Pfu-Sso7d in the pH 10.0 PCR reaction buffer with a 30 second per kb extension time (FIG. 4). The significant difference between these PCR reactions, since they all use the pH 10.0 buffer, is the amounts of Pfu-Sso7d in each reaction (i.e. 0.25 U Pfu-Sso7d for the blends and 0.83 U and 1.3 U Pfu-Sso7d for the non-blend reactions). The reactions which have 0.83 U and 1.3 U Pfu-Sso7d without any cloned Pfu DNA polymerase (#3 and #4 FIG. 4) generated dramatically higher yields than the blend reactions (#1 and #2 FIG. 4) which only had 0.25 U Pfu-Sso7d even though the total units of DNA polymerase were higher for the blend reactions (2.75 U #1, 5.25 U #2 for the blends and 0.83 U #3 and 1.3 U #4 for the Pfu-Sso7d reactions—FIG. 4).

PCR Performance Using a Reaction Buffer at pH 10.0.

Figure 5:
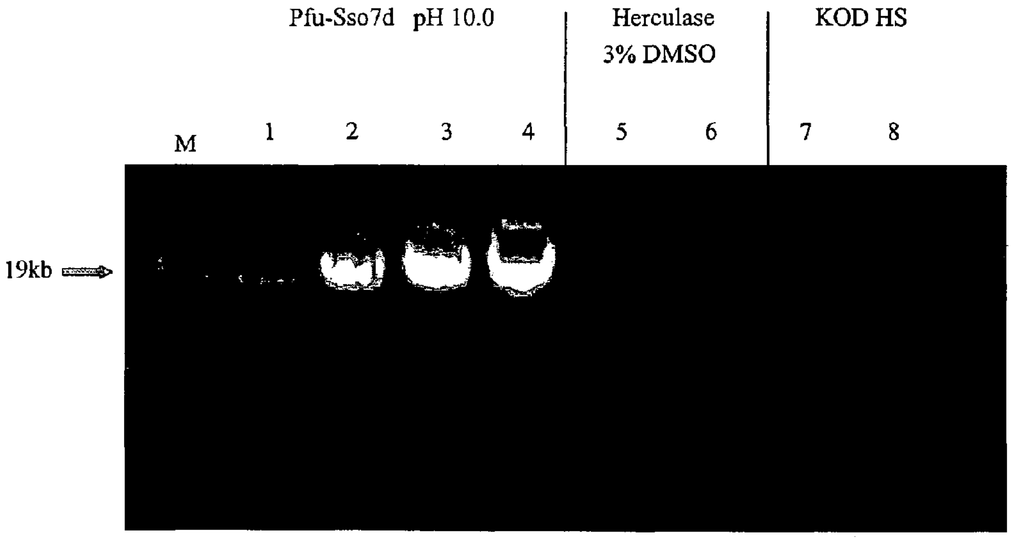
FIG. 5: Unit titration of chimeric Pfu DNA polymerase in high pH PCR reaction buffer and performance comparison to Herculase DNA polymerase and KOD hot start for the amplification of the 19 kb human beta globin with an extension time of 30 seconds per kb. #1-4, chimeric Pfu-Sso7d DNA polymerase in pH 10.0 PCR reaction buffer. #1-0.25 U; #2-0.5 U; #3-0.83 U; #4-1.3 U. #5-6, 5.0 U of Herculase DNA polymerase in 1× Herculase PCR reaction buffer and 3% DMSO. #7-8, KOD hot start DNA polymerase in KOD hot start DNA polymerase PCR reaction buffer. #7-1.25 U; #8-2.5 U. M is the Lambda/Hind III DNA marker (Stratagene).

The amplification efficiency of the 19 kb human beta globin target with Herculase DNA polymerase, KOD hot start DNA polymerase and a unit titration of the Pfu-Sso7d chimeric DNA polymerase was compared (FIG. 5). All enzymes were used in their optimal reaction buffers. The pH 10.0 buffer was used for Pfu-Sso7d, KOD hot start buffer for KOD hot start, and Herculase buffer for Herculase. 3% DMSO was added to the Herculase reactions which is optimal for the amplification of genomic targets over 10 kb in length. A 30 second per kb extension time was used. Most PCR enzymes require an extension time of 1-2 minutes per kb for a target of this length. All unit amounts (0.25-1.3 U) of Pfu-Sso7d in the pH 10 buffer generated PCR product. The Herculase and KOD hot start reactions did not generate any PCR product at this extension time.

Figure 6:
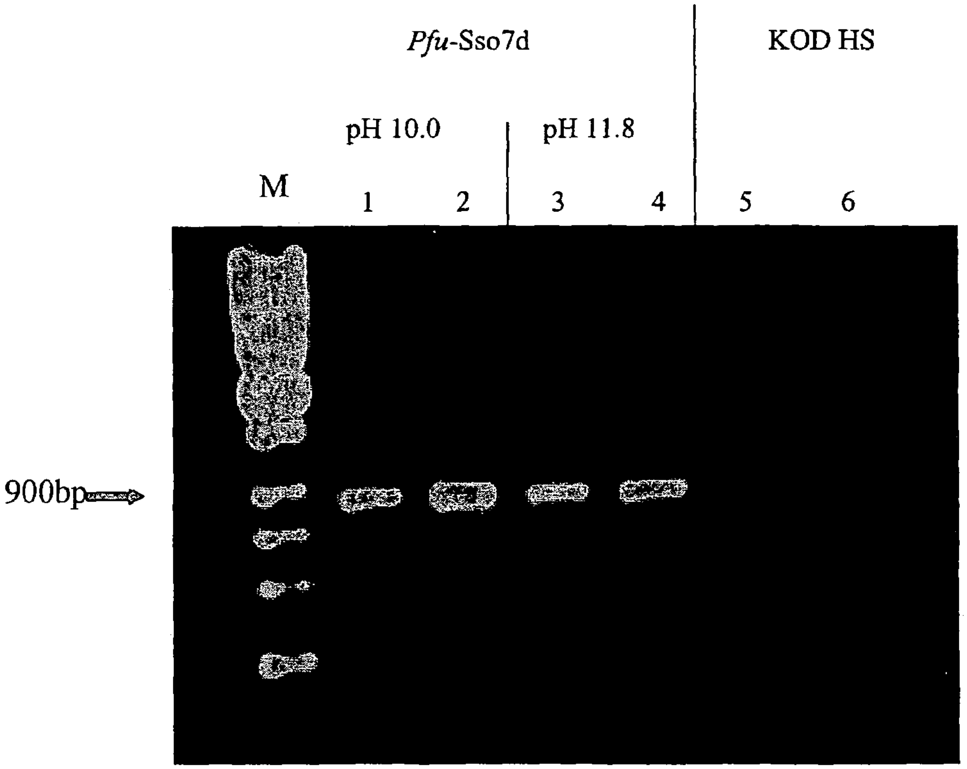
FIG. 6: Performance comparison of chimeric Pfu DNA polymerase in the pH 10.0 PCR reaction buffer and KOD hot start in KOD hot start PCR reaction buffer for the amplification of 900 bp Human alpha-1 antitrypsin (Hα1AT) with a 1 second total extension time. #1-2, chimeric Pfu-Sso7d DNA polymerase in pH 10.0 PCR reaction buffer. #3-4, Pfu-Sso7d DNA polymerase in pH 11.8 PCR reaction buffer. #5-6, 1.0 U KOD hot start in KOD hot start PCR reaction buffer. #1-0.5 U; #2-0.83 U; #3-0.5 U; #4-0.83 U. M-1 kb DNA marker (Stratagene).
Figure 7:
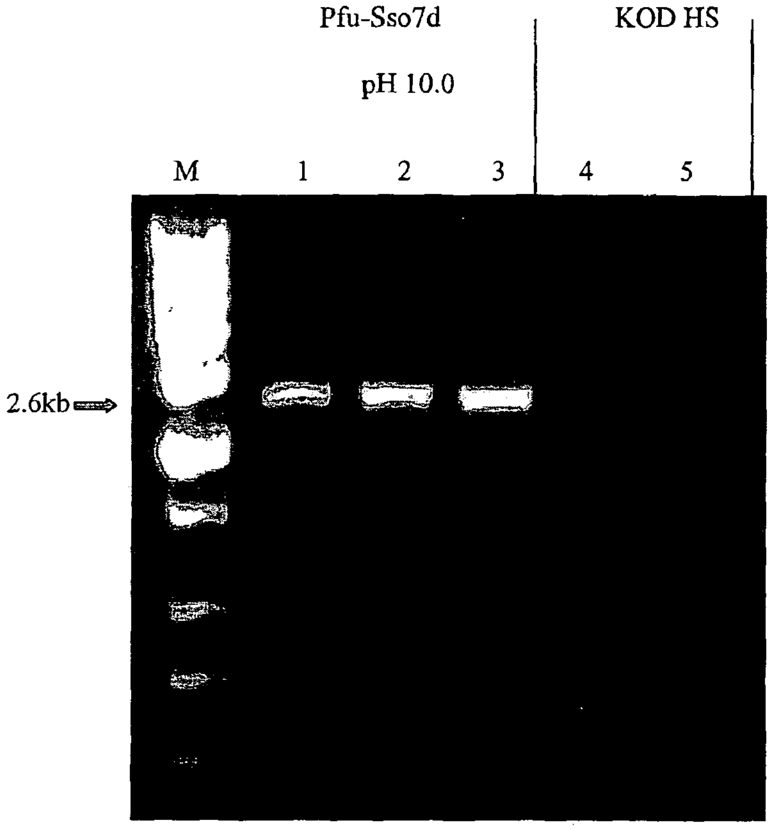
FIG. 7: PCR performance comparison of chimeric Pfu-Sso7d DNA polymerase in pH 10.0 PCR reaction buffer and KOD hot start DNA polymerase in KOD hot start PCR reaction buffer for the amplification of 2.6 kb Human alpha-1 antitrypsin (Hα1AT) with an extension time of 2 seconds per kb (5 second total extension time). #1-3, Pfu-Sso7d DNA polymerase in pH 10.0 PCR reaction buffer. #4-5, KOD hot start DNA polymerase in KOD hot start PCR reaction buffer. #1-0.5 U; #2-0.83 U; #3-1.3 U; #4-1.25 U; #5-2.5 U. M-1 kb DNA ladder (Stratagene).
Figure 8:
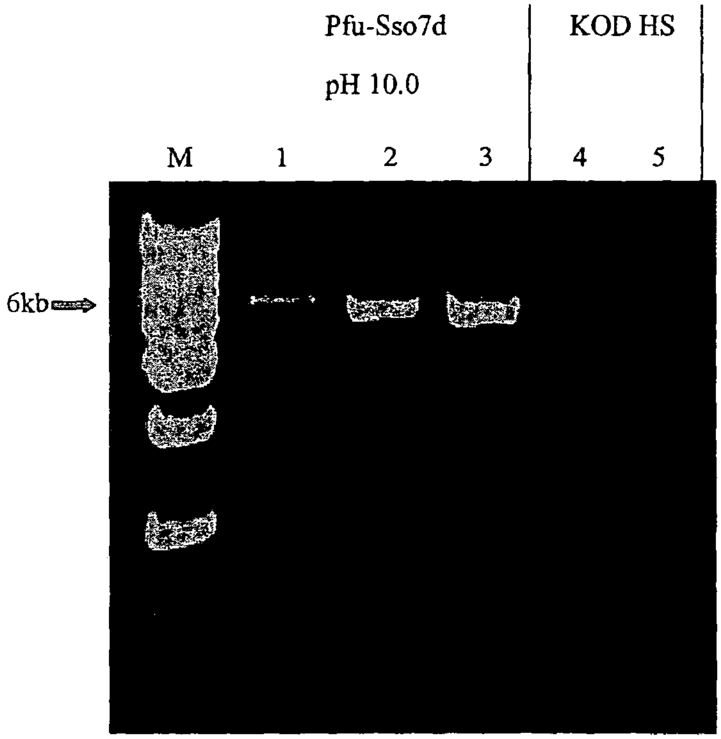
FIG. 8: PCR performance comparison of chimeric Pfu-Sso7d DNA polymerase in pH 10.0 PCR reaction buffer and KOD hot start in KOD hot start PCR reaction buffer for the amplification of 6 kb human beta globin with an extension time of 10 seconds per kb. #1-3, chimeric Pfu-Sso7d DNA polymerase in pH 10.0 PCR reaction buffer. #4-5. KOD hot start DNA polymerase in KOD hot start PCR reaction buffer. #1-0.5 U; #2-0.83 U; #3-1.3 U; #4-1.25 U; #5-2.5 U. M-1 kb DNA ladder (Stratagene).
Figure 9:
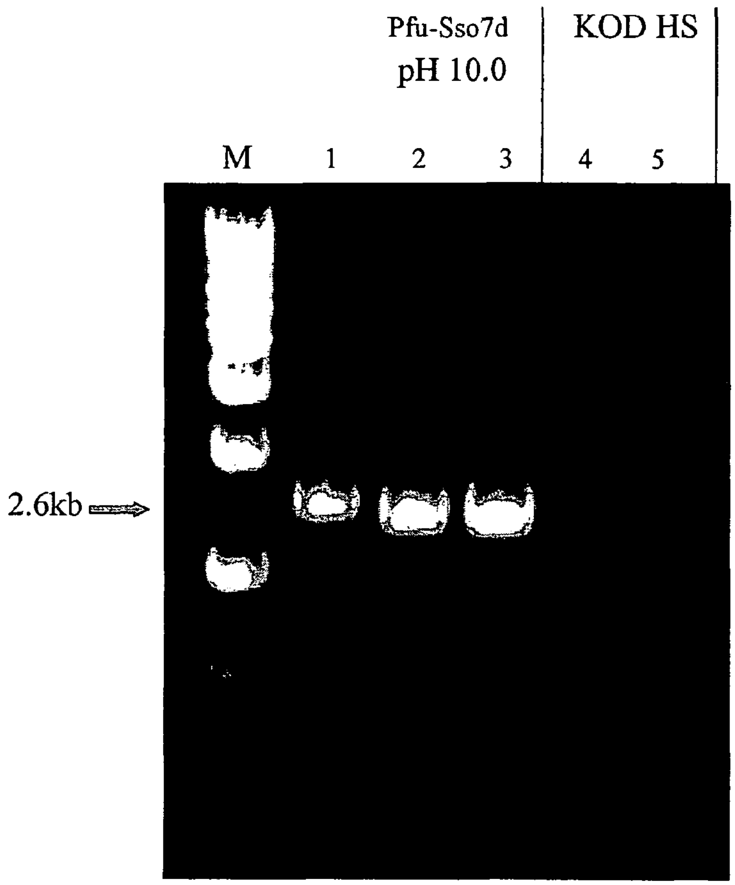
FIG. 9: PCR performance comparison of chimeric Pfu-Sso7d DNA polymerase in pH 10.0 PCR reaction buffer and KOD hot start in KOD hot start PCR reaction buffer for, the amplification of 2.6 kb Hα1AT with an extension of 30 seconds per kb (1 minute 18 seconds total extension time). #1-3, Pfu-Sso7d DNA polymerase. #4-5, KOD hot start DNA polymerase. #1-0.5 U; #2-0.83 U; #3-1.3 U; #4-1.25 U; #5-2.5 U. M-1 kb DNA ladder (Stratagene).

The amplification of smaller genomic targets was also compared using the Pfu-Sso7d chimeric DNA polymerase in the high pH 10.0 PCR reaction buffer and KOD hot start DNA polymerase in KOD hot start PCR reaction buffer. A 900 bp fragment of human alpha-1 anti trypsin (Hα1AT) was amplified with a 1 second total extension time using 1) 0.5 U or 0.83 U of Pfu-Sso7d in pH 10.0 or pH 11.8 PCR reaction buffers, and 2) 1 U of KOD hot start in KOD hot start PCR reaction buffer (FIG. 6). A 2.6 kb fragment of Hα1AT was amplified with a 2 second per kb extension time (5 second total extension time) (FIG. 7) and a 30 second per kb extension time (1 minute 18 second total extension time) (FIG. 9) using 0.5 U, 0.83 U and 1.3 U of Pfu-Sso7d in the pH 10.0 PCR reaction buffer and 1.25 U and 2.5 U of KOD hot start in KOD hot start PCR reaction buffer. A 6 kb fragment of human beta globin was amplified with a 10 second per kb extension time (1 minute total extension time) (FIG. 8) using 0.5 U, 0.83 U and 1.3 U of Pfu-Sso7d in the pH 10.0 PCR reaction buffer and 1.25 U and 2.5 U of KOD hot start in KOD hot start PCR reaction buffer. The extension times for all targets were shorter than the standard time for most PCR enzymes. 30 seconds to 2 minutes per kb is standard for most PCR enzymes. For all targets, the chimeric Pfu-Sso7d DNA polymerase in the high pH PCR reaction buffers displayed vastly superior performance at all unit amounts (0.25-1.3Upper reaction).

By the use of a high pH PCR reaction buffer with a processive chimeric Pfu DNA polymerase (in the presence of PEF/dUTPase), PCR extension times were substantially reduced for the amplification of genomic targets. For genomic targets between 1-6 kb an extension time of 1 min/kb for a non-chimeric DNA polymerase/DNA polymerase formulation was reduced to 1-10 seconds per kb. For genomic targets between 17-19 kb an extension time of 2 min/kb for a non-chimeric DNA polymerase/polymerase formulation was reduced to 30 sec/kb. The high pH reaction buffer/chimeric DNA polymerase/chimeric DNA polymerase blend combination is used in the same way as a conventional PCR reaction buffer/DNA polymerase/DNA polymerase blend combination and can be used in any primer extension application, including PCR, to produce high product yields with shortened extension times. The main application would be for the amplification of genomic targets, which typically require extension times of 1-2 minutes per kb and can take hours to amplify. Extension times could be reduced to 1-30 seconds per kb, or shorter, with the high pH buffer and chimeric DNA polymerase. Amplification times could be dramatically reduced, substantially improving PCR applications. Other applications include RT-PCR, site-directed mutagensis and random mutagenesis. A high pH reaction buffer/chimera combination used in all of these applications would increase length capability and shorten reaction times and highly increase overall performance in all standard protocols.

The practice of the present invention will employ, unless otherwise indicated, conventional techniques of molecular biology, cell biology, microbiology and recombinant DNA techniques, which are within the skill of the art. Such techniques are explained fully in the literature. See, e.g., Sambrook, Fritsch & Maniatis, 1989*, Molecular Cloning: A Laboratory Manual*, Second Edition; *Oligonucleotide Synthesis* (M. J. Gait, ed., 1984); *Nucleic Acid Hybridization* (B. D. Hames & S. J. Higgins, eds., 1984); *A Practical Guide to Molecular Cloning* (B. Perbal, 1984); (Harlow, E. and Lane, D.) Using Antibodies: A Laboratory Manual (1999) Cold Spring Harbor Laboratory Press; and a series, *Methods in Enzymology* (Academic Press, Inc.); *Short Protocols In Molecular Biology*, (Ausubel et al., ed., 1995).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method for DNA synthesis at a pH from 9.5 to 12, comprising:

(a) providing a DNA polymerase fusion comprising a chimeric archaeal DNA polymerase fused to an Sso7D protein, wherein the chimeric archaeal DNA polymerase comprises a first amino acid sequence derived from a first polymerase species and a second amino acid sequence derived from a second polymerase species and wherein the first amino acid sequence or the second amino acid sequence is derived from an archaeal polymerase;

(b) contacting said fusion with a nucleic acid template, wherein said fusion has enhanced DNA polymerase activity at a pH from 9.5 to 12 as compared to at a pH lower than 9.5 and permits DNA synthesis, and (c) synthesizing said DNA from said nucleic acid template.

2. The method of claim 1, further comprising contacting a PCR enhancing factor and/or an additive with said DNA polymerase fusion and said nucleic acid template.

3. A kit for performing at a pH from 9.5 to 12 a method selected from the group consisting of DNA synthesis, cloning of a DNA synthesis product, sequencing DNA, RT PCR, and linear or exponential PCR amplification, said kit comprising:

a DNA polymerase fusion comprising a chimeric archaeal DNA polymerase fused to an Sso7D protein, wherein the chimeric archaeal DNA polymerase comprises a first amino acid sequence derived from a first polymerase species and a second amino acid sequence derived from a second polymerase species and has enhanced DNA polymerase activity at a pH from 9.5 to 12 as compared to at a pH lower than 9.5 and wherein the first amino acid sequence or the second amino acid sequence is derived from an archaeal polymerase;

a buffer with a pH from 9.5 to 12; and packaging materials therefor.

4. The kit of claim 3, further comprising a PCR enhancing factor and/or an additive.

5. A composition for any one of DNA synthesis, cloning of a DNA synthesis product, sequencing DNA, linear or exponential PCR amplification, and RT-PCR, said composition comprising:

a DNA polymerase fusion and a buffer with a pH from 9.5 to 12, wherein the DNA polymerase fusion comprises a chimeric archaeal DNA polymerase fused to an Sso7D protein, wherein the chimeric archaeal DNA polymerase comprises a first amino acid sequence derived from a first polymerase species and a second amino acid sequence derived from a second polymerase species and has enhanced DNA polymerase activity at a pH from 9.5 to 12 as compared to at a pH lower than 9.5 and wherein the first amino acid sequence or the second amino acid sequence is derived from an archaeal polymerase.

6. The composition of claim 5, wherein the buffer is a DNA synthesis buffer, a DNA cloning buffer a DNA sequencing buffer, a DNA sequencing buffer, or a PCR reaction buffer.

7. The composition of claim 5, further comprising a PCR enhancing factor and/or an additive.

8. The method of claim 1, wherein both the first polymerase species and the second polymerase species are derived from archaeal DNA polymerases.

9. The method of claim 1, wherein the first polymerase species or the second polymerase species is selected from the group consisting of Pfu, KOD, Pfx, Vent, Deep Vent, Tgo, Pwo, and *Pyrococcus furiosus* DP1/DP2.

10. The kit of claim 3, wherein both the first polymerase species and the second polymerase species are derived from archaeal DNA polymerases.

11. The kit of claim 3, wherein the first polymerase species or the second polymerase species is selected from the group consisting of Pfu, KOD, Pfx, Vent, Deep Vent, Tgo, Pwo, and *Pyrococcus furiosus* DP1/DP2.

12. The composition of claim 5, wherein both the first polymerase species and the second polymerase species are derived from archaeal DNA polymerases.

13. The composition of claim 5, wherein the first polymerase species or the second polymerase species is selected from the group consisting of Pfu, KOD, Pfx, Vent, Deep Vent, Tgo, Pwo, and *Pyrococcus furiosus* DP1/DP2.

* * * * *

SEQUENCE LISTING

```
<160> NUMBER OF SEQ ID NOS: 148

<210> SEQ ID NO 1
<211> LENGTH: 30
<212> TYPE: DNA
<213> ORGANISM: Artificial sequence
<220> FEATURE:
<223> OTHER INFORMATION: primer

<400> SEQUENCE: 1

gacgacgaca agatgatttt agatgtggat                                    30


<210> SEQ ID NO 2
```

<211> LENGTH: 30
<212> TYPE: DNA
<213> ORGANISM: Artificial sequence
<220> FEATURE:
<223> OTHER INFORMATION: primer

<400> SEQUENCE: 2
ggaacaagac ccgtctagga ttttttaatg 30

<210> SEQ ID NO 3
<211> LENGTH: 30
<212> TYPE: DNA
<213> ORGANISM: Artificial sequence
<220> FEATURE:
<223> OTHER INFORMATION: primer

<400> SEQUENCE: 3
agagcttgag gagagcagga aaggtggaac 30

<210> SEQ ID NO 4
<211> LENGTH: 30
<212> TYPE: DNA
<213> ORGANISM: Artificial sequence
<220> FEATURE:
<223> OTHER INFORMATION: primer

<400> SEQUENCE: 4
gggaggggag gtacagggtt gaggctagtg 30

<210> SEQ ID NO 5
<211> LENGTH: 37
<212> TYPE: DNA
<213> ORGANISM: Artificial sequence
<220> FEATURE:
<223> OTHER INFORMATION: primer

<400> SEQUENCE: 5
gaacatcccc aagatgaacc cactattaga gaaaaag 37

<210> SEQ ID NO 6
<211> LENGTH: 37
<212> TYPE: DNA
<213> ORGANISM: Artificial sequence
<220> FEATURE:
<223> OTHER INFORMATION: primer

<400> SEQUENCE: 6
ctttttctct aatagtgggt tcatcttggg gatgttc 37

<210> SEQ ID NO 7
<211> LENGTH: 37
<212> TYPE: DNA
<213> ORGANISM: Artificial sequence
<220> FEATURE:
<223> OTHER INFORMATION: primer

<400> SEQUENCE: 7
gaacatcccc aagatagacc cactattaga gaaaaag 37

<210> SEQ ID NO 8
<211> LENGTH: 37
<212> TYPE: DNA
<213> ORGANISM: Artificial sequence
<220> FEATURE:
<223> OTHER INFORMATION: primer

<400> SEQUENCE: 8

```
ctttttctct aatagtgggt ctatcttggg gatgttc                            37


<210> SEQ ID NO 9
<211> LENGTH: 37
<212> TYPE: DNA
<213> ORGANISM: Artificial sequence
<220> FEATURE:
<223> OTHER INFORMATION: primer

<400> SEQUENCE: 9

gaacatcccc aagataaccc cactattaga gaaaaag                            37


<210> SEQ ID NO 10
<211> LENGTH: 37
<212> TYPE: DNA
<213> ORGANISM: Artificial sequence
<220> FEATURE:
<223> OTHER INFORMATION: primer

<400> SEQUENCE: 10

ctttttctct aatagtgggg ttatcttggg gatgttc                            37


<210> SEQ ID NO 11
<211> LENGTH: 37
<212> TYPE: DNA
<213> ORGANISM: Artificial sequence
<220> FEATURE:
<223> OTHER INFORMATION: primer

<400> SEQUENCE: 11

gaacatcccc aagatcaccc cactattaga gaaaaag                            37


<210> SEQ ID NO 12
<211> LENGTH: 37
<212> TYPE: DNA
<213> ORGANISM: Artificial sequence
<220> FEATURE:
<223> OTHER INFORMATION: primer

<400> SEQUENCE: 12

ctttttctct aatagtgggg tgatcttggg gatgttc                            37


<210> SEQ ID NO 13
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate
<220> FEATURE:
<221> NAME/KEY: misc_feature
<222> LOCATION: (16)..(18)
<223> OTHER INFORMATION: NNK where N=any nucleotide

<400> SEQUENCE: 13

gaacatcccc aagatnnkcc cactattaga gaaaaag                            37


<210> SEQ ID NO 14
<211> LENGTH: 31
<212> TYPE: DNA
<213> ORGANISM: Artificial sequence
<220> FEATURE:
<223> OTHER INFORMATION: primer
```

<400> SEQUENCE: 14
gaacatcccc aagataaacc cactattaga g 31

<210> SEQ ID NO 15
<211> LENGTH: 31
<212> TYPE: DNA
<213> ORGANISM: Artificial sequence
<220> FEATURE:
<223> OTHER INFORMATION: primer

<400> SEQUENCE: 15
ctctaatagt gggtttatct tggggatgtt c 31

<210> SEQ ID NO 16
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 16
gaacatcccc aagatgcacc cactattaga gaaaaag 37

<210> SEQ ID NO 17
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 17
gaacatcccc aagatgaccc cactattaga gaaaaag 37

<210> SEQ ID NO 18
<211> LENGTH: 38
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 18
gaacatcccc aagattgccc ccactattag agaaaaag 38

<210> SEQ ID NO 19
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 19
gaacatcccc aagatatacc cactattaga gaaaaag 37

```
<210> SEQ ID NO 20
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 20

gaacatcccc aagatatgcc cactattaga gaaaaag                              37


<210> SEQ ID NO 21
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 21

gaacatcccc aagatttccc cactattaga gaaaaag                              37


<210> SEQ ID NO 22
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 22

gaacatcccc aagatcctcc cactattaga gaaaaag                              37


<210> SEQ ID NO 23
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 23

gaacatcccc aagatagccc cactattaga gaaaaag                              37


<210> SEQ ID NO 24
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 24
```

-continued gaacatcccc aagatacacc cactattaga gaaaaag 37

<210> SEQ ID NO 25
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 25
gaacatcccc aagattaccc cactattaga gaaaaag 37

<210> SEQ ID NO 26
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 26
gaacatcccc aagattggcc cactattaga gaaaaag 37

<210> SEQ ID NO 27
<211> LENGTH: 2328
<212> TYPE: DNA
<213> ORGANISM: Pyrococcus furiosus
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL POSSIBLE CODONS FOR ARGININE)

<400> SEQUENCE: 27
atgattttag atgtggatta cataactgaa gaaggaaaac ctgttattag gctattcaaa 60
aaagagaacg gaaaatttaa gatagagcat gatagaactt ttagaccata catttacgct 120
cttctcaggg atgattcaaa gattgaagaa gttaagaaaa taacggggga aaggcatgga 180
aagattgtga gaattgttga tgtagagaag gttgagaaaa agtttctcgg caagcctatt 240
accgtgtgga aactttattt ggaacatccc caagatnnnc ccactattag agaaaaagtt 300
agagaacatc cagcagttgt ggacatcttc gaatacgata ttccatttgc aaagagatac 360
ctcatcgaca aaggcctaat accaatggag ggggaagaag agctaaagat tcttgccttc 420
gatatagaaa ccctctatca cgaaggagaa gagtttggaa aaggcccaat tataatgatt 480
agttatgcag atgaaaatga agcaaaggtg attacttgga aaaacataga tcttccatac 540
gttgaggttg tatcaagcga gagagagatg ataaagagat ttctcaggat tatcagggag 600
aaggatcctg acattatagt tacttataat ggagactcat tcgcattccc atatttagcg 660
aaaagggcag aaaaacttgg gattaaatta accattggaa gagatggaag cgagcccaag 720
atgcagagaa taggcgatat gacggctgta gaagtcaagg gaagaataca tttcgacttg 780
tatcatgtaa taacaaggac aataaatctc ccaacataca cactagaggc tgtatatgaa 840
gcaatttttg gaaagccaaa ggagaaggta tacgccgacg agatagcaaa agcctgggaa 900
agtggagaga accttgagag agttgccaaa tactcgatgg aagatgcaaa ggcaacttat 960

```
gaactcggga aagaattcct tccaatggaa attcagcttt caagattagt tggacaacct   1020

ttatgggatg tttcaaggtc aagcacaggg aaccttgtag agtggttctt acttaggaaa   1080

gcctacgaaa gaaacgaagt agctccaaac aagccaagtg aagaggagta tcaaagaagg   1140

ctcagggaga gctacacagg tggattcgtt aaagagccag aaaaggggtt gtgggaaaac   1200

atagtatacc tagattttag agccctatat ccctcgatta taattaccca caatgtttct   1260

cccgatactc taaatcttga gggatgcaag aactatgata tcgctcctca agtaggccac   1320

aagttctgca aggacatccc tggtttttata ccaagtctct tgggacattt gttagaggaa   1380

agacaaaaga ttaagacaaa aatgaaggaa actcaagatc ctatagaaaa aatactcctt   1440

gactatagac aaaaagcgat aaaactctta gcaaattctt tctacggata ttatggctat   1500

gcaaaagcaa gatggtactg taaggagtgt gctgagagcg ttactgcctg gggaagaaag   1560

tacatcgagt tagtatggaa ggagctcgaa gaaaagtttg gatttaaagt cctctacatt   1620

gacactgatg gtctctatgc aactatccca ggaggagaaa gtgaggaaat aaagaaaaag   1680

gctctagaat ttgtaaaata cataaattca aagctccctg gactgctaga gcttgaatat   1740

gaagggtttt ataagagggg attcttcgtt acgaagaaga ggtatgcagt aatagatgaa   1800

gaaggaaaag tcattactcg tggtttagag atagttagga gagattggag tgaaattgca   1860

aaagaaactc aagctagagt tttggagaca atactaaaac acggagatgt tgaagaagct   1920

gtgagaatag taaaagaagt aatacaaaag cttgccaatt atgaaattcc accagagaag   1980

ctcgcaatat atgagcagat aacaagacca ttacatgagt ataaggcgat aggtcctcac   2040

gtagctgttg caaagaaact agctgctaaa ggagttaaaa taaagccagg aatggtaatt   2100

ggatacatag tacttagagg cgatggtcca attagcaata gggcaattct agctgaggaa   2160

tacgatccca aaaagcacaa gtatgacgca gaatattaca tggagaacca ggttcttcca   2220

gcggtactta ggatattgga gggatttgga tacagaaagg aagacctcag ataccaaaag   2280

acaagacaag tcggcctaac ttcctggctt aacattaaaa aatcctag                2328
```

<210> SEQ ID NO 28
<211> LENGTH: 2328
<212> TYPE: DNA
<213> ORGANISM: Pyrococcus furiosus
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 28

```
atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacgggggga aaggcatgga    180

aagattgtga gaattgttga tgtagagaag gttgagaaaa agtttctcgg caagcctatt    240

accgtgtgga aactttattt ggaacatccc caagatnnnc ccactattag agaaaaagtt    300

agagaacatc cagcagttgt ggacatcttc gaatacgata ttccatttgc aaagagatac    360

ctcatcgaca aaggcctaat accaatggag ggggaagaag agctaaagat tcttgccttc    420

gatatagaaa ccctctatca cgaaggagaa gagtttggaa aaggcccaat tataatgatt    480

agttatgcag atgaaaatga agcaaaggtg attacttgga aaaacataga tcttccatac    540

gttgaggttg tatcaagcga gagagagatg ataaagagat ttctcaggat tatcagggag    600

aaggatcctg acattatagt tacttataat ggagactcat tcgcattccc atatttagcg    660
```

```
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
gcaatttttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga aagaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaaggggtt gtgggaaaac   1200
atagtatacc tagattttag agccctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca tggagaacca ggttcttcca   2220
gcggtactta ggatattgga gggatttgga tacagaaagg aagacctcag ataccaaaag   2280
acaagacaag tcggcctaac ttcctggctt aacattaaaa aatcctag                2328
```

<210> SEQ ID NO 29
<211> LENGTH: 2328
<212> TYPE: DNA
<213> ORGANISM: Pyrococcus furiosus
<220> FEATURE:
<221> NAME/KEY: misc_feature
<222> LOCATION: (1161)..(1161)
<223> OTHER INFORMATION: N = C, G, A, or T
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL POSSIBLE CODONS FOR ARGININE)

<400> SEQUENCE: 29

```
atgattttag atgtggatta cataactgaa gaaggaaaac ctgttattag gctattcaaa     60
aaagagaacg gaaaatttaa gatagagcat gatagaactt ttagaccata catttacgct    120
cttctcaggg atgattcaaa gattgaagaa gttaagaaaa taacggggga aaggcatgga    180
```

```
aagattgtga gaattgttga tgtagagaag gttgagaaaa agtttctcgg caagcctatt    240
accgtgtgga aactttattt ggaacatccc caagatnnnc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gatatagaaa ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgcattccc atatttagcg    660
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
gcaatttttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga aagaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacacc nggattcgtt aaagagccag aaaaggggtt gtgggaaaac   1200
atagtatacc tagattttag agccctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg ggggaagaaag  1560
tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca tggagaacca ggttcttcca   2220
gcggtactta ggatattgga gggatttgga tacagaaagg aagacctcag ataccaaaag   2280
acaagacaag tcggcctaac ttcctggctt aacattaaaa aatcctag                2328
```

<210> SEQ ID NO 30
<211> LENGTH: 2328
<212> TYPE: DNA
<213> ORGANISM: Pyrococcus furiosus
<220> FEATURE:

<221> NAME/KEY: misc_feature
<222> LOCATION: (1161)..(1161)
<223> OTHER INFORMATION: N= A,T,C or G
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 30

```
atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacggggga aaggcatgga    180

aagattgtga gaattgttga tgtagagaag gttgagaaaa agtttctcgg caagcctatt    240

accgtgtgga aactttattt ggaacatccc caagatnnnc ccactattag agaaaaagtt    300

agagaacatc cagcagttgt ggacatcttc gaatacgata ttccatttgc aaagagatac    360

ctcatcgaca aaggcctaat accaatggag ggggaagaag agctaaagat tcttgccttc    420

gatatagaaa ccctctatca cgaaggagaa gagtttggaa aaggcccaat tataatgatt    480

agttatgcag atgaaaatga agcaaaggtg attacttgga aaaacataga tcttccatac    540

gttgaggttg tatcaagcga gagagagatg ataaagagat ttctcaggat tatcagggag    600

aaggatcctg acattatagt tacttataat ggagactcat tcgcattccc atatttagcg    660

aaaagggcag aaaaacttgg gattaaatta accattggaa gagatggaag cgagcccaag    720

atgcagagaa taggcgatat gacggctgta gaagtcaagg gaagaataca tttcgacttg    780

tatcatgtaa taacaaggac aataaatctc ccaacataca cactagaggc tgtatatgaa    840

gcaatttttg gaaagccaaa ggagaaggta tacgccgacg agatagcaaa agcctgggaa    900

agtggagaga accttgagag agttgccaaa tactcgatgg aagatgcaaa ggcaacttat    960

gaactcggga aagaattcct tccaatggaa attcagcttt caagattagt tggacaacct   1020

ttatgggatg tttcaaggtc aagcacaggg aaccttgtag agtggttctt acttaggaaa   1080

gcctacgaaa gaaacgaagt agctccaaac aagccaagtg aagaggagta tcaaagaagg   1140

ctcagggaga gctacacacc nggattcgtt aaagagccag aaaaggggtt gtgggaaaac   1200

atagtatacc tagattttag agccctatat ccctcgatta taattaccca caatgtttct   1260

cccgatactc taaatcttga gggatgcaag aactatgata tcgctcctca agtaggccac   1320

aagttctgca aggacatccc tggttttata ccaagtctct tgggacattt gttagaggaa   1380

agacaaaaga ttaagacaaa aatgaaggaa actcaagatc ctatagaaaa aatactcctt   1440

gactatagac aaaaagcgat aaaactctta gcaaattctt tctacggata ttatggctat   1500

gcaaaagcaa gatggtactg taaggagtgt gctgagagcg ttactgcctg ggggaagaaag   1560

tacatcgagt tagtatggaa ggagctcgaa gaaaagtttg gatttaaagt cctctacatt   1620

gacactgatg gtctctatgc aactatccca ggaggagaaa gtgaggaaat aaagaaaaag   1680

gctctagaat ttgtaaaata cataaattca aagctccctg gactgctaga gcttgaatat   1740

gaagggtttt ataagagggg attcttcgtt acgaagaaga ggtatgcagt aatagatgaa   1800

gaaggaaaag tcattactcg tggtttagag atagttagga gagattggag tgaaattgca   1860

aaagaaactc aagctagagt tttggagaca atactaaaac acggagatgt tgaagaagct   1920

gtgagaatag taaaagaagt aatacaaaag cttgccaatt atgaaattcc accagagaag   1980

ctcgcaatat atgagcagat aacaagacca ttacatgagt ataaggcgat aggtcctcac   2040

gtagctgttg caaagaaact agctgctaaa ggagttaaaa taaagccagg aatggtaatt   2100
```

```
ggatacatag tacttagagg cgatggtcca attagcaata gggcaattct agctgaggaa   2160

tacgatccca aaaagcacaa gtatgacgca gaatattaca tggagaacca ggttcttcca   2220

gcggtactta ggatattgga gggatttgga tacagaaagg aagacctcag ataccaaaag   2280

acaagacaag tcggcctaac ttcctggctt aacattaaaa aatcctag                2328


<210> SEQ ID NO 31
<211> LENGTH: 2328
<212> TYPE: DNA
<213> ORGANISM: Pyrococcus furiosus
<220> FEATURE:
<221> NAME/KEY: misc_feature
<222> LOCATION: (423)..(423)
<223> OTHER INFORMATION: N = C, G, A, or T
<220> FEATURE:
<221> NAME/KEY: misc_feature
<222> LOCATION: (429)..(429)
<223> OTHER INFORMATION: N = C, G, A, or T
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL
      POSSIBLE CODONS FOR ARGININE)

<400> SEQUENCE: 31

atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacgggga aaggcatgga    180

aagattgtga gaattgttga tgtagagaag gttgagaaaa agtttctcgg caagcctatt    240

accgtgtgga aactttattt ggaacatccc caagatnnnc ccactattag agaaaaagtt    300

agagaacatc cagcagttgt ggacatcttc gaatacgata ttccatttgc aaagagatac    360

ctcatcgaca aaggcctaat accaatggag ggggaagaag agctaaagat tcttgccttc    420

gcnatagcna ccctctatca cgaaggagaa gagtttggaa aaggcccaat tataatgatt    480

agttatgcag atgaaaatga agcaaaggtg attacttgga aaaacataga tcttccatac    540

gttgaggttg tatcaagcga gagagagatg ataaagagat ttctcaggat tatcagggag    600

aaggatcctg acattatagt tacttataat ggagactcat tcgcattccc atatttagcg    660

aaaagggcag aaaaacttgg gattaaatta accattggaa gagatggaag cgagcccaag    720

atgcagagaa taggcgatat gacggctgta gaagtcaagg gaagaataca tttcgacttg    780

tatcatgtaa taacaaggac aataaatctc ccaacataca cactagaggc tgtatatgaa    840

gcaatttttg gaaagccaaa ggagaaggta tacgccgacg agatagcaaa agcctgggaa    900

agtggagaga accttgagag agttgccaaa tactcgatgg aagatgcaaa ggcaacttat    960

gaactcggga aagaattcct tccaatggaa attcagcttt caagattagt tggacaacct   1020

ttatgggatg tttcaaggtc aagcacaggg aaccttgtag agtggttctt acttaggaaa   1080

gcctacgaaa gaaacgaagt agctccaaac aagccaagtg aagaggagta tcaaagaagg   1140

ctcagggaga gctacacagg tggattcgtt aaagagccag aaaaggggtt gtgggaaaac   1200

atagtatacc tagattttag agccctatat ccctcgatta taattaccca caatgtttct   1260

cccgatactc taaatcttga gggatgcaag aactatgata tcgctcctca agtaggccac   1320

aagttctgca aggacatccc tggttttata ccaagtctct tgggacattt gttagaggaa   1380

agacaaaaga ttaagacaaa aatgaaggaa actcaagatc ctatagaaaa aatactcctt   1440

gactatagac aaaaagcgat aaaactctta gcaaattctt tctacggata ttatggctat   1500
```

-continued

```
gcaaaagcaa gatggtactg taaggagtgt gctgagagcg ttactgcctg gggaagaaag   1560

tacatcgagt tagtatggaa ggagctcgaa gaaaagtttg gatttaaagt cctctacatt   1620

gacactgatg gtctctatgc aactatccca ggaggagaaa gtgaggaaat aaagaaaaag   1680

gctctagaat ttgtaaaata cataaattca aagctccctg gactgctaga gcttgaatat   1740

gaagggtttt ataagagggg attcttcgtt acgaagaaga ggtatgcagt aatagatgaa   1800

gaaggaaaag tcattactcg tggtttagag atagttagga gagattggag tgaaattgca   1860

aaagaaactc aagctagagt tttggagaca atactaaaac acggagatgt tgaagaagct   1920

gtgagaatag taaaagaagt aatacaaaag cttgccaatt atgaaattcc accagagaag   1980

ctcgcaatat atgagcagat aacaagacca ttacatgagt ataaggcgat aggtcctcac   2040

gtagctgttg caaagaaact agctgctaaa ggagttaaaa taaagccagg aatggtaatt   2100

ggatacatag tacttagagg cgatggtcca attagcaata gggcaattct agctgaggaa   2160

tacgatccca aaaagcacaa gtatgacgca gaatattaca tggagaacca ggttcttcca   2220

gcggtactta ggatattgga gggatttgga tacagaaagg aagacctcag ataccaaaag   2280

acaagacaag tcggcctaac ttcctggctt aacattaaaa aatcctag                2328
```

```
<210> SEQ ID NO 32
<211> LENGTH: 2328
<212> TYPE: DNA
<213> ORGANISM: Pyrococcus furiosus
<220> FEATURE:
<221> NAME/KEY: misc_feature
<222> LOCATION: (423)..(423)
<223> OTHER INFORMATION: N = C, G, A, or T
<220> FEATURE:
<221> NAME/KEY: misc_feature
<222> LOCATION: (429)..(429)
<223> OTHER INFORMATION: N = C, G, A, or T
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 32

atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacgggggga aaggcatgga    180

aagattgtga gaattgttga tgtagagaag gttgagaaaa agtttctcgg caagcctatt    240

accgtgtgga aactttattt ggaacatccc caagatnnnc ccactattag agaaaaagtt    300

agagaacatc cagcagttgt ggacatcttc gaatacgata ttccatttgc aaagagatac    360

ctcatcgaca aaggcctaat accaatggag ggggaagaag agctaaagat tcttgccttc    420

gcnatagcna ccctctatca cgaaggagaa gagtttggaa aaggcccaat tataatgatt    480

agttatgcag atgaaaatga agcaaaggtg attacttgga aaaacataga tcttccatac    540

gttgaggttg tatcaagcga gagagagatg ataaagagat ttctcaggat tatcagggag    600

aaggatcctg acattatagt tacttataat ggagactcat tcgcattccc atatttagcg    660

aaaagggcag aaaaacttgg gattaaatta accattggaa gagatggaag cgagcccaag    720

atgcagagaa taggcgatat gacggctgta gaagtcaagg gaagaataca tttcgacttg    780

tatcatgtaa taacaaggac aataaatctc ccaacataca cactagaggc tgtatatgaa    840

gcaatttttg gaaagccaaa ggagaaggta tacgccgacg agatagcaaa agcctgggaa    900
```

```
agtggagaga accttgagag agttgccaaa tactcgatgg aagatgcaaa ggcaacttat    960

gaactcggga aagaattcct tccaatggaa attcagcttt caagattagt tggacaacct   1020

ttatgggatg tttcaaggtc aagcacaggg aaccttgtag agtggttctt acttaggaaa   1080

gcctacgaaa gaaacgaagt agctccaaac aagccaagtg aagaggagta tcaaagaagg   1140

ctcagggaga gctacacagg tggattcgtt aaagagccag aaaaggggtt gtgggaaaac   1200

atagtatacc tagattttag agccctatat ccctcgatta taattaccca caatgtttct   1260

cccgatactc taaatcttga gggatgcaag aactatgata tcgctcctca agtaggccac   1320

aagttctgca aggacatccc tggtttttata ccaagtctct tgggacattt gttagaggaa   1380

agacaaaaga ttaagacaaa aatgaaggaa actcaagatc ctatagaaaa aatactcctt   1440

gactatagac aaaaagcgat aaaactctta gcaaattctt tctacggata ttatggctat   1500

gcaaaagcaa gatggtactg taaggagtgt gctgagagcg ttactgcctg gggaagaaag   1560

tacatcgagt tagtatggaa ggagctcgaa gaaaagtttg gatttaaagt cctctacatt   1620

gacactgatg gtctctatgc aactatccca ggaggagaaa gtgaggaaat aaagaaaaag   1680

gctctagaat ttgtaaaata cataaattca aagctccctg gactgctaga gcttgaatat   1740

gaagggtttt ataagagggg attcttcgtt acgaagaaga ggtatgcagt aatagatgaa   1800

gaaggaaaag tcattactcg tggtttagag atagttagga gagattggag tgaaattgca   1860

aaagaaactc aagctagagt tttggagaca atactaaaac acggagatgt tgaagaagct   1920

gtgagaatag taaaagaagt aatacaaaag cttgccaatt atgaaattcc accagagaag   1980

ctcgcaatat atgagcagat aacaagacca ttacatgagt ataaggcgat aggtcctcac   2040

gtagctgttg caaagaaact agctgctaaa ggagttaaaa taaagccagg aatggtaatt   2100

ggatacatag tacttagagg cgatggtcca attagcaata gggcaattct agctgaggaa   2160

tacgatccca aaaagcacaa gtatgacgca gaatattaca tggagaacca ggttcttcca   2220

gcggtactta ggatattgga gggatttgga tacagaaagg aagacctcag ataccaaaag   2280

acaagacaag tcggcctaac ttcctggctt aacattaaaa aatcctag                2328
```

<210> SEQ ID NO 33
<211> LENGTH: 2325
<212> TYPE: DNA
<213> ORGANISM: Thermococcus kodakaraensis
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL POSSIBLE CODONS FOR ARGININE)

<400> SEQUENCE: 33

```
atgatcctcg acactgacta cataaccgag gatggaaagc ctgtcataag aattttcaag     60

aaggaaaacg gcgagtttaa gattgagtac gaccggactt ttgaacccta cttctacgcc    120

ctcctgaagg acgattctgc cattgaggaa gtcaagaaga taaccgccga gaggcacggg    180

acggttgtaa cggttaagcg ggttgaaaag gttcagaaga agttcctcgg gagaccagtt    240

gaggtctgga aactctactt tactcatccg caggacnnnc cagcgataag ggacaagata    300

cgagagcatc cagcagttat tgacatctac gagtacgaca tacccttcgc caagcgctac    360

ctcatagaca agggattagt gccaatggaa ggcgacgagg agctgaaaat gctcgccttc    420

gacattgaaa ctctctacca tgagggcgag gagttcgccg aggggccaat ccttatgata    480

agctacgccg acgaggaagg ggccagggtg ataacttgga agaacgtgga tctcccctac    540
```

```
gttgacgtcg tctcgacgga gagggagatg ataaagcgct tcctccgtgt tgtgaaggag    600

aaagacccgg acgttctcat aacctacaac ggcgacaact tcgacttcgc ctatctgaaa    660

aagcgctgtg aaaagctcgg aataaacttc gccctcggaa gggatggaag cgagccgaag    720

attcagagga tgggcgacag gtttgccgtc gaagtgaagg gacggataca cttcgatctc    780

tatcctgtga taagacggac gataaacctg cccacataca cgcttgaggc cgtttatgaa    840

gccgtcttcg gtcagccgaa ggagaaggtt tacgctgagg aaataaccac agcctgggaa    900

accggcgaga accttgagag agtcgcccgc tactcgatgg aagatgcgaa ggtcacatac    960

gagcttggga aggagttcct tccgatggag gcccagcttt ctcgcttaat cggccagtcc   1020

ctctgggacg tctcccgctc cagcactggc aacctcgttg agtggttcct cctcaggaag   1080

gcctatgaga ggaatgagct ggccccgaac aagcccgatg aaaaggagct ggccagaaga   1140

cggcagagct atgaaggagg ctatgtaaaa gagcccgaga gagggttgtg ggagaacata   1200

gtgtacctag attttagatc cctgtacccc tcaatcatca tcacccacaa cgtctcgccg   1260

gatacgctca acagagaagg atgcaaggaa tatgacgttg ccccacaggt cggccaccgc   1320

ttctgcaagg acttcccagg atttatcccg agcctgcttg gagacctcct agaggagagg   1380

cagaagataa agaagaagat gaaggccacg attgacccga tcgagaggaa gctcctcgat   1440

tacaggcaga gggccatcaa gatcctggca aacagctact acggttacta cggctatgca   1500

agggcgcgct ggtactgcaa ggagtgtgca gagagcgtaa cggcctgggg aagggagtac   1560

ataacgatga ccatcaagga gatagaggaa aagtacggct ttaaggtaat ctacagcgac   1620

accgacggat tttttgccac aatacctgga gccgatgctg aaaccgtcaa aaagaaggct   1680

atggagttcc tcaagtatat caacgccaaa cttccgggcg cgcttgagct cgagtacgag   1740

ggcttctaca aacgcggctt cttcgtcacg aagaagaagt atgcggtgat agacgaggaa   1800

ggcaagataa caacgcgcgg acttgagatt gtgaggcgtg actggagcga gatagcgaaa   1860

gagacgcagg cgagggttct tgaagctttg ctaaaggacg gtgacgtcga gaaggccgtg   1920

aggatagtca aagaagttac cgaaaagctg agcaagtacg aggttccgcc ggagaagctg   1980

gtgatccacg agcagataac gagggattta aaggactaca aggcaaccgg tccccacgtt   2040

gccgttgcca agaggttggc cgcgagagga gtcaaaatac gccctggaac ggtgataagc   2100

tacatcgtgc tcaagggctc tgggaggata ggcgacaggg cgataccgtt cgacgagttc   2160

gacccgacga agcacaagta cgacgccgag tactacattg agaaccaggt tctcccagcc   2220

gttgagagaa ttctgagagc cttcggttac cgcaaggaag acctgcgcta ccagaagacg   2280

agacaggttg gtttgagtgc ttggctgaag ccgaagggaa cttga                   2325
```

<210> SEQ ID NO 34
<211> LENGTH: 2325
<212> TYPE: DNA
<213> ORGANISM: Thermococcus kodakaraensis
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 34

```
atgatcctcg acactgacta cataaccgag gatggaaagc ctgtcataag aattttcaag     60

aaggaaaacg gcgagtttaa gattgagtac gaccggactt ttgaacccta cttctacgcc    120

ctcctgaagg acgattctgc cattgaggaa gtcaagaaga taaccgccga gaggcacggg    180

acggttgtaa cggttaagcg ggttgaaaag gttcagaaga agttcctcgg gagaccagtt    240
```

gaggtctgga aactctactt tactcatccg caggacnnnc cagcgataag ggacaagata 300
cgagagcatc cagcagttat tgacatctac gagtacgaca taccccttcgc caagcgctac 360 ctcatagaca agggattagt gccaatggaa ggcgacgagg agctgaaaat gctcgccttc 420
gacattgaaa ctctctacca tgagggcgag gagttcgccg aggggccaat ccttatgata 480
agctacgccg acgaggaagg ggccagggtg ataacttgga agaacgtgga tctcccctac 540
gttgacgtcg tctcgacgga gagggagatg ataaagcgct tcctccgtgt tgtgaaggag 600
aaagacccgg acgttctcat aacctacaac ggcgacaact tcgacttcgc ctatctgaaa 660
aagcgctgtg aaaagctcgg aataaacttc gccctcggaa gggatggaag cgagccgaag 720
attcagagga tgggcgacag gtttgccgtc gaagtgaagg gacggataca cttcgatctc 780
tatcctgtga taagacggac gataaacctg cccacataca cgcttgaggc cgtttatgaa 840
gccgtcttcg gtcagccgaa ggagaaggtt tacgctgagg aaataaccac agcctgggaa 900
accggcgaga accttgagag agtcgcccgc tactcgatgg aagatgcgaa ggtcacatac 960
gagcttggga aggagttcct tccgatggag gcccagcttt ctcgcttaat cggccagtcc 1020
ctctgggacg tctcccgctc cagcactggc aacctcgttg agtggttcct cctcaggaag 1080
gcctatgaga ggaatgagct ggccccgaac aagcccgatg aaaaggagct ggccagaaga 1140
cggcagagct atgaaggagg ctatgtaaaa gagcccgaga gagggttgtg ggagaacata 1200
gtgtacctag attttagatc cctgtacccc tcaatcatca tcacccacaa cgtctcgccg 1260
gatacgctca acagagaagg atgcaaggaa tatgacgttg ccccacaggt cggccaccgc 1320
ttctgcaagg acttcccagg atttatcccg agcctgcttg gagacctcct agaggagagg 1380
cagaagataa agaagaagat gaaggccacg attgacccga tcgagaggaa gctcctcgat 1440
tacaggcaga gggccatcaa gatcctggca aacagctact acggttacta cggctatgca 1500
agggcgcgct ggtactgcaa ggagtgtgca gagagcgtaa cggcctgggg aagggagtac 1560
ataacgatga ccatcaagga gatagaggaa aagtacggct ttaaggtaat ctacagcgac 1620
accgacggat tttttgccac aatacctgga gccgatgctg aaaccgtcaa aaagaaggct 1680
atggagttcc tcaagtatat caacgccaaa cttccgggcg cgcttgagct cgagtacgag 1740
ggcttctaca aacgcggctt cttcgtcacg aagaagaagt atgcggtgat agacgaggaa 1800
ggcaagataa caacgcgcgg acttgagatt gtgaggcgtg actggagcga gatagcgaaa 1860
gagacgcagg cgagggttct tgaagctttg ctaaaggacg gtgacgtcga gaaggccgtg 1920
aggatagtca aagaagttac cgaaaagctg agcaagtacg aggttccgcc ggagaagctg 1980
gtgatccacg agcagataac gagggattta aaggactaca aggcaaccgg tccccacgtt 2040
gccgttgcca agaggttggc cgcgagagga gtcaaaatac gccctggaac ggtgataagc 2100
tacatcgtgc tcaagggctc tgggaggata ggcgacaggg cgataccgtt cgacgagttc 2160
gacccgacga agcacaagta cgacgccgag tactacattg agaaccaggt tctcccagcc 2220
gttgagagaa ttctgagagc cttcggttac cgcaaggaag acctgcgcta ccagaagacg 2280
agacaggttg gtttgagtgc ttggctgaag ccgaaggaa cttga 2325

<210> SEQ ID NO 35
<211> LENGTH: 2325
<212> TYPE: DNA
<213> ORGANISM: Thermococcus litoralis
<220> FEATURE:
<221> NAME/KEY: misc_feature
<222> LOCATION: (277)..(279)

-continued

<223> OTHER INFORMATION: NNN = AGA, AGG, CGA, CGC, CGG, CGT (ALL POSSIBLE CODONS FOR ARGININE)

<400> SEQUENCE: 35

```
atgatactgg acactgatta cataacaaaa gatggcaagc ctataatccg aatttttaag     60
aaagagaacg gggagtttaa aatagaactt gaccctcatt ttcagcccta tatatatgct    120
cttctcaaag atgactccgc tattgaggag ataaaggcaa taaagggcga gagacatgga    180
aaaactgtga gagtgctcga tgcagtgaaa gtcaggaaaa aatttttggg aagggaagtt    240
gaagtctgga agctcatttt cgagcatccc caagacnnnc cagctatgcg gggcaaaata    300
agggaacatc cagctgtggt tgacatttac gaatatgaca taccctttgc caagcgttat    360
ctcatagaca agggcttgat tcccatggag ggagacgagg agcttaagct ccttgccttt    420
gatattgaaa cgttttatca tgagggagat gaatttggaa agggcgagat aataatgatt    480
agttatgccg atgaagaaga ggccagagta atcacatgga aaaatatcga tttgccgtat    540
gtcgatgttg tgtccaatga aagagaaatg ataaagcgtt ttgttcaagt tgttaaagaa    600
aaagaccccg atgtgataat aacttacaat ggggacaatt ttgatttgcc gtatctcata    660
aaacgggcag aaaagctggg agttcggctt gtcttaggaa gggacaaaga acatcccgaa    720
cccaagattc agaggatggg tgatagtttt gctgtggaaa tcaagggtag aatccacttt    780
gatcttttcc cagttgtgcg aaggacgata aacctcccaa cgtatacgct tgaggcagtt    840
tatgaagcag ttttaggaaa aaccaaaagc aaattaggag cagaggaaat tgccgctata    900
tgggaaacag aagaaagcat gaaaaaacta gcccagtact caatggaaga tgctagggca    960
acgtatgagc tcgggaagga attcttcccc atggaagctg agctggcaaa gctgataggt   1020
caaagtgtat gggacgtctc gagatcaagc accggcaacc tcgtggagtg gtatctttta   1080
agggtggcat acgcgaggaa tgaacttgca ccgaacaaac ctgatgagga agagtataaa   1140
cggcgcttaa gaacaactta cctgggagga tatgtaaaag agccagaaaa aggtttgtgg   1200
gaaaatatca tttatttgga tttccgcagt ctgtaccctt caataatagt tactcacaac   1260
gtatccccag ataccccttga aaaagagggc tgtaagaatt acgatgttgc tccgatagta   1320
ggatataggt tctgcaagga ctttccgggc tttattccct ccatactcgg ggacttaatt   1380
gcaatgaggc aagatataaa gaagaaaatg aaatccacaa ttgacccgat cgaaaagaaa   1440
atgctcgatt ataggcaaag ggctattaaa ttgcttgcaa acagctatta cggctatatg   1500
gggtatccta aggcaagatg gtactcgaag gaatgtgctg aaagcgttac cgcatggggg   1560
agacactaca tagagatgac gataagagaa atagaggaaa agttcggctt taaggttctt   1620
tatgcggaca ctgacggctt ttatgccaca atacccgggg aaaagcctga actcattaaa   1680
aagaaagcca aggaattcct aaactacata aactccaaac ttccaggtct gcttgagctt   1740
gagtatgagg gcttttactt gagaggattc tttgttacaa aaaagcgcta tgcagtcata   1800
gatgaagagg gcaggataac aacaaggggc ttggaagtag taaggagaga ttggagtgag   1860
atagctaagg agactcaggc aaaggtttta gaggctatac ttaaagaggg aagtgttgaa   1920
aaagctgtag aagttgttag agatgttgta gagaaaatag caaaatacag ggttccactt   1980
gaaaagcttg ttatccatga gcagattacc agggatttaa aggactacaa agccattggc   2040
cctcatgtcg cgatagcaaa aagacttgcc gcaagaggga taaaagtgaa accgggcaca   2100
ataataagct atatcgttct caaagggagc ggaaagataa gcgatagggt aattttactt   2160
acagaatacg atcctagaaa acacaagtac gatccggact actacataga aaaccaagtt   2220
```

-continued

```
ttgccggcag tacttaggat actcgaagcg tttggataca gaaaggagga tttaaggtat   2280

caaagctcaa aacaaaccgg cttagatgca tggctcaaga ggtag                   2325


<210> SEQ ID NO 36
<211> LENGTH: 2325
<212> TYPE: DNA
<213> ORGANISM: Thermococcus litoralis
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 36

atgatactgg acactgatta cataacaaaa gatggcaagc ctataatccg aatttttaag     60

aaagagaacg ggagtttaa aatagaactt gaccctcatt ttcagcccta tatatatgct    120

cttctcaaag atgactccgc tattgaggag ataaaggcaa taaagggcga gagacatgga    180

aaaactgtga gagtgctcga tgcagtgaaa gtcaggaaaa aatttttggg aagggaagtt    240

gaagtctgga agctcatttt cgagcatccc caagacnnnc cagctatgcg ggcaaaata    300

agggaacatc cagctgtggt tgacatttac gaatatgaca taccctttgc caagcgttat    360

ctcatagaca agggcttgat tcccatggag ggagacgagg agcttaagct ccttgccttt    420

gatattgaaa cgttttatca tgagggagat gaatttggaa agggcgagat aataatgatt    480

agttatgccg atgaagaaga ggccagagta atcacatgga aaaatatcga tttgccgtat    540

gtcgatgttg tgtccaatga aagagaaatg ataaagcgtt ttgttcaagt tgttaaagaa    600

aaagaccccg atgtgataat aacttacaat ggggacaatt ttgatttgcc gtatctcata    660

aaacgggcag aaaagctggg agttcggctt gtcttaggaa gggacaaaga acatcccgaa    720

cccaagattc agaggatggg tgatagtttt gctgtggaaa tcaagggtag aatccacttt    780

gatcttttcc cagttgtgcg aaggacgata aacctcccaa cgtatacgct tgaggcagtt    840

tatgaagcag ttttaggaaa aaccaaaagc aaattaggag cagaggaaat tgccgctata    900

tgggaaacag aagaaagcat gaaaaaacta gcccagtact caatggaaga tgctagggca    960

acgtatgagc tcgggaagga attcttcccc atggaagctg agctggcaaa gctgataggt   1020

caaagtgtat gggacgtctc gagatcaagc accggcaacc tcgtggagtg gtatcttta   1080

agggtggcat acgcgaggaa tgaacttgca ccgaacaaac ctgatgagga agagtataaa   1140

cggcgcttaa gaacaactta cctgggagga tatgtaaaag agccagaaaa aggtttgtgg   1200

gaaaatatca tttatttgga tttccgcagt ctgtaccctt caataatagt tactcacaac   1260

gtatccccag ataccttga aaaagagggc tgtaagaatt acgatgttgc tccgatagta   1320

ggatataggt tctgcaagga ctttccgggc tttattccct ccatactcgg ggacttaatt   1380

gcaatgaggc aagatataaa gaagaaaatg aaatccacaa ttgacccgat cgaaaagaaa   1440

atgctcgatt ataggcaaag ggctattaaa ttgcttgcaa acagctatta cggctatatg   1500

gggtatccta aggcaagatg gtactcgaag gaatgtgctg aaagcgttac cgcatggggg   1560

agacactaca tagagatgac gataagagaa atagaggaaa agttcggctt taaggttctt   1620

tatgcggaca ctgacggctt ttatgccaca atacccgggg aaaagcctga actcattaaa   1680

aagaaagcca aggaattcct aaactacata aactccaaac ttccaggtct gcttgagctt   1740

gagtatgagg gcttttactt gagaggattc tttgttacaa aaaagcgcta tgcagtcata   1800

gatgaagagg gcaggataac aacaaggggc ttggaagtag taaggagaga ttggagtgag   1860

atagctaagg agactcaggc aaaggtttta gaggctatac ttaaagaggg aagtgttgaa   1920
```

```
aaagctgtag aagttgttag agatgttgta gagaaaatag caaaatacag ggttccactt   1980

gaaaagcttg ttatccatga gcagattacc agggatttaa aggactacaa agccattggc   2040

cctcatgtcg cgatagcaaa aagacttgcc gcaagaggga taaaagtgaa accgggcaca   2100

ataataagct atatcgttct caaagggagc ggaaagataa gcgatagggt aattttactt   2160

acagaatacg atcctagaaa acacaagtac gatccggact actacataga aaaccaagtt   2220

ttgccggcag tacttaggat actcgaagcg tttggataca gaaaggagga tttaaggtat   2280

caaagctcaa aacaaaccgg cttagatgca tggctcaaga ggtag                   2325


<210> SEQ ID NO 37
<211> LENGTH: 2328
<212> TYPE: DNA
<213> ORGANISM: Pyrococcus GB-D
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL
      POSSIBLE CODONS FOR ARGININE)

<400> SEQUENCE: 37

atgatacttg acgctgacta catcaccgag gatgggaagc cgattataag gattttcaag     60

aaagaaaacg gcgagtttaa ggttgagtac gacagaaact ttagacctta catttacgct    120

ctcctcaaag atgactcgca gattgatgag gttaggaaga taaccgccga gaggcatggg    180

aagatagtga gaattataga tgccgaaaag gtaaggaaga agttcctggg gaggccgatt    240

gaggtatgga ggctgtactt tgaacaccct caggacnnnc ccgcaataag ggataagata    300

agagagcatt ccgcagttat tgacatcttt gagtacgaca ttccgttcgc gaagaggtac    360

ctaatagaca aaggcctaat tccaatggaa ggcgatgaag agctcaagtt gctcgcattt    420

gacatagaaa ccctctatca cgaaggggag gagttcgcga aggggcccat tataatgata    480

agctatgctg atgaggaaga agccaaagtc ataacgtgga aaaagatcga tctcccgtac    540

gtcgaggtag tttccagcga gagggagatg ataaagcggt tcctcaaggt gataagggag    600

aaagatcccg atgttataat tacctacaac ggcgattctt tcgaccttcc ctatctagtt    660

aagagggccg aaaagctcgg gataaagcta cccctgggaa gggacggtag tgagccaaag    720

atgcagaggc ttggggatat gacagcggtg gagataaagg gaaggataca ctttgacctc    780

taccacgtga ttaggagaac gataaacctc ccaacataca ccctcgaggc agtttatgag    840

gcaatcttcg gaaagccaaa ggagaaagtt tacgctcacg agatagctga ggcctgggag    900

actggaaagg gactggagag agttgcaaag tattcaatgg aggatgcaaa ggtaacgtac    960

gagctcggta gggagttctt cccaatggag gcccagcttt caaggttagt cggccagccc   1020

ctgtgggatg tttctaggtc ttcaactggc aacttggtgg agtggtacct cctcaggaag   1080

gcctacgaga ggaatgaatt ggctccaaac aagccggatg agagggagta cgagagaagg   1140

ctaagggaga gctacgctgg gggatacgtt aaggagccgg agaaagggct ctgggagggg   1200

ttagtttccc tagatttcag gagcctgtac ccctcgataa taatcaccca taacgtctca   1260

ccggatacgc tgaacaggga agggtgtagg gaatacgatg tcgccccaga ggttgggcac   1320

aagttctgca aggacttccc ggggtttatc cccagcctgc tcaagaggtt attggatgaa   1380

aggcaagaaa taaaaaggaa gatgaaagct tctaaagacc caatcgagaa gaagatgctt   1440

gattacaggc aacgggcaat caaaatcctg gcaaacagct attatgggta ttatgggtac   1500

gcaaaagccc gttggtactg taaggagtgc gcagagagcg ttacggcctg gggagggaa    1560
```

```
tatatagagt tcgtaaggaa ggaactggag gaaaagttcg ggttcaaagt cttatacata   1620

gacacagatg gactctacgc cacaattcct ggggcaaaac ccgaggagat aaagaagaaa   1680

gccctagagt tcgtagatta tataaacgcc aagctcccag ggctgttgga gcttgagtac   1740

gagggcttct acgtgagagg gttcttcgtg acgaagaaga agtatgcgtt gatagatgag   1800

gaagggaaga taatcactag gggggcttgaa atagtcagga gggactggag cgaaatagcc   1860

aaagaaaccc aagcaaaagt cctagaggct atcctaaagc atggcaacgt tgaggaggca   1920

gtaaagatag ttaaggaggt aactgaaaag ctgagcaagt acgaaatacc tccagaaaag   1980

ctagttattt acgagcagat cacgaggccc cttcacgagt acaaggctat aggtccgcac   2040

gttgccgtgg caaaaaggtt agccgctaga ggagtaaagg tgaggcctgg catggtgata   2100

gggtacatag tgctgagggg agacgggcca ataagcaaga gggctatcct tgcagaggag   2160

ttcgatctca ggaagcataa gtatgacgct gagtattaca tagaaaatca ggttttacct   2220

gccgttctta gaatattaga ggcctttggg tacaggaaag aagacctcag gtggcagaag   2280

actaaacaga caggtcttac ggcatggctt aacatcaaga agaagtaa                2328
```

<210> SEQ ID NO 38
<211> LENGTH: 2328
<212> TYPE: DNA
<213> ORGANISM: Pyrococcus GB-D
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 38

```
atgatacttg acgctgacta catcaccgag gatgggaagc cgattataag gattttcaag     60

aaagaaaacg gcgagtttaa ggttgagtac gacagaaact ttagacctta catttacgct    120

ctcctcaaag atgactcgca gattgatgag gttaggaaga taaccgccga gaggcatggg    180

aagatagtga gaattataga tgccgaaaag gtaaggaaga agttcctggg gaggccgatt    240

gaggtatgga ggctgtactt tgaacaccct caggacnnnc ccgcaataag ggataagata    300

agagagcatt ccgcagttat tgacatcttt gagtacgaca ttccgttcgc gaagaggtac    360

ctaatagaca aaggcctaat tccaatggaa ggcgatgaag agctcaagtt gctcgcattt    420

gacatagaaa ccctctatca cgaaggggag gagttcgcga aggggcccat tataatgata    480

agctatgctg atgaggaaga agccaaagtc ataacgtgga aaaagatcga tctcccgtac    540

gtcgaggtag tttccagcga gagggagatg ataaagcggt tcctcaaggt gataagggag    600

aaagatcccg atgttataat tacctacaac ggcgattctt tcgaccttcc ctatctagtt    660

aagagggccg aaaagctcgg gataaagcta cccctgggaa gggacggtag tgagccaaag    720

atgcagaggc ttggggatat gacagcggtg gagataaagg gaaggataca ctttgacctc    780

taccacgtga ttaggagaac gataaacctc ccaacataca ccctcgaggc agtttatgag    840

gcaatcttcg gaaagccaaa ggagaaagtt tacgctcacg agatagctga ggcctgggag    900

actggaaagg gactggagag agttgcaaag tattcaatgg aggatgcaaa ggtaacgtac    960

gagctcggta gggagttctt cccaatggag gcccagcttt caaggttagt cggccagccc   1020

ctgtgggatg tttctaggtc ttcaactggc aacttggtgg agtggtacct cctcaggaag   1080

gcctacgaga ggaatgaatt ggctccaaac aagccggatg agagggagta cgagagaagg   1140

ctaagggaga gctacgctgg gggatacgtt aaggagccgg agaaagggct ctgggagggg   1200
```

```
ttagtttccc tagatttcag gagcctgtac ccctcgataa taatcaccca taacgtctca   1260

ccggatacgc tgaacaggga agggtgtagg gaatacgatg tcgccccaga ggttgggcac   1320

aagttctgca aggacttccc ggggtttatc cccagcctgc tcaagaggtt attggatgaa   1380

aggcaagaaa taaaaaggaa gatgaaagct tctaaagacc caatcgagaa gaagatgctt   1440

gattacaggc aacgggcaat caaaatcctg gcaaacagct attatgggta ttatgggtac   1500

gcaaaagccc gttggtactg taaggagtgc gcagagagcg ttacggcctg gggagaggaa   1560

tatatagagt tcgtaaggaa ggaactggag gaaaagttcg ggttcaaagt cttatacata   1620

gacacagatg gactctacgc cacaattcct ggggcaaaac ccgaggagat aaagaagaaa   1680

gccctagagt tcgtagatta tataaacgcc aagctcccag ggctgttgga gcttgagtac   1740

gagggcttct acgtgagagg gttcttcgtg acgaagaaga agtatgcgtt gatagatgag   1800

gaagggaaga taatcactag gggcttgaa atagtcagga gggactggag cgaaatagcc   1860

aaagaaaccc aagcaaaagt cctagaggct atcctaaagc atggcaacgt tgaggaggca   1920

gtaaagatag ttaaggaggt aactgaaaag ctgagcaagt acgaaatacc tccagaaaag   1980

ctagttattt acgagcagat cacgaggccc cttcacgagt acaaggctat aggtccgcac   2040

gttgccgtgg caaaaaggtt agccgctaga ggagtaaagg tgaggcctgg catggtgata   2100

gggtacatag tgctgagggg agacgggcca ataagcaaga gggctatcct tgcagaggag   2160

ttcgatctca ggaagcataa gtatgacgct gagtattaca tagaaaatca ggttttacct   2220

gccgttctta gaatattaga ggcctttggg tacaggaaag aagacctcag gtggcagaag   2280

actaaacaga caggtcttac ggcatggctt aacatcaaga agaagtaa               2328
```

```
<210> SEQ ID NO 39
<211> LENGTH: 2331
<212> TYPE: DNA
<213> ORGANISM: Thermococcus sp.
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL
      POSSIBLE CODONS FOR ARGININE)

<400> SEQUENCE: 39

atgatccttg acgttgatta catcaccgag aatggaaagc ccgtcatcag ggtcttcaag     60

aaggagaacg gcgagttcag gattgaatac gaccgcgagt tcgagcccta cttctacgcg    120

ctcctcaggg acgactctgc catcgaagaa atcaaaaaga taaccgcgga gaggcacggc    180

agggtcgtta aggttaagcg cgcggagaag gtgaagaaaa agttcctcgg caggtctgtg    240

gaggtctggg tcctctactt cacgcacccg caggacnnnc cggcaatccg cgacaaaata    300

aggaagcacc ccgcggtcat cgacatctac gagtacgaca tacccttcgc caagcgctac    360

ctcatagaca agggcctaat cccgatggaa ggtgaggaag agcttaaact catgtccttc    420

gacatcgaga cgctctacca cgagggagaa gagtttggaa ccgggccgat tctgatgata    480

agctacgccg atgaaagcga ggcgcgcgtg ataacctgga agaagatcga ccttccttac    540

gttgaggttg tctccaccga gaaggagatg attaagcgct tcttgagggt cgttaaggag    600

aaggacccgg acgtgctgat aacatacaac ggcgacaact tcgacttcgc ctacctgaaa    660

aagcgctgtg agaagcttgg cgtgagcttt accctcggga gggacgggag cgagccgaag    720

atacagcgca tgggggacag gtttgcggtc gaggtgaagg gcagggtaca cttcgacctt    780

tatccagtca taaggcgcac cataaacctc ccgacctaca cccttgaggc tgtatacgag    840
```

```
gcggttttcg gcaagcccaa ggagaaggtc tacgccgagg agatagccac cgcctgggag    900

accggcgagg ggcttgagag ggtcgcgcgc tactcgatgg aggacgcgag ggttacctac    960

gagcttggca gggagttctt cccgatggag gcccagcttt ccaggctcat cggccaaggc   1020

ctctgggacg tttcccgctc cagcaccggc aacctcgtcg agtggttcct cctaaggaag   1080

gcctacgaga ggaacgaact cgctcccaac aagcccgacg agagggagct ggcgaggaga   1140

aggggggcgct acgccggtgg ctacgtcaag gagccggagc ggggactgtg ggacaatatc   1200

gtgtatctag actttcgtag tctctaccct tcaatcataa tcacccacaa cgtctcgcca   1260

gatacgctca accgcgaggg gtgtaggagc tacgacgttg cccccgaggt cggtcacaag   1320

ttctgcaagg acttccccgg cttcattccg agcctgctcg gaaacctgct ggaggaaagg   1380

cagaagataa agaggaagat gaaggcaact ctcgacccgc tggagaagaa tctcctcgat   1440

tacaggcaac gcgccatcaa gattctcgcc aacagctact acggctacta cggctatgcc   1500

agggcaagat ggtactgcag ggagtgcgcc gagagcgtta cggcatgggg aagggagtac   1560

atcgaaatgg tcatcagaga gcttgaggaa aagttcggtt ttaaagtcct ctatgcagac   1620

acagacggtc tccatgccac cattcctgga gcggacgctg aaacagtcaa gaaaaaggca   1680

atggagttct taaactatat caatcccaaa ctgcccggcc ttctcgaact cgaatacgag   1740

ggcttctacg tcaggggctt cttcgtcacg aagaaaaagt acgcggtcat cgacgaggag   1800

ggcaagataa ccacgcgcgg gcttgagata gtcaggcgcg actggagcga gatagcgaag   1860

gagacgcagg cgagggtttt ggaggcgata ctcaggcacg gtgacgttga agaggccgtc   1920

agaattgtca gggaagtcac cgaaaagctg agcaagtacg aggttccgcc ggagaagctg   1980

gttatccacg agcagataac gcgcgagctc aaggactaca aggccaccgg cccgcacgta   2040

gccatagcga agcgtttggc cgccagaggt gttaaaatcc ggcccggaac tgtgataagc   2100

tacatcgttc tgaagggctc cggaaggata ggcgacaggg cgattccctt cgacgagttc   2160

gacccgacga agcacaagta cgatgcggac tactacatcg agaaccaggt tctgccggca   2220

gttgagagaa tcctcagggc cttcggctac cgcaaggaag acctgcgcta ccagaagacg   2280

aggcaggtcg ggcttggcgc gtggctgaag ccgaagggga agaagaagtg a            2331
```

```
<210> SEQ ID NO 40
<211> LENGTH: 2331
<212> TYPE: DNA
<213> ORGANISM: Thermococcus sp.
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 40
```

```
atgatccttg acgttgatta catcaccgag aatggaaagc ccgtcatcag ggtcttcaag     60

aaggagaacg gcgagttcag gattgaatac gaccgcgagt tcgagcccta cttctacgcg    120

ctcctcaggg acgactctgc catcgaagaa atcaaaaaga taaccgcgga gaggcacggc    180

agggtcgtta aggttaagcg cgcggagaag gtgaagaaaa agttcctcgg caggtctgtg    240

gaggtctggg tcctctactt cacgcacccg caggacnnnc cggcaatccg cgacaaaata    300

aggaagcacc ccgcggtcat cgacatctac gagtacgaca taccccttcgc caagcgctac    360

ctcatagaca agggcctaat cccgatggaa ggtgaggaag agcttaaact catgtccttc    420

gacatcgaga cgctctacca cgagggagaa gagtttggaa ccgggccgat tctgatgata    480

agctacgccg atgaaagcga ggcgcgcgtg ataacctgga agaagatcga ccttccttac    540
```

```
gttgaggttg tctccaccga gaaggagatg attaagcgct tcttgagggt cgttaaggag    600
aaggacccgg acgtgctgat aacatacaac ggcgacaact tcgacttcgc ctacctgaaa    660
aagcgctgtg agaagcttgg cgtgagcttt accctcggga gggacgggag cgagccgaag    720
atacagcgca tgggggacag gtttgcggtc gaggtgaagg gcagggtaca cttcgacctt    780
tatccagtca taaggcgcac cataaacctc ccgacctaca cccttgaggc tgtatacgag    840
gcggttttcg gcaagcccaa ggagaaggtc tacgccgagg agatagccac cgcctgggag    900
accggcgagg ggcttgagag ggtcgcgcgc tactcgatgg aggacgcgag ggttacctac    960
gagcttggca gggagttctt cccgatggag gcccagcttt ccaggctcat cggccaaggc   1020
ctctgggacg tttcccgctc cagcaccggc aacctcgtcg agtggttcct cctaaggaag   1080
gcctacgaga ggaacgaact cgctcccaac aagcccgacg agagggagct ggcgaggaga   1140
agggggggct acgccggtgg ctacgtcaag gagccggagc ggggactgtg ggacaatatc   1200
gtgtatctag actttcgtag tctctaccct tcaatcataa tcacccacaa cgtctcgcca   1260
gatacgctca accgcgaggg gtgtaggagc tacgacgttg cccccgaggt cggtcacaag   1320
ttctgcaagg acttccccgg cttcattccg agcctgctcg gaaacctgct ggaggaaagg   1380
cagaagataa agaggaagat gaaggcaact ctcgacccgc tggagaagaa tctcctcgat   1440
tacaggcaac gcgccatcaa gattctcgcc aacagctact acggctacta cggctatgcc   1500
agggcaagat ggtactgcag ggagtgcgcc gagagcgtta cggcatgggg aagggagtac   1560
atcgaaatgg tcatcagaga gcttgaggaa aagttcggtt ttaaagtcct ctatgcagac   1620
acagacggtc tccatgccac cattcctgga gcggacgctg aaacagtcaa gaaaaaggca   1680
atggagttct taaactatat caatcccaaa ctgcccggcc ttctcgaact cgaatacgag   1740
ggcttctacg tcaggggctt cttcgtcacg aagaaaaagt acgcggtcat cgacgaggag   1800
ggcaagataa ccacgcgcgg gcttgagata gtcaggcgcg actggagcga gatagcgaag   1860
gagacgcagg cgagggtttt ggaggcgata ctcaggcacg gtgacgttga agaggccgtc   1920
agaattgtca gggaagtcac cgaaaagctg agcaagtacg aggttccgcc ggagaagctg   1980
gttatccacg agcagataac gcgcgagctc aaggactaca aggccaccgg cccgcacgta   2040
gccatagcga agcgtttggc cgccagaggt gttaaaatcc ggcccggaac tgtgataagc   2100
tacatcgttc tgaagggctc cggaaggata ggcgacaggg cgattccctt cgacgagttc   2160
gacccgacga agcacaagta cgatgcggac tactacatcg agaaccaggt tctgccggca   2220
gttgagagaa tcctcagggc cttcggctac cgcaaggaag acctgcgcta ccagaagacg   2280
aggcaggtcg ggcttggcgc gtggctgaag ccgaagggga agaagaagtg a             2331
```

<210> SEQ ID NO 41
<211> LENGTH: 775
<212> TYPE: PRT
<213> ORGANISM: Pyrococcus furiosus

<400> SEQUENCE: 41

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
```

-continued

```
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Arg Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480
```

```
Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 42
<211> LENGTH: 775
<212> TYPE: PRT
<213> ORGANISM: Pyrococcus furiosus

<400> SEQUENCE: 42

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
```

-continued

```
65                  70                  75                  80

Thr Val Trp Lys Leu Tyr Leu Glu His Pro Gln Asp Glu Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495
```

```
Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 43
<211> LENGTH: 775
<212> TYPE: PRT
<213> ORGANISM: Pyrococcus furiosus

<400> SEQUENCE: 43

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Arg Pro Thr Ile
```

-continued

```
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
    370                 375                 380

Tyr Thr Pro Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510
```

```
Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 44
<211> LENGTH: 775
<212> TYPE: PRT
<213> ORGANISM: Pyrococcus furiosus

<400> SEQUENCE: 44

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Arg Pro Thr Ile
                85                  90                  95

Arg Glu Lys Val Arg Glu His Pro Ala Val Val Asp Ile Phe Glu Tyr
```

-continued

```
        100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525
```

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 45
<211> LENGTH: 775
<212> TYPE: PRT
<213> ORGANISM: Pyrococcus furiosus

<400> SEQUENCE: 45

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Glu Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro

```
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Pro Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540
```

```
Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 46
<211> LENGTH: 775
<212> TYPE: PRT
<213> ORGANISM: Pyrococcus furiosus

<400> SEQUENCE: 46

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Arg Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
```

```
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560
```

```
Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 47
<211> LENGTH: 775
<212> TYPE: PRT
<213> ORGANISM: Thermococcus sp.

<400> SEQUENCE: 47

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Arg Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
```

-continued

```
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575
```

Glu Leu Glu Tyr Glu Gly Phe Tyr Val Arg Gly Phe Phe Val Thr Lys
580 585 590

Lys Lys Tyr Ala Leu Ile Asp Glu Glu Gly Lys Ile Ile Thr Arg Gly
595 600 605

Leu Glu Ile Val Arg Arg Asp Trp Ser Glu Ile Ala Lys Glu Thr Gln
610 615 620

Ala Lys Val Leu Glu Ala Ile Leu Lys His Gly Asn Val Glu Glu Ala
625 630 635 640

Val Lys Ile Val Lys Glu Val Thr Glu Lys Leu Ser Lys Tyr Glu Ile
645 650 655

Pro Pro Glu Lys Leu Val Ile Tyr Glu Gln Ile Thr Arg Pro Leu His
660 665 670

Glu Tyr Lys Ala Ile Gly Pro His Val Ala Val Ala Lys Arg Leu Ala
675 680 685

Ala Arg Gly Val Lys Val Arg Pro Gly Met Val Ile Gly Tyr Ile Val
690 695 700

Leu Arg Gly Asp Gly Pro Ile Ser Lys Arg Ala Ile Leu Ala Glu Glu
705 710 715 720

Phe Asp Leu Arg Lys His Lys Tyr Asp Ala Glu Tyr Tyr Ile Glu Asn
725 730 735

Gln Val Leu Pro Ala Val Leu Arg Ile Leu Glu Ala Phe Gly Tyr Arg
740 745 750

Lys Glu Asp Leu Arg Trp Gln Lys Thr Lys Gln Thr Gly Leu Thr Ala
755 760 765

Trp Leu Asn Ile Lys Lys Lys
770 775

<210> SEQ ID NO 48
<211> LENGTH: 775
<212> TYPE: PRT
<213> ORGANISM: Thermococcus sp.

<400> SEQUENCE: 48

Met Ile Leu Asp Ala Asp Tyr Ile Thr Glu Asp Gly Lys Pro Ile Ile
1 5 10 15

Arg Ile Phe Lys Lys Glu Asn Gly Glu Phe Lys Val Glu Tyr Asp Arg
20 25 30

Asn Phe Arg Pro Tyr Ile Tyr Ala Leu Leu Lys Asp Asp Ser Gln Ile
35 40 45

Asp Glu Val Arg Lys Ile Thr Ala Glu Arg His Gly Lys Ile Val Arg
50 55 60

Ile Ile Asp Ala Glu Lys Val Arg Lys Lys Phe Leu Gly Arg Pro Ile
65 70 75 80

Glu Val Trp Arg Leu Tyr Phe Glu His Pro Gln Asp Glu Pro Ala Ile
85 90 95

Arg Asp Lys Ile Arg Glu His Ser Ala Val Ile Asp Ile Phe Glu Tyr
100 105 110

Asp Ile Pro Phe Ala Lys Arg Tyr Leu Ile Asp Lys Gly Leu Ile Pro
115 120 125

Met Glu Gly Asp Glu Glu Leu Lys Leu Leu Ala Phe Asp Ile Glu Thr
130 135 140

Leu Tyr His Glu Gly Glu Glu Phe Ala Lys Gly Pro Ile Ile Met Ile
145 150 155 160

Ser Tyr Ala Asp Glu Glu Glu Ala Lys Val Ile Thr Trp Lys Lys Ile

-continued

```
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590
```

Lys Lys Tyr Ala Leu Ile Asp Glu Glu Gly Lys Ile Ile Thr Arg Gly
595 600 605

Leu Glu Ile Val Arg Arg Asp Trp Ser Glu Ile Ala Lys Glu Thr Gln
610 615 620

Ala Lys Val Leu Glu Ala Ile Leu Lys His Gly Asn Val Glu Glu Ala
625 630 635 640

Val Lys Ile Val Lys Glu Val Thr Glu Lys Leu Ser Lys Tyr Glu Ile
645 650 655

Pro Pro Glu Lys Leu Val Ile Tyr Glu Gln Ile Thr Arg Pro Leu His
660 665 670

Glu Tyr Lys Ala Ile Gly Pro His Val Ala Val Ala Lys Arg Leu Ala
675 680 685

Ala Arg Gly Val Lys Val Arg Pro Gly Met Val Ile Gly Tyr Ile Val
690 695 700

Leu Arg Gly Asp Gly Pro Ile Ser Lys Arg Ala Ile Leu Ala Glu Glu
705 710 715 720

Phe Asp Leu Arg Lys His Lys Tyr Asp Ala Glu Tyr Tyr Ile Glu Asn
725 730 735

Gln Val Leu Pro Ala Val Leu Arg Ile Leu Glu Ala Phe Gly Tyr Arg
740 745 750

Lys Glu Asp Leu Arg Trp Gln Lys Thr Lys Gln Thr Gly Leu Thr Ala
755 760 765

Trp Leu Asn Ile Lys Lys Lys
770 775

<210> SEQ ID NO 49
<211> LENGTH: 773
<212> TYPE: PRT
<213> ORGANISM: Thermococcus gorgonarius

<400> SEQUENCE: 49

Met Ile Leu Asp Thr Asp Tyr Ile Thr Glu Asp Gly Lys Pro Val Ile
1 5 10 15

Arg Ile Phe Lys Lys Glu Asn Gly Glu Phe Lys Ile Asp Tyr Asp Arg
20 25 30

Asn Phe Glu Pro Tyr Ile Tyr Ala Leu Leu Lys Asp Asp Ser Ala Ile
35 40 45

Glu Asp Val Lys Lys Ile Thr Ala Glu Arg His Gly Thr Thr Val Arg
50 55 60

Val Val Arg Ala Glu Lys Val Lys Lys Lys Phe Leu Gly Arg Pro Ile
65 70 75 80

Glu Val Trp Lys Leu Tyr Phe Thr His Pro Gln Asp Arg Pro Ala Ile
85 90 95

Arg Asp Lys Ile Lys Glu His Pro Ala Val Val Asp Ile Tyr Glu Tyr
100 105 110

Asp Ile Pro Phe Ala Lys Arg Tyr Leu Ile Asp Lys Gly Leu Ile Pro
115 120 125

Met Glu Gly Asp Glu Glu Leu Lys Met Leu Ala Phe Asp Ile Glu Thr
130 135 140

Leu Tyr His Glu Gly Glu Glu Phe Ala Glu Gly Pro Ile Leu Met Ile
145 150 155 160

Ser Tyr Ala Asp Glu Glu Gly Ala Arg Val Ile Thr Trp Lys Asn Ile
165 170 175

Asp Leu Pro Tyr Val Asp Val Val Ser Thr Glu Lys Glu Met Ile Lys

```
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605
```

```
Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770
```

<210> SEQ ID NO 50
<211> LENGTH: 773
<212> TYPE: PRT
<213> ORGANISM: Thermococcus gorgonarius

<400> SEQUENCE: 50

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Glu Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
```

-continued

```
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620
```

```
Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 51
<211> LENGTH: 774
<212> TYPE: PRT
<213> ORGANISM: Thermococcus kodakaraensis

<400> SEQUENCE: 51

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Arg Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
```

-continued

```
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640
```

```
Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770
```

<210> SEQ ID NO 52
<211> LENGTH: 774
<212> TYPE: PRT
<213> ORGANISM: Thermococcus kodakaraensis

<400> SEQUENCE: 52

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Glu Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
```

```
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655
```

```
Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770


<210> SEQ ID NO 53
<211> LENGTH: 774
<212> TYPE: PRT
<213> ORGANISM: Thermococcus litoralis

<400> SEQUENCE: 53

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Arg Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
```

```
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
    370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
    450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
    530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670
```

```
Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770


<210> SEQ ID NO 54
<211> LENGTH: 774
<212> TYPE: PRT
<213> ORGANISM: Thermococcus litoralis

<400> SEQUENCE: 54

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Glu Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
```

```
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
    370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
    450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
    530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685
```

Leu Ala Ala Arg Gly Ile Lys Val Lys Pro Gly Thr Ile Ile Ser Tyr
690 695 700

Ile Val Leu Lys Gly Ser Gly Lys Ile Ser Asp Arg Val Ile Leu Leu
705 710 715 720

Thr Glu Tyr Asp Pro Arg Lys His Lys Tyr Asp Pro Asp Tyr Tyr Ile
725 730 735

Glu Asn Gln Val Leu Pro Ala Val Leu Arg Ile Leu Glu Ala Phe Gly
740 745 750

Tyr Arg Lys Glu Asp Leu Arg Tyr Gln Ser Ser Lys Gln Thr Gly Leu
755 760 765

Asp Ala Trp Leu Lys Arg
770

<210> SEQ ID NO 55
<211> LENGTH: 776
<212> TYPE: PRT
<213> ORGANISM: Pyrococcus GB-D

<400> SEQUENCE: 55

Met Ile Leu Asp Val Asp Tyr Ile Thr Glu Asn Gly Lys Pro Val Ile
1 5 10 15

Arg Val Phe Lys Lys Glu Asn Gly Glu Phe Arg Ile Glu Tyr Asp Arg
20 25 30

Glu Phe Glu Pro Tyr Phe Tyr Ala Leu Leu Arg Asp Asp Ser Ala Ile
35 40 45

Glu Glu Ile Lys Lys Ile Thr Ala Glu Arg His Gly Arg Val Val Lys
50 55 60

Val Lys Arg Ala Glu Lys Val Lys Lys Lys Phe Leu Gly Arg Ser Val
65 70 75 80

Glu Val Trp Val Leu Tyr Phe Thr His Pro Gln Asp Arg Pro Ala Ile
85 90 95

Arg Asp Lys Ile Arg Lys His Pro Ala Val Ile Asp Ile Tyr Glu Tyr
100 105 110

Asp Ile Pro Phe Ala Lys Arg Tyr Leu Ile Asp Lys Gly Leu Ile Pro
115 120 125

Met Glu Gly Glu Glu Glu Leu Lys Leu Met Ser Phe Asp Ile Glu Thr
130 135 140

Leu Tyr His Glu Gly Glu Glu Phe Gly Thr Gly Pro Ile Leu Met Ile
145 150 155 160

Ser Tyr Ala Asp Glu Ser Glu Ala Arg Val Ile Thr Trp Lys Lys Ile
165 170 175

Asp Leu Pro Tyr Val Glu Val Val Ser Thr Glu Lys Glu Met Ile Lys
180 185 190

Arg Phe Leu Arg Val Val Lys Glu Lys Asp Pro Asp Val Leu Ile Thr
195 200 205

Tyr Asn Gly Asp Asn Phe Asp Phe Ala Tyr Leu Lys Lys Arg Cys Glu
210 215 220

Lys Leu Gly Val Ser Phe Thr Leu Gly Arg Asp Gly Ser Glu Pro Lys
225 230 235 240

Ile Gln Arg Met Gly Asp Arg Phe Ala Val Glu Val Lys Gly Arg Val
245 250 255

His Phe Asp Leu Tyr Pro Val Ile Arg Arg Thr Ile Asn Leu Pro Thr
260 265 270

Tyr Thr Leu Glu Ala Val Tyr Glu Ala Val Phe Gly Lys Pro Lys Glu

-continued

```
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
    690                 695                 700
```

```
Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Gly Lys Lys Lys
    770                 775


<210> SEQ ID NO 56
<211> LENGTH: 776
<212> TYPE: PRT
<213> ORGANISM: Pyrococcus GB-D

<400> SEQUENCE: 56

Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Lys Phe Leu Gly Arg Ser Val
65                  70                  75                  80

Glu Val Trp Val Leu Tyr Phe Thr His Pro Gln Asp Glu Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Leu Met Ser Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
```

```
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720
```

```
Asp Pro Thr Lys His Lys Tyr Asp Ala Asp Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Gly Lys Lys Lys
    770                 775


<210> SEQ ID NO 57
<211> LENGTH: 2322
<212> TYPE: DNA
<213> ORGANISM: Thermococcus gorgonarius
<220> FEATURE:
<221> NAME/KEY: misc_feature
<222> LOCATION: (277)..(279)
<223> OTHER INFORMATION: NNN = AGA, AGG, CGA, CGC, CGG, CGT
<220> FEATURE:
<221> NAME/KEY: CDS
<222> LOCATION: (1)..(2322)
<223> OTHER INFORMATION:

<400> SEQUENCE: 57

atg atc ctc gat aca gac tac ata act gag gat gga aag ccc gtc atc       48
Met Ile Leu Asp Thr Asp Tyr Ile Thr Glu Asp Gly Lys Pro Val Ile
1               5                   10                  15

agg atc ttc aag aag gag aac ggc gag ttc aaa ata gac tac gac aga       96
Arg Ile Phe Lys Lys Glu Asn Gly Glu Phe Lys Ile Asp Tyr Asp Arg
            20                  25                  30

aac ttt gag cca tac atc tac gcg ctc ttg aag gac gac tct gcg att      144
Asn Phe Glu Pro Tyr Ile Tyr Ala Leu Leu Lys Asp Asp Ser Ala Ile
        35                  40                  45

gag gac gtc aag aag ata act gcc gag agg cac ggc act acc gtt agg      192
Glu Asp Val Lys Lys Ile Thr Ala Glu Arg His Gly Thr Thr Val Arg
    50                  55                  60

gtt gtc agg gcc gag aaa gtg aag aag aag ttc cta ggc agg ccg ata      240
Val Val Arg Ala Glu Lys Val Lys Lys Lys Phe Leu Gly Arg Pro Ile
65                  70                  75                  80

gag gtc tgg aag ctc tac ttc act cac ccc cag gac nnn ccc gca atc      288
Glu Val Trp Lys Leu Tyr Phe Thr His Pro Gln Asp Xaa Pro Ala Ile
                85                  90                  95

agg gac aag ata aag gag cat cct gcc gtt gtg gac atc tac gag tac      336
Arg Asp Lys Ile Lys Glu His Pro Ala Val Val Asp Ile Tyr Glu Tyr
            100                 105                 110

gac atc ccc ttc gcg aag cgc tac ctc ata gac aaa ggc tta atc ccg      384
Asp Ile Pro Phe Ala Lys Arg Tyr Leu Ile Asp Lys Gly Leu Ile Pro
        115                 120                 125

atg gag ggc gac gag gaa ctt aag atg ctc gcc ttc gac atc gag acg      432
Met Glu Gly Asp Glu Glu Leu Lys Met Leu Ala Phe Asp Ile Glu Thr
    130                 135                 140

ctc tat cac gag ggc gag gag ttc gcc gaa ggg cct atc ctg atg ata      480
Leu Tyr His Glu Gly Glu Glu Phe Ala Glu Gly Pro Ile Leu Met Ile
145                 150                 155                 160

agc tac gcc gac gag gaa ggg gcg cgc gtt att acc tgg aag aat atc      528
Ser Tyr Ala Asp Glu Glu Gly Ala Arg Val Ile Thr Trp Lys Asn Ile
                165                 170                 175

gac ctt ccc tat gtc gac gtc gtt tcc acc gag aag gag atg ata aag      576
Asp Leu Pro Tyr Val Asp Val Val Ser Thr Glu Lys Glu Met Ile Lys
            180                 185                 190

cgc ttc ctc aag gtc gtc aag gaa aag gat ccc gac gtc ctc ata acc      624
Arg Phe Leu Lys Val Val Lys Glu Lys Asp Pro Asp Val Leu Ile Thr
```

-continued

```
        195                 200                 205

tac aac ggc gac aac ttc gac ttc gcc tac ctc aag aag cgc tcc gag      672
Tyr Asn Gly Asp Asn Phe Asp Phe Ala Tyr Leu Lys Lys Arg Ser Glu
    210                 215                 220

aag ctc gga gtc aag ttc atc ctc gga agg gaa ggg agc gag ccg aaa      720
Lys Leu Gly Val Lys Phe Ile Leu Gly Arg Glu Gly Ser Glu Pro Lys
225                 230                 235                 240

atc cag cgc atg ggc gat cgc ttt gcg gtg gag gtc aag gga agg att      768
Ile Gln Arg Met Gly Asp Arg Phe Ala Val Glu Val Lys Gly Arg Ile
                245                 250                 255

cac ttc gac ctc tac ccc gtc att agg aga acg att aac ctc ccc act      816
His Phe Asp Leu Tyr Pro Val Ile Arg Arg Thr Ile Asn Leu Pro Thr
            260                 265                 270

tac acc ctt gag gca gta tat gaa gcc atc ttt gga cag ccg aag gag      864
Tyr Thr Leu Glu Ala Val Tyr Glu Ala Ile Phe Gly Gln Pro Lys Glu
        275                 280                 285

aag gtc tac gct gag gag ata gcg cag gcc tgg gaa acg ggc gag gga      912
Lys Val Tyr Ala Glu Glu Ile Ala Gln Ala Trp Glu Thr Gly Glu Gly
    290                 295                 300

tta gaa agg gtg gcc cgc tac tcg atg gag gac gca aag gta acc tat      960
Leu Glu Arg Val Ala Arg Tyr Ser Met Glu Asp Ala Lys Val Thr Tyr
305                 310                 315                 320

gaa ctc gga aaa gag ttc ttc cct atg gaa gcc cag ctc tcg cgc ctc     1008
Glu Leu Gly Lys Glu Phe Phe Pro Met Glu Ala Gln Leu Ser Arg Leu
                325                 330                 335

gta ggc cag agc ctc tgg gat gta tct cgc tcg agt acc gga aac ctc     1056
Val Gly Gln Ser Leu Trp Asp Val Ser Arg Ser Ser Thr Gly Asn Leu
            340                 345                 350

gtc gag tgg ttt ttg ctg agg aag gcc tac gag agg aat gaa ctt gca     1104
Val Glu Trp Phe Leu Leu Arg Lys Ala Tyr Glu Arg Asn Glu Leu Ala
        355                 360                 365

cca aac aag ccg gac gag agg gag ctg gca aga aga agg gag agc tac     1152
Pro Asn Lys Pro Asp Glu Arg Glu Leu Ala Arg Arg Arg Glu Ser Tyr
    370                 375                 380

gcg ggt gga tac gtc aag gag ccc gaa agg gga ctg tgg gag aac atc     1200
Ala Gly Gly Tyr Val Lys Glu Pro Glu Arg Gly Leu Trp Glu Asn Ile
385                 390                 395                 400

gtg tat ctg gac ttc cgc tcc ctg tat cct tcg ata ata atc acc cat     1248
Val Tyr Leu Asp Phe Arg Ser Leu Tyr Pro Ser Ile Ile Ile Thr His
                405                 410                 415

aac gtc tcc cct gat aca ctc aac agg gag ggt tgt gag gag tac gac     1296
Asn Val Ser Pro Asp Thr Leu Asn Arg Glu Gly Cys Glu Glu Tyr Asp
            420                 425                 430

gtg gct cct cag gta ggc cat aag ttc tgc aag gac ttc ccc ggc ttc     1344
Val Ala Pro Gln Val Gly His Lys Phe Cys Lys Asp Phe Pro Gly Phe
        435                 440                 445

atc cca agc ctc ctc gga gac ctc ttg gag gag aga cag aag gta aag     1392
Ile Pro Ser Leu Leu Gly Asp Leu Leu Glu Glu Arg Gln Lys Val Lys
    450                 455                 460

aag aag atg aag gcc act ata gac cca atc gag aag aaa ctc ctc gat     1440
Lys Lys Met Lys Ala Thr Ile Asp Pro Ile Glu Lys Lys Leu Leu Asp
465                 470                 475                 480

tac agg caa cga gca atc aaa atc ctt gct aat agc ttc tac ggt tac     1488
Tyr Arg Gln Arg Ala Ile Lys Ile Leu Ala Asn Ser Phe Tyr Gly Tyr
                485                 490                 495

tac ggc tat gca aag gcc cgc tgg tac tgc aag gag tgc gcc gag agc     1536
Tyr Gly Tyr Ala Lys Ala Arg Trp Tyr Cys Lys Glu Cys Ala Glu Ser
            500                 505                 510

gtt acc gct tgg ggc agg cag tac atc gag acc acg ata agg gaa ata     1584
```

```
Val Thr Ala Trp Gly Arg Gln Tyr Ile Glu Thr Thr Ile Arg Glu Ile
        515                 520                 525

gag gag aaa ttt ggc ttt aaa gtc ctc tac gcg gac aca gat gga ttt      1632
Glu Glu Lys Phe Gly Phe Lys Val Leu Tyr Ala Asp Thr Asp Gly Phe
    530                 535                 540

ttc gca aca ata cct gga gcg gac gcc gaa acc gtc aaa aag aag gca      1680
Phe Ala Thr Ile Pro Gly Ala Asp Ala Glu Thr Val Lys Lys Lys Ala
545                 550                 555                 560

aag gag ttc ctg gac tac atc aac gcc aaa ctg ccc ggc ctg ctc gaa      1728
Lys Glu Phe Leu Asp Tyr Ile Asn Ala Lys Leu Pro Gly Leu Leu Glu
                565                 570                 575

ctc gaa tac gag ggc ttc tac aag cgc ggc ttc ttc gtg acg aag aag      1776
Leu Glu Tyr Glu Gly Phe Tyr Lys Arg Gly Phe Phe Val Thr Lys Lys
            580                 585                 590

aag tac gcg gtt ata gac gag gag gac aag ata acg acg cgc ggg ctt      1824
Lys Tyr Ala Val Ile Asp Glu Glu Asp Lys Ile Thr Thr Arg Gly Leu
        595                 600                 605

gaa ata gtt agg cgt gac tgg agc gag ata gcg aag gag acg cag gcg      1872
Glu Ile Val Arg Arg Asp Trp Ser Glu Ile Ala Lys Glu Thr Gln Ala
    610                 615                 620

agg gtt ctt gag gcg ata cta aag cac ggt gac gtt gaa gaa gcg gta      1920
Arg Val Leu Glu Ala Ile Leu Lys His Gly Asp Val Glu Glu Ala Val
625                 630                 635                 640

agg att gtc aaa gag gtt acg gag aag ctg agc aag tac gag gtt cca      1968
Arg Ile Val Lys Glu Val Thr Glu Lys Leu Ser Lys Tyr Glu Val Pro
                645                 650                 655

ccg gag aag ctg gtc atc tac gag cag ata acc cgc gac ctg aag gac      2016
Pro Glu Lys Leu Val Ile Tyr Glu Gln Ile Thr Arg Asp Leu Lys Asp
            660                 665                 670

tac aag gcc acc ggg ccg cat gtg gct gtt gca aaa cgc ctc gcc gca      2064
Tyr Lys Ala Thr Gly Pro His Val Ala Val Ala Lys Arg Leu Ala Ala
        675                 680                 685

agg ggg ata aaa atc cgg ccc gga acg gtc ata agc tac atc gtg ctc      2112
Arg Gly Ile Lys Ile Arg Pro Gly Thr Val Ile Ser Tyr Ile Val Leu
    690                 695                 700

aaa ggc tcg gga agg att ggg gac agg gct ata ccc ttt gac gaa ttt      2160
Lys Gly Ser Gly Arg Ile Gly Asp Arg Ala Ile Pro Phe Asp Glu Phe
705                 710                 715                 720

gac ccg gca aag cac aag tac gat gca gaa tac tac atc gag aac cag      2208
Asp Pro Ala Lys His Lys Tyr Asp Ala Glu Tyr Tyr Ile Glu Asn Gln
                725                 730                 735

gtt ctt cca gct gtg gag agg att ctg agg gcc ttt ggt tac cgt aaa      2256
Val Leu Pro Ala Val Glu Arg Ile Leu Arg Ala Phe Gly Tyr Arg Lys
            740                 745                 750

gaa gat tta agg tat cag aaa acg cgg cag gtt ggc ttg ggg gcg tgg      2304
Glu Asp Leu Arg Tyr Gln Lys Thr Arg Gln Val Gly Leu Gly Ala Trp
        755                 760                 765

cta aaa cct aag aca tga                                              2322
Leu Lys Pro Lys Thr
    770


<210> SEQ ID NO 58
<211> LENGTH: 773
<212> TYPE: PRT
<213> ORGANISM: Thermococcus gorgonarius
<220> FEATURE:
<221> NAME/KEY: misc_feature
<222> LOCATION: (93)..(93)
<223> OTHER INFORMATION: The 'Xaa' at location 93 stands for Lys, Asn,
      Arg, Ser, Thr, Ile, Met, Glu, Asp, Gly, Ala, Val, Gln, His, Pro,
      Leu, Tyr, Trp, Cys, or Phe.
```

<400> SEQUENCE: 58

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Xaa Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415
```

Asn Val Ser Pro Asp Thr Leu Asn Arg Glu Gly Cys Glu Glu Tyr Asp
420 425 430

Val Ala Pro Gln Val Gly His Lys Phe Cys Lys Asp Phe Pro Gly Phe
435 440 445

Ile Pro Ser Leu Leu Gly Asp Leu Leu Glu Glu Arg Gln Lys Val Lys
450 455 460

Lys Lys Met Lys Ala Thr Ile Asp Pro Ile Glu Lys Lys Leu Leu Asp
465 470 475 480

Tyr Arg Gln Arg Ala Ile Lys Ile Leu Ala Asn Ser Phe Tyr Gly Tyr
485 490 495

Tyr Gly Tyr Ala Lys Ala Arg Trp Tyr Cys Lys Glu Cys Ala Glu Ser
500 505 510

Val Thr Ala Trp Gly Arg Gln Tyr Ile Glu Thr Thr Ile Arg Glu Ile
515 520 525

Glu Glu Lys Phe Gly Phe Lys Val Leu Tyr Ala Asp Thr Asp Gly Phe
530 535 540

Phe Ala Thr Ile Pro Gly Ala Asp Ala Glu Thr Val Lys Lys Lys Ala
545 550 555 560

Lys Glu Phe Leu Asp Tyr Ile Asn Ala Lys Leu Pro Gly Leu Leu Glu
565 570 575

Leu Glu Tyr Glu Gly Phe Tyr Lys Arg Gly Phe Phe Val Thr Lys Lys
580 585 590

Lys Tyr Ala Val Ile Asp Glu Glu Asp Lys Ile Thr Thr Arg Gly Leu
595 600 605

Glu Ile Val Arg Arg Asp Trp Ser Glu Ile Ala Lys Glu Thr Gln Ala
610 615 620

Arg Val Leu Glu Ala Ile Leu Lys His Gly Asp Val Glu Glu Ala Val
625 630 635 640

Arg Ile Val Lys Glu Val Thr Glu Lys Leu Ser Lys Tyr Glu Val Pro
645 650 655

Pro Glu Lys Leu Val Ile Tyr Glu Gln Ile Thr Arg Asp Leu Lys Asp
660 665 670

Tyr Lys Ala Thr Gly Pro His Val Ala Val Ala Lys Arg Leu Ala Ala
675 680 685

Arg Gly Ile Lys Ile Arg Pro Gly Thr Val Ile Ser Tyr Ile Val Leu
690 695 700

Lys Gly Ser Gly Arg Ile Gly Asp Arg Ala Ile Pro Phe Asp Glu Phe
705 710 715 720

Asp Pro Ala Lys His Lys Tyr Asp Ala Glu Tyr Tyr Ile Glu Asn Gln
725 730 735

Val Leu Pro Ala Val Glu Arg Ile Leu Arg Ala Phe Gly Tyr Arg Lys
740 745 750

Glu Asp Leu Arg Tyr Gln Lys Thr Arg Gln Val Gly Leu Gly Ala Trp
755 760 765

Leu Lys Pro Lys Thr
770

<210> SEQ ID NO 59
<211> LENGTH: 2322
<212> TYPE: DNA
<213> ORGANISM: Thermococcus gorgonarius
<220> FEATURE:
<221> NAME/KEY: CDS
<222> LOCATION: (1)..(2322)
<223> OTHER INFORMATION:

```
<220> FEATURE:
<221> NAME/KEY: misc_feature
<222> LOCATION: (277)..(279)
<223> OTHER INFORMATION: NNN = GAA, GAG

<400> SEQUENCE: 59

atg atc ctc gat aca gac tac ata act gag gat gga aag ccc gtc atc       48
Met Ile Leu Asp Thr Asp Tyr Ile Thr Glu Asp Gly Lys Pro Val Ile
1               5                   10                  15

agg atc ttc aag aag gag aac ggc gag ttc aaa ata gac tac gac aga       96
Arg Ile Phe Lys Lys Glu Asn Gly Glu Phe Lys Ile Asp Tyr Asp Arg
            20                  25                  30

aac ttt gag cca tac atc tac gcg ctc ttg aag gac gac tct gcg att      144
Asn Phe Glu Pro Tyr Ile Tyr Ala Leu Leu Lys Asp Asp Ser Ala Ile
        35                  40                  45

gag gac gtc aag aag ata act gcc gag agg cac ggc act acc gtt agg      192
Glu Asp Val Lys Lys Ile Thr Ala Glu Arg His Gly Thr Thr Val Arg
    50                  55                  60

gtt gtc agg gcc gag aaa gtg aag aag aag ttc cta ggc agg ccg ata      240
Val Val Arg Ala Glu Lys Val Lys Lys Lys Phe Leu Gly Arg Pro Ile
65                  70                  75                  80

gag gtc tgg aag ctc tac ttc act cac ccc cag gac nnn ccc gca atc      288
Glu Val Trp Lys Leu Tyr Phe Thr His Pro Gln Asp Xaa Pro Ala Ile
                85                  90                  95

agg gac aag ata aag gag cat cct gcc gtt gtg gac atc tac gag tac      336
Arg Asp Lys Ile Lys Glu His Pro Ala Val Val Asp Ile Tyr Glu Tyr
            100                 105                 110

gac atc ccc ttc gcg aag cgc tac ctc ata gac aaa ggc tta atc ccg      384
Asp Ile Pro Phe Ala Lys Arg Tyr Leu Ile Asp Lys Gly Leu Ile Pro
        115                 120                 125

atg gag ggc gac gag gaa ctt aag atg ctc gcc ttc gac atc gag acg      432
Met Glu Gly Asp Glu Glu Leu Lys Met Leu Ala Phe Asp Ile Glu Thr
    130                 135                 140

ctc tat cac gag ggc gag gag ttc gcc gaa ggg cct atc ctg atg ata      480
Leu Tyr His Glu Gly Glu Glu Phe Ala Glu Gly Pro Ile Leu Met Ile
145                 150                 155                 160

agc tac gcc gac gag gaa ggg gcg cgc gtt att acc tgg aag aat atc      528
Ser Tyr Ala Asp Glu Glu Gly Ala Arg Val Ile Thr Trp Lys Asn Ile
                165                 170                 175

gac ctt ccc tat gtc gac gtc gtt tcc acc gag aag gag atg ata aag      576
Asp Leu Pro Tyr Val Asp Val Val Ser Thr Glu Lys Glu Met Ile Lys
            180                 185                 190

cgc ttc ctc aag gtc gtc aag gaa aag gat ccc gac gtc ctc ata acc      624
Arg Phe Leu Lys Val Val Lys Glu Lys Asp Pro Asp Val Leu Ile Thr
        195                 200                 205

tac aac ggc gac aac ttc gac ttc gcc tac ctc aag aag cgc tcc gag      672
Tyr Asn Gly Asp Asn Phe Asp Phe Ala Tyr Leu Lys Lys Arg Ser Glu
    210                 215                 220

aag ctc gga gtc aag ttc atc ctc gga agg gaa ggg agc gag ccg aaa      720
Lys Leu Gly Val Lys Phe Ile Leu Gly Arg Glu Gly Ser Glu Pro Lys
225                 230                 235                 240

atc cag cgc atg ggc gat cgc ttt gcg gtg gag gtc aag gga agg att      768
Ile Gln Arg Met Gly Asp Arg Phe Ala Val Glu Val Lys Gly Arg Ile
                245                 250                 255

cac ttc gac ctc tac ccc gtc att agg aga acg att aac ctc ccc act      816
His Phe Asp Leu Tyr Pro Val Ile Arg Arg Thr Ile Asn Leu Pro Thr
            260                 265                 270

tac acc ctt gag gca gta tat gaa gcc atc ttt gga cag ccg aag gag      864
Tyr Thr Leu Glu Ala Val Tyr Glu Ala Ile Phe Gly Gln Pro Lys Glu
        275                 280                 285
```

```
aag gtc tac gct gag gag ata gcg cag gcc tgg gaa acg ggc gag gga      912
Lys Val Tyr Ala Glu Glu Ile Ala Gln Ala Trp Glu Thr Gly Glu Gly
    290                 295                 300

tta gaa agg gtg gcc cgc tac tcg atg gag gac gca aag gta acc tat      960
Leu Glu Arg Val Ala Arg Tyr Ser Met Glu Asp Ala Lys Val Thr Tyr
305                 310                 315                 320

gaa ctc gga aaa gag ttc ttc cct atg gaa gcc cag ctc tcg cgc ctc     1008
Glu Leu Gly Lys Glu Phe Phe Pro Met Glu Ala Gln Leu Ser Arg Leu
                325                 330                 335

gta ggc cag agc ctc tgg gat gta tct cgc tcg agt acc gga aac ctc     1056
Val Gly Gln Ser Leu Trp Asp Val Ser Arg Ser Ser Thr Gly Asn Leu
            340                 345                 350

gtc gag tgg ttt ttg ctg agg aag gcc tac gag agg aat gaa ctt gca     1104
Val Glu Trp Phe Leu Leu Arg Lys Ala Tyr Glu Arg Asn Glu Leu Ala
        355                 360                 365

cca aac aag ccg gac gag agg gag ctg gca aga aga agg gag agc tac     1152
Pro Asn Lys Pro Asp Glu Arg Glu Leu Ala Arg Arg Arg Glu Ser Tyr
    370                 375                 380

gcg ggt gga tac gtc aag gag ccc gaa agg gga ctg tgg gag aac atc     1200
Ala Gly Gly Tyr Val Lys Glu Pro Glu Arg Gly Leu Trp Glu Asn Ile
385                 390                 395                 400

gtg tat ctg gac ttc cgc tcc ctg tat cct tcg ata ata atc acc cat     1248
Val Tyr Leu Asp Phe Arg Ser Leu Tyr Pro Ser Ile Ile Ile Thr His
                405                 410                 415

aac gtc tcc cct gat aca ctc aac agg gag ggt tgt gag gag tac gac     1296
Asn Val Ser Pro Asp Thr Leu Asn Arg Glu Gly Cys Glu Glu Tyr Asp
            420                 425                 430

gtg gct cct cag gta ggc cat aag ttc tgc aag gac ttc ccc ggc ttc     1344
Val Ala Pro Gln Val Gly His Lys Phe Cys Lys Asp Phe Pro Gly Phe
        435                 440                 445

atc cca agc ctc ctc gga gac ctc ttg gag gag aga cag aag gta aag     1392
Ile Pro Ser Leu Leu Gly Asp Leu Leu Glu Glu Arg Gln Lys Val Lys
    450                 455                 460

aag aag atg aag gcc act ata gac cca atc gag aag aaa ctc ctc gat     1440
Lys Lys Met Lys Ala Thr Ile Asp Pro Ile Glu Lys Lys Leu Leu Asp
465                 470                 475                 480

tac agg caa cga gca atc aaa atc ctt gct aat agc ttc tac ggt tac     1488
Tyr Arg Gln Arg Ala Ile Lys Ile Leu Ala Asn Ser Phe Tyr Gly Tyr
                485                 490                 495

tac ggc tat gca aag gcc cgc tgg tac tgc aag gag tgc gcc gag agc     1536
Tyr Gly Tyr Ala Lys Ala Arg Trp Tyr Cys Lys Glu Cys Ala Glu Ser
            500                 505                 510

gtt acc gct tgg ggc agg cag tac atc gag acc acg ata agg gaa ata     1584
Val Thr Ala Trp Gly Arg Gln Tyr Ile Glu Thr Thr Ile Arg Glu Ile
        515                 520                 525

gag gag aaa ttt ggc ttt aaa gtc ctc tac gcg gac aca gat gga ttt     1632
Glu Glu Lys Phe Gly Phe Lys Val Leu Tyr Ala Asp Thr Asp Gly Phe
    530                 535                 540

ttc gca aca ata cct gga gcg gac gcc gaa acc gtc aaa aag aag gca     1680
Phe Ala Thr Ile Pro Gly Ala Asp Ala Glu Thr Val Lys Lys Lys Ala
545                 550                 555                 560

aag gag ttc ctg gac tac atc aac gcc aaa ctg ccc ggc ctg ctc gaa     1728
Lys Glu Phe Leu Asp Tyr Ile Asn Ala Lys Leu Pro Gly Leu Leu Glu
                565                 570                 575

ctc gaa tac gag ggc ttc tac aag cgc ggc ttc ttc gtg acg aag aag     1776
Leu Glu Tyr Glu Gly Phe Tyr Lys Arg Gly Phe Phe Val Thr Lys Lys
            580                 585                 590

aag tac gcg gtt ata gac gag gag gac aag ata acg acg cgc ggg ctt     1824
Lys Tyr Ala Val Ile Asp Glu Glu Asp Lys Ile Thr Thr Arg Gly Leu
        595                 600                 605
```

```
gaa ata gtt agg cgt gac tgg agc gag ata gcg aag gag acg cag gcg     1872
Glu Ile Val Arg Arg Asp Trp Ser Glu Ile Ala Lys Glu Thr Gln Ala
    610                 615                 620

agg gtt ctt gag gcg ata cta aag cac ggt gac gtt gaa gaa gcg gta     1920
Arg Val Leu Glu Ala Ile Leu Lys His Gly Asp Val Glu Glu Ala Val
625                 630                 635                 640

agg att gtc aaa gag gtt acg gag aag ctg agc aag tac gag gtt cca     1968
Arg Ile Val Lys Glu Val Thr Glu Lys Leu Ser Lys Tyr Glu Val Pro
                645                 650                 655

ccg gag aag ctg gtc atc tac gag cag ata acc cgc gac ctg aag gac     2016
Pro Glu Lys Leu Val Ile Tyr Glu Gln Ile Thr Arg Asp Leu Lys Asp
            660                 665                 670

tac aag gcc acc ggg ccg cat gtg gct gtt gca aaa cgc ctc gcc gca     2064
Tyr Lys Ala Thr Gly Pro His Val Ala Val Ala Lys Arg Leu Ala Ala
        675                 680                 685

agg ggg ata aaa atc cgg ccc gga acg gtc ata agc tac atc gtg ctc     2112
Arg Gly Ile Lys Ile Arg Pro Gly Thr Val Ile Ser Tyr Ile Val Leu
    690                 695                 700

aaa ggc tcg gga agg att ggg gac agg gct ata ccc ttt gac gaa ttt     2160
Lys Gly Ser Gly Arg Ile Gly Asp Arg Ala Ile Pro Phe Asp Glu Phe
705                 710                 715                 720

gac ccg gca aag cac aag tac gat gca gaa tac tac atc gag aac cag     2208
Asp Pro Ala Lys His Lys Tyr Asp Ala Glu Tyr Tyr Ile Glu Asn Gln
                725                 730                 735

gtt ctt cca gct gtg gag agg att ctg agg gcc ttt ggt tac cgt aaa     2256
Val Leu Pro Ala Val Glu Arg Ile Leu Arg Ala Phe Gly Tyr Arg Lys
            740                 745                 750

gaa gat tta agg tat cag aaa acg cgg cag gtt ggc ttg ggg gcg tgg     2304
Glu Asp Leu Arg Tyr Gln Lys Thr Arg Gln Val Gly Leu Gly Ala Trp
        755                 760                 765

cta aaa cct aag aca tga                                             2322
Leu Lys Pro Lys Thr
    770


<210> SEQ ID NO 60
<211> LENGTH: 773
<212> TYPE: PRT
<213> ORGANISM: Thermococcus gorgonarius
<220> FEATURE:
<221> NAME/KEY: misc_feature
<222> LOCATION: (93)..(93)
<223> OTHER INFORMATION: The 'Xaa' at location 93 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 60

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Xaa Pro Ala Ile
                85                  90                  95

Arg Asp Lys Ile Lys Glu His Pro Ala Val Val Asp Ile Tyr Glu Tyr
            100                 105                 110
```

-continued

```
Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525
```

```
Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 61
<211> LENGTH: 3499
<212> TYPE: DNA
<213> ORGANISM: Pyrococcus furiosus
<220> FEATURE:
<221> NAME/KEY: misc_feature
<222> LOCATION: (1)..(3499)
<223> OTHER INFORMATION: n = A, T, G or C
<220> FEATURE:
<221> NAME/KEY: CDS
<222> LOCATION: (224)..(2551)
<223> OTHER INFORMATION:

<400> SEQUENCE: 61

ccctggtcct gggtccacat atatgttctt actcgccttt atgaagaatc ccccagtcgc      60

tctaacctgg gttatagtga caaatcttcc tccaccaccg cccaagaagg ttatttctat     120

caactctaca cctcccctat tttctctctt atgagatttt taagtatagt tatagagaag     180

gttttatact ccaaactgag ttagtagata tgtggggagc ata atg att tta gat       235
                                                Met Ile Leu Asp
                                                1

gtg gat tac ata act gaa gaa gga aaa cct gtt att agg cta ttc aaa       283
Val Asp Tyr Ile Thr Glu Glu Gly Lys Pro Val Ile Arg Leu Phe Lys
5                   10                  15                  20

aaa gag aac gga aaa ttt aag ata gag cat gat aga act ttt aga cca       331
```

-continued

```
Lys Glu Asn Gly Lys Phe Lys Ile Glu His Asp Arg Thr Phe Arg Pro
                25                  30                  35

tac att tac gct ctt ctc agg gat gat tca aag att gaa gaa gtt aag      379
Tyr Ile Tyr Ala Leu Leu Arg Asp Asp Ser Lys Ile Glu Glu Val Lys
            40                  45                  50

aaa ata acg ggg gaa agg cat gga aag att gtg aga att gtt gat gta      427
Lys Ile Thr Gly Glu Arg His Gly Lys Ile Val Arg Ile Val Asp Val
        55                  60                  65

gag aag gtt gag aaa aag ttt ctc ggc aag cct att acc gtg tgg aaa      475
Glu Lys Val Glu Lys Lys Phe Leu Gly Lys Pro Ile Thr Val Trp Lys
    70                  75                  80

ctt tat ttg gaa cat ccc caa gat gtt ccc act att aga gaa aaa gtt      523
Leu Tyr Leu Glu His Pro Gln Asp Val Pro Thr Ile Arg Glu Lys Val
85                  90                  95                  100

aga gaa cat cca gca gtt gtg gac atc ttc gaa tac gat att cca ttt      571
Arg Glu His Pro Ala Val Val Asp Ile Phe Glu Tyr Asp Ile Pro Phe
                105                 110                 115

gca aag aga tac ctc atc gac aaa ggc cta ata cca atg gag ggg gaa      619
Ala Lys Arg Tyr Leu Ile Asp Lys Gly Leu Ile Pro Met Glu Gly Glu
            120                 125                 130

gaa gag cta aag att ctt gcc ttc gat ata gaa acc ctc tat cac gaa      667
Glu Glu Leu Lys Ile Leu Ala Phe Asp Ile Glu Thr Leu Tyr His Glu
        135                 140                 145

gga gaa gag ttt gga aaa ggc cca att ata atg att agt tat gca gat      715
Gly Glu Glu Phe Gly Lys Gly Pro Ile Ile Met Ile Ser Tyr Ala Asp
    150                 155                 160

gaa aat gaa gca aag gtg att act tgg aaa aac ata gat ctt cca tac      763
Glu Asn Glu Ala Lys Val Ile Thr Trp Lys Asn Ile Asp Leu Pro Tyr
165                 170                 175                 180

gtt gag gtt gta tca agc gag aga gag atg ata aag aga ttt ctc agg      811
Val Glu Val Val Ser Ser Glu Arg Glu Met Ile Lys Arg Phe Leu Arg
                185                 190                 195

att atc agg gag aag gat cct gac att ata gtt act tat aat gga gac      859
Ile Ile Arg Glu Lys Asp Pro Asp Ile Ile Val Thr Tyr Asn Gly Asp
            200                 205                 210

tca ttc gac ttc cca tat tta gcg aaa agg gca gaa aaa ctt ggg att      907
Ser Phe Asp Phe Pro Tyr Leu Ala Lys Arg Ala Glu Lys Leu Gly Ile
        215                 220                 225

aaa tta acc att gga aga gat gga agc gag ccc aag atg cag aga ata      955
Lys Leu Thr Ile Gly Arg Asp Gly Ser Glu Pro Lys Met Gln Arg Ile
    230                 235                 240

ggc gat atg acg gct gta gaa gtc aag gga aga ata cat ttc gac ttg     1003
Gly Asp Met Thr Ala Val Glu Val Lys Gly Arg Ile His Phe Asp Leu
245                 250                 255                 260

tat cat gta ata aca agg aca ata aat ctc cca aca tac aca cta gag     1051
Tyr His Val Ile Thr Arg Thr Ile Asn Leu Pro Thr Tyr Thr Leu Glu
                265                 270                 275

gct gta tat gaa gca att ttt gga aag cca aag gag aag gta tac gcc     1099
Ala Val Tyr Glu Ala Ile Phe Gly Lys Pro Lys Glu Lys Val Tyr Ala
            280                 285                 290

gac gag ata gca aaa gcc tgg gaa agt gga gag aac ctt gag aga gtt     1147
Asp Glu Ile Ala Lys Ala Trp Glu Ser Gly Glu Asn Leu Glu Arg Val
        295                 300                 305

gcc aaa tac tcg atg gaa gat gca aag gca act tat gaa ctc ggg aaa     1195
Ala Lys Tyr Ser Met Glu Asp Ala Lys Ala Thr Tyr Glu Leu Gly Lys
    310                 315                 320

gaa ttc ctt cca atg gaa att cag ctt tca aga tta gtt gga caa cct     1243
Glu Phe Leu Pro Met Glu Ile Gln Leu Ser Arg Leu Val Gly Gln Pro
325                 330                 335                 340
```

-continued tta tgg gat gtt tca agg tca agc aca ggg aac ctt gta gag tgg ttc 1291
Leu Trp Asp Val Ser Arg Ser Ser Thr Gly Asn Leu Val Glu Trp Phe
345 350 355 tta ctt agg aaa gcc tac gaa aga aac gaa gta gct cca aac aag cca 1339
Leu Leu Arg Lys Ala Tyr Glu Arg Asn Glu Val Ala Pro Asn Lys Pro
360 365 370 agt gaa gag gag tat caa aga agg ctc agg gag agc tac aca ggt gga 1387
Ser Glu Glu Glu Tyr Gln Arg Arg Leu Arg Glu Ser Tyr Thr Gly Gly
375 380 385 ttc gtt aaa gag cca gaa aag ggg ttg tgg gaa aac ata gta tac cta 1435
Phe Val Lys Glu Pro Glu Lys Gly Leu Trp Glu Asn Ile Val Tyr Leu
390 395 400 gat ttt aga gcc cta tat ccc tcg att ata att acc cac aat gtt tct 1483
Asp Phe Arg Ala Leu Tyr Pro Ser Ile Ile Ile Thr His Asn Val Ser
405 410 415 420 ccc gat act cta aat ctt gag gga tgc aag aac tat gat atc gct cct 1531
Pro Asp Thr Leu Asn Leu Glu Gly Cys Lys Asn Tyr Asp Ile Ala Pro
425 430 435 caa gta ggc cac aag ttc tgc aag gac atc cct ggt ttt ata cca agt 1579
Gln Val Gly His Lys Phe Cys Lys Asp Ile Pro Gly Phe Ile Pro Ser
440 445 450 ctc ttg gga cat ttg tta gag gaa aga caa aag att aag aca aaa atg 1627
Leu Leu Gly His Leu Leu Glu Glu Arg Gln Lys Ile Lys Thr Lys Met
455 460 465 aag gaa act caa gat cct ata gaa aaa ata ctc ctt gac tat aga caa 1675
Lys Glu Thr Gln Asp Pro Ile Glu Lys Ile Leu Leu Asp Tyr Arg Gln
470 475 480 aaa gcg ata aaa ctc tta gca aat tct ttc tac gga tat tat ggc tat 1723
Lys Ala Ile Lys Leu Leu Ala Asn Ser Phe Tyr Gly Tyr Tyr Gly Tyr
485 490 495 500 gca aaa gca aga tgg tac tgt aag gag tgt gct gag agc gtt act gcc 1771
Ala Lys Ala Arg Trp Tyr Cys Lys Glu Cys Ala Glu Ser Val Thr Ala
505 510 515 tgg gga aga aag tac atc gag tta gta tgg aag gag ctc gaa gaa aag 1819
Trp Gly Arg Lys Tyr Ile Glu Leu Val Trp Lys Glu Leu Glu Glu Lys
520 525 530 ttt gga ttt aaa gtc ctc tac att gac act gat ggt ctc tat gca act 1867
Phe Gly Phe Lys Val Leu Tyr Ile Asp Thr Asp Gly Leu Tyr Ala Thr
535 540 545 atc cca gga gga gaa agt gag gaa ata aag aaa aag gct cta gaa ttt 1915
Ile Pro Gly Gly Glu Ser Glu Glu Ile Lys Lys Lys Ala Leu Glu Phe
550 555 560 gta aaa tac ata aat tca aag ctc cct gga ctg cta gag ctt gaa tat 1963
Val Lys Tyr Ile Asn Ser Lys Leu Pro Gly Leu Leu Glu Leu Glu Tyr
565 570 575 580 gaa ggg ttt tat aag agg gga ttc ttc gtt acg aag aag agg tat gca 2011
Glu Gly Phe Tyr Lys Arg Gly Phe Phe Val Thr Lys Lys Arg Tyr Ala
585 590 595 gta ata gat gaa gaa gga aaa gtc att act cgt ggt tta gag ata gtt 2059
Val Ile Asp Glu Glu Gly Lys Val Ile Thr Arg Gly Leu Glu Ile Val
600 605 610 agg aga gat tgg agt gaa att gca aaa gaa act caa gct aga gtt ttg 2107
Arg Arg Asp Trp Ser Glu Ile Ala Lys Glu Thr Gln Ala Arg Val Leu
615 620 625 gag aca ata cta aaa cac gga gat gtt gaa gaa gct gtg aga ata gta 2155
Glu Thr Ile Leu Lys His Gly Asp Val Glu Glu Ala Val Arg Ile Val
630 635 640 aaa gaa gta ata caa aag ctt gcc aat tat gaa att cca cca gag aag 2203
Lys Glu Val Ile Gln Lys Leu Ala Asn Tyr Glu Ile Pro Pro Glu Lys
645 650 655 660

```
ctc gca ata tat gag cag ata aca aga cca tta cat gag tat aag gcg     2251
Leu Ala Ile Tyr Glu Gln Ile Thr Arg Pro Leu His Glu Tyr Lys Ala
                665                 670                 675

ata ggt cct cac gta gct gtt gca aag aaa cta gct gct aaa gga gtt     2299
Ile Gly Pro His Val Ala Val Ala Lys Lys Leu Ala Ala Lys Gly Val
            680                 685                 690

aaa ata aag cca gga atg gta att gga tac ata gta ctt aga ggc gat     2347
Lys Ile Lys Pro Gly Met Val Ile Gly Tyr Ile Val Leu Arg Gly Asp
        695                 700                 705

ggt cca att agc aat agg gca att cta gct gag gaa tac gat ccc aaa     2395
Gly Pro Ile Ser Asn Arg Ala Ile Leu Ala Glu Glu Tyr Asp Pro Lys
    710                 715                 720

aag cac aag tat gac gca gaa tat tac att gag aac cag gtt ctt cca     2443
Lys His Lys Tyr Asp Ala Glu Tyr Tyr Ile Glu Asn Gln Val Leu Pro
725                 730                 735                 740

gcg gta ctt agg ata ttg gag gga ttt gga tac aga aag gaa gac ctc     2491
Ala Val Leu Arg Ile Leu Glu Gly Phe Gly Tyr Arg Lys Glu Asp Leu
                745                 750                 755

aga tac caa aag aca aga caa gtc ggc cta act tcc tgg ctt aac att     2539
Arg Tyr Gln Lys Thr Arg Gln Val Gly Leu Thr Ser Trp Leu Asn Ile
            760                 765                 770

aaa aaa tcc tag aaaagcgata gatatcaact tttattcttt ctaacctttt         2591
Lys Lys Ser
        775

tctatgaaag aagaactgag caggaattac cagttcttcc gttattttat gggtaattaa   2651

aaacccatgc tcttgggaga atcttcgaat aaaatcccta acttcaggct ttgctaagtg   2711

aatagaataa acaacatcac tcacttcaaa cgccttcgtt agaaatggtc tatctgcatg   2771

cttctctggc tcggaanngg aggattcata acaacagtat caacattctc agagaattga   2831

gaaacatcag aaactttgac ttctacaaca tttctaactt tgcaactctt caagattttc   2891

taaaagaatt ttaacggcct cctcgtcaat ttcgacgacg tagatctttt ttgctccaag   2951

cagagccgct ccaatggata acacccctgt tcccgcaccc aagtccgcta caatttttc    3011

cttgtatctc ctaatgtata agcaagccaa aggagagtag atgctacctt tccgggagtt   3071

ttgtattgct ctagccaagg tttgggattt ttgaatcctt taactctgga aagtataatt   3131

tcaagctcct tcttcttcat gacagatgaa aaattgtttt gtctcttttt aacttttaca   3191

gaaataactg tctcaaatta tgacaactct tgacattttt acttcattac cagggtaatg   3251

tttttaagta tgaaattttt ctttcataga ggaggnnnnn ngtcctctcc tcgatttcct   3311

tggttgtgct ccatatgata agcttccaaa gtgggtgttc agacttttag acactcaaat   3371

accagacgac aatggtgtgc tcactcaagc cccatatggg ttgagaaaag tagaagcggc   3431

actactcaga tgcttcccca ggaatgaggt tgttgtagct cntcccngaa agattgagat   3491

gttcttgg                                                            3499
```

<210> SEQ ID NO 62
<211> LENGTH: 775
<212> TYPE: PRT
<213> ORGANISM: Pyrococcus furiosus

<400> SEQUENCE: 62

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30
```

```
Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
```

```
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 63
<211> LENGTH: 207
<212> TYPE: DNA
<213> ORGANISM: Pyrococcus furiosus
<220> FEATURE:
<221> NAME/KEY: CDS
<222> LOCATION: (1)..(207)
<223> OTHER INFORMATION:

<400> SEQUENCE: 63

atg atg gga gaa tta cca att gcc cca gtt gac aga ctt ata aga aag       48
Met Met Gly Glu Leu Pro Ile Ala Pro Val Asp Arg Leu Ile Arg Lys
1               5                   10                  15

gct ggt gct cag aga gtt agc gag caa gca gct aag gta ctt gca gag       96
```

```
Ala Gly Ala Gln Arg Val Ser Glu Gln Ala Ala Lys Val Leu Ala Glu
            20                  25                  30

cac ctt gag gaa aaa gct att gag atc gca aaa aag gca gta gat ctt      144
His Leu Glu Glu Lys Ala Ile Glu Ile Ala Lys Lys Ala Val Asp Leu
        35                  40                  45

gca aag cac gca ggt aga aag acc gtt aag gtc gaa gac att aag ctc      192
Ala Lys His Ala Gly Arg Lys Thr Val Lys Val Glu Asp Ile Lys Leu
    50                  55                  60

gca att aag agc tga                                                  207
Ala Ile Lys Ser
65


<210> SEQ ID NO 64
<211> LENGTH: 68
<212> TYPE: PRT
<213> ORGANISM: Pyrococcus furiosus

<400> SEQUENCE: 64

Met Met Gly Glu Leu Pro Ile Ala Pro Val Asp Arg Leu Ile Arg Lys
1               5                   10                  15

Ala Gly Ala Gln Arg Val Ser Glu Gln Ala Ala Lys Val Leu Ala Glu
            20                  25                  30

His Leu Glu Glu Lys Ala Ile Glu Ile Ala Lys Lys Ala Val Asp Leu
        35                  40                  45

Ala Lys His Ala Gly Arg Lys Thr Val Lys Val Glu Asp Ile Lys Leu
    50                  55                  60

Ala Ile Lys Ser
65


<210> SEQ ID NO 65
<211> LENGTH: 2556
<212> TYPE: DNA
<213> ORGANISM: Thermus aquaticus
<220> FEATURE:
<221> NAME/KEY: CDS
<222> LOCATION: (1)..(2556)
<223> OTHER INFORMATION:

<400> SEQUENCE: 65

ggc ggc ggt gtc act agt ggg atg ctg ccc ctc ttt gag ccc aag ggc       48
Gly Gly Gly Val Thr Ser Gly Met Leu Pro Leu Phe Glu Pro Lys Gly
1               5                   10                  15

cgg gtc ctc ctg gtg gac ggc cac cac ctg gcc tac cgc acc ttc cac       96
Arg Val Leu Leu Val Asp Gly His His Leu Ala Tyr Arg Thr Phe His
            20                  25                  30

gcc ctg aag ggc ctc acc acc agc cgg ggg gag ccg gtg cag gcg gtc      144
Ala Leu Lys Gly Leu Thr Thr Ser Arg Gly Glu Pro Val Gln Ala Val
        35                  40                  45

tac ggc ttc gcc aag agc ctc ctc aag gcc ctc aag gag gac ggg gac      192
Tyr Gly Phe Ala Lys Ser Leu Leu Lys Ala Leu Lys Glu Asp Gly Asp
    50                  55                  60

gcg gtg atc gtg gtc ttt gac gcc aag gcc ccc tcc ttc cgc cac gag      240
Ala Val Ile Val Val Phe Asp Ala Lys Ala Pro Ser Phe Arg His Glu
65                  70                  75                  80

gcc tac ggg ggg tac aag gcg ggc cgg gcc ccc acg cca gag gac ttt      288
Ala Tyr Gly Gly Tyr Lys Ala Gly Arg Ala Pro Thr Pro Glu Asp Phe
                85                  90                  95

ccc cgg caa ctc gcc ctc atc aag gag ctg gtg gac ctc ctg ggg ctg      336
Pro Arg Gln Leu Ala Leu Ile Lys Glu Leu Val Asp Leu Leu Gly Leu
            100                 105                 110

gcg cgc ctc gag gtc ccg ggc tac gag gcg gac gac gtc ctg gcc agc      384
```

```
Ala Arg Leu Glu Val Pro Gly Tyr Glu Ala Asp Asp Val Leu Ala Ser
        115                 120                 125

ctg gcc aag aag gcg gaa aag gag ggc tac gag gtc cgc atc ctc acc      432
Leu Ala Lys Lys Ala Glu Lys Glu Gly Tyr Glu Val Arg Ile Leu Thr
    130                 135                 140

gcc gac aaa gac ctt tac cag ctc ctt tcc gac cgc atc cac gtc ctc      480
Ala Asp Lys Asp Leu Tyr Gln Leu Leu Ser Asp Arg Ile His Val Leu
145                 150                 155                 160

cac ccc gag ggg tac ctc atc acc ccg gcc tgg ctt tgg gaa aag tac      528
His Pro Glu Gly Tyr Leu Ile Thr Pro Ala Trp Leu Trp Glu Lys Tyr
                165                 170                 175

ggc ctg agg ccc gac cag tgg gcc gac tac cgg gcc ctg acc ggg gac      576
Gly Leu Arg Pro Asp Gln Trp Ala Asp Tyr Arg Ala Leu Thr Gly Asp
            180                 185                 190

gag tcc gac aac ctt ccc ggg gtc aag ggc atc ggg gag aag acg gcg      624
Glu Ser Asp Asn Leu Pro Gly Val Lys Gly Ile Gly Glu Lys Thr Ala
        195                 200                 205

agg aag ctt ctg gag gag tgg ggg agc ctg gaa gcc ctc ctc aag aac      672
Arg Lys Leu Leu Glu Glu Trp Gly Ser Leu Glu Ala Leu Leu Lys Asn
    210                 215                 220

ctg gac cgg ctg aag ccc gcc atc cgg gag aag atc ctg gcc cac atg      720
Leu Asp Arg Leu Lys Pro Ala Ile Arg Glu Lys Ile Leu Ala His Met
225                 230                 235                 240

gac gat ctg aag ctc tcc tgg gac ctg gcc aag gtg cgc acc gac ctg      768
Asp Asp Leu Lys Leu Ser Trp Asp Leu Ala Lys Val Arg Thr Asp Leu
                245                 250                 255

ccc ctg gag gtg gac ttc gcc aaa agg cgg gag ccc gac cgg gag agg      816
Pro Leu Glu Val Asp Phe Ala Lys Arg Arg Glu Pro Asp Arg Glu Arg
            260                 265                 270

ctt agg gcc ttt ctg gag agg ctt gag ttt ggc agc ctc ctc cac gag      864
Leu Arg Ala Phe Leu Glu Arg Leu Glu Phe Gly Ser Leu Leu His Glu
        275                 280                 285

ttc ggc ctt ctg gaa agc ccc aag gcc ctg gag gag gcc ccc tgg ccc      912
Phe Gly Leu Leu Glu Ser Pro Lys Ala Leu Glu Glu Ala Pro Trp Pro
    290                 295                 300

ccg ccg gaa ggg gcc ttc gtg ggc ttt gtg ctt tcc cgc aag gag ccc      960
Pro Pro Glu Gly Ala Phe Val Gly Phe Val Leu Ser Arg Lys Glu Pro
305                 310                 315                 320

atg tgg gcc gat ctt ctg gcc ctg gcc gcc gcc agg ggg ggc cgg gtc     1008
Met Trp Ala Asp Leu Leu Ala Leu Ala Ala Ala Arg Gly Gly Arg Val
                325                 330                 335

cac cgg gcc ccc gag cct tat aaa gcc ctc agg gac ctg aag gag gcg     1056
His Arg Ala Pro Glu Pro Tyr Lys Ala Leu Arg Asp Leu Lys Glu Ala
            340                 345                 350

cgg ggg ctt ctc gcc aaa gac ctg agc gtt ctg gcc ctg agg gaa ggc     1104
Arg Gly Leu Leu Ala Lys Asp Leu Ser Val Leu Ala Leu Arg Glu Gly
        355                 360                 365

ctt ggc ctc ccg ccc ggc gac gac ccc atg ctc ctc gcc tac ctc ctg     1152
Leu Gly Leu Pro Pro Gly Asp Asp Pro Met Leu Leu Ala Tyr Leu Leu
    370                 375                 380

gac cct tcc aac acc acc ccc gag ggg gtg gcc cgg cgc tac ggc ggg     1200
Asp Pro Ser Asn Thr Thr Pro Glu Gly Val Ala Arg Arg Tyr Gly Gly
385                 390                 395                 400

gag tgg acg gag gag gcg ggg gag cgg gcc gcc ctt tcc gag agg ctc     1248
Glu Trp Thr Glu Glu Ala Gly Glu Arg Ala Ala Leu Ser Glu Arg Leu
                405                 410                 415

ttc gcc aac ctg tgg ggg agg ctt gag ggg gag gag agg ctc ctt tgg     1296
Phe Ala Asn Leu Trp Gly Arg Leu Glu Gly Glu Glu Arg Leu Leu Trp
            420                 425                 430
```

-continued

```
ctt tac cgg gag gtg gag agg ccc ctt tcc gct gtc ctg gcc cac atg      1344
Leu Tyr Arg Glu Val Glu Arg Pro Leu Ser Ala Val Leu Ala His Met
        435                 440                 445

gag gcc acg ggg gtg cgc ctg gac gtg gcc tat ctc agg gcc ttg tcc      1392
Glu Ala Thr Gly Val Arg Leu Asp Val Ala Tyr Leu Arg Ala Leu Ser
    450                 455                 460

ctg gag gtg gcc gag gag atc gcc cgc ctc gag gcc gag gtc ttc cgc      1440
Leu Glu Val Ala Glu Glu Ile Ala Arg Leu Glu Ala Glu Val Phe Arg
465                 470                 475                 480

ctg gcc ggc cac ccc ttc aac ctc aac tcc cgg gac cag ctg gaa agg      1488
Leu Ala Gly His Pro Phe Asn Leu Asn Ser Arg Asp Gln Leu Glu Arg
                485                 490                 495

gtc ctc ttt gac gag cta ggg ctt ccc gcc atc ggc aag acg gag aag      1536
Val Leu Phe Asp Glu Leu Gly Leu Pro Ala Ile Gly Lys Thr Glu Lys
            500                 505                 510

acc ggc aag cgc tcc acc agc gcc gcc gtc ctg gag gcc ctc cgc gag      1584
Thr Gly Lys Arg Ser Thr Ser Ala Ala Val Leu Glu Ala Leu Arg Glu
        515                 520                 525

gcc cac ccc atc gtg gag aag atc ctg cag tac cgg gag ctc acc aag      1632
Ala His Pro Ile Val Glu Lys Ile Leu Gln Tyr Arg Glu Leu Thr Lys
    530                 535                 540

ctg aag agc acc tac att gac ccc ttg ccg gac ctc atc cac ccc agg      1680
Leu Lys Ser Thr Tyr Ile Asp Pro Leu Pro Asp Leu Ile His Pro Arg
545                 550                 555                 560

acg ggc cgc ctc cac acc cgc ttc aac cag acg gcc acg gcc acg ggc      1728
Thr Gly Arg Leu His Thr Arg Phe Asn Gln Thr Ala Thr Ala Thr Gly
                565                 570                 575

agg cta agt agc tcc gat ccc aac ctc cag aac atc ccc gtc cgc acc      1776
Arg Leu Ser Ser Ser Asp Pro Asn Leu Gln Asn Ile Pro Val Arg Thr
            580                 585                 590

ccg ctt ggg cag agg atc cgc cgg gcc ttc atc gcc gag gag ggg tgg      1824
Pro Leu Gly Gln Arg Ile Arg Arg Ala Phe Ile Ala Glu Glu Gly Trp
        595                 600                 605

cta ttg gtg gcc ctg gac tat agc cag ata gag ctc agg gtg ctg gcc      1872
Leu Leu Val Ala Leu Asp Tyr Ser Gln Ile Glu Leu Arg Val Leu Ala
    610                 615                 620

cac ctc tcc ggc gac gag aac ctg atc cgg gtc ttc cag gag ggg cgg      1920
His Leu Ser Gly Asp Glu Asn Leu Ile Arg Val Phe Gln Glu Gly Arg
625                 630                 635                 640

gac atc cac acg gag acc gcc agc tgg atg ttc ggc gtc ccc cgg gag      1968
Asp Ile His Thr Glu Thr Ala Ser Trp Met Phe Gly Val Pro Arg Glu
                645                 650                 655

gcc gtg gac ccc ctg atg cgc cgg gcg gcc aag acc atc aac ttc ggg      2016
Ala Val Asp Pro Leu Met Arg Arg Ala Ala Lys Thr Ile Asn Phe Gly
            660                 665                 670

gtc ctc tac ggc atg tcg gcc cac cgc ctc tcc cag gag cta gcc atc      2064
Val Leu Tyr Gly Met Ser Ala His Arg Leu Ser Gln Glu Leu Ala Ile
        675                 680                 685

cct tac gag gag gcc cag gcc ttc att gag cgc tac ttt cag agc ttc      2112
Pro Tyr Glu Glu Ala Gln Ala Phe Ile Glu Arg Tyr Phe Gln Ser Phe
    690                 695                 700

ccc aag gtg cgg gcc tgg att gag aag acc ctg gag gag ggc agg agg      2160
Pro Lys Val Arg Ala Trp Ile Glu Lys Thr Leu Glu Glu Gly Arg Arg
705                 710                 715                 720

cgg ggg tac gtg gag acc ctc ttc ggc cgc cgc cgc tac gtg cca gac      2208
Arg Gly Tyr Val Glu Thr Leu Phe Gly Arg Arg Arg Tyr Val Pro Asp
                725                 730                 735

cta gag gcc cgg gtg aag agc gtg cgg gag gcg gcc gag cgc atg gcc      2256
Leu Glu Ala Arg Val Lys Ser Val Arg Glu Ala Ala Glu Arg Met Ala
            740                 745                 750
```

```
ttc aac atg ccc gtc cag ggc acc gcc gcc gac ctc atg aag ctg gct      2304
Phe Asn Met Pro Val Gln Gly Thr Ala Ala Asp Leu Met Lys Leu Ala
        755                 760                 765

atg gtg aag ctc ttc ccc agg ctg gag gaa atg ggg gcc agg atg ctc      2352
Met Val Lys Leu Phe Pro Arg Leu Glu Glu Met Gly Ala Arg Met Leu
    770                 775                 780

ctt cag gtc cac gac gag ctg gtc ctc gag gcc cca aaa gag agg gcg      2400
Leu Gln Val His Asp Glu Leu Val Leu Glu Ala Pro Lys Glu Arg Ala
785                 790                 795                 800

gag gcc gtg gcc cgg ctg gcc aag gag gtc atg gag ggg gtg tat ccc      2448
Glu Ala Val Ala Arg Leu Ala Lys Glu Val Met Glu Gly Val Tyr Pro
                805                 810                 815

ctg gcc gtg ccc ctg gag gtg gag gtg ggg ata ggg gag gac tgg ctc      2496
Leu Ala Val Pro Leu Glu Val Glu Val Gly Ile Gly Glu Asp Trp Leu
            820                 825                 830

tcc gcc aag gag ggc att gat ggc cgc ggc gga ggc ggg cat cat cat      2544
Ser Ala Lys Glu Gly Ile Asp Gly Arg Gly Gly Gly Gly His His His
        835                 840                 845

cat cat cat taa                                                      2556
His His His
    850


<210> SEQ ID NO 66
<211> LENGTH: 851
<212> TYPE: PRT
<213> ORGANISM: Thermus aquaticus

<400> SEQUENCE: 66

Gly Gly Gly Val Thr Ser Gly Met Leu Pro Leu Phe Glu Pro Lys Gly
1               5                   10                  15

Arg Val Leu Leu Val Asp Gly His His Leu Ala Tyr Arg Thr Phe His
            20                  25                  30

Ala Leu Lys Gly Leu Thr Thr Ser Arg Gly Glu Pro Val Gln Ala Val
        35                  40                  45

Tyr Gly Phe Ala Lys Ser Leu Leu Lys Ala Leu Lys Glu Asp Gly Asp
    50                  55                  60

Ala Val Ile Val Val Phe Asp Ala Lys Ala Pro Ser Phe Arg His Glu
65                  70                  75                  80

Ala Tyr Gly Gly Tyr Lys Ala Gly Arg Ala Pro Thr Pro Glu Asp Phe
                85                  90                  95

Pro Arg Gln Leu Ala Leu Ile Lys Glu Leu Val Asp Leu Leu Gly Leu
            100                 105                 110

Ala Arg Leu Glu Val Pro Gly Tyr Glu Ala Asp Asp Val Leu Ala Ser
        115                 120                 125

Leu Ala Lys Lys Ala Glu Lys Glu Gly Tyr Glu Val Arg Ile Leu Thr
    130                 135                 140

Ala Asp Lys Asp Leu Tyr Gln Leu Leu Ser Asp Arg Ile His Val Leu
145                 150                 155                 160

His Pro Glu Gly Tyr Leu Ile Thr Pro Ala Trp Leu Trp Glu Lys Tyr
                165                 170                 175

Gly Leu Arg Pro Asp Gln Trp Ala Asp Tyr Arg Ala Leu Thr Gly Asp
            180                 185                 190

Glu Ser Asp Asn Leu Pro Gly Val Lys Gly Ile Gly Glu Lys Thr Ala
        195                 200                 205

Arg Lys Leu Leu Glu Glu Trp Gly Ser Leu Glu Ala Leu Leu Lys Asn
    210                 215                 220
```

-continued

```
Leu Asp Arg Leu Lys Pro Ala Ile Arg Glu Lys Ile Leu Ala His Met
225                 230                 235                 240

Asp Asp Leu Lys Leu Ser Trp Asp Leu Ala Lys Val Arg Thr Asp Leu
                245                 250                 255

Pro Leu Glu Val Asp Phe Ala Lys Arg Arg Glu Pro Asp Arg Glu Arg
            260                 265                 270

Leu Arg Ala Phe Leu Glu Arg Leu Glu Phe Gly Ser Leu Leu His Glu
        275                 280                 285

Phe Gly Leu Leu Glu Ser Pro Lys Ala Leu Glu Glu Ala Pro Trp Pro
    290                 295                 300

Pro Pro Glu Gly Ala Phe Val Gly Phe Val Leu Ser Arg Lys Glu Pro
305                 310                 315                 320

Met Trp Ala Asp Leu Leu Ala Leu Ala Ala Ala Arg Gly Gly Arg Val
                325                 330                 335

His Arg Ala Pro Glu Pro Tyr Lys Ala Leu Arg Asp Leu Lys Glu Ala
            340                 345                 350

Arg Gly Leu Leu Ala Lys Asp Leu Ser Val Leu Ala Leu Arg Glu Gly
        355                 360                 365

Leu Gly Leu Pro Pro Gly Asp Asp Pro Met Leu Leu Ala Tyr Leu Leu
    370                 375                 380

Asp Pro Ser Asn Thr Thr Pro Glu Gly Val Ala Arg Arg Tyr Gly Gly
385                 390                 395                 400

Glu Trp Thr Glu Glu Ala Gly Glu Arg Ala Ala Leu Ser Glu Arg Leu
                405                 410                 415

Phe Ala Asn Leu Trp Gly Arg Leu Glu Gly Glu Glu Arg Leu Leu Trp
            420                 425                 430

Leu Tyr Arg Glu Val Glu Arg Pro Leu Ser Ala Val Leu Ala His Met
        435                 440                 445

Glu Ala Thr Gly Val Arg Leu Asp Val Ala Tyr Leu Arg Ala Leu Ser
    450                 455                 460

Leu Glu Val Ala Glu Glu Ile Ala Arg Leu Glu Ala Glu Val Phe Arg
465                 470                 475                 480

Leu Ala Gly His Pro Phe Asn Leu Asn Ser Arg Asp Gln Leu Glu Arg
                485                 490                 495

Val Leu Phe Asp Glu Leu Gly Leu Pro Ala Ile Gly Lys Thr Glu Lys
            500                 505                 510

Thr Gly Lys Arg Ser Thr Ser Ala Ala Val Leu Glu Ala Leu Arg Glu
        515                 520                 525

Ala His Pro Ile Val Glu Lys Ile Leu Gln Tyr Arg Glu Leu Thr Lys
    530                 535                 540

Leu Lys Ser Thr Tyr Ile Asp Pro Leu Pro Asp Leu Ile His Pro Arg
545                 550                 555                 560

Thr Gly Arg Leu His Thr Arg Phe Asn Gln Thr Ala Thr Ala Thr Gly
                565                 570                 575

Arg Leu Ser Ser Ser Asp Pro Asn Leu Gln Asn Ile Pro Val Arg Thr
            580                 585                 590

Pro Leu Gly Gln Arg Ile Arg Arg Ala Phe Ile Ala Glu Glu Gly Trp
        595                 600                 605

Leu Leu Val Ala Leu Asp Tyr Ser Gln Ile Glu Leu Arg Val Leu Ala
    610                 615                 620

His Leu Ser Gly Asp Glu Asn Leu Ile Arg Val Phe Gln Glu Gly Arg
625                 630                 635                 640

Asp Ile His Thr Glu Thr Ala Ser Trp Met Phe Gly Val Pro Arg Glu
```

```
                645                 650                 655

Ala Val Asp Pro Leu Met Arg Arg Ala Ala Lys Thr Ile Asn Phe Gly
            660                 665                 670

Val Leu Tyr Gly Met Ser Ala His Arg Leu Ser Gln Glu Leu Ala Ile
        675                 680                 685

Pro Tyr Glu Glu Ala Gln Ala Phe Ile Glu Arg Tyr Phe Gln Ser Phe
    690                 695                 700

Pro Lys Val Arg Ala Trp Ile Glu Lys Thr Leu Glu Glu Gly Arg Arg
705                 710                 715                 720

Arg Gly Tyr Val Glu Thr Leu Phe Gly Arg Arg Arg Tyr Val Pro Asp
                725                 730                 735

Leu Glu Ala Arg Val Lys Ser Val Arg Glu Ala Ala Glu Arg Met Ala
            740                 745                 750

Phe Asn Met Pro Val Gln Gly Thr Ala Ala Asp Leu Met Lys Leu Ala
        755                 760                 765

Met Val Lys Leu Phe Pro Arg Leu Glu Glu Met Gly Ala Arg Met Leu
    770                 775                 780

Leu Gln Val His Asp Glu Leu Val Leu Glu Ala Pro Lys Glu Arg Ala
785                 790                 795                 800

Glu Ala Val Ala Arg Leu Ala Lys Glu Val Met Glu Gly Val Tyr Pro
                805                 810                 815

Leu Ala Val Pro Leu Glu Val Glu Val Gly Ile Gly Glu Asp Trp Leu
            820                 825                 830

Ser Ala Lys Glu Gly Ile Asp Gly Arg Gly Gly Gly Gly His His His
        835                 840                 845

His His His
    850


<210> SEQ ID NO 67
<211> LENGTH: 750
<212> TYPE: DNA
<213> ORGANISM: Pyrococcus furiosus
<220> FEATURE:
<221> NAME/KEY: CDS
<222> LOCATION: (1)..(750)
<223> OTHER INFORMATION:

<400> SEQUENCE: 67

atg cca ttt gaa atc gta ttt gaa ggt gca aaa gag ttt gcc caa ctt       48
Met Pro Phe Glu Ile Val Phe Glu Gly Ala Lys Glu Phe Ala Gln Leu
1               5                   10                  15

ata gac acc gca agt aag tta ata gat gag gcc gcg ttt aaa gtt aca       96
Ile Asp Thr Ala Ser Lys Leu Ile Asp Glu Ala Ala Phe Lys Val Thr
            20                  25                  30

gaa gat ggg ata agc atg agg gcc atg gat cca agt aga gtt gtc ctg      144
Glu Asp Gly Ile Ser Met Arg Ala Met Asp Pro Ser Arg Val Val Leu
        35                  40                  45

att gac cta aat ctc ccg tca agc ata ttt agc aaa tat gaa gtt gtt      192
Ile Asp Leu Asn Leu Pro Ser Ser Ile Phe Ser Lys Tyr Glu Val Val
    50                  55                  60

gaa cca gaa aca att gga gtt aac atg gac cac cta aag aag atc cta      240
Glu Pro Glu Thr Ile Gly Val Asn Met Asp His Leu Lys Lys Ile Leu
65                  70                  75                  80

aag aga ggt aaa gca aag gac acc tta ata ctc aag aaa gga gag gaa      288
Lys Arg Gly Lys Ala Lys Asp Thr Leu Ile Leu Lys Lys Gly Glu Glu
                85                  90                  95

aac ttc tta gag ata aca att caa gga act gca aca aga aca ttt aga      336
Asn Phe Leu Glu Ile Thr Ile Gln Gly Thr Ala Thr Arg Thr Phe Arg
```

```
            100                 105                 110

gtt ccc cta ata gat gta gaa gag atg gaa gtt gac ctc cca gaa ctt      384
Val Pro Leu Ile Asp Val Glu Glu Met Glu Val Asp Leu Pro Glu Leu
        115                 120                 125

cca ttc act gca aag gtt gta gtt ctt gga gaa gtc cta aaa gat gct      432
Pro Phe Thr Ala Lys Val Val Val Leu Gly Glu Val Leu Lys Asp Ala
    130                 135                 140

gtt aaa gat gcc tct cta gtg agt gac agc ata aaa ttt att gcc agg      480
Val Lys Asp Ala Ser Leu Val Ser Asp Ser Ile Lys Phe Ile Ala Arg
145                 150                 155                 160

gaa aat gaa ttt ata atg aag gca gag gga gaa acc cag gaa gtt gag      528
Glu Asn Glu Phe Ile Met Lys Ala Glu Gly Glu Thr Gln Glu Val Glu
                165                 170                 175

ata aag cta act ctt gaa gat gag gga tta ttg gac atc gag gtt caa      576
Ile Lys Leu Thr Leu Glu Asp Glu Gly Leu Leu Asp Ile Glu Val Gln
            180                 185                 190

gag gag aca aag agc gca tat gga gtc agc tat ctc tcc gac atg gtt      624
Glu Glu Thr Lys Ser Ala Tyr Gly Val Ser Tyr Leu Ser Asp Met Val
        195                 200                 205

aaa gga ctt gga aag gcc gat gaa gtt aca ata aag ttt gga aat gaa      672
Lys Gly Leu Gly Lys Ala Asp Glu Val Thr Ile Lys Phe Gly Asn Glu
    210                 215                 220

atg ccc atg caa atg gag tat tac att aga gat gaa gga aga ctt aca      720
Met Pro Met Gln Met Glu Tyr Tyr Ile Arg Asp Glu Gly Arg Leu Thr
225                 230                 235                 240

ttc cta ctg gct cca aga gtt gaa gag tga                              750
Phe Leu Leu Ala Pro Arg Val Glu Glu
                245


<210> SEQ ID NO 68
<211> LENGTH: 249
<212> TYPE: PRT
<213> ORGANISM: Pyrococcus furiosus

<400> SEQUENCE: 68

Met Pro Phe Glu Ile Val Phe Glu Gly Ala Lys Glu Phe Ala Gln Leu
1               5                   10                  15

Ile Asp Thr Ala Ser Lys Leu Ile Asp Glu Ala Ala Phe Lys Val Thr
            20                  25                  30

Glu Asp Gly Ile Ser Met Arg Ala Met Asp Pro Ser Arg Val Val Leu
        35                  40                  45

Ile Asp Leu Asn Leu Pro Ser Ser Ile Phe Ser Lys Tyr Glu Val Val
    50                  55                  60

Glu Pro Glu Thr Ile Gly Val Asn Met Asp His Leu Lys Lys Ile Leu
65                  70                  75                  80

Lys Arg Gly Lys Ala Lys Asp Thr Leu Ile Leu Lys Lys Gly Glu Glu
                85                  90                  95

Asn Phe Leu Glu Ile Thr Ile Gln Gly Thr Ala Thr Arg Thr Phe Arg
            100                 105                 110

Val Pro Leu Ile Asp Val Glu Glu Met Glu Val Asp Leu Pro Glu Leu
        115                 120                 125

Pro Phe Thr Ala Lys Val Val Val Leu Gly Glu Val Leu Lys Asp Ala
    130                 135                 140

Val Lys Asp Ala Ser Leu Val Ser Asp Ser Ile Lys Phe Ile Ala Arg
145                 150                 155                 160

Glu Asn Glu Phe Ile Met Lys Ala Glu Gly Glu Thr Gln Glu Val Glu
                165                 170                 175
```

```
Ile Lys Leu Thr Leu Glu Asp Glu Gly Leu Leu Asp Ile Glu Val Gln
            180                 185                 190

Glu Glu Thr Lys Ser Ala Tyr Gly Val Ser Tyr Leu Ser Asp Met Val
        195                 200                 205

Lys Gly Leu Gly Lys Ala Asp Glu Val Thr Ile Lys Phe Gly Asn Glu
    210                 215                 220

Met Pro Met Gln Met Glu Tyr Tyr Ile Arg Asp Glu Gly Arg Leu Thr
225                 230                 235                 240

Phe Leu Leu Ala Pro Arg Val Glu Glu
                245


<210> SEQ ID NO 69
<211> LENGTH: 201
<212> TYPE: DNA
<213> ORGANISM: Sulfolobus acidocaldarius
<220> FEATURE:
<221> NAME/KEY: CDS
<222> LOCATION: (1)..(201)
<223> OTHER INFORMATION:

<400> SEQUENCE: 69

atg gtg aag gta aag ttc aag tat aag ggt gaa gag aaa gaa gta gac       48
Met Val Lys Val Lys Phe Lys Tyr Lys Gly Glu Glu Lys Glu Val Asp
1               5                   10                  15

act tca aag ata aag aag gtt tgg aga gta ggc aaa atg gtg tcc ttt       96
Thr Ser Lys Ile Lys Lys Val Trp Arg Val Gly Lys Met Val Ser Phe
            20                  25                  30

acc tat gac gac aat ggt aag aca ggt aga gga gct gta agc gag aaa      144
Thr Tyr Asp Asp Asn Gly Lys Thr Gly Arg Gly Ala Val Ser Glu Lys
        35                  40                  45

gat gct cca aaa gaa tta tta gac atg tta gca aga gca gaa aga gag      192
Asp Ala Pro Lys Glu Leu Leu Asp Met Leu Ala Arg Ala Glu Arg Glu
    50                  55                  60

aag aaa taa                                                          201
Lys Lys
65


<210> SEQ ID NO 70
<211> LENGTH: 66
<212> TYPE: PRT
<213> ORGANISM: Sulfolobus acidocaldarius

<400> SEQUENCE: 70

Met Val Lys Val Lys Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Asp Met Leu Ala Arg Ala Glu Arg Glu
    50                  55                  60

Lys Lys
65


<210> SEQ ID NO 71
<211> LENGTH: 189
<212> TYPE: DNA
<213> ORGANISM: Sulfolobus solfactaricus
<220> FEATURE:
<221> NAME/KEY: CDS
<222> LOCATION: (1)..(189)
<223> OTHER INFORMATION:
```

<400> SEQUENCE: 71

```
gca acc gta aag ttc aag tac aaa ggc gaa gaa aaa gag gta gac atc       48
Ala Thr Val Lys Phe Lys Tyr Lys Gly Glu Glu Lys Glu Val Asp Ile
1               5                   10                  15

tcc aag atc aag aaa gta tgg cgt gtg ggc aag atg atc tcc ttc acc       96
Ser Lys Ile Lys Lys Val Trp Arg Val Gly Lys Met Ile Ser Phe Thr
            20                  25                  30

tac gac gag ggc ggt ggc aag acc ggc cgt ggt gcg gta agc gaa aag      144
Tyr Asp Glu Gly Gly Gly Lys Thr Gly Arg Gly Ala Val Ser Glu Lys
        35                  40                  45

gac gcg ccg aag gag ctg ctg cag atg ctg gag aag cag aaa aag          189
Asp Ala Pro Lys Glu Leu Leu Gln Met Leu Glu Lys Gln Lys Lys
    50                  55                  60
```

<210> SEQ ID NO 72
<211> LENGTH: 63
<212> TYPE: PRT
<213> ORGANISM: Sulfolobus solfactaricus

<400> SEQUENCE: 72

```
Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60
```

<210> SEQ ID NO 73
<211> LENGTH: 57
<212> TYPE: PRT
<213> ORGANISM: Methanopyrus kandleri

<400> SEQUENCE: 73

```
Val Ala Leu Val Tyr Asp Ala Glu Phe Val Gly Ser Glu Arg Glu Phe
1               5                   10                  15

Glu Glu Glu Arg Glu Thr Phe Leu Lys Gly Val Lys Ala Tyr Asp Gly
            20                  25                  30

Val Leu Ala Thr Arg Tyr Leu Met Glu Arg Ser Ser Ser Ala Lys Asn
        35                  40                  45

Asp Glu Glu Leu Leu Glu Leu His Gln
    50                  55
```

<210> SEQ ID NO 74
<211> LENGTH: 29
<212> TYPE: PRT
<213> ORGANISM: Escherichia coli

<400> SEQUENCE: 74

```
Gly Gly Asn Ala Leu Lys Phe Tyr Ala Ser Val Arg Leu Asp Ile Arg
1               5                   10                  15

Arg Ile Gly Ala Ile Lys Asp Gly Asp Glu Val Val Gly
            20                  25
```

<210> SEQ ID NO 75
<211> LENGTH: 57
<212> TYPE: PRT
<213> ORGANISM: Methanopyrus kandleri

<400> SEQUENCE: 75

Val Pro Ile Asp Glu Lys Glu Glu Arg Ile Leu Glu Ile Leu Arg Glu
1 5 10 15

Asn Pro Trp Thr Pro His Asp Glu Ile Ala Arg Arg Gly Gly Leu Ser
20 25 30

Val Ser Glu Val Glu Gly Glu Lys Asp Pro Glu Ser Ser Gly Ile Tyr
35 40 45

Ser Leu Trp Ser Arg Val Val Val Asn
50 55

<210> SEQ ID NO 76
<211> LENGTH: 40
<212> TYPE: PRT
<213> ORGANISM: Escherichia coli

<400> SEQUENCE: 76

Ile Asp Arg Ile Asp Arg Lys Ile Leu Asn Glu Leu Gln Lys Asp Gly
1 5 10 15

Arg Arg Ile Ser Asn Glu Leu Ala Lys Arg Val Gly Leu Ser Val Ser
20 25 30

Thr Val Arg Glu Arg Val Arg Arg
35 40

<210> SEQ ID NO 77
<211> LENGTH: 40
<212> TYPE: PRT
<213> ORGANISM: Methanopyrus kandleri

<400> SEQUENCE: 77

Leu Lys Leu Gln Asp Arg Tyr Gly Ile Arg Glu Asp Val Ala Leu Cys
1 5 10 15

Leu Ala Arg Ala Phe Asp Gly Ser Ile Ser Met Ile Ala Thr Thr Pro
20 25 30

Tyr Arg Thr Leu Lys Asp Val Cys
35 40

<210> SEQ ID NO 78
<211> LENGTH: 15
<212> TYPE: PRT
<213> ORGANISM: Methanopyrus kandleri

<400> SEQUENCE: 78

Pro Asp Leu Thr Leu Glu Glu Ala Lys Ser Val Asn Arg Thr Leu
1 5 10 15

<210> SEQ ID NO 79
<211> LENGTH: 30
<212> TYPE: PRT
<213> ORGANISM: Methanopyrus kandleri

<400> SEQUENCE: 79

Ala Thr Leu Ile Asp Glu His Gly Leu Ser Pro Ala Asp Ala Ala Asp
1 5 10 15

Glu Leu Ile Glu His Phe Glu Ser Ile Ala Gly Ile Leu Ala
20 25 30

<210> SEQ ID NO 80
<211> LENGTH: 11
<212> TYPE: PRT
<213> ORGANISM: Methanopyrus kandleri

<400> SEQUENCE: 80

Thr Asp Leu Glu Glu Ile Glu Arg Met Tyr Glu
1 5 10

<210> SEQ ID NO 81
<211> LENGTH: 15
<212> TYPE: PRT
<213> ORGANISM: Methanopyrus kandleri

<400> SEQUENCE: 81

Glu Gly Arg Leu Ser Glu Glu Ala Tyr Arg Ala Ala Val Glu Ile
1 5 10 15

<210> SEQ ID NO 82
<211> LENGTH: 57
<212> TYPE: PRT
<213> ORGANISM: Thermococcus kodakaraensis

<400> SEQUENCE: 82

Ala Glu Leu Thr Lys Lys Glu Gly Val Gly Arg Lys Thr Ala Glu Arg
1 5 10 15

Leu Leu Arg Ala Phe Gly Asn Pro Glu Arg Val Lys Gln Leu Ala Arg
20 25 30

Glu Phe Glu Ile Glu Lys Leu Ala Ser Val Glu Gly Val Gly Glu Arg
35 40 45

Val Leu Arg Ser Leu Val Pro Gly Tyr
50 55

<210> SEQ ID NO 83
<211> LENGTH: 27
<212> TYPE: PRT
<213> ORGANISM: Methanopyrus kandleri

<400> SEQUENCE: 83

Ala Ser Leu Ile Ser Ile Arg Gly Ile Asp Arg Glu Arg Ala Glu Arg
1 5 10 15

Leu Leu Lys Lys Tyr Gly Gly Tyr Ser Lys Val
20 25

<210> SEQ ID NO 84
<211> LENGTH: 10
<212> TYPE: PRT
<213> ORGANISM: Methanopyrus kandleri

<400> SEQUENCE: 84

Arg Glu Ala Gly Val Glu Glu Leu Arg Glu
1 5 10

<210> SEQ ID NO 85
<211> LENGTH: 13
<212> TYPE: PRT
<213> ORGANISM: Methanopyrus kandleri

<400> SEQUENCE: 85

Asp Gly Leu Thr Asp Ala Gln Ile Arg Glu Leu Lys Gly
1 5 10

<210> SEQ ID NO 86
<211> LENGTH: 27
<212> TYPE: PRT
<213> ORGANISM: Methanopyrus kandleri

<400> SEQUENCE: 86

Leu Lys Thr Leu Glu Ser Ile Val Gly Asp Leu Glu Lys Ala Asp Glu
1 5 10 15

Leu Lys Arg Lys Tyr Gly Ser Ala Ser Ala Val
20 25

<210> SEQ ID NO 87
<211> LENGTH: 10
<212> TYPE: PRT
<213> ORGANISM: Methanopyrus kandleri

<400> SEQUENCE: 87

Arg Arg Leu Pro Val Glu Glu Leu Arg Glu
1 5 10

<210> SEQ ID NO 88
<211> LENGTH: 13
<212> TYPE: PRT
<213> ORGANISM: Methanopyrus kandleri

<400> SEQUENCE: 88

Leu Gly Phe Ser Asp Asp Glu Ile Ala Glu Ile Lys Gly
1 5 10

<210> SEQ ID NO 89
<211> LENGTH: 28
<212> TYPE: PRT
<213> ORGANISM: Methanopyrus kandleri

<400> SEQUENCE: 89

Ile Pro Lys Lys Leu Arg Glu Ala Phe Asp Leu Glu Thr Ala Ala Glu
1 5 10 15

Leu Tyr Glu Arg Tyr Gly Ser Leu Lys Glu Ile Gly
20 25

<210> SEQ ID NO 90
<211> LENGTH: 10
<212> TYPE: PRT
<213> ORGANISM: Methanopyrus kandleri

<400> SEQUENCE: 90

Arg Arg Leu Ser Tyr Asp Asp Leu Leu Glu
1 5 10

<210> SEQ ID NO 91
<211> LENGTH: 15
<212> TYPE: PRT
<213> ORGANISM: Methanopyrus kandleri

<400> SEQUENCE: 91

Leu Gly Ala Thr Pro Lys Ala Ala Ala Glu Ile Lys Gly Pro Glu
1 5 10 15

<210> SEQ ID NO 92
<211> LENGTH: 28
<212> TYPE: PRT
<213> ORGANISM: Methanopyrus kandleri

<400> SEQUENCE: 92

Lys Phe Leu Leu Asn Ile Glu Gly Val Gly Pro Lys Leu Ala Glu Arg
1 5 10 15

Ile Leu Glu Ala Val Asp Tyr Asp Leu Glu Arg Leu
20 25

<210> SEQ ID NO 93
<211> LENGTH: 26
<212> TYPE: PRT
<213> ORGANISM: Methanopyrus kandleri

<400> SEQUENCE: 93

```
Ala Ser Leu Asn Pro Glu Glu Leu Ala Glu Val Glu Gly Leu Gly Glu
1               5                   10                  15

Glu Leu Ala Glu Arg Val Val Tyr Ala Ala
            20                  25
```

<210> SEQ ID NO 94
<211> LENGTH: 40
<212> TYPE: PRT
<213> ORGANISM: Methanopyrus kandleri

<400> SEQUENCE: 94

```
Trp Lys Glu Trp Leu Glu Arg Lys Val Gly Glu Gly Arg Ala Arg Arg
1               5                   10                  15

Leu Ile Glu Tyr Phe Gly Ser Ala Gly Glu Val Gly Lys Leu Val Glu
            20                  25                  30

Asn Ala Glu Val Ser Lys Leu Leu
        35                  40
```

<210> SEQ ID NO 95
<211> LENGTH: 15
<212> TYPE: PRT
<213> ORGANISM: Methanopyrus kandleri

<400> SEQUENCE: 95

```
Val Pro Gly Ile Gly Asp Glu Ala Val Ala Arg Leu Val Pro Gly
1               5                   10                  15
```

<210> SEQ ID NO 96
<211> LENGTH: 28
<212> TYPE: PRT
<213> ORGANISM: Methanopyrus kandleri

<400> SEQUENCE: 96

```
Tyr Lys Thr Leu Arg Asp Ala Gly Leu Thr Pro Ala Glu Ala Glu Arg
1               5                   10                  15

Val Leu Lys Arg Tyr Gly Ser Val Ser Lys Val Gln
            20                  25
```

<210> SEQ ID NO 97
<211> LENGTH: 10
<212> TYPE: PRT
<213> ORGANISM: Methanopyrus kandleri

<400> SEQUENCE: 97

```
Glu Gly Ala Thr Pro Asp Glu Leu Arg Glu
1               5                   10
```

<210> SEQ ID NO 98
<211> LENGTH: 13
<212> TYPE: PRT
<213> ORGANISM: Methanopyrus kandleri

<400> SEQUENCE: 98

```
Leu Gly Leu Gly Asp Ala Lys Ile Ala Arg Ile Leu Gly
1               5                   10
```

<210> SEQ ID NO 99
<211> LENGTH: 27
<212> TYPE: PRT
<213> ORGANISM: Methanopyrus kandleri

<400> SEQUENCE: 99

Leu Arg Ser Leu Val Asn Lys Arg Leu Asp Val Asp Thr Ala Tyr Glu
1 5 10 15

Leu Lys Arg Arg Tyr Gly Ser Val Ser Ala Val
20 25

<210> SEQ ID NO 100
<211> LENGTH: 10
<212> TYPE: PRT
<213> ORGANISM: Methanopyrus kandleri

<400> SEQUENCE: 100

Arg Lys Ala Pro Val Lys Glu Leu Arg Glu
1 5 10

<210> SEQ ID NO 101
<211> LENGTH: 15
<212> TYPE: PRT
<213> ORGANISM: Methanopyrus kandleri

<400> SEQUENCE: 101

Leu Gly Leu Ser Asp Arg Lys Ile Ala Arg Ile Lys Gly Ile Pro
1 5 10 15

<210> SEQ ID NO 102
<211> LENGTH: 27
<212> TYPE: PRT
<213> ORGANISM: Methanopyrus kandleri

<400> SEQUENCE: 102

Glu Thr Met Leu Gln Val Arg Gly Met Ser Val Glu Lys Ala Glu Arg
1 5 10 15

Leu Leu Glu Arg Phe Asp Thr Trp Thr Lys Val
20 25

<210> SEQ ID NO 103
<211> LENGTH: 9
<212> TYPE: PRT
<213> ORGANISM: Methanopyrus kandleri

<400> SEQUENCE: 103

Lys Glu Ala Pro Val Ser Glu Leu Val
1 5

<210> SEQ ID NO 104
<211> LENGTH: 16
<212> TYPE: PRT
<213> ORGANISM: Methanopyrus kandleri

<400> SEQUENCE: 104

Val Pro Gly Val Gly Leu Ser Leu Val Lys Glu Ile Lys Ala Gln Val
1 5 10 15

<210> SEQ ID NO 105
<211> LENGTH: 27
<212> TYPE: PRT
<213> ORGANISM: Methanopyrus kandleri

<400> SEQUENCE: 105

-continued

Lys Ala Leu Leu Asp Val Lys Gly Val Ser Pro Glu Leu Ala Asp Arg
1 5 10 15

Leu Val Glu Glu Leu Gly Ser Pro Tyr Arg Val
20 25

<210> SEQ ID NO 106
<211> LENGTH: 9
<212> TYPE: PRT
<213> ORGANISM: Methanopyrus kandleri

<400> SEQUENCE: 106

Leu Thr Ala Lys Lys Ser Asp Leu Met
1 5

<210> SEQ ID NO 107
<211> LENGTH: 16
<212> TYPE: PRT
<213> ORGANISM: Methanopyrus kandleri

<400> SEQUENCE: 107

Val Glu Arg Val Gly Pro Lys Leu Ala Glu Arg Ile Arg Ala Ala Gly
1 5 10 15

<210> SEQ ID NO 108
<211> LENGTH: 27
<212> TYPE: PRT
<213> ORGANISM: Escherichia coli

<400> SEQUENCE: 108

Lys Glu Leu Ile Lys Thr Asn Gly Val Gly Pro Lys Leu Ala Leu Ala
1 5 10 15

Ile Leu Ser Gly Met Ser Ala Gln Gln Phe Val
20 25

<210> SEQ ID NO 109
<211> LENGTH: 26
<212> TYPE: PRT
<213> ORGANISM: Escherichia coli

<400> SEQUENCE: 109

Asn Ala Val Glu Arg Glu Glu Val Gly Ala Leu Pro Gly Ile Gly Lys
1 5 10 15

Lys Thr Ala Glu Arg Leu Ile Val Glu Met
20 25

<210> SEQ ID NO 110
<211> LENGTH: 57
<212> TYPE: PRT
<213> ORGANISM: Homo sapiens

<400> SEQUENCE: 110

Ala Glu Ala Lys Lys Leu Pro Gly Val Gly Thr Lys Ile Ala Glu Lys
1 5 10 15

Ile Asp Glu Phe Leu Ala Thr Gly Lys Leu Arg Lys Leu Glu Lys Ile
20 25 30

Arg Gln Asp Asp Thr Ser Ser Ser Ile Val Ser Gly Ile Gly Pro Ser
35 40 45

Ala Ala Arg Lys Phe Val Asp Glu Gly
50 55

<210> SEQ ID NO 111
<211> LENGTH: 27

<212> TYPE: PRT
<213> ORGANISM: Escherichia coli

<400> SEQUENCE: 111

Leu Glu Val Met Glu Val Pro Gly Val Gly Pro Lys Thr Ala Arg Gly
1 5 10 15

Leu Tyr Glu Ala Leu Gly Ile Asp Ser Leu Glu
20 25

<210> SEQ ID NO 112
<211> LENGTH: 12
<212> TYPE: PRT
<213> ORGANISM: Escherichia coli

<400> SEQUENCE: 112

Lys Leu Lys Glu Ala Leu Glu Arg Gly Asp Leu Leu
1 5 10

<210> SEQ ID NO 113
<211> LENGTH: 16
<212> TYPE: PRT
<213> ORGANISM: Escherichia coli

<400> SEQUENCE: 113

Leu Lys Gly Phe Gly Ala Lys Lys Ala Glu Arg Ile Lys Glu Gly Leu
1 5 10 15

<210> SEQ ID NO 114
<211> LENGTH: 30
<212> TYPE: DNA
<213> ORGANISM: artificial sequence
<220> FEATURE:
<223> OTHER INFORMATION: primer

<400> SEQUENCE: 114
agagcttgag gagagcagga aaggtggaac 30

<210> SEQ ID NO 115
<211> LENGTH: 24
<212> TYPE: DNA
<213> ORGANISM: artificial sequence
<220> FEATURE:
<223> OTHER INFORMATION: primer

<400> SEQUENCE: 115
tgcagagcga ttattcagga atgc 24

<210> SEQ ID NO 116
<211> LENGTH: 30
<212> TYPE: DNA
<213> ORGANISM: artificial sequence
<220> FEATURE:
<223> OTHER INFORMATION: primer

<400> SEQUENCE: 116
acaagggcta ctggttgccg atttttattg 30

<210> SEQ ID NO 117
<211> LENGTH: 27
<212> TYPE: DNA
<213> ORGANISM: artificial sequence
<220> FEATURE:
<223> OTHER INFORMATION: primer

<400> SEQUENCE: 117
gggactggcc tcagaggaaa cttcagg 27

<210> SEQ ID NO 118
<211> LENGTH: 30
<212> TYPE: DNA
<213> ORGANISM: artificial sequence
<220> FEATURE:
<223> OTHER INFORMATION: primer

<400> SEQUENCE: 118
acaagggcta ctggttgccg atttttattg 30

<210> SEQ ID NO 119
<211> LENGTH: 28
<212> TYPE: DNA
<213> ORGANISM: artificial sequence
<220> FEATURE:
<223> OTHER INFORMATION: primer

<400> SEQUENCE: 119
cctgcatttg tggggtgaat tccttgcc 28

<210> SEQ ID NO 120
<211> LENGTH: 189
<212> TYPE: DNA
<213> ORGANISM: artificial sequence
<220> FEATURE:
<223> OTHER INFORMATION: Synthetic Sso7d gene
<220> FEATURE:
<221> NAME/KEY: CDS
<222> LOCATION: (1)..(189)
<223> OTHER INFORMATION:

<400> SEQUENCE: 120

```
gca acc gta aag ttc aag tac aaa ggc gaa gaa aaa gag gta gac atc       48
Ala Thr Val Lys Phe Lys Tyr Lys Gly Glu Glu Lys Glu Val Asp Ile
1               5                   10                  15

tcc aag atc aag aaa gta tgg cgt gtg ggc aag atg atc tcc ttc acc       96
Ser Lys Ile Lys Lys Val Trp Arg Val Gly Lys Met Ile Ser Phe Thr
            20                  25                  30

tac gac gag ggc ggt ggc aag acc ggc cgt ggt gcg gta agc gaa aag      144
Tyr Asp Glu Gly Gly Gly Lys Thr Gly Arg Gly Ala Val Ser Glu Lys
        35                  40                  45

gac gcg ccg aag gag ctg ctg cag atg ctg gag aag cag aaa aag          189
Asp Ala Pro Lys Glu Leu Leu Gln Met Leu Glu Lys Gln Lys Lys
    50                  55                  60
```

<210> SEQ ID NO 121
<211> LENGTH: 63
<212> TYPE: PRT
<213> ORGANISM: artificial sequence
<220> FEATURE:
<223> OTHER INFORMATION: Synthetic Sso7d gene

<400> SEQUENCE: 121

```
Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60
```

```
<210> SEQ ID NO 122
<211> LENGTH: 1899
<212> TYPE: DNA
<213> ORGANISM: artificial sequence
<220> FEATURE:
<223> OTHER INFORMATION: The DNA sequence encoding the Sso7d-ATaq fusion
      protein
<220> FEATURE:
<221> NAME/KEY: CDS
<222> LOCATION: (1)..(1899)
<223> OTHER INFORMATION:

<400> SEQUENCE: 122

atg att acg aat tcg agc gca acc gta aag ttc aag tac aaa ggc gaa       48
Met Ile Thr Asn Ser Ser Ala Thr Val Lys Phe Lys Tyr Lys Gly Glu
1               5                   10                  15

gaa aaa gag gta gac atc tcc aag atc aag aaa gta tgg cgt gtg ggc       96
Glu Lys Glu Val Asp Ile Ser Lys Ile Lys Lys Val Trp Arg Val Gly
            20                  25                  30

aag atg atc tcc ttc acc tac gac gag ggc ggt ggc aag acc ggc cgt      144
Lys Met Ile Ser Phe Thr Tyr Asp Glu Gly Gly Gly Lys Thr Gly Arg
        35                  40                  45

ggt gcg gta agc gaa aag gac gcg ccg aag gag ctg ctg cag atg ctg      192
Gly Ala Val Ser Glu Lys Asp Ala Pro Lys Glu Leu Leu Gln Met Leu
    50                  55                  60

gag aag cag aaa aag ggc ggc ggt gtc act agt ccc aag gcc ctg gag      240
Glu Lys Gln Lys Lys Gly Gly Gly Val Thr Ser Pro Lys Ala Leu Glu
65                  70                  75                  80

gag gcc ccc tgg ccc ccg ccg gaa ggg gcc ttc gtg ggc ttt gtg ctt      288
Glu Ala Pro Trp Pro Pro Pro Glu Gly Ala Phe Val Gly Phe Val Leu
                85                  90                  95

tcc cgc aag gag ccc atg tgg gcc gat ctt ctg gcc ctg gcc gcc gcc      336
Ser Arg Lys Glu Pro Met Trp Ala Asp Leu Leu Ala Leu Ala Ala Ala
            100                 105                 110

agg ggg ggc cgg gtc cac cgg gcc ccc gag cct tat aaa gcc ctc agg      384
Arg Gly Gly Arg Val His Arg Ala Pro Glu Pro Tyr Lys Ala Leu Arg
        115                 120                 125

gac ctg aag gag gcg cgg ggg ctt ctc gcc aaa gac ctg agc gtt ctg      432
Asp Leu Lys Glu Ala Arg Gly Leu Leu Ala Lys Asp Leu Ser Val Leu
    130                 135                 140

gcc ctg agg gaa ggc ctt ggc ctc ccg ccc ggc gac gac ccc atg ctc      480
Ala Leu Arg Glu Gly Leu Gly Leu Pro Pro Gly Asp Asp Pro Met Leu
145                 150                 155                 160

ctc gcc tac ctc ctg gac cct tcc aac acc acc ccc gag ggg gtg gcc      528
Leu Ala Tyr Leu Leu Asp Pro Ser Asn Thr Thr Pro Glu Gly Val Ala
                165                 170                 175

cgg cgc tac ggc ggg gag tgg acg gag gag gcg ggg gag cgg gcc gcc      576
Arg Arg Tyr Gly Gly Glu Trp Thr Glu Glu Ala Gly Glu Arg Ala Ala
            180                 185                 190

ctt tcc gag agg ctc ttc gcc aac ctg tgg ggg agg ctt gag ggg gag      624
Leu Ser Glu Arg Leu Phe Ala Asn Leu Trp Gly Arg Leu Glu Gly Glu
        195                 200                 205

gag agg ctc ctt tgg ctt tac cgg gag gtg gag agg ccc ctt tcc gct      672
Glu Arg Leu Leu Trp Leu Tyr Arg Glu Val Glu Arg Pro Leu Ser Ala
    210                 215                 220

gtc ctg gcc cac atg gag gcc acg ggg gtg cgc ctg gac gtg gcc tat      720
Val Leu Ala His Met Glu Ala Thr Gly Val Arg Leu Asp Val Ala Tyr
225                 230                 235                 240

ctc agg gcc ttg tcc ctg gag gtg gcc gag gag atc gcc cgc ctc gag      768
Leu Arg Ala Leu Ser Leu Glu Val Ala Glu Glu Ile Ala Arg Leu Glu
                245                 250                 255

gcc gag gtc ttc cgc ctg gcc ggc cac ccc ttc aac ctc aac tcc cgg      816
```

-continued

```
Ala Glu Val Phe Arg Leu Ala Gly His Pro Phe Asn Leu Asn Ser Arg
            260                 265                 270

gac cag ctg gaa agg gtc ctc ttt gac gag cta ggg ctt ccc gcc atc      864
Asp Gln Leu Glu Arg Val Leu Phe Asp Glu Leu Gly Leu Pro Ala Ile
        275                 280                 285

ggc aag acg gag aag acc ggc aag cgc tcc acc agc gcc gcc gtc ctg      912
Gly Lys Thr Glu Lys Thr Gly Lys Arg Ser Thr Ser Ala Ala Val Leu
    290                 295                 300

gag gcc ctc cgc gag gcc cac ccc atc gtg gag aag atc ctg cag tac      960
Glu Ala Leu Arg Glu Ala His Pro Ile Val Glu Lys Ile Leu Gln Tyr
305                 310                 315                 320

cgg gag ctc acc aag ctg aag agc acc tac att gac ccc ttg ccg gac     1008
Arg Glu Leu Thr Lys Leu Lys Ser Thr Tyr Ile Asp Pro Leu Pro Asp
                325                 330                 335

ctc atc cac ccc agg acg ggc cgc ctc cac acc cgc ttc aac cag acg     1056
Leu Ile His Pro Arg Thr Gly Arg Leu His Thr Arg Phe Asn Gln Thr
            340                 345                 350

gcc acg gcc acg ggc agg cta agt agc tcc gat ccc aac ctc cag aac     1104
Ala Thr Ala Thr Gly Arg Leu Ser Ser Ser Asp Pro Asn Leu Gln Asn
        355                 360                 365

atc ccc gtc cgc acc ccg ctt ggg cag agg atc cgc cgg gcc ttc atc     1152
Ile Pro Val Arg Thr Pro Leu Gly Gln Arg Ile Arg Arg Ala Phe Ile
    370                 375                 380

gcc gag gag ggg tgg cta ttg gtg gcc ctg gac tat agc cag ata gag     1200
Ala Glu Glu Gly Trp Leu Leu Val Ala Leu Asp Tyr Ser Gln Ile Glu
385                 390                 395                 400

ctc agg gtg ctg gcc cac ctc tcc ggc gac gag aac ctg atc cgg gtc     1248
Leu Arg Val Leu Ala His Leu Ser Gly Asp Glu Asn Leu Ile Arg Val
                405                 410                 415

ttc cag gag ggg cgg gac atc cac acg gag acc gcc agc tgg atg ttc     1296
Phe Gln Glu Gly Arg Asp Ile His Thr Glu Thr Ala Ser Trp Met Phe
            420                 425                 430

ggc gtc ccc cgg gag gcc gtg gac ccc ctg atg cgc cgg gcg gcc aag     1344
Gly Val Pro Arg Glu Ala Val Asp Pro Leu Met Arg Arg Ala Ala Lys
        435                 440                 445

acc atc aac ttc ggg gtc ctc tac ggc atg tcg gcc cac cgc ctc tcc     1392
Thr Ile Asn Phe Gly Val Leu Tyr Gly Met Ser Ala His Arg Leu Ser
    450                 455                 460

cag gag cta gcc atc cct tac gag gag gcc cag gcc ttc att gag cgc     1440
Gln Glu Leu Ala Ile Pro Tyr Glu Glu Ala Gln Ala Phe Ile Glu Arg
465                 470                 475                 480

tac ttt cag agc ttc ccc aag gtg cgg gcc tgg att gag aag acc ctg     1488
Tyr Phe Gln Ser Phe Pro Lys Val Arg Ala Trp Ile Glu Lys Thr Leu
                485                 490                 495

gag gag ggc agg agg cgg ggg tac gtg gag acc ctc ttc ggc cgc cgc     1536
Glu Glu Gly Arg Arg Arg Gly Tyr Val Glu Thr Leu Phe Gly Arg Arg
            500                 505                 510

cgc tac gtg cca gac cta gag gcc cgg gtg aag agc gtg cgg gag gcg     1584
Arg Tyr Val Pro Asp Leu Glu Ala Arg Val Lys Ser Val Arg Glu Ala
        515                 520                 525

gcc gag cgc atg gcc ttc aac atg ccc gtc cag ggc acc gcc gcc gac     1632
Ala Glu Arg Met Ala Phe Asn Met Pro Val Gln Gly Thr Ala Ala Asp
    530                 535                 540

ctc atg aag ctg gct atg gtg aag ctc ttc ccc agg ctg gag gaa atg     1680
Leu Met Lys Leu Ala Met Val Lys Leu Phe Pro Arg Leu Glu Glu Met
545                 550                 555                 560

ggg gcc agg atg ctc ctt cag gtc cac gac gag ctg gtc ctc gag gcc     1728
Gly Ala Arg Met Leu Leu Gln Val His Asp Glu Leu Val Leu Glu Ala
                565                 570                 575
```

```
cca aaa gag agg gcg gag gcc gtg gcc cgg ctg gcc aag gag gtc atg     1776
Pro Lys Glu Arg Ala Glu Ala Val Ala Arg Leu Ala Lys Glu Val Met
            580                 585                 590

gag ggg gtg tat ccc ctg gcc gtg ccc ctg gag gtg gag gtg ggg ata     1824
Glu Gly Val Tyr Pro Leu Ala Val Pro Leu Glu Val Glu Val Gly Ile
        595                 600                 605

ggg gag gac tgg ctc tcc gcc aag gag ggc att gat ggc cgc ggc gga     1872
Gly Glu Asp Trp Leu Ser Ala Lys Glu Gly Ile Asp Gly Arg Gly Gly
    610                 615                 620

ggc ggg cat cat cat cat cat cat taa                                 1899
Gly Gly His His His His His His
625                 630


<210> SEQ ID NO 123
<211> LENGTH: 632
<212> TYPE: PRT
<213> ORGANISM: artificial sequence
<220> FEATURE:
<223> OTHER INFORMATION: The DNA sequence encoding the Sso7d-ATaq fusion
      protein

<400> SEQUENCE: 123

Met Ile Thr Asn Ser Ser Ala Thr Val Lys Phe Lys Tyr Lys Gly Glu
1               5                   10                  15

Glu Lys Glu Val Asp Ile Ser Lys Ile Lys Lys Val Trp Arg Val Gly
            20                  25                  30

Lys Met Ile Ser Phe Thr Tyr Asp Glu Gly Gly Gly Lys Thr Gly Arg
        35                  40                  45

Gly Ala Val Ser Glu Lys Asp Ala Pro Lys Glu Leu Leu Gln Met Leu
    50                  55                  60

Glu Lys Gln Lys Lys Gly Gly Gly Val Thr Ser Pro Lys Ala Leu Glu
65                  70                  75                  80

Glu Ala Pro Trp Pro Pro Pro Glu Gly Ala Phe Val Gly Phe Val Leu
                85                  90                  95

Ser Arg Lys Glu Pro Met Trp Ala Asp Leu Leu Ala Leu Ala Ala Ala
            100                 105                 110

Arg Gly Gly Arg Val His Arg Ala Pro Glu Pro Tyr Lys Ala Leu Arg
        115                 120                 125

Asp Leu Lys Glu Ala Arg Gly Leu Leu Ala Lys Asp Leu Ser Val Leu
    130                 135                 140

Ala Leu Arg Glu Gly Leu Gly Leu Pro Pro Gly Asp Asp Pro Met Leu
145                 150                 155                 160

Leu Ala Tyr Leu Leu Asp Pro Ser Asn Thr Thr Pro Glu Gly Val Ala
                165                 170                 175

Arg Arg Tyr Gly Gly Glu Trp Thr Glu Glu Ala Gly Glu Arg Ala Ala
            180                 185                 190

Leu Ser Glu Arg Leu Phe Ala Asn Leu Trp Gly Arg Leu Glu Gly Glu
        195                 200                 205

Glu Arg Leu Leu Trp Leu Tyr Arg Glu Val Glu Arg Pro Leu Ser Ala
    210                 215                 220

Val Leu Ala His Met Glu Ala Thr Gly Val Arg Leu Asp Val Ala Tyr
225                 230                 235                 240

Leu Arg Ala Leu Ser Leu Glu Val Ala Glu Glu Ile Ala Arg Leu Glu
                245                 250                 255

Ala Glu Val Phe Arg Leu Ala Gly His Pro Phe Asn Leu Asn Ser Arg
            260                 265                 270

Asp Gln Leu Glu Arg Val Leu Phe Asp Glu Leu Gly Leu Pro Ala Ile
```

```
        275                 280                 285

Gly Lys Thr Glu Lys Thr Gly Lys Arg Ser Thr Ser Ala Ala Val Leu
    290                 295                 300

Glu Ala Leu Arg Glu Ala His Pro Ile Val Glu Lys Ile Leu Gln Tyr
305                 310                 315                 320

Arg Glu Leu Thr Lys Leu Lys Ser Thr Tyr Ile Asp Pro Leu Pro Asp
                325                 330                 335

Leu Ile His Pro Arg Thr Gly Arg Leu His Thr Arg Phe Asn Gln Thr
            340                 345                 350

Ala Thr Ala Thr Gly Arg Leu Ser Ser Ser Asp Pro Asn Leu Gln Asn
        355                 360                 365

Ile Pro Val Arg Thr Pro Leu Gly Gln Arg Ile Arg Arg Ala Phe Ile
    370                 375                 380

Ala Glu Glu Gly Trp Leu Leu Val Ala Leu Asp Tyr Ser Gln Ile Glu
385                 390                 395                 400

Leu Arg Val Leu Ala His Leu Ser Gly Asp Glu Asn Leu Ile Arg Val
                405                 410                 415

Phe Gln Glu Gly Arg Asp Ile His Thr Glu Thr Ala Ser Trp Met Phe
            420                 425                 430

Gly Val Pro Arg Glu Ala Val Asp Pro Leu Met Arg Arg Ala Ala Lys
        435                 440                 445

Thr Ile Asn Phe Gly Val Leu Tyr Gly Met Ser Ala His Arg Leu Ser
    450                 455                 460

Gln Glu Leu Ala Ile Pro Tyr Glu Glu Ala Gln Ala Phe Ile Glu Arg
465                 470                 475                 480

Tyr Phe Gln Ser Phe Pro Lys Val Arg Ala Trp Ile Glu Lys Thr Leu
                485                 490                 495

Glu Glu Gly Arg Arg Arg Gly Tyr Val Glu Thr Leu Phe Gly Arg Arg
            500                 505                 510

Arg Tyr Val Pro Asp Leu Glu Ala Arg Val Lys Ser Val Arg Glu Ala
        515                 520                 525

Ala Glu Arg Met Ala Phe Asn Met Pro Val Gln Gly Thr Ala Ala Asp
    530                 535                 540

Leu Met Lys Leu Ala Met Val Lys Leu Phe Pro Arg Leu Glu Glu Met
545                 550                 555                 560

Gly Ala Arg Met Leu Leu Gln Val His Asp Glu Leu Val Leu Glu Ala
                565                 570                 575

Pro Lys Glu Arg Ala Glu Ala Val Ala Arg Leu Ala Lys Glu Val Met
            580                 585                 590

Glu Gly Val Tyr Pro Leu Ala Val Pro Leu Glu Val Glu Val Gly Ile
        595                 600                 605

Gly Glu Asp Trp Leu Ser Ala Lys Glu Gly Ile Asp Gly Arg Gly Gly
    610                 615                 620

Gly Gly His His His His His His
625                 630
```

<210> SEQ ID NO 124
<211> LENGTH: 2763
<212> TYPE: DNA
<213> ORGANISM: artificial sequence
<220> FEATURE:
<223> OTHER INFORMATION: The DNA sequence encoding the Sso7d-Taq fusion protein
<220> FEATURE:
<221> NAME/KEY: CDS
<222> LOCATION: (1)..(2763)

```
<223> OTHER INFORMATION:

<400> SEQUENCE: 124

atg att acg aat tcg agc gca acc gta aag ttc aag tac aaa ggc gaa       48
Met Ile Thr Asn Ser Ser Ala Thr Val Lys Phe Lys Tyr Lys Gly Glu
1               5                   10                  15

gaa aaa gag gta gac atc tcc aag atc aag aaa gta tgg cgt gtg ggc       96
Glu Lys Glu Val Asp Ile Ser Lys Ile Lys Lys Val Trp Arg Val Gly
            20                  25                  30

aag atg atc tcc ttc acc tac gac gag ggc ggt ggc aag acc ggc cgt      144
Lys Met Ile Ser Phe Thr Tyr Asp Glu Gly Gly Gly Lys Thr Gly Arg
        35                  40                  45

ggt gcg gta agc gaa aag gac gcg ccg aag gag ctg ctg cag atg ctg      192
Gly Ala Val Ser Glu Lys Asp Ala Pro Lys Glu Leu Leu Gln Met Leu
    50                  55                  60

gag aag cag aaa aag ggc ggc ggt gtc act agt ggg atg ctg ccc ctc      240
Glu Lys Gln Lys Lys Gly Gly Gly Val Thr Ser Gly Met Leu Pro Leu
65                  70                  75                  80

ttt gag ccc aag ggc cgg gtc ctc ctg gtg gac ggc cac cac ctg gcc      288
Phe Glu Pro Lys Gly Arg Val Leu Leu Val Asp Gly His His Leu Ala
                85                  90                  95

tac cgc acc ttc cac gcc ctg aag ggc ctc acc acc agc cgg ggg gag      336
Tyr Arg Thr Phe His Ala Leu Lys Gly Leu Thr Thr Ser Arg Gly Glu
            100                 105                 110

ccg gtg cag gcg gtc tac ggc ttc gcc aag agc ctc ctc aag gcc ctc      384
Pro Val Gln Ala Val Tyr Gly Phe Ala Lys Ser Leu Leu Lys Ala Leu
        115                 120                 125

aag gag gac ggg gac gcg gtg atc gtg gtc ttt gac gcc aag gcc ccc      432
Lys Glu Asp Gly Asp Ala Val Ile Val Val Phe Asp Ala Lys Ala Pro
    130                 135                 140

tcc ttc cgc cac gag gcc tac ggg ggg tac aag gcg ggc cgg gcc ccc      480
Ser Phe Arg His Glu Ala Tyr Gly Gly Tyr Lys Ala Gly Arg Ala Pro
145                 150                 155                 160

acg cca gag gac ttt ccc cgg caa ctc gcc ctc atc aag gag ctg gtg      528
Thr Pro Glu Asp Phe Pro Arg Gln Leu Ala Leu Ile Lys Glu Leu Val
                165                 170                 175

gac ctc ctg ggg ctg gcg cgc ctc gag gtc ccg ggc tac gag gcg gac      576
Asp Leu Leu Gly Leu Ala Arg Leu Glu Val Pro Gly Tyr Glu Ala Asp
            180                 185                 190

gac gtc ctg gcc agc ctg gcc aag aag gcg gaa aag gag ggc tac gag      624
Asp Val Leu Ala Ser Leu Ala Lys Lys Ala Glu Lys Glu Gly Tyr Glu
        195                 200                 205

gtc cgc atc ctc acc gcc gac aaa gac ctt tac cag ctc ctt tcc gac      672
Val Arg Ile Leu Thr Ala Asp Lys Asp Leu Tyr Gln Leu Leu Ser Asp
    210                 215                 220

cgc atc cac gtc ctc cac ccc gag ggg tac ctc atc acc ccg gcc tgg      720
Arg Ile His Val Leu His Pro Glu Gly Tyr Leu Ile Thr Pro Ala Trp
225                 230                 235                 240

ctt tgg gaa aag tac ggc ctg agg ccc gac cag tgg gcc gac tac cgg      768
Leu Trp Glu Lys Tyr Gly Leu Arg Pro Asp Gln Trp Ala Asp Tyr Arg
                245                 250                 255

gcc ctg acc ggg gac gag tcc gac aac ctt ccc ggg gtc aag ggc atc      816
Ala Leu Thr Gly Asp Glu Ser Asp Asn Leu Pro Gly Val Lys Gly Ile
            260                 265                 270

ggg gag aag acg gcg agg aag ctt ctg gag gag tgg ggg agc ctg gaa      864
Gly Glu Lys Thr Ala Arg Lys Leu Leu Glu Glu Trp Gly Ser Leu Glu
        275                 280                 285

gcc ctc ctc aag aac ctg gac cgg ctg aag ccc gcc atc cgg gag aag      912
Ala Leu Leu Lys Asn Leu Asp Arg Leu Lys Pro Ala Ile Arg Glu Lys
    290                 295                 300
```

```
atc ctg gcc cac atg gac gat ctg aag ctc tcc tgg gac ctg gcc aag      960
Ile Leu Ala His Met Asp Asp Leu Lys Leu Ser Trp Asp Leu Ala Lys
305                 310                 315                 320

gtg cgc acc gac ctg ccc ctg gag gtg gac ttc gcc aaa agg cgg gag     1008
Val Arg Thr Asp Leu Pro Leu Glu Val Asp Phe Ala Lys Arg Arg Glu
                325                 330                 335

ccc gac cgg gag agg ctt agg gcc ttt ctg gag agg ctt gag ttt ggc     1056
Pro Asp Arg Glu Arg Leu Arg Ala Phe Leu Glu Arg Leu Glu Phe Gly
            340                 345                 350

agc ctc ctc cac gag ttc ggc ctt ctg gaa agc ccc aag gcc ctg gag     1104
Ser Leu Leu His Glu Phe Gly Leu Leu Glu Ser Pro Lys Ala Leu Glu
        355                 360                 365

gag gcc ccc tgg ccc ccg ccg gaa ggg gcc ttc gtg ggc ttt gtg ctt     1152
Glu Ala Pro Trp Pro Pro Pro Glu Gly Ala Phe Val Gly Phe Val Leu
    370                 375                 380

tcc cgc aag gag ccc atg tgg gcc gat ctt ctg gcc ctg gcc gcc gcc     1200
Ser Arg Lys Glu Pro Met Trp Ala Asp Leu Leu Ala Leu Ala Ala Ala
385                 390                 395                 400

agg ggg ggc cgg gtc cac cgg gcc ccc gag cct tat aaa gcc ctc agg     1248
Arg Gly Gly Arg Val His Arg Ala Pro Glu Pro Tyr Lys Ala Leu Arg
                405                 410                 415

gac ctg aag gag gcg cgg ggg ctt ctc gcc aaa gac ctg agc gtt ctg     1296
Asp Leu Lys Glu Ala Arg Gly Leu Leu Ala Lys Asp Leu Ser Val Leu
            420                 425                 430

gcc ctg agg gaa ggc ctt ggc ctc ccg ccc ggc gac gac ccc atg ctc     1344
Ala Leu Arg Glu Gly Leu Gly Leu Pro Pro Gly Asp Asp Pro Met Leu
        435                 440                 445

ctc gcc tac ctc ctg gac cct tcc aac acc acc ccc gag ggg gtg gcc     1392
Leu Ala Tyr Leu Leu Asp Pro Ser Asn Thr Thr Pro Glu Gly Val Ala
    450                 455                 460

cgg cgc tac ggc ggg gag tgg acg gag gag gcg ggg gag cgg gcc gcc     1440
Arg Arg Tyr Gly Gly Glu Trp Thr Glu Glu Ala Gly Glu Arg Ala Ala
465                 470                 475                 480

ctt tcc gag agg ctc ttc gcc aac ctg tgg ggg agg ctt gag ggg gag     1488
Leu Ser Glu Arg Leu Phe Ala Asn Leu Trp Gly Arg Leu Glu Gly Glu
                485                 490                 495

gag agg ctc ctt tgg ctt tac cgg gag gtg gag agg ccc ctt tcc gct     1536
Glu Arg Leu Leu Trp Leu Tyr Arg Glu Val Glu Arg Pro Leu Ser Ala
            500                 505                 510

gtc ctg gcc cac atg gag gcc acg ggg gtg cgc ctg gac gtg gcc tat     1584
Val Leu Ala His Met Glu Ala Thr Gly Val Arg Leu Asp Val Ala Tyr
        515                 520                 525

ctc agg gcc ttg tcc ctg gag gtg gcc gag gag atc gcc cgc ctc gag     1632
Leu Arg Ala Leu Ser Leu Glu Val Ala Glu Glu Ile Ala Arg Leu Glu
    530                 535                 540

gcc gag gtc ttc cgc ctg gcc ggc cac ccc ttc aac ctc aac tcc cgg     1680
Ala Glu Val Phe Arg Leu Ala Gly His Pro Phe Asn Leu Asn Ser Arg
545                 550                 555                 560

gac cag ctg gaa agg gtc ctc ttt gac gag cta ggg ctt ccc gcc atc     1728
Asp Gln Leu Glu Arg Val Leu Phe Asp Glu Leu Gly Leu Pro Ala Ile
                565                 570                 575

ggc aag acg gag aag acc ggc aag cgc tcc acc agc gcc gcc gtc ctg     1776
Gly Lys Thr Glu Lys Thr Gly Lys Arg Ser Thr Ser Ala Ala Val Leu
            580                 585                 590

gag gcc ctc cgc gag gcc cac ccc atc gtg gag aag atc ctg cag tac     1824
Glu Ala Leu Arg Glu Ala His Pro Ile Val Glu Lys Ile Leu Gln Tyr
        595                 600                 605

cgg gag ctc acc aag ctg aag agc acc tac att gac ccc ttg ccg gac     1872
Arg Glu Leu Thr Lys Leu Lys Ser Thr Tyr Ile Asp Pro Leu Pro Asp
```

```
    610                 615                 620

ctc atc cac ccc agg acg ggc cgc ctc cac acc cgc ttc aac cag acg      1920
Leu Ile His Pro Arg Thr Gly Arg Leu His Thr Arg Phe Asn Gln Thr
625                 630                 635                 640

gcc acg gcc acg ggc agg cta agt agc tcc gat ccc aac ctc cag aac      1968
Ala Thr Ala Thr Gly Arg Leu Ser Ser Ser Asp Pro Asn Leu Gln Asn
                645                 650                 655

atc ccc gtc cgc acc ccg ctt ggg cag agg atc cgc cgg gcc ttc atc      2016
Ile Pro Val Arg Thr Pro Leu Gly Gln Arg Ile Arg Arg Ala Phe Ile
            660                 665                 670

gcc gag gag ggg tgg cta ttg gtg gcc ctg gac tat agc cag ata gag      2064
Ala Glu Glu Gly Trp Leu Leu Val Ala Leu Asp Tyr Ser Gln Ile Glu
        675                 680                 685

ctc agg gtg ctg gcc cac ctc tcc ggc gac gag aac ctg atc cgg gtc      2112
Leu Arg Val Leu Ala His Leu Ser Gly Asp Glu Asn Leu Ile Arg Val
    690                 695                 700

ttc cag gag ggg cgg gac atc cac acg gag acc gcc agc tgg atg ttc      2160
Phe Gln Glu Gly Arg Asp Ile His Thr Glu Thr Ala Ser Trp Met Phe
705                 710                 715                 720

ggc gtc ccc cgg gag gcc gtg gac ccc ctg atg cgc cgg gcg gcc aag      2208
Gly Val Pro Arg Glu Ala Val Asp Pro Leu Met Arg Arg Ala Ala Lys
                725                 730                 735

acc atc aac ttc ggg gtc ctc tac ggc atg tcg gcc cac cgc ctc tcc      2256
Thr Ile Asn Phe Gly Val Leu Tyr Gly Met Ser Ala His Arg Leu Ser
            740                 745                 750

cag gag cta gcc atc cct tac gag gag gcc cag gcc ttc att gag cgc      2304
Gln Glu Leu Ala Ile Pro Tyr Glu Glu Ala Gln Ala Phe Ile Glu Arg
        755                 760                 765

tac ttt cag agc ttc ccc aag gtg cgg gcc tgg att gag aag acc ctg      2352
Tyr Phe Gln Ser Phe Pro Lys Val Arg Ala Trp Ile Glu Lys Thr Leu
    770                 775                 780

gag gag ggc agg agg cgg ggg tac gtg gag acc ctc ttc ggc cgc cgc      2400
Glu Glu Gly Arg Arg Arg Gly Tyr Val Glu Thr Leu Phe Gly Arg Arg
785                 790                 795                 800

cgc tac gtg cca gac cta gag gcc cgg gtg aag agc gtg cgg gag gcg      2448
Arg Tyr Val Pro Asp Leu Glu Ala Arg Val Lys Ser Val Arg Glu Ala
                805                 810                 815

gcc gag cgc atg gcc ttc aac atg ccc gtc cag ggc acc gcc gcc gac      2496
Ala Glu Arg Met Ala Phe Asn Met Pro Val Gln Gly Thr Ala Ala Asp
            820                 825                 830

ctc atg aag ctg gct atg gtg aag ctc ttc ccc agg ctg gag gaa atg      2544
Leu Met Lys Leu Ala Met Val Lys Leu Phe Pro Arg Leu Glu Glu Met
        835                 840                 845

ggg gcc agg atg ctc ctt cag gtc cac gac gag ctg gtc ctc gag gcc      2592
Gly Ala Arg Met Leu Leu Gln Val His Asp Glu Leu Val Leu Glu Ala
    850                 855                 860

cca aaa gag agg gcg gag gcc gtg gcc cgg ctg gcc aag gag gtc atg      2640
Pro Lys Glu Arg Ala Glu Ala Val Ala Arg Leu Ala Lys Glu Val Met
865                 870                 875                 880

gag ggg gtg tat ccc ctg gcc gtg ccc ctg gag gtg gag gtg ggg ata      2688
Glu Gly Val Tyr Pro Leu Ala Val Pro Leu Glu Val Glu Val Gly Ile
                885                 890                 895

ggg gag gac tgg ctc tcc gcc aag gag ggc att gat ggc cgc ggc gga      2736
Gly Glu Asp Trp Leu Ser Ala Lys Glu Gly Ile Asp Gly Arg Gly Gly
            900                 905                 910

ggc ggg cat cat cat cat cat cat taa                                  2763
Gly Gly His His His His His His
        915                 920
```

```
<210> SEQ ID NO 125
<211> LENGTH: 920
<212> TYPE: PRT
<213> ORGANISM: artificial sequence
<220> FEATURE:
<223> OTHER INFORMATION: The DNA sequence encoding the Sso7d-Taq fusion
      protein

<400> SEQUENCE: 125

Met Ile Thr Asn Ser Ser Ala Thr Val Lys Phe Lys Tyr Lys Gly Glu
1               5                   10                  15

Glu Lys Glu Val Asp Ile Ser Lys Ile Lys Lys Val Trp Arg Val Gly
            20                  25                  30

Lys Met Ile Ser Phe Thr Tyr Asp Glu Gly Gly Gly Lys Thr Gly Arg
        35                  40                  45

Gly Ala Val Ser Glu Lys Asp Ala Pro Lys Glu Leu Leu Gln Met Leu
    50                  55                  60

Glu Lys Gln Lys Lys Gly Gly Gly Val Thr Ser Gly Met Leu Pro Leu
65                  70                  75                  80

Phe Glu Pro Lys Gly Arg Val Leu Leu Val Asp Gly His His Leu Ala
                85                  90                  95

Tyr Arg Thr Phe His Ala Leu Lys Gly Leu Thr Thr Ser Arg Gly Glu
            100                 105                 110

Pro Val Gln Ala Val Tyr Gly Phe Ala Lys Ser Leu Leu Lys Ala Leu
        115                 120                 125

Lys Glu Asp Gly Asp Ala Val Ile Val Val Phe Asp Ala Lys Ala Pro
    130                 135                 140

Ser Phe Arg His Glu Ala Tyr Gly Gly Tyr Lys Ala Gly Arg Ala Pro
145                 150                 155                 160

Thr Pro Glu Asp Phe Pro Arg Gln Leu Ala Leu Ile Lys Glu Leu Val
                165                 170                 175

Asp Leu Leu Gly Leu Ala Arg Leu Glu Val Pro Gly Tyr Glu Ala Asp
            180                 185                 190

Asp Val Leu Ala Ser Leu Ala Lys Lys Ala Glu Lys Glu Gly Tyr Glu
        195                 200                 205

Val Arg Ile Leu Thr Ala Asp Lys Asp Leu Tyr Gln Leu Leu Ser Asp
    210                 215                 220

Arg Ile His Val Leu His Pro Glu Gly Tyr Leu Ile Thr Pro Ala Trp
225                 230                 235                 240

Leu Trp Glu Lys Tyr Gly Leu Arg Pro Asp Gln Trp Ala Asp Tyr Arg
                245                 250                 255

Ala Leu Thr Gly Asp Glu Ser Asp Asn Leu Pro Gly Val Lys Gly Ile
            260                 265                 270

Gly Glu Lys Thr Ala Arg Lys Leu Leu Glu Glu Trp Gly Ser Leu Glu
        275                 280                 285

Ala Leu Leu Lys Asn Leu Asp Arg Leu Lys Pro Ala Ile Arg Glu Lys
    290                 295                 300

Ile Leu Ala His Met Asp Asp Leu Lys Leu Ser Trp Asp Leu Ala Lys
305                 310                 315                 320

Val Arg Thr Asp Leu Pro Leu Glu Val Asp Phe Ala Lys Arg Arg Glu
                325                 330                 335

Pro Asp Arg Glu Arg Leu Arg Ala Phe Leu Glu Arg Leu Glu Phe Gly
            340                 345                 350

Ser Leu Leu His Glu Phe Gly Leu Leu Glu Ser Pro Lys Ala Leu Glu
        355                 360                 365
```

```
Glu Ala Pro Trp Pro Pro Pro Glu Gly Ala Phe Val Gly Phe Val Leu
    370                 375                 380

Ser Arg Lys Glu Pro Met Trp Ala Asp Leu Leu Ala Leu Ala Ala Ala
385                 390                 395                 400

Arg Gly Gly Arg Val His Arg Ala Pro Glu Pro Tyr Lys Ala Leu Arg
                405                 410                 415

Asp Leu Lys Glu Ala Arg Gly Leu Leu Ala Lys Asp Leu Ser Val Leu
            420                 425                 430

Ala Leu Arg Glu Gly Leu Gly Leu Pro Pro Gly Asp Asp Pro Met Leu
        435                 440                 445

Leu Ala Tyr Leu Leu Asp Pro Ser Asn Thr Thr Pro Glu Gly Val Ala
    450                 455                 460

Arg Arg Tyr Gly Gly Glu Trp Thr Glu Glu Ala Gly Glu Arg Ala Ala
465                 470                 475                 480

Leu Ser Glu Arg Leu Phe Ala Asn Leu Trp Gly Arg Leu Glu Gly Glu
                485                 490                 495

Glu Arg Leu Leu Trp Leu Tyr Arg Glu Val Glu Arg Pro Leu Ser Ala
            500                 505                 510

Val Leu Ala His Met Glu Ala Thr Gly Val Arg Leu Asp Val Ala Tyr
        515                 520                 525

Leu Arg Ala Leu Ser Leu Glu Val Ala Glu Glu Ile Ala Arg Leu Glu
    530                 535                 540

Ala Glu Val Phe Arg Leu Ala Gly His Pro Phe Asn Leu Asn Ser Arg
545                 550                 555                 560

Asp Gln Leu Glu Arg Val Leu Phe Asp Glu Leu Gly Leu Pro Ala Ile
                565                 570                 575

Gly Lys Thr Glu Lys Thr Gly Lys Arg Ser Thr Ser Ala Ala Val Leu
            580                 585                 590

Glu Ala Leu Arg Glu Ala His Pro Ile Val Glu Lys Ile Leu Gln Tyr
        595                 600                 605

Arg Glu Leu Thr Lys Leu Lys Ser Thr Tyr Ile Asp Pro Leu Pro Asp
    610                 615                 620

Leu Ile His Pro Arg Thr Gly Arg Leu His Thr Arg Phe Asn Gln Thr
625                 630                 635                 640

Ala Thr Ala Thr Gly Arg Leu Ser Ser Ser Asp Pro Asn Leu Gln Asn
                645                 650                 655

Ile Pro Val Arg Thr Pro Leu Gly Gln Arg Ile Arg Arg Ala Phe Ile
            660                 665                 670

Ala Glu Glu Gly Trp Leu Leu Val Ala Leu Asp Tyr Ser Gln Ile Glu
        675                 680                 685

Leu Arg Val Leu Ala His Leu Ser Gly Asp Glu Asn Leu Ile Arg Val
    690                 695                 700

Phe Gln Glu Gly Arg Asp Ile His Thr Glu Thr Ala Ser Trp Met Phe
705                 710                 715                 720

Gly Val Pro Arg Glu Ala Val Asp Pro Leu Met Arg Arg Ala Ala Lys
                725                 730                 735

Thr Ile Asn Phe Gly Val Leu Tyr Gly Met Ser Ala His Arg Leu Ser
            740                 745                 750

Gln Glu Leu Ala Ile Pro Tyr Glu Glu Ala Gln Ala Phe Ile Glu Arg
        755                 760                 765

Tyr Phe Gln Ser Phe Pro Lys Val Arg Ala Trp Ile Glu Lys Thr Leu
    770                 775                 780

Glu Glu Gly Arg Arg Arg Gly Tyr Val Glu Thr Leu Phe Gly Arg Arg
```

```
785                 790                 795                 800

Arg Tyr Val Pro Asp Leu Glu Ala Arg Val Lys Ser Val Arg Glu Ala
                805                 810                 815

Ala Glu Arg Met Ala Phe Asn Met Pro Val Gln Gly Thr Ala Ala Asp
            820                 825                 830

Leu Met Lys Leu Ala Met Val Lys Leu Phe Pro Arg Leu Glu Glu Met
        835                 840                 845

Gly Ala Arg Met Leu Leu Gln Val His Asp Glu Leu Val Leu Glu Ala
    850                 855                 860

Pro Lys Glu Arg Ala Glu Ala Val Ala Arg Leu Ala Lys Glu Val Met
865                 870                 875                 880

Glu Gly Val Tyr Pro Leu Ala Val Pro Leu Glu Val Glu Val Gly Ile
                885                 890                 895

Gly Glu Asp Trp Leu Ser Ala Lys Glu Gly Ile Asp Gly Arg Gly Gly
            900                 905                 910

Gly Gly His His His His His His
        915                 920


<210> SEQ ID NO 126
<211> LENGTH: 2481
<212> TYPE: DNA
<213> ORGANISM: artificial sequence
<220> FEATURE:
<223> OTHER INFORMATION: The DNA sequence encoding the Pfu-Sso7d fusion
      protein
<220> FEATURE:
<221> NAME/KEY: CDS
<222> LOCATION: (1)..(2481)
<223> OTHER INFORMATION:

<400> SEQUENCE: 126

atg att tta gat gtg gat tac ata act gaa gaa gga aaa cct gtt att       48
Met Ile Leu Asp Val Asp Tyr Ile Thr Glu Glu Gly Lys Pro Val Ile
1               5                   10                  15

agg cta ttc aaa aaa gag aac gga aaa ttt aag ata gag cat gat aga       96
Arg Leu Phe Lys Lys Glu Asn Gly Lys Phe Lys Ile Glu His Asp Arg
            20                  25                  30

act ttt aga cca tac att tac gct ctt ctc agg gat gat tca aag att      144
Thr Phe Arg Pro Tyr Ile Tyr Ala Leu Leu Arg Asp Asp Ser Lys Ile
        35                  40                  45

gaa gaa gtt aag aaa ata acg ggg gaa agg cat gga aag att gtg aga      192
Glu Glu Val Lys Lys Ile Thr Gly Glu Arg His Gly Lys Ile Val Arg
    50                  55                  60

att gtt gat gta gag aag gtt gag aaa aag ttt ctc ggc aag cct att      240
Ile Val Asp Val Glu Lys Val Glu Lys Lys Phe Leu Gly Lys Pro Ile
65                  70                  75                  80

acc gtg tgg aaa ctt tat ttg gaa cat ccc caa gat gtt ccc act att      288
Thr Val Trp Lys Leu Tyr Leu Glu His Pro Gln Asp Val Pro Thr Ile
                85                  90                  95

aga gaa aaa gtt aga gaa cat cca gca gtt gtg gac atc ttc gaa tac      336
Arg Glu Lys Val Arg Glu His Pro Ala Val Val Asp Ile Phe Glu Tyr
            100                 105                 110

gat att cca ttt gca aag aga tac ctc atc gac aaa ggc cta ata cca      384
Asp Ile Pro Phe Ala Lys Arg Tyr Leu Ile Asp Lys Gly Leu Ile Pro
        115                 120                 125

atg gag ggg gaa gaa gag cta aag att ctt gcc ttc gat ata gaa acc      432
Met Glu Gly Glu Glu Glu Leu Lys Ile Leu Ala Phe Asp Ile Glu Thr
    130                 135                 140

ctc tat cac gaa gga gaa gag ttt gga aaa ggc cca att ata atg att      480
Leu Tyr His Glu Gly Glu Glu Phe Gly Lys Gly Pro Ile Ile Met Ile
```

-continued

```
145                 150                 155                 160

agt tat gca gat gaa aat gaa gca aag gtg att act tgg aaa aac ata      528
Ser Tyr Ala Asp Glu Asn Glu Ala Lys Val Ile Thr Trp Lys Asn Ile
                165                 170                 175

gat ctt cca tac gtt gag gtt gta tca agc gag aga gag atg ata aag      576
Asp Leu Pro Tyr Val Glu Val Val Ser Ser Glu Arg Glu Met Ile Lys
            180                 185                 190

aga ttt ctc agg att atc agg gag aag gat cct gac att ata gtt act      624
Arg Phe Leu Arg Ile Ile Arg Glu Lys Asp Pro Asp Ile Ile Val Thr
        195                 200                 205

tat aat gga gac tca ttc gac ttc cca tat tta gcg aaa agg gca gaa      672
Tyr Asn Gly Asp Ser Phe Asp Phe Pro Tyr Leu Ala Lys Arg Ala Glu
    210                 215                 220

aaa ctt ggg att aaa tta acc att gga aga gat gga agc gag ccc aag      720
Lys Leu Gly Ile Lys Leu Thr Ile Gly Arg Asp Gly Ser Glu Pro Lys
225                 230                 235                 240

atg cag aga ata ggc gat atg acg gct gta gaa gtc aag gga aga ata      768
Met Gln Arg Ile Gly Asp Met Thr Ala Val Glu Val Lys Gly Arg Ile
                245                 250                 255

cat ttc gac ttg tat cat gta ata aca agg aca ata aat ctc cca aca      816
His Phe Asp Leu Tyr His Val Ile Thr Arg Thr Ile Asn Leu Pro Thr
            260                 265                 270

tac aca cta gag gct gta tat gaa gca att ttt gga aag cca aag gag      864
Tyr Thr Leu Glu Ala Val Tyr Glu Ala Ile Phe Gly Lys Pro Lys Glu
        275                 280                 285

aag gta tac gcc gac gag ata gca aaa gcc tgg gaa agt gga gag aac      912
Lys Val Tyr Ala Asp Glu Ile Ala Lys Ala Trp Glu Ser Gly Glu Asn
    290                 295                 300

ctt gag aga gtt gcc aaa tac tcg atg gaa gat gca aag gca act tat      960
Leu Glu Arg Val Ala Lys Tyr Ser Met Glu Asp Ala Lys Ala Thr Tyr
305                 310                 315                 320

gaa ctc ggg aaa gaa ttc ctt cca atg gaa att cag ctt tca aga tta     1008
Glu Leu Gly Lys Glu Phe Leu Pro Met Glu Ile Gln Leu Ser Arg Leu
                325                 330                 335

gtt gga caa cct tta tgg gat gtt tca agg tca agc aca ggg aac ctt     1056
Val Gly Gln Pro Leu Trp Asp Val Ser Arg Ser Ser Thr Gly Asn Leu
            340                 345                 350

gta gag tgg ttc tta ctt agg aaa gcc tac gaa aga aac gaa gta gct     1104
Val Glu Trp Phe Leu Leu Arg Lys Ala Tyr Glu Arg Asn Glu Val Ala
        355                 360                 365

cca aac aag cca agt gaa gag gag tat caa aga agg ctc agg gag agc     1152
Pro Asn Lys Pro Ser Glu Glu Glu Tyr Gln Arg Arg Leu Arg Glu Ser
    370                 375                 380

tac aca ggt gga ttc gtt aaa gag cca gaa aag ggg ttg tgg gaa aac     1200
Tyr Thr Gly Gly Phe Val Lys Glu Pro Glu Lys Gly Leu Trp Glu Asn
385                 390                 395                 400

ata gta tac cta gat ttt aga gcc cta tat ccc tcg att ata att acc     1248
Ile Val Tyr Leu Asp Phe Arg Ala Leu Tyr Pro Ser Ile Ile Ile Thr
                405                 410                 415

cac aat gtt tct ccc gat act cta aat ctt gag gga tgc aag aac tat     1296
His Asn Val Ser Pro Asp Thr Leu Asn Leu Glu Gly Cys Lys Asn Tyr
            420                 425                 430

gat atc gct cct caa gta ggc cac aag ttc tgc aag gac atc cct ggt     1344
Asp Ile Ala Pro Gln Val Gly His Lys Phe Cys Lys Asp Ile Pro Gly
        435                 440                 445

ttt ata cca agt ctc ttg gga cat ttg tta gag gaa aga caa aag att     1392
Phe Ile Pro Ser Leu Leu Gly His Leu Leu Glu Glu Arg Gln Lys Ile
    450                 455                 460

aag aca aaa atg aag gaa act tta gca aat tct ttc tac gga tat tat     1440
```

```
Lys Thr Lys Met Lys Glu Thr Leu Ala Asn Ser Phe Tyr Gly Tyr Tyr
465                 470                 475                 480

ggc tat gca aaa gca aga tgg tac tgt aag gag tgt gct gag agc gtt      1488
Gly Tyr Ala Lys Ala Arg Trp Tyr Cys Lys Glu Cys Ala Glu Ser Val
                485                 490                 495

act gcc tgg gga aga aag tac atc gag tta gta tgg aag gag ctc gaa      1536
Thr Ala Trp Gly Arg Lys Tyr Ile Glu Leu Val Trp Lys Glu Leu Glu
            500                 505                 510

gaa aag ttt gga ttt aaa gtc ctc tac att gac act gat ggt ctc tat      1584
Glu Lys Phe Gly Phe Lys Val Leu Tyr Ile Asp Thr Asp Gly Leu Tyr
        515                 520                 525

gca act atc cca gga gga gaa agt gag gaa ata aag aaa aag gct cta      1632
Ala Thr Ile Pro Gly Gly Glu Ser Glu Glu Ile Lys Lys Lys Ala Leu
    530                 535                 540

gaa ttt gta aaa tac ata aat tca aag ctc cct gga ctg cta gag ctt      1680
Glu Phe Val Lys Tyr Ile Asn Ser Lys Leu Pro Gly Leu Leu Glu Leu
545                 550                 555                 560

gaa tat gaa ggg ttt tat aag agg gga ttc ttc gtt acg aag aag agg      1728
Glu Tyr Glu Gly Phe Tyr Lys Arg Gly Phe Phe Val Thr Lys Lys Arg
                565                 570                 575

tat gca gta ata gat gaa gaa gga aaa gtc att act cgt ggt tta gag      1776
Tyr Ala Val Ile Asp Glu Glu Gly Lys Val Ile Thr Arg Gly Leu Glu
            580                 585                 590

ata gtt agg aga gat tgg agt gaa att gca aaa gaa act caa gct aga      1824
Ile Val Arg Arg Asp Trp Ser Glu Ile Ala Lys Glu Thr Gln Ala Arg
        595                 600                 605

gtt ttg gag aca ata cta aaa cac gga gat gtt gaa gaa gct gtg aga      1872
Val Leu Glu Thr Ile Leu Lys His Gly Asp Val Glu Glu Ala Val Arg
    610                 615                 620

ata gta aaa gaa gta ata caa aag ctt gcc aat tat gaa att cca cca      1920
Ile Val Lys Glu Val Ile Gln Lys Leu Ala Asn Tyr Glu Ile Pro Pro
625                 630                 635                 640

gag aag ctc gca ata tat gag cag ata aca aga cca tta cat gag tat      1968
Glu Lys Leu Ala Ile Tyr Glu Gln Ile Thr Arg Pro Leu His Glu Tyr
                645                 650                 655

aag gcg ata ggt cct cac gta gct gtt gca aag aaa cta gct gct aaa      2016
Lys Ala Ile Gly Pro His Val Ala Val Ala Lys Lys Leu Ala Ala Lys
            660                 665                 670

gga gtt aaa ata aag cca gga atg gta att gga tac ata gta ctt aga      2064
Gly Val Lys Ile Lys Pro Gly Met Val Ile Gly Tyr Ile Val Leu Arg
        675                 680                 685

ggc gat ggt cca att agc aat agg gca att cta gct gag gaa tac gat      2112
Gly Asp Gly Pro Ile Ser Asn Arg Ala Ile Leu Ala Glu Glu Tyr Asp
    690                 695                 700

ccc aaa aag cac aag tat gac gca gaa tat tac att gag aac cag gtt      2160
Pro Lys Lys His Lys Tyr Asp Ala Glu Tyr Tyr Ile Glu Asn Gln Val
705                 710                 715                 720

ctt cca gcg gta ctt agg ata ttg gag gga ttt gga tac aga aag gaa      2208
Leu Pro Ala Val Leu Arg Ile Leu Glu Gly Phe Gly Tyr Arg Lys Glu
                725                 730                 735

gac ctc aga tac caa aag aca aga caa gtc ggc cta act tcc tgg ctt      2256
Asp Leu Arg Tyr Gln Lys Thr Arg Gln Val Gly Leu Thr Ser Trp Leu
            740                 745                 750

aac att aaa aaa tcc ggt acc ggc ggt ggc ggt gca acc gta aag ttc      2304
Asn Ile Lys Lys Ser Gly Thr Gly Gly Gly Gly Ala Thr Val Lys Phe
        755                 760                 765

aag tac aaa ggc gaa gaa aaa gag gta gac atc tcc aag atc aag aaa      2352
Lys Tyr Lys Gly Glu Glu Lys Glu Val Asp Ile Ser Lys Ile Lys Lys
    770                 775                 780
```

-continued

```
gta tgg cgt gtg ggc aag atg atc tcc ttc acc tac gac gag ggc ggt     2400
Val Trp Arg Val Gly Lys Met Ile Ser Phe Thr Tyr Asp Glu Gly Gly
785                 790                 795                 800

ggc aag acc ggc cgt ggt gcg gta agc gaa aag gac gcg ccg aag gag     2448
Gly Lys Thr Gly Arg Gly Ala Val Ser Glu Lys Asp Ala Pro Lys Glu
                805                 810                 815

ctg ctg cag atg ctg gag aag cag aaa aag tga                         2481
Leu Leu Gln Met Leu Glu Lys Gln Lys Lys
            820                 825
```

<210> SEQ ID NO 127
<211> LENGTH: 826
<212> TYPE: PRT
<213> ORGANISM: artificial sequence
<220> FEATURE:
<223> OTHER INFORMATION: The DNA sequence encoding the Pfu-Sso7d fusion protein

<400> SEQUENCE: 127

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300
```

-continued

```
Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Leu Ala Asn Ser Phe Tyr Gly Tyr Tyr
465                 470                 475                 480

Gly Tyr Ala Lys Ala Arg Trp Tyr Cys Lys Glu Cys Ala Glu Ser Val
                485                 490                 495

Thr Ala Trp Gly Arg Lys Tyr Ile Glu Leu Val Trp Lys Glu Leu Glu
            500                 505                 510

Glu Lys Phe Gly Phe Lys Val Leu Tyr Ile Asp Thr Asp Gly Leu Tyr
        515                 520                 525

Ala Thr Ile Pro Gly Gly Glu Ser Glu Glu Ile Lys Lys Lys Ala Leu
    530                 535                 540

Glu Phe Val Lys Tyr Ile Asn Ser Lys Leu Pro Gly Leu Leu Glu Leu
545                 550                 555                 560

Glu Tyr Glu Gly Phe Tyr Lys Arg Gly Phe Phe Val Thr Lys Lys Arg
                565                 570                 575

Tyr Ala Val Ile Asp Glu Glu Gly Lys Val Ile Thr Arg Gly Leu Glu
            580                 585                 590

Ile Val Arg Arg Asp Trp Ser Glu Ile Ala Lys Glu Thr Gln Ala Arg
        595                 600                 605

Val Leu Glu Thr Ile Leu Lys His Gly Asp Val Glu Glu Ala Val Arg
    610                 615                 620

Ile Val Lys Glu Val Ile Gln Lys Leu Ala Asn Tyr Glu Ile Pro Pro
625                 630                 635                 640

Glu Lys Leu Ala Ile Tyr Glu Gln Ile Thr Arg Pro Leu His Glu Tyr
                645                 650                 655

Lys Ala Ile Gly Pro His Val Ala Val Ala Lys Lys Leu Ala Ala Lys
            660                 665                 670

Gly Val Lys Ile Lys Pro Gly Met Val Ile Gly Tyr Ile Val Leu Arg
        675                 680                 685

Gly Asp Gly Pro Ile Ser Asn Arg Ala Ile Leu Ala Glu Glu Tyr Asp
    690                 695                 700

Pro Lys Lys His Lys Tyr Asp Ala Glu Tyr Tyr Ile Glu Asn Gln Val
705                 710                 715                 720
```

-continued

```
Leu Pro Ala Val Leu Arg Ile Leu Glu Gly Phe Gly Tyr Arg Lys Glu
                725                 730                 735

Asp Leu Arg Tyr Gln Lys Thr Arg Gln Val Gly Leu Thr Ser Trp Leu
            740                 745                 750

Asn Ile Lys Lys Ser Gly Thr Gly Gly Gly Gly Ala Thr Val Lys Phe
        755                 760                 765

Lys Tyr Lys Gly Glu Glu Lys Glu Val Asp Ile Ser Lys Ile Lys Lys
    770                 775                 780

Val Trp Arg Val Gly Lys Met Ile Ser Phe Thr Tyr Asp Glu Gly Gly
785                 790                 795                 800

Gly Lys Thr Gly Arg Gly Ala Val Ser Glu Lys Asp Ala Pro Lys Glu
                805                 810                 815

Leu Leu Gln Met Leu Glu Lys Gln Lys Lys
            820                 825


<210> SEQ ID NO 128
<211> LENGTH: 1905
<212> TYPE: DNA
<213> ORGANISM: artificial sequence
<220> FEATURE:
<223> OTHER INFORMATION: The DNA sequence encoding the Sac7d-ATaq fusion
      protein

<400> SEQUENCE: 128

atgattacga attcgacggt gaaggtaaag ttcaagtata agggtgaaga gaaagaagta      60

gacacttcaa agataaagaa ggtttggaga gtaggcaaaa tggtgtcctt tacctatgac     120

gacaatggta agacaggtag aggagctgta agcgagaaag atgctccaaa agaattatta     180

gacatgttag caagagcaga aagagagaag aaaggcggcg gtgtcactag ccccaaggcc     240

ctggaggagg ccccctggcc cccgccggaa ggggccttcg tgggctttgt gctttcccgc     300

aaggagccca tgtgggccga tcttctggcc ctggccgccg ccaggggggg ccgggtccac     360

cgggcccccg agccttataa agccctcagg gacctgaagg aggcgcgggg gcttctcgcc     420

aaagacctga gcgttctggc cctgagggaa ggccttggcc tcccgcccgg cgacgacccc     480

atgctcctcg cctacctcct ggacccttcc aacaccaccc ccgagggggt ggcccggcgc     540

tacggcgggg agtggacgga ggaggcgggg gagcgggccg ccctttccga gaggctcttc     600

gccaacctgt gggggaggct tgagggggag gagaggctcc tttggcttta ccgggaggtg     660

gagaggcccc tttccgctgt cctggcccac atggaggcca cgggggtgcg cctggacgtg     720

gcctatctca gggccttgtc cctggaggtg gccgaggaga tcgcccgcct cgaggccgag     780

gtcttccgcc tggccggcca ccccttcaac ctcaactccc gggaccagct ggaaagggtc     840

ctctttgacg agctagggct tcccgccatc ggcaagacgg agaagaccgg caagcgctcc     900

accagcgccg ccgtcctgga ggccctccgc gaggcccacc ccatcgtgga gaagatcctg     960

cagtaccggg agctcaccaa gctgaagagc acctacattg acccccttgcc ggacctcatc    1020

caccccagga cgggccgcct ccacacccgc ttcaaccaga cggccacggc cacgggcagg    1080

ctaagtagct ccgatcccaa cctccagaac atccccgtcc gcaccccgct tgggcagagg    1140

atccgccggg ccttcatcgc cgaggagggg tggctattgg tggccctgga ctatagccag    1200

atagagctca gggtgctggc ccacctctcc ggcgacgaga acctgatccg ggtcttccag    1260

gaggggcggg acatccacac ggagaccgcc agctggatgt tcggcgtccc ccgggaggcc    1320

gtggaccccc tgatgcgccg ggcggccaag accatcaact tcggggtcct ctacggcatg    1380

tcggcccacc gcctctccca ggagctagcc atcccttacg aggaggccca ggccttcatt    1440
```

```
gagcgctact ttcagagctt ccccaaggtg cgggcctgga ttgagaagac cctggaggag   1500

ggcaggaggc gggggtacgt ggagaccctc ttcggccgcc gccgctacgt gccagaccta   1560

gaggcccggg tgaagagcgt gcgggaggcg gccgagcgca tggccttcaa catgcccgtc   1620

cagggcaccg ccgccgacct catgaagctg gctatggtga agctcttccc caggctggag   1680

gaaatggggg ccaggatgct ccttcaggtc cacgacgagc tggtcctcga ggccccaaaa   1740

gagagggcgg aggccgtggc ccggctggcc aaggaggtca tggagggggt gtatcccctg   1800

gccgtgcccc tggaggtgga ggtggggata ggggaggact ggctctccgc caaggagggc   1860

attgatggcc gcggcggagg cgggcatcat catcatcatc attaa                   1905
```

<210> SEQ ID NO 129
<211> LENGTH: 634
<212> TYPE: PRT
<213> ORGANISM: artificial sequence
<220> FEATURE:
<223> OTHER INFORMATION: The amino acid sequence of the Sac7d-ATaq
      fusion protein

<400> SEQUENCE: 129

```
Met Ile Thr Asn Ser Thr Val Lys Val Lys Phe Lys Tyr Lys Gly Glu
1               5                   10                  15

Glu Lys Glu Val Asp Thr Ser Lys Ile Lys Lys Val Trp Arg Val Gly
            20                  25                  30

Lys Met Val Ser Phe Thr Tyr Asp Asp Asn Gly Lys Thr Gly Arg Gly
        35                  40                  45

Ala Val Ser Glu Lys Asp Ala Pro Lys Glu Leu Leu Asp Met Leu Ala
    50                  55                  60

Arg Ala Glu Arg Glu Lys Lys Gly Gly Gly Val Thr Ser Pro Lys Ala
65                  70                  75                  80

Leu Glu Glu Ala Pro Trp Pro Pro Pro Glu Gly Ala Phe Val Gly Phe
                85                  90                  95

Val Leu Ser Arg Lys Glu Pro Met Trp Ala Asp Leu Leu Ala Leu Ala
            100                 105                 110

Ala Ala Arg Gly Gly Arg Val His Arg Ala Pro Glu Pro Tyr Lys Ala
        115                 120                 125

Leu Arg Asp Leu Lys Glu Ala Arg Gly Leu Leu Ala Lys Asp Leu Ser
    130                 135                 140

Val Leu Ala Leu Arg Glu Gly Leu Gly Leu Pro Pro Gly Asp Asp Pro
145                 150                 155                 160

Met Leu Leu Ala Tyr Leu Leu Asp Pro Ser Asn Thr Thr Pro Glu Gly
                165                 170                 175

Val Ala Arg Arg Tyr Gly Gly Glu Trp Thr Glu Glu Ala Gly Glu Arg
            180                 185                 190

Ala Ala Leu Ser Glu Arg Leu Phe Ala Asn Leu Trp Gly Arg Leu Glu
        195                 200                 205

Gly Glu Glu Arg Leu Leu Trp Leu Tyr Arg Glu Val Glu Arg Pro Leu
    210                 215                 220

Ser Ala Val Leu Ala His Met Glu Ala Thr Gly Val Arg Leu Asp Val
225                 230                 235                 240

Ala Tyr Leu Arg Ala Leu Ser Leu Glu Val Ala Glu Glu Ile Ala Arg
                245                 250                 255

Leu Glu Ala Glu Val Phe Arg Leu Ala Gly His Pro Phe Asn Leu Asn
            260                 265                 270
```

```
Ser Arg Asp Gln Leu Glu Arg Val Leu Phe Asp Glu Leu Gly Leu Pro
        275                 280                 285

Ala Ile Gly Lys Thr Glu Lys Thr Gly Lys Arg Ser Thr Ser Ala Ala
    290                 295                 300

Val Leu Glu Ala Leu Arg Glu Ala His Pro Ile Val Glu Lys Ile Leu
305                 310                 315                 320

Gln Tyr Arg Glu Leu Thr Lys Leu Lys Ser Thr Tyr Ile Asp Pro Leu
                325                 330                 335

Pro Asp Leu Ile His Pro Arg Thr Gly Arg Leu His Thr Arg Phe Asn
            340                 345                 350

Gln Thr Ala Thr Ala Thr Gly Arg Leu Ser Ser Ser Asp Pro Asn Leu
        355                 360                 365

Gln Asn Ile Pro Val Arg Thr Pro Leu Gly Gln Arg Ile Arg Arg Ala
    370                 375                 380

Phe Ile Ala Glu Glu Gly Trp Leu Leu Val Ala Leu Asp Tyr Ser Gln
385                 390                 395                 400

Ile Glu Leu Arg Val Leu Ala His Leu Ser Gly Asp Glu Asn Leu Ile
                405                 410                 415

Arg Val Phe Gln Glu Gly Arg Asp Ile His Thr Glu Thr Ala Ser Trp
            420                 425                 430

Met Phe Gly Val Pro Arg Glu Ala Val Asp Pro Leu Met Arg Arg Ala
        435                 440                 445

Ala Lys Thr Ile Asn Phe Gly Val Leu Tyr Gly Met Ser Ala His Arg
    450                 455                 460

Leu Ser Gln Glu Leu Ala Ile Pro Tyr Glu Glu Ala Gln Ala Phe Ile
465                 470                 475                 480

Glu Arg Tyr Phe Gln Ser Phe Pro Lys Val Arg Ala Trp Ile Glu Lys
                485                 490                 495

Thr Leu Glu Glu Gly Arg Arg Arg Gly Tyr Val Glu Thr Leu Phe Gly
            500                 505                 510

Arg Arg Arg Tyr Val Pro Asp Leu Glu Ala Arg Val Lys Ser Val Arg
        515                 520                 525

Glu Ala Ala Glu Arg Met Ala Phe Asn Met Pro Val Gln Gly Thr Ala
    530                 535                 540

Ala Asp Leu Met Lys Leu Ala Met Val Lys Leu Phe Pro Arg Leu Glu
545                 550                 555                 560

Glu Met Gly Ala Arg Met Leu Leu Gln Val His Asp Glu Leu Val Leu
                565                 570                 575

Glu Ala Pro Lys Glu Arg Ala Glu Ala Val Ala Arg Leu Ala Lys Glu
            580                 585                 590

Val Met Glu Gly Val Tyr Pro Leu Ala Val Pro Leu Glu Val Glu Val
        595                 600                 605

Gly Ile Gly Glu Asp Trp Leu Ser Ala Lys Glu Gly Ile Asp Gly Arg
    610                 615                 620

Gly Gly Gly Gly His His His His His His
625                 630
```

<210> SEQ ID NO 130
<211> LENGTH: 1965
<212> TYPE: DNA
<213> ORGANISM: artificial sequence
<220> FEATURE:
<223> OTHER INFORMATION: The DNA sequence encoding the PL-delta Taq fusion protein

<400> SEQUENCE: 130

```
atgattacga attcgaagaa aaagaaaaag aaaaagcgta agaaacgcaa aaagaaaaag     60
aaaggcggcg gtgtcactag tggcgcaacc gtaaagttca agtacaaagg cgaagaaaaa    120
gaggtagaca tctccaagat caagaaagta tggcgtgtgg gcaagatgat ctccttcacc    180
tacgacgagg gcggtggcaa gaccggccgt ggtgcggtaa gcgaaaagga cgcgccgaag    240
gagctgctgc agatgctgga gaagcagaaa aagggcggcg gtgtcaccag tcccaaggcc    300
ctggaggagg ccccctggcc cccgccggaa ggggccttcg tgggctttgt gctttcccgc    360
aaggagccca tgtgggccga tcttctggcc ctggccgccg ccaggggggg ccgggtccac    420
cgggcccccg agccttataa agccctcagg gacctgaagg aggcgcgggg gcttctcgcc    480
aaagacctga gcgttctggc cctgagggaa ggccttggcc tcccgcccgg cgacgacccc    540
atgctcctcg cctacctcct ggacccttcc aacaccaccc ccgagggggt ggcccggcgc    600
tacggcgggg agtggacgga ggaggcgggg gagcgggccg ccctttccga gaggctcttc    660
gccaacctgt gggggaggct tgaggggag gagaggctcc tttggcttta ccgggaggtg    720
gagaggcccc tttccgctgt cctggcccac atggaggcca cgggggtgcg cctggacgtg    780
gcctatctca gggccttgtc cctggaggtg gccgaggaga tcgcccgcct cgaggccgag    840
gtcttccgcc tggccggcca ccccttcaac ctcaactccc gggaccagct ggaaagggtc    900
ctctttgacg agctagggct tcccgccatc ggcaagacgg agaagaccgg caagcgctcc    960
accagcgccg ccgtcctgga ggccctccgc gaggcccacc ccatcgtgga gaagatcctg   1020
cagtaccggg agctcaccaa gctgaagagc acctacattg accccttgcc ggacctcatc   1080
caccccagga cgggccgcct ccacacccgc ttcaaccaga cggccacggc cacgggcagg   1140
ctaagtagct ccgatcccaa cctccagaac atccccgtcc gcaccccgct tgggcagagg   1200
atccgccggg ccttcatcgc cgaggagggg tggctattgg tggccctgga ctatagccag   1260
atagagctca gggtgctggc ccacctctcc ggcgacgaga acctgatccg ggtcttccag   1320
gaggggcggg acatccacac ggagaccgcc agctggatgt tcggcgtccc ccgggaggcc   1380
gtggaccccc tgatgcgccg ggcggccaag accatcaact tcggggtcct ctacggcatg   1440
tcggcccacc gcctctccca ggagctagcc atcccttacg aggaggccca ggccttcatt   1500
gagcgctact ttcagagctt ccccaaggtg cgggcctgga ttgagaagac cctggaggag   1560
ggcaggaggc gggggtacgt ggagaccctc ttcggccgcc gccgctacgt gccagaccta   1620
gaggcccggg tgaagagcgt gcgggaggcg gccgagcgca tggccttcaa catgcccgtc   1680
cagggcaccg ccgccgacct catgaagctg gctatggtga agctcttccc caggctggag   1740
gaaatggggg ccaggatgct ccttcaggtc cacgacgagc tggtcctcga ggccccaaaa   1800
gagagggcgg aggccgtggc ccggctggcc aaggaggtca tggagggggt gtatcccctg   1860
gccgtgcccc tggaggtgga ggtggggata ggggaggact ggctctccgc caaggagggc   1920
attgatggcc gcggcggagg cgggcatcat catcatcatc attaa                   1965
```

<210> SEQ ID NO 131
<211> LENGTH: 654
<212> TYPE: PRT
<213> ORGANISM: artificial sequence
<220> FEATURE:
<223> OTHER INFORMATION: The amino acid sequence of PL- delta Taq fusion
      protein

<400> SEQUENCE: 131

Met Ile Thr Asn Ser Lys Lys Lys Lys Lys Lys Lys Arg Lys Lys Arg

-continued

```
1               5                   10                  15

Lys Lys Lys Lys Lys Gly Gly Gly Val Thr Ser Gly Ala Thr Val Lys
            20                  25                  30

Phe Lys Tyr Lys Gly Glu Glu Lys Glu Val Asp Ile Ser Lys Ile Lys
        35                  40                  45

Lys Val Trp Arg Val Gly Lys Met Ile Ser Phe Thr Tyr Asp Glu Gly
    50                  55                  60

Gly Gly Lys Thr Gly Arg Gly Ala Val Ser Glu Lys Asp Ala Pro Lys
65                  70                  75                  80

Glu Leu Leu Gln Met Leu Glu Lys Gln Lys Lys Gly Gly Gly Val Thr
                85                  90                  95

Ser Pro Lys Ala Leu Glu Glu Ala Pro Trp Pro Pro Pro Glu Gly Ala
            100                 105                 110

Phe Val Gly Phe Val Leu Ser Arg Lys Glu Pro Met Trp Ala Asp Leu
        115                 120                 125

Leu Ala Leu Ala Ala Ala Arg Gly Gly Arg Val His Arg Ala Pro Glu
    130                 135                 140

Pro Tyr Lys Ala Leu Arg Asp Leu Lys Glu Ala Arg Gly Leu Leu Ala
145                 150                 155                 160

Lys Asp Leu Ser Val Leu Ala Leu Arg Glu Gly Leu Gly Leu Pro Pro
                165                 170                 175

Gly Asp Asp Pro Met Leu Leu Ala Tyr Leu Leu Asp Pro Ser Asn Thr
            180                 185                 190

Thr Pro Glu Gly Val Ala Arg Arg Tyr Gly Gly Glu Trp Thr Glu Glu
        195                 200                 205

Ala Gly Glu Arg Ala Ala Leu Ser Glu Arg Leu Phe Ala Asn Leu Trp
    210                 215                 220

Gly Arg Leu Glu Gly Glu Glu Arg Leu Leu Trp Leu Tyr Arg Glu Val
225                 230                 235                 240

Glu Arg Pro Leu Ser Ala Val Leu Ala His Met Glu Ala Thr Gly Val
                245                 250                 255

Arg Leu Asp Val Ala Tyr Leu Arg Ala Leu Ser Leu Glu Val Ala Glu
            260                 265                 270

Glu Ile Ala Arg Leu Glu Ala Glu Val Phe Arg Leu Ala Gly His Pro
        275                 280                 285

Phe Asn Leu Asn Ser Arg Asp Gln Leu Glu Arg Val Leu Phe Asp Glu
    290                 295                 300

Leu Gly Leu Pro Ala Ile Gly Lys Thr Glu Lys Thr Gly Lys Arg Ser
305                 310                 315                 320

Thr Ser Ala Ala Val Leu Glu Ala Leu Arg Glu Ala His Pro Ile Val
                325                 330                 335

Glu Lys Ile Leu Gln Tyr Arg Glu Leu Thr Lys Leu Lys Ser Thr Tyr
            340                 345                 350

Ile Asp Pro Leu Pro Asp Leu Ile His Pro Arg Thr Gly Arg Leu His
        355                 360                 365

Thr Arg Phe Asn Gln Thr Ala Thr Ala Thr Gly Arg Leu Ser Ser Ser
    370                 375                 380

Asp Pro Asn Leu Gln Asn Ile Pro Val Arg Thr Pro Leu Gly Gln Arg
385                 390                 395                 400

Ile Arg Arg Ala Phe Ile Ala Glu Glu Gly Trp Leu Leu Val Ala Leu
                405                 410                 415

Asp Tyr Ser Gln Ile Glu Leu Arg Val Leu Ala His Leu Ser Gly Asp
            420                 425                 430
```

```
Glu Asn Leu Ile Arg Val Phe Gln Glu Gly Arg Asp Ile His Thr Glu
        435                 440                 445

Thr Ala Ser Trp Met Phe Gly Val Pro Arg Glu Ala Val Asp Pro Leu
    450                 455                 460

Met Arg Arg Ala Ala Lys Thr Ile Asn Phe Gly Val Leu Tyr Gly Met
465                 470                 475                 480

Ser Ala His Arg Leu Ser Gln Glu Leu Ala Ile Pro Tyr Glu Glu Ala
                485                 490                 495

Gln Ala Phe Ile Glu Arg Tyr Phe Gln Ser Phe Pro Lys Val Arg Ala
            500                 505                 510

Trp Ile Glu Lys Thr Leu Glu Glu Gly Arg Arg Arg Gly Tyr Val Glu
        515                 520                 525

Thr Leu Phe Gly Arg Arg Arg Tyr Val Pro Asp Leu Glu Ala Arg Val
    530                 535                 540

Lys Ser Val Arg Glu Ala Ala Glu Arg Met Ala Phe Asn Met Pro Val
545                 550                 555                 560

Gln Gly Thr Ala Ala Asp Leu Met Lys Leu Ala Met Val Lys Leu Phe
                565                 570                 575

Pro Arg Leu Glu Glu Met Gly Ala Arg Met Leu Leu Gln Val His Asp
            580                 585                 590

Glu Leu Val Leu Glu Ala Pro Lys Glu Arg Ala Glu Ala Val Ala Arg
        595                 600                 605

Leu Ala Lys Glu Val Met Glu Gly Val Tyr Pro Leu Ala Val Pro Leu
    610                 615                 620

Glu Val Glu Val Gly Ile Gly Glu Asp Trp Leu Ser Ala Lys Glu Gly
625                 630                 635                 640

Ile Asp Gly Arg Gly Gly Gly Gly His His His His His His
                645                 650
```

<210> SEQ ID NO 132
<211> LENGTH: 20
<212> TYPE: DNA
<213> ORGANISM: artificial sequence
<220> FEATURE:
<223> OTHER INFORMATION: primer

<400> SEQUENCE: 132
cctgctctgc cgcttcacgc 20

<210> SEQ ID NO 133
<211> LENGTH: 20
<212> TYPE: DNA
<213> ORGANISM: artificial sequence
<220> FEATURE:
<223> OTHER INFORMATION: primer

<400> SEQUENCE: 133
gcacagcggc tggctgagga 20

<210> SEQ ID NO 134
<211> LENGTH: 22
<212> TYPE: DNA
<213> ORGANISM: artificial sequence
<220> FEATURE:
<223> OTHER INFORMATION: primer

<400> SEQUENCE: 134
tgacggagga taacgccagc ag 22

<210> SEQ ID NO 135
<211> LENGTH: 25
<212> TYPE: DNA
<213> ORGANISM: artificial sequence
<220> FEATURE:
<223> OTHER INFORMATION: primer

<400> SEQUENCE: 135
gaaagacgat gggtcgctaa tacgc 25

<210> SEQ ID NO 136
<211> LENGTH: 22
<212> TYPE: DNA
<213> ORGANISM: artificial sequence
<220> FEATURE:
<223> OTHER INFORMATION: primer

<400> SEQUENCE: 136
tgacggagga taacgccagc ag 22

<210> SEQ ID NO 137
<211> LENGTH: 22
<212> TYPE: DNA
<213> ORGANISM: artificial sequence
<220> FEATURE:
<223> OTHER INFORMATION: primer

<400> SEQUENCE: 137
ggggttggag gtcaatgggt tc 22

<210> SEQ ID NO 138
<211> LENGTH: 20
<212> TYPE: DNA
<213> ORGANISM: artificial sequence
<220> FEATURE:
<223> OTHER INFORMATION: primer

<400> SEQUENCE: 138
cctgctctgc cgcttcacgc 20

<210> SEQ ID NO 139
<211> LENGTH: 22
<212> TYPE: DNA
<213> ORGANISM: artificial sequence
<220> FEATURE:
<223> OTHER INFORMATION: primer

<400> SEQUENCE: 139
cacatggtac agcaagcctg gc 22

<210> SEQ ID NO 140
<211> LENGTH: 23
<212> TYPE: DNA
<213> ORGANISM: artificial sequence
<220> FEATURE:
<223> OTHER INFORMATION: primer

<400> SEQUENCE: 140
cccgtatctg ctgggatact ggc 23

<210> SEQ ID NO 141
<211> LENGTH: 23
<212> TYPE: DNA
<213> ORGANISM: artificial sequence
<220> FEATURE:
<223> OTHER INFORMATION: primer

<400> SEQUENCE: 141
cagcggtgct gactgaatca tgg 23

<210> SEQ ID NO 142
<211> LENGTH: 19
<212> TYPE: DNA
<213> ORGANISM: artificial sequence
<220> FEATURE:
<223> OTHER INFORMATION: primer

<400> SEQUENCE: 142
cctgcctgcc gcttcacgc 19

<210> SEQ ID NO 143
<211> LENGTH: 22
<212> TYPE: DNA
<213> ORGANISM: artificial sequence
<220> FEATURE:
<223> OTHER INFORMATION: primer

<400> SEQUENCE: 143
ccaatacccg tttcatcgcg gc 22

<210> SEQ ID NO 144
<211> LENGTH: 19
<212> TYPE: DNA
<213> ORGANISM: artificial sequence
<220> FEATURE:
<223> OTHER INFORMATION: primer

<400> SEQUENCE: 144
ccacctcatc ctgggcacc 19

<210> SEQ ID NO 145
<211> LENGTH: 22
<212> TYPE: DNA
<213> ORGANISM: artificial sequence
<220> FEATURE:
<223> OTHER INFORMATION: primer

<400> SEQUENCE: 145
gcttgaggcc aaccatcaga gc 22

<210> SEQ ID NO 146
<211> LENGTH: 22
<212> TYPE: DNA
<213> ORGANISM: artificial sequence
<220> FEATURE:
<223> OTHER INFORMATION: prmer

<400> SEQUENCE: 146
ggttggccaa tctactccca gg 22

<210> SEQ ID NO 147
<211> LENGTH: 20
<212> TYPE: DNA
<213> ORGANISM: artificial sequence
<220> FEATURE:
<223> OTHER INFORMATION: primer

<400> SEQUENCE: 147
gctcactcag tgtggcaaag 20

<210> SEQ ID NO 148

-continued

```
<211> LENGTH: 24
<212> TYPE: DNA
<213> ORGANISM: artificial sequence
<220> FEATURE:
<223> OTHER INFORMATION: primer

<400> SEQUENCE: 148

gattagcaaa agggcctagc ttgg                                              24
```